US 9,550,805 B2
Jan. 24, 2017

(12) United States Patent
Banta et al.

(54) PRECIPITABLE PEPTIDES

(71) Applicant: THE TRUSTEES OF COLUMBIA UNIVERSITY IN THE CITY OF NEW YORK, New York, NY (US)

(72) Inventors: Scott Banta, Fairfield, CT (US); Oren Shur, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,367

(22) Filed: Oct. 11, 2013

(65) Prior Publication Data

US 2014/0187746 A1 Jul. 3, 2014

Related U.S. Application Data

(63) Continuation-in-part of application No. PCT/US2012/033293, filed on Apr. 12, 2012.

(60) Provisional application No. 61/475,042, filed on Apr. 13, 2011, provisional application No. 61/616,341, filed on Mar. 27, 2012.

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 1/30* | (2006.01) | |
| *C07K 7/06* | (2006.01) | |

(52) U.S. Cl.
CPC .............. *C07K 1/30* (2013.01); *C07K 1/303* (2013.01); *C07K 7/06* (2013.01); *C07K 2319/00* (2013.01); *C07K 2319/24* (2013.01); *C07K 2319/50* (2013.01)

(58) Field of Classification Search
CPC ....... C07K 1/30; C07K 1/303; C07K 2319/00; C07K 2319/24; C07K 2319/50; C07K 7/06

See application file for complete search history.

(56) References Cited

U.S. PATENT DOCUMENTS

| | | | | |
|---|---|---|---|---|
| 7,642,079 | B2* | 1/2010 | Cayouette et al. | 435/212 |
| 9,127,267 | B2* | 9/2015 | Banta | C12N 9/88 |
| 2004/0019919 | A1* | 1/2004 | Sonderegger et al. | 800/14 |
| 2009/0075335 | A1 | 3/2009 | Banta et al. | |
| 2013/0237612 | A1* | 9/2013 | Banta | C12N 9/88 514/773 |
| 2016/0152966 | A1* | 6/2016 | Banta | C12N 9/88 424/94.5 |

OTHER PUBLICATIONS

Giraud et al. Legumes Symbioses: Absence of Nod Genes in Photosynthetic Bradyrhizobia. Science, 2007. vol. 316, pp. 1307-1312.*
Livingstone et al. Protein sequence alignments: a strategy for the hierarchichal analysis of residue conservation. CABIOS, 1993. vol. 9, No. 6, pp. 745-756.*
Nemoto et al. R2D5 Antigen: a Calcium-binding Phosphoprotein Predominantly Expressed in Olfactory Receptor Neurons. J Cell Biol., 1993. vol. 123, No. 4, pp. 963-976.*
Scoffer, A.J., et al., "Metal ion-dependent, reversible, protein filament formation by designed beta-roll polypeptides," BMC Structural Biology, vol. 7:63, pp. 1-13, Oct. 2007.
Tebo, et al., UniProt Accession, Jul. 13, 2010, downloaded from www.uniprot.org/uniprot/A5PAU7.txt?version=14 on Sep. 14, 2012.
Blenner, M.A., et al., "Calcium-Induced Folding of a Beta Roll Motif Requires C-Terminal Entropic Stabilization," J. Molecular Biology, vol. 400, pp. 244-256, May 11, 2010.
International Search Report and the Written Opinion of the International Searching Authority, International Application No. PCT/US20121033293, filed Oct. 1, 2012.

* cited by examiner

*Primary Examiner* — Marcela M Cordero Garcia
(74) *Attorney, Agent, or Firm* — Murtha Cullina LLP; Anthony P. Gangemi

(57) ABSTRACT

The invention is directed to a Ca2+ precipitable polypeptide tags and cassettes useful for purification of molecules from heterogeneous samples. The invention also relates to methods for bioseparation of molecules comprising Ca2+ precipitable tags and cassettes.

11 Claims, 25 Drawing Sheets

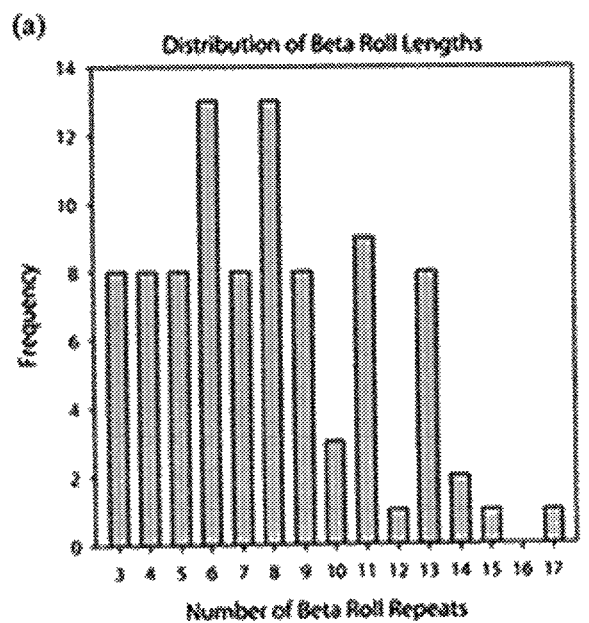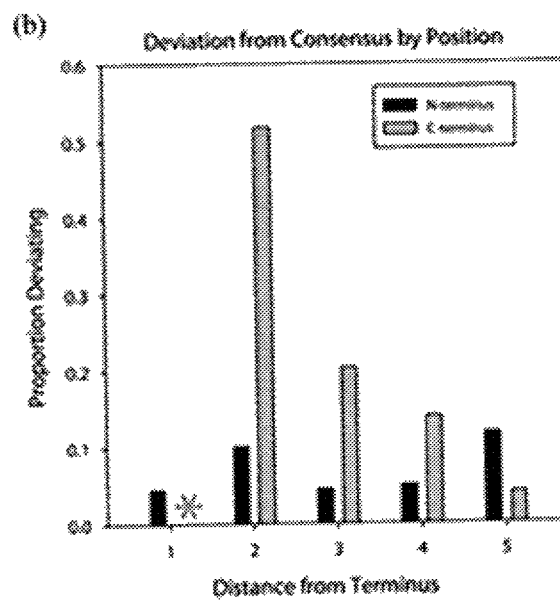
Figure 8A-B

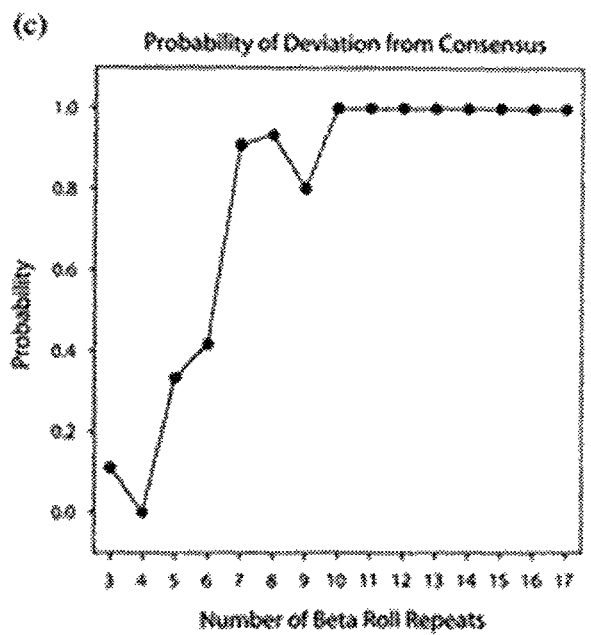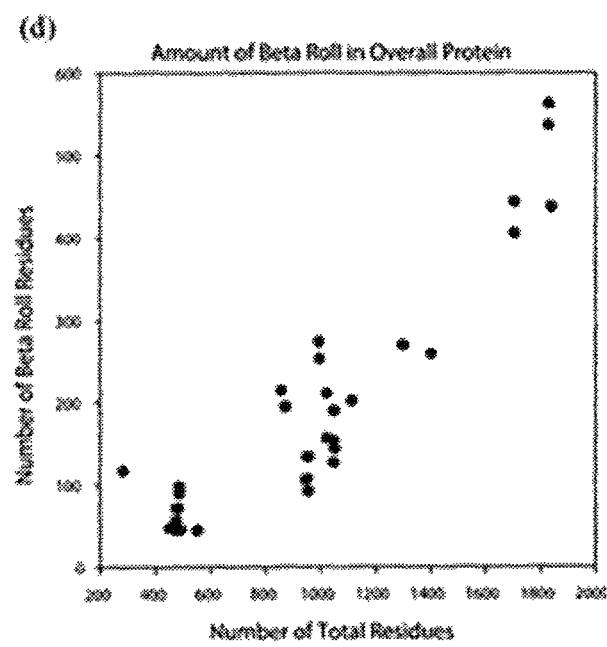
Figure 8C-D

SEQUENCE LISTING

<160> NUMBER OF SEQ ID NOS: 1372

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Ala Gly Asn Asp Thr Leu Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<223> OTHER INFORMATION: see specification as filed for detailed
      description of substitutions and preferred embodiments

<400> SEQUENCE: 2

Gly Gly Xaa Gly Xaa Asp Xaa Xaa Xaa
1               5

<210> SEQ ID NO 3
<211> LENGTH: 68
<212> TYPE: PRT
<213> ORGANISM: Bordetella pertussis

<400> SEQUENCE: 3

Ile Asn Ala Gly Ala Asp Gln Leu Trp Phe Ala Arg Gln Gly Asn Asp
1               5                   10                  15

Leu Glu Ile Arg Ile Leu Gly Thr Asp Asp Ala Leu Thr Val His Asp
            20                  25                  30

Trp Tyr Arg Asp Ala Asp His Arg Val Glu Ile Ile His Ala Ala Asn
        35                  40                  45

Gln Ala Val Asp Gln Ala Gly Ile Glu Lys Leu Val Glu Ala Met Ala
    50                  55                  60

Gln Tyr Pro Asp
65

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Gly Gly Ala Gly Asn Asp Thr Leu Tyr Gly Gly Ala Gly Asn Asp Thr
1               5                   10                  15

Leu Tyr Gly Gly Ala Gly Asn Asp Thr Leu Tyr Gly Gly Ala Gly Asn
            20                  25                  30

Asp Thr Leu Tyr Gly Gly Ala Gly Asn Asp Thr Leu Tyr Ile Asn Ala
        35                  40                  45

Gly Ala Asp Gln Leu Trp Phe Ala Arg Gln Gly Asn Asp Leu Glu Ile
    50                  55                  60

Arg Ile Leu Gly Thr Asp Ala Leu Thr Val His Asp Trp Tyr Arg
65                  70                  75                  80

Asp Ala Asp His Arg Val Glu Ile Ile His Ala Ala Asn Gln Ala Val
                85                  90                  95

Asp Gln Ala Gly Ile Glu Lys Leu Val Glu Ala Met Ala Gln Tyr Pro
            100                 105                 110

Asp

<210> SEQ ID NO 5
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Gly Ala Gly Asn Asp Thr Leu Tyr Gly Gly Ala Gly Asn Asp Thr
1               5                   10                  15

Leu Tyr Gly Gly Ala Gly Asn Asp Thr Leu Tyr Gly Gly Ala Gly Asn
            20                  25                  30

Asp Thr Leu Tyr Gly Gly Ala Gly Asn Asp Thr Leu Tyr Gly Gly Ala
        35                  40                  45

Gly Asn Asp Thr Leu Tyr Gly Gly Ala Gly Asn Asp Thr Leu Tyr Gly
    50                  55                  60

Gly Ala Gly Asn Asp Thr Leu Tyr Gly Gly Ala Gly Asn Asp Thr Leu
65                  70                  75                  80

Tyr Gly Gly Ala Gly Asn Asp Thr Leu Tyr Gly Gly Ala Gly Asn Asp
                85                  90                  95

Thr Leu Tyr Gly Gly Ala Gly Asn Asp Thr Leu Tyr Gly Gly Ala Gly
            100                 105                 110

Asn Asp Thr Leu Tyr Gly Gly Ala Gly Asn Asp Thr Leu Tyr Gly Gly
            115                 120                 125

Ala Gly Asn Asp Thr Leu Tyr Gly Gly Ala Gly Asn Asp Thr Leu Tyr
        130                 135                 140

Gly Gly Ala Gly Asn Asp Thr Leu Tyr Ile Asn Ala Gly Ala Asp Gln
145                 150                 155                 160

Leu Trp Phe Ala Arg Gln Gly Asn Asp Leu Glu Ile Arg Ile Leu Gly
                165                 170                 175

Thr Asp Asp Ala Leu Thr Val His Asp Trp Tyr Arg Asp Ala Asp His
            180                 185                 190

Arg Val Glu Ile Ile His Ala Ala Asn Gln Ala Val Asp Gln Ala Gly
        195                 200                 205

Ile Glu Lys Leu Val Glu Ala Met Ala Gln Tyr Pro Asp
        210                 215                 220

<210> SEQ ID NO 6
<211> LENGTH: 68

```
<212> TYPE: PRT
<213> ORGANISM: Bordetella bronchiseptica

<400> SEQUENCE: 6

Ile Asn Ala Gly Ala Asp Gln Leu Trp Phe Ala Arg Gln Gly Asn Asp
1               5                   10                  15

Leu Glu Ile Arg Ile Leu Gly Thr Asp Asp Ala Leu Thr Val His Asp
            20                  25                  30

Trp Tyr Arg Asp Ala Asp His Arg Val Glu Ala Ile His Ala Ala Asn
        35                  40                  45

Gln Ala Ile Asp Pro Ala Gly Ile Glu Lys Leu Val Glu Ala Met Ala
    50                  55                  60

Gln Tyr Pro Asp
65

<210> SEQ ID NO 7
<211> LENGTH: 68
<212> TYPE: PRT
<213> ORGANISM: Bordetella bronchiseptica

<400> SEQUENCE: 7

Ile Asn Ala Gly Ala Asp Gln Leu Trp Phe Ala Arg Gln Gly Asn Asp
1               5                   10                  15

Leu Glu Ile Arg Ile Leu Gly Thr Asp Asp Ala Leu Thr Val His Asp
            20                  25                  30

Trp Tyr Arg Asp Ala Asp His Arg Val Glu Ala Ile His Ala Ala Asn
        35                  40                  45

Gln Ala Ile Asp Pro Ala Gly Ile Glu Lys Leu Val Glu Ala Met Ala
    50                  55                  60

Gln Tyr Pro Asp
65

<210> SEQ ID NO 8
<211> LENGTH: 68
<212> TYPE: PRT
<213> ORGANISM: Bordetella bronchiseptica

<400> SEQUENCE: 8

Ile Asn Ala Gly Ala Asp Gln Leu Trp Phe Ala Arg Gln Gly Asn Asp
1               5                   10                  15

Leu Glu Ile Arg Ile Leu Gly Thr Asp Asp Ala Leu Thr Val His Asp
            20                  25                  30

Trp Tyr Arg Asp Ala Asp His Arg Val Glu Ala Ile His Ala Ala Asn
        35                  40                  45

Gln Thr Val Asp Pro Ala Gly Ile Glu Lys Leu Val Glu Ala Met Ala
    50                  55                  60

Gln Tyr Pro Asp
65

<210> SEQ ID NO 9
<211> LENGTH: 61
<212> TYPE: PRT
<213> ORGANISM: Azospirillum sp.

<400> SEQUENCE: 9

Gln Leu Trp Phe Ser Lys Ser Gly Ser Asp Leu Glu Val Arg Val Val
1               5                   10                  15

Gly Thr Asp Ala Val Thr Val Ala Gly Trp Tyr Ser Gly Ala Glu
            20                  25                  30
```

```
His His Met Asp Ser Ile Glu Thr Ala Asp Gly Thr Val Leu Leu Asp
            35                  40                  45

Ser Met Val Asp Arg Leu Val Gln Ala Met Ala Gly Phe
 50                  55                  60

<210> SEQ ID NO 10
<211> LENGTH: 61
<212> TYPE: PRT
<213> ORGANISM: Burkholderia cenocepacia

<400> SEQUENCE: 10

Ala Asp Gln Leu Trp Phe Arg His Val Gly Asn Asp Leu Glu Ile Ser
 1               5                  10                  15

Ile Leu Gly Thr Gly Asp Thr Ala Thr Val Arg Asp Trp Tyr Leu Gly
            20                  25                  30

Ser Arg Tyr Gln Ile Glu Gln Ile Arg Val Asp Asp Gly Arg Thr Leu
        35                  40                  45

Val Asn Ala Asp Val Glu Lys Leu Val Gln Ala Met Ala
 50                  55                  60

<210> SEQ ID NO 11
<211> LENGTH: 61
<212> TYPE: PRT
<213> ORGANISM: Burkholderia ambifaria

<400> SEQUENCE: 11

Ala Asp Gln Leu Trp Phe Arg His Val Gly Asn Asp Leu Glu Ile Ser
 1               5                  10                  15

Ile Leu Gly Ser Ser Asp Thr Ala Thr Val Arg Asp Trp Tyr Ser Gly
            20                  25                  30

Ser Arg Tyr Gln Ile Glu Gln Ile Arg Leu Asp Asp Gly Arg Thr Leu
        35                  40                  45

Val Asn Ala Asp Val Glu Lys Leu Val Gln Ala Met Ala
 50                  55                  60

<210> SEQ ID NO 12
<211> LENGTH: 66
<212> TYPE: PRT
<213> ORGANISM: Herbaspirillum seropedicae

<400> SEQUENCE: 12

Asp Ala Arg Gln Thr Asn Leu Trp Phe Ser Gln Val Gly Lys Asp Leu
 1               5                  10                  15

Gln Ile Asp Val Leu Gly Ser Thr Asp Gln Val Thr Val Lys Asp Trp
            20                  25                  30

Tyr Ala Gly Ala Asp Asn Arg Val Glu Arg Ile Lys Thr Ala Asp Gly
        35                  40                  45

Lys Thr Leu Tyr Asp Ser Asp Val Asp Lys Leu Val Gln Ala Met Ala
 50                  55                  60

Ser Phe
 65

<210> SEQ ID NO 13
<211> LENGTH: 66
<212> TYPE: PRT
<213> ORGANISM: Herbaspirillum seropedicae

<400> SEQUENCE: 13

Asp Ala Arg Gln Thr Asn Leu Trp Phe Ser Gln Val Gly Lys Asp Leu
```

```
                1               5                  10                 15
        Gln Ile Asp Val Leu Gly Ser Thr Asp Gln Val Thr Val Lys Asp Trp
                        20                  25                  30

Tyr Ala Gly Ala Asp Asn Arg Val Glu Arg Ile Lys Thr Ala Asp Gly
                        35                  40                  45

Lys Thr Leu Tyr Asp Ser Asp Val Asp Lys Leu Val Gln Ala Met Ala
                50                      55                  60

Ser Phe
        65
```

<210> SEQ ID NO 14
<211> LENGTH: 61
<212> TYPE: PRT
<213> ORGANISM: Actinobacillus pleuropneumoniae

<400> SEQUENCE: 14

```
        Glu Leu Trp Phe Ser Arg Glu Asn Asn Asp Leu Ile Ile Lys Ser Leu
        1               5                   10                  15

Leu Ser Glu Asp Lys Val Thr Val Gln Asn Trp Tyr Ser His Gln Asp
                        20                  25                  30

His Lys Ile Glu Asn Ile Arg Leu Ser Asn Glu Gln Thr Leu Val Ser
                    35                  40                  45

Thr Gln Val Glu Lys Met Val Glu Ser Met Ala Gly Phe
                50                  55                  60
```

<210> SEQ ID NO 15
<211> LENGTH: 61
<212> TYPE: PRT
<213> ORGANISM: Shewanella piezotolerans

<400> SEQUENCE: 15

```
        Glu Glu Leu Trp Phe Ser Arg Asp Gly Asn Asp Leu Gln Ile Asn Val
        1               5                   10                  15

Ile Gly Thr Asp Asn Gln Val Glu Ile Ser Asp Trp Tyr Ser Gly Val
                        20                  25                  30

Asn Tyr Gln Leu Asp Lys Val Gln Val Gly Asp Ser Val Leu Leu Asn
                    35                  40                  45

Thr Gln Leu Glu Gln Leu Val Ser Ala Met Ala Ser Phe
                50                  55                  60
```

<210> SEQ ID NO 16
<211> LENGTH: 64
<212> TYPE: PRT
<213> ORGANISM: Actinobacillus pleuropneumoniae

<400> SEQUENCE: 16

```
        Gly Leu Ser Glu Leu Trp Phe Ser Arg Glu Asn Asn Asp Leu Ile Ile
        1               5                   10                  15

Lys Ser Leu Leu Ser Glu Asp Lys Val Thr Val Gln Asn Trp Tyr Ser
                        20                  25                  30

His Gln Asp His Lys Ile Glu Asn Ile Arg Leu Ser Asn Glu Gln Met
                    35                  40                  45

Leu Val Ser Thr Gln Val Glu Lys Met Val Glu Ser Met Ala Gly Phe
                50                  55                  60
```

<210> SEQ ID NO 17
<211> LENGTH: 61
<212> TYPE: PRT
<213> ORGANISM: Shewanella violacea

<400> SEQUENCE: 17

| Glu | Asp | Leu | Trp | Phe | Ser | Arg | Asp | Gly | Asn | Asn | Leu | Gln | Ile | Asn | Ile |
| 1 | | | | 5 | | | | | 10 | | | | | 15 | |

| Ile | Gly | Thr | Asp | Asp | Gln | Val | Glu | Val | Asn | Asn | Trp | Tyr | Asn | Asp | Thr |
| | | | 20 | | | | | 25 | | | | | 30 | | |

| Asn | Tyr | Gln | Leu | Asp | Gln | Ile | Gln | Val | Gly | Gly | Ser | Val | Leu | Leu | Asn |
| | | | 35 | | | | | 40 | | | | | 45 | | |

| Asn | Gln | Leu | Glu | Gln | Leu | Val | Ser | Ala | Met | Ala | Ser | Phe |
| | 50 | | | | | 55 | | | | | 60 | |

<210> SEQ ID NO 18
<211> LENGTH: 61
<212> TYPE: PRT
<213> ORGANISM: Actinobacillus pleuropneumoniae

<400> SEQUENCE: 18

| Glu | Leu | Trp | Phe | Ser | Arg | Glu | Asn | Asn | Asp | Leu | Ile | Ile | Lys | Ser | Leu |
| 1 | | | | 5 | | | | | 10 | | | | | 15 | |

| Leu | Ser | Glu | Asp | Lys | Val | Thr | Val | Gln | Asn | Trp | Tyr | Ser | His | Gln | Asp |
| | | | 20 | | | | | 25 | | | | | 30 | | |

| His | Lys | Ile | Glu | Asn | Ile | Arg | Leu | Ser | Asn | Glu | Gln | Thr | Leu | Val | Ser |
| | | | 35 | | | | | 40 | | | | | 45 | | |

| Thr | Gln | Val | Glu | Lys | Met | Val | Glu | Ser | Met | Ala | Ser | Phe |
| | 50 | | | | | 55 | | | | | 60 | |

<210> SEQ ID NO 19
<211> LENGTH: 61
<212> TYPE: PRT
<213> ORGANISM: Bradyrhizobium sp.

<400> SEQUENCE: 19

| Ala | Asp | Asn | Phe | Trp | Phe | Val | Lys | Ser | Gly | Asn | Asp | Leu | Glu | Ile | Asp |
| 1 | | | | 5 | | | | | 10 | | | | | 15 | |

| Ile | Leu | Gly | Thr | His | Gln | Gln | Val | Thr | Val | Ala | Asp | Trp | Phe | Leu | Gly |
| | | | 20 | | | | | 25 | | | | | 30 | | |

| Gly | Ser | Tyr | Gln | Leu | Gln | Glu | Ile | Lys | Ala | Gly | Gly | Leu | Glu | Leu | Asp |
| | | | 35 | | | | | 40 | | | | | 45 | | |

| Thr | Gln | Val | Thr | Gln | Leu | Val | Gln | Ala | Met | Ala | Thr | Tyr |
| | 50 | | | | | 55 | | | | | 60 | |

<210> SEQ ID NO 20
<211> LENGTH: 61
<212> TYPE: PRT
<213> ORGANISM: Actinobacillus pleuropneumoniae

<400> SEQUENCE: 20

| Glu | Leu | Trp | Phe | Ser | Arg | Glu | Asn | Asn | Asp | Leu | Ile | Ile | Lys | Ser | Leu |
| 1 | | | | 5 | | | | | 10 | | | | | 15 | |

| Leu | Ser | Glu | Asp | Lys | Val | Thr | Val | Gln | Asn | Trp | Tyr | Ser | His | Gln | Asp |
| | | | 20 | | | | | 25 | | | | | 30 | | |

| His | Lys | Ile | Glu | Asn | Ile | Arg | Leu | Ser | Asn | Glu | Gln | Thr | Leu | Val | Ser |
| | | | 35 | | | | | 40 | | | | | 45 | | |

| Thr | Gln | Val | Glu | Lys | Met | Val | Glu | Ser | Met | Ala | Gly | Phe |
| | 50 | | | | | 55 | | | | | 60 | |

<210> SEQ ID NO 21
<211> LENGTH: 60
<212> TYPE: PRT

<213> ORGANISM: Actinobacillus pleuropneumoniae

<400> SEQUENCE: 21

Leu Trp Phe Ser Arg Glu Asn Asn Asp Leu Ile Ile Lys Ser Leu Leu
1               5                   10                  15

Ser Glu Asp Lys Val Thr Val Gln Asn Trp Tyr Ser His Gln Asp His
            20                  25                  30

Lys Ile Glu Asn Ile Arg Leu Ser Asn Glu Gln Thr Leu Val Ser Thr
        35                  40                  45

Gln Val Glu Lys Met Val Glu Ser Met Ala Gly Phe
    50                  55                  60

<210> SEQ ID NO 22
<211> LENGTH: 60
<212> TYPE: PRT
<213> ORGANISM: Xanthomonas axonopodis

<400> SEQUENCE: 22

Leu Trp Phe Arg Lys Ser Gly Asn Asn Leu Glu Val Ser Ile Ile Gly
1               5                   10                  15

Thr Ser Asp Lys Leu Val Met Ser Asn Trp Tyr Ala Gly Ser Gln Tyr
            20                  25                  30

Gln Val Glu Arg Phe Gln Ala Gly Asp Gly Lys Ala Leu Gln Ala Asn
        35                  40                  45

Gln Val Gln Ser Leu Val Gln Ala Met Ala Ser Phe
    50                  55                  60

<210> SEQ ID NO 23
<211> LENGTH: 61
<212> TYPE: PRT
<213> ORGANISM: Actinobacillus pleuropneumoniae

<400> SEQUENCE: 23

Glu Leu Trp Phe Ser Arg Glu Asn Asn Asp Leu Ile Ile Lys Ser Leu
1               5                   10                  15

Leu Ser Glu Asp Lys Val Thr Val Gln Asn Trp Tyr Ser His Gln Asp
            20                  25                  30

His Lys Ile Glu Asn Ile Arg Leu Ser Asn Glu Gln Thr Leu Val Ser
        35                  40                  45

Thr Gln Val Glu Lys Met Val Glu Ser Met Ala Gly Phe
    50                  55                  60

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)

```
<223> OTHER INFORMATION: Leu, Phe or Ile
<220> FEATURE:
<221> NAME/KEY: MOD_RES
<222> LOCATION: (9)..(9)
<223> OTHER INFORMATION: Any amino acid

<400> SEQUENCE: 24

Gly Gly Xaa Gly Xaa Asp Xaa Xaa Xaa
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Asp Asn Ala Ser Asp Leu Phe Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Asn Ala Gly Asn Asp Thr Leu Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Asp Ala Gly Asn Asp Thr Leu Tyr
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Ser Gly Asn Asp Thr Leu Tyr
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Asn Ser Gly Asn Asp Thr Leu Tyr
```

```
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Asp Ser Gly Asn Asp Thr Leu Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Gly Asn Asp Thr Leu Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Asn Gly Gly Asn Asp Thr Leu Tyr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Asp Gly Gly Asn Asp Thr Leu Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Asp Gly Asn Asp Thr Leu Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 35

Gly Asn Asp Gly Asn Asp Thr Leu Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Asp Asp Gly Asn Asp Thr Leu Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Ala Gly Asp Asp Thr Leu Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Ala Gly Asp Asp Thr Leu Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Asp Ala Gly Asp Asp Thr Leu Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Ser Gly Asp Asp Thr Leu Tyr
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Asn Ser Gly Asp Asp Thr Leu Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Asp Ser Gly Asp Asp Thr Leu Tyr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Gly Gly Asp Asp Thr Leu Tyr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Asn Gly Gly Asp Asp Thr Leu Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Asp Gly Gly Asp Asp Thr Leu Tyr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

Gly Gly Asp Gly Asp Asp Thr Leu Tyr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Asn Asp Gly Asp Asp Thr Leu Tyr
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Asp Asp Gly Asp Asp Thr Leu Tyr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Ala Gly Ala Asp Thr Leu Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Asn Ala Gly Ala Asp Thr Leu Tyr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Asp Ala Gly Ala Asp Thr Leu Tyr
1               5

<210> SEQ ID NO 52
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 52

Gly Gly Ser Gly Ala Asp Thr Leu Tyr
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Asn Ser Gly Ala Asp Thr Leu Tyr
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Asp Ser Gly Ala Asp Thr Leu Tyr
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Gly Ala Asp Thr Leu Tyr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Asn Gly Gly Ala Asp Thr Leu Tyr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Asp Gly Gly Ala Asp Thr Leu Tyr
1               5
```

```
<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Asp Gly Ala Asp Thr Leu Tyr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Asn Asp Gly Ala Asp Thr Leu Tyr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Asp Asp Gly Ala Asp Thr Leu Tyr
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Ala Gly Asn Asn Thr Leu Tyr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Asn Ala Gly Asn Asn Thr Leu Tyr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

```
Gly Asp Ala Gly Asn Asn Thr Leu Tyr
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Ser Gly Asn Asn Thr Leu Tyr
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Asn Ser Gly Asn Asn Thr Leu Tyr
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Asp Ser Gly Asn Asn Thr Leu Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Gly Gly Asn Asn Thr Leu Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Asn Gly Gly Asn Asn Thr Leu Tyr
1               5

<210> SEQ ID NO 69
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 69

Gly Asp Gly Gly Asn Asn Thr Leu Tyr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Asp Gly Asn Asn Thr Leu Tyr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Asn Asp Gly Asn Asn Thr Leu Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Asp Asp Gly Asn Asn Thr Leu Tyr
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Ala Gly Asp Asn Thr Leu Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Asn Ala Gly Asp Asn Thr Leu Tyr
1               5
```

```
<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Asp Ala Gly Asp Asn Thr Leu Tyr
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Ser Gly Asp Asn Thr Leu Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Asn Ser Gly Asp Asn Thr Leu Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asp Ser Gly Asp Asn Thr Leu Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Gly Gly Asp Asn Thr Leu Tyr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Gly Asn Gly Gly Asp Asn Thr Leu Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Asp Gly Gly Asp Asn Thr Leu Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Asp Gly Asp Asn Thr Leu Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Asn Asp Gly Asp Asn Thr Leu Tyr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Asp Asp Gly Asp Asn Thr Leu Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Ala Gly Ala Asn Thr Leu Tyr
1               5

<210> SEQ ID NO 86
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 86

Gly Asn Ala Gly Ala Asn Thr Leu Tyr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Asp Ala Gly Ala Asn Thr Leu Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Ser Gly Ala Asn Thr Leu Tyr
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Asn Ser Gly Ala Asn Thr Leu Tyr
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Asp Ser Gly Ala Asn Thr Leu Tyr
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Gly Gly Ala Asn Thr Leu Tyr
1               5
```

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gly Asn Gly Gly Ala Asn Thr Leu Tyr
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Gly Asp Gly Gly Ala Asn Thr Leu Tyr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Gly Asp Gly Ala Asn Thr Leu Tyr
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Asn Asp Gly Ala Asn Thr Leu Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Gly Asp Asp Gly Ala Asn Thr Leu Tyr
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 97

Gly Gly Ala Gly Asn Asp Ile Leu Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Asn Ala Gly Asn Asp Ile Leu Tyr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Asp Ala Gly Asn Asp Ile Leu Tyr
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly Ser Gly Asn Asp Ile Leu Tyr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Asn Ser Gly Asn Asp Ile Leu Tyr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Asp Ser Gly Asn Asp Ile Leu Tyr
1               5

<210> SEQ ID NO 103
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Gly Asn Asp Ile Leu Tyr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Asn Gly Gly Asn Asp Ile Leu Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Asp Gly Gly Asn Asp Ile Leu Tyr
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Asp Gly Asn Asp Ile Leu Tyr
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Asn Asp Gly Asn Asp Ile Leu Tyr
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Asp Asp Gly Asn Asp Ile Leu Tyr
```

```
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Ala Gly Asp Asp Ile Leu Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Asn Ala Gly Asp Asp Ile Leu Tyr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Asp Ala Gly Asp Asp Ile Leu Tyr
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gly Ser Gly Asp Asp Ile Leu Tyr
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Asn Ser Gly Asp Asp Ile Leu Tyr
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 114

Gly Asp Ser Gly Asp Asp Ile Leu Tyr
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gly Gly Gly Asp Asp Ile Leu Tyr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Asn Gly Gly Asp Asp Ile Leu Tyr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Asp Gly Gly Asp Asp Ile Leu Tyr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Asp Gly Asp Asp Ile Leu Tyr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Asn Asp Gly Asp Asp Ile Leu Tyr
1               5

<210> SEQ ID NO 120
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Asp Asp Gly Asp Asp Ile Leu Tyr
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Gly Ala Gly Ala Asp Ile Leu Tyr
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Asn Ala Gly Ala Asp Ile Leu Tyr
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Asp Ala Gly Ala Asp Ile Leu Tyr
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Ser Gly Ala Asp Ile Leu Tyr
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125
```

```
Gly Asn Ser Gly Ala Asp Ile Leu Tyr
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Asp Ser Gly Ala Asp Ile Leu Tyr
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Gly Gly Ala Asp Ile Leu Tyr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Asn Gly Gly Ala Asp Ile Leu Tyr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Asp Gly Gly Ala Asp Ile Leu Tyr
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Asp Gly Ala Asp Ile Leu Tyr
1               5

<210> SEQ ID NO 131
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 131

Gly Asn Asp Gly Ala Asp Ile Leu Tyr
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Asp Asp Gly Ala Asp Ile Leu Tyr
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Ala Gly Asn Asn Ile Leu Tyr
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Asn Ala Gly Asn Asn Ile Leu Tyr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Asp Ala Gly Asn Asn Ile Leu Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Ser Gly Asn Asn Ile Leu Tyr
1               5
```

```
<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Asn Ser Gly Asn Asn Ile Leu Tyr
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Asp Ser Gly Asn Asn Ile Leu Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Gly Gly Asn Asn Ile Leu Tyr
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Asn Gly Gly Asn Asn Ile Leu Tyr
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Asp Gly Gly Asn Asn Ile Leu Tyr
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142
```

```
Gly Gly Asp Gly Asn Asn Ile Leu Tyr
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Asn Asp Gly Asn Asn Ile Leu Tyr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Asp Asp Gly Asn Asn Ile Leu Tyr
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Ala Gly Asp Asn Ile Leu Tyr
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Asn Ala Gly Asp Asn Ile Leu Tyr
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Asp Ala Gly Asp Asn Ile Leu Tyr
1               5

<210> SEQ ID NO 148
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 148

Gly Gly Ser Gly Asp Asn Ile Leu Tyr
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Asn Ser Gly Asp Asn Ile Leu Tyr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Asp Ser Gly Asp Asn Ile Leu Tyr
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Gly Gly Asp Asn Ile Leu Tyr
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Asn Gly Gly Asp Asn Ile Leu Tyr
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Asp Gly Gly Asp Asn Ile Leu Tyr
1               5
```

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Gly Asp Gly Asp Asn Ile Leu Tyr
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Asn Asp Gly Asp Asn Ile Leu Tyr
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Asp Asp Gly Asp Asn Ile Leu Tyr
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Ala Gly Ala Asn Ile Leu Tyr
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Asn Ala Gly Ala Asn Ile Leu Tyr
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 159

Gly Asp Ala Gly Ala Asn Ile Leu Tyr
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Ser Gly Ala Asn Ile Leu Tyr
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Asn Ser Gly Ala Asn Ile Leu Tyr
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Asp Ser Gly Ala Asn Ile Leu Tyr
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Gly Gly Ala Asn Ile Leu Tyr
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Asn Gly Gly Ala Asn Ile Leu Tyr
1               5

<210> SEQ ID NO 165
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 165

Gly Asp Gly Gly Ala Asn Ile Leu Tyr
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Gly Asp Gly Ala Asn Ile Leu Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Asn Asp Gly Ala Asn Ile Leu Tyr
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Asp Asp Gly Ala Asn Ile Leu Tyr
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Gly Ala Gly Asn Asp Val Leu Tyr
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Asn Ala Gly Asn Asp Val Leu Tyr
1               5
```

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Asp Ala Gly Asn Asp Val Leu Tyr
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Ser Gly Asn Asp Val Leu Tyr
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Asn Ser Gly Asn Asp Val Leu Tyr
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Asp Ser Gly Asn Asp Val Leu Tyr
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Gly Gly Gly Asn Asp Val Leu Tyr
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 176

Gly Asn Gly Gly Asn Asp Val Leu Tyr
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Asp Gly Gly Asn Asp Val Leu Tyr
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Gly Asp Gly Asn Asp Val Leu Tyr
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Asn Asp Gly Asn Asp Val Leu Tyr
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Asp Asp Gly Asn Asp Val Leu Tyr
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Gly Ala Gly Asp Asp Val Leu Tyr
1               5

<210> SEQ ID NO 182
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Asn Ala Gly Asp Asp Val Leu Tyr
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Asp Ala Gly Asp Asp Val Leu Tyr
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Gly Ser Gly Asp Asp Val Leu Tyr
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Asn Ser Gly Asp Asp Val Leu Tyr
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Asp Ser Gly Asp Asp Val Leu Tyr
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Gly Gly Gly Asp Asp Val Leu Tyr
```

```
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Asn Gly Gly Asp Asp Val Leu Tyr
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Asp Gly Gly Asp Asp Val Leu Tyr
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Gly Asp Gly Asp Asp Val Leu Tyr
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Asn Asp Gly Asp Asp Val Leu Tyr
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Asp Asp Gly Asp Asp Val Leu Tyr
1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 193

Gly Gly Ala Gly Ala Asp Val Leu Tyr
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Asn Ala Gly Ala Asp Val Leu Tyr
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Asp Ala Gly Ala Asp Val Leu Tyr
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Gly Ser Gly Ala Asp Val Leu Tyr
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Asn Ser Gly Ala Asp Val Leu Tyr
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Asp Ser Gly Ala Asp Val Leu Tyr
1               5

<210> SEQ ID NO 199
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Gly Gly Gly Ala Asp Val Leu Tyr
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Asn Gly Gly Ala Asp Val Leu Tyr
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Asp Gly Gly Ala Asp Val Leu Tyr
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gly Asp Gly Ala Asp Val Leu Tyr
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Asn Asp Gly Ala Asp Val Leu Tyr
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204
```

```
Gly Asp Asp Gly Ala Asp Val Leu Tyr
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gly Ala Gly Asn Asn Val Leu Tyr
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Asn Ala Gly Asn Asn Val Leu Tyr
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Asp Ala Gly Asn Asn Val Leu Tyr
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Gly Ser Gly Asn Asn Val Leu Tyr
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Asn Ser Gly Asn Asn Val Leu Tyr
1               5

<210> SEQ ID NO 210
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 210

Gly Asp Ser Gly Asn Asn Val Leu Tyr
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Gly Gly Asn Asn Val Leu Tyr
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Asn Gly Gly Asn Asn Val Leu Tyr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Asp Gly Gly Asn Asn Val Leu Tyr
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Asp Gly Asn Asn Val Leu Tyr
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Asn Asp Gly Asn Asn Val Leu Tyr
1               5
```

```
<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Asp Asp Gly Asn Asn Val Leu Tyr
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Ala Gly Asp Asn Val Leu Tyr
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Asn Ala Gly Asp Asn Val Leu Tyr
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Asp Ala Gly Asp Asn Val Leu Tyr
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gly Ser Gly Asp Asn Val Leu Tyr
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221
```

Gly Asn Ser Gly Asp Asn Val Leu Tyr
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Asp Ser Gly Asp Asn Val Leu Tyr
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Gly Gly Asp Asn Val Leu Tyr
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Asn Gly Gly Asp Asn Val Leu Tyr
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Asp Gly Gly Asp Asn Val Leu Tyr
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Asp Gly Asp Asn Val Leu Tyr
1               5

<210> SEQ ID NO 227
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 227

Gly Asn Asp Gly Asp Asn Val Leu Tyr
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Asp Asp Gly Asp Asn Val Leu Tyr
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Gly Ala Gly Ala Asn Val Leu Tyr
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Asn Ala Gly Ala Asn Val Leu Tyr
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Asp Ala Gly Ala Asn Val Leu Tyr
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Gly Ser Gly Ala Asn Val Leu Tyr
1               5
```

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Asn Ser Gly Ala Asn Val Leu Tyr
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Asp Ser Gly Ala Asn Val Leu Tyr
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Gly Gly Gly Ala Asn Val Leu Tyr
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Asn Gly Gly Ala Asn Val Leu Tyr
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Asp Gly Gly Ala Asn Val Leu Tyr
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 238

Gly Gly Asp Gly Ala Asn Val Leu Tyr
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Asn Asp Gly Ala Asn Val Leu Tyr
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Asp Asp Gly Ala Asn Val Leu Tyr
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Gly Ala Gly Asn Asp Thr Ile Tyr
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Asn Ala Gly Asn Asp Thr Ile Tyr
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Asp Ala Gly Asn Asp Thr Ile Tyr
1               5

<210> SEQ ID NO 244
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 244

Gly Gly Ser Gly Asn Asp Thr Ile Tyr
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Asn Ser Gly Asn Asp Thr Ile Tyr
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Asp Ser Gly Asn Asp Thr Ile Tyr
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Gly Gly Asn Asp Thr Ile Tyr
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Asn Gly Gly Asn Asp Thr Ile Tyr
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Asp Gly Gly Asn Asp Thr Ile Tyr
1               5
```

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Gly Asp Gly Asn Asp Thr Ile Tyr
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Asn Asp Gly Asn Asp Thr Ile Tyr
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Asp Asp Gly Asn Asp Thr Ile Tyr
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Gly Ala Gly Asp Asp Thr Ile Tyr
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Asn Ala Gly Asp Asp Thr Ile Tyr
1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 255

Gly Asp Ala Gly Asp Asp Thr Ile Tyr
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Gly Ser Gly Asp Asp Thr Ile Tyr
1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Asn Ser Gly Asp Asp Thr Ile Tyr
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Asp Ser Gly Asp Asp Thr Ile Tyr
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Gly Gly Gly Asp Asp Thr Ile Tyr
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Asn Gly Gly Asp Asp Thr Ile Tyr
1               5

<210> SEQ ID NO 261
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Asp Gly Gly Asp Asp Thr Ile Tyr
1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Gly Asp Gly Asp Asp Thr Ile Tyr
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Asn Asp Gly Asp Asp Thr Ile Tyr
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Asp Asp Gly Asp Asp Thr Ile Tyr
1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gly Ala Gly Ala Asp Thr Ile Tyr
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Asn Ala Gly Ala Asp Thr Ile Tyr
```

```
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Asp Ala Gly Ala Asp Thr Ile Tyr
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Gly Ser Gly Ala Asp Thr Ile Tyr
1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Asn Ser Gly Ala Asp Thr Ile Tyr
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Asp Ser Gly Ala Asp Thr Ile Tyr
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Gly Gly Gly Ala Asp Thr Ile Tyr
1               5

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 272

Gly Asn Gly Gly Ala Asp Thr Ile Tyr
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Asp Gly Gly Ala Asp Thr Ile Tyr
1               5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gly Gly Asp Gly Ala Asp Thr Ile Tyr
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gly Asn Asp Gly Ala Asp Thr Ile Tyr
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Asp Asp Gly Ala Asp Thr Ile Tyr
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Gly Ala Gly Asn Asn Thr Ile Tyr
1               5

<210> SEQ ID NO 278
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Asn Ala Gly Asn Asn Thr Ile Tyr
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Asp Ala Gly Asn Asn Thr Ile Tyr
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Gly Ser Gly Asn Asn Thr Ile Tyr
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Asn Ser Gly Asn Asn Thr Ile Tyr
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Asp Ser Gly Asn Asn Thr Ile Tyr
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

```
Gly Gly Gly Gly Asn Asn Thr Ile Tyr
1               5
```

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

```
Gly Asn Gly Gly Asn Asn Thr Ile Tyr
1               5
```

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

```
Gly Asp Gly Gly Asn Asn Thr Ile Tyr
1               5
```

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

```
Gly Gly Asp Gly Asn Asn Thr Ile Tyr
1               5
```

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

```
Gly Asn Asp Gly Asn Asn Thr Ile Tyr
1               5
```

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

```
Gly Asp Asp Gly Asn Asn Thr Ile Tyr
1               5
```

<210> SEQ ID NO 289
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 289

Gly Gly Ala Gly Asp Asn Thr Ile Tyr
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Asn Ala Gly Asp Asn Thr Ile Tyr
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Asp Ala Gly Asp Asn Thr Ile Tyr
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Gly Ser Gly Asp Asn Thr Ile Tyr
1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Asn Ser Gly Asp Asn Thr Ile Tyr
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Asp Ser Gly Asp Asn Thr Ile Tyr
1               5

```
<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Gly Gly Gly Asp Asn Thr Ile Tyr
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gly Asn Gly Gly Asp Asn Thr Ile Tyr
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Asp Gly Gly Asp Asn Thr Ile Tyr
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Gly Asp Gly Asp Asn Thr Ile Tyr
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Asn Asp Gly Asp Asn Thr Ile Tyr
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300
```

```
Gly Asp Asp Gly Asp Asn Thr Ile Tyr
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gly Gly Ala Gly Ala Asn Thr Ile Tyr
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Asn Ala Gly Ala Asn Thr Ile Tyr
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Asp Ala Gly Ala Asn Thr Ile Tyr
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Gly Ser Gly Ala Asn Thr Ile Tyr
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Asn Ser Gly Ala Asn Thr Ile Tyr
1               5

<210> SEQ ID NO 306
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 306

Gly Asp Ser Gly Ala Asn Thr Ile Tyr
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Gly Gly Gly Ala Asn Thr Ile Tyr
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Asn Gly Gly Ala Asn Thr Ile Tyr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Asp Gly Gly Ala Asn Thr Ile Tyr
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Gly Asp Gly Ala Asn Thr Ile Tyr
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Asn Asp Gly Ala Asn Thr Ile Tyr
1               5
```

```
<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Asp Asp Gly Ala Asn Thr Ile Tyr
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Gly Ala Gly Asn Asp Ile Ile Tyr
1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Asn Ala Gly Asn Asp Ile Ile Tyr
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Asp Ala Gly Asn Asp Ile Ile Tyr
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Gly Ser Gly Asn Asp Ile Ile Tyr
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 317

Gly Asn Ser Gly Asn Asp Ile Ile Tyr
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gly Asp Ser Gly Asn Asp Ile Ile Tyr
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Gly Gly Gly Asn Asp Ile Ile Tyr
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Asn Gly Gly Asn Asp Ile Ile Tyr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gly Asp Gly Gly Asn Asp Ile Ile Tyr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Gly Asp Gly Asn Asp Ile Ile Tyr
1               5

<210> SEQ ID NO 323
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 323

Gly Asn Asp Gly Asn Asp Ile Ile Tyr
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gly Asp Asp Gly Asn Asp Ile Ile Tyr
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gly Gly Ala Gly Asp Asp Ile Ile Tyr
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Asn Ala Gly Asp Asp Ile Ile Tyr
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gly Asp Ala Gly Asp Asp Ile Ile Tyr
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Gly Ser Gly Asp Asp Ile Ile Tyr
1               5
```

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Asn Ser Gly Asp Asp Ile Ile Tyr
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gly Asp Ser Gly Asp Asp Ile Ile Tyr
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gly Gly Gly Gly Asp Asp Ile Ile Tyr
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly Asn Gly Gly Asp Asp Ile Ile Tyr
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Asp Gly Gly Asp Asp Ile Ile Tyr
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 334

Gly Gly Asp Gly Asp Asp Ile Ile Tyr
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Asn Asp Gly Asp Asp Ile Ile Tyr
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Asp Asp Gly Asp Asp Ile Ile Tyr
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Gly Gly Ala Gly Ala Asp Ile Ile Tyr
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Asn Ala Gly Ala Asp Ile Ile Tyr
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gly Asp Ala Gly Ala Asp Ile Ile Tyr
1               5

<210> SEQ ID NO 340
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Gly Ser Gly Ala Asp Ile Ile Tyr
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gly Asn Ser Gly Ala Asp Ile Ile Tyr
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Gly Asp Ser Gly Ala Asp Ile Ile Tyr
1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Gly Gly Gly Ala Asp Ile Ile Tyr
1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Asn Gly Gly Ala Asp Ile Ile Tyr
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Asp Gly Gly Ala Asp Ile Ile Tyr
```

-continued 1               5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Gly Gly Asp Gly Ala Asp Ile Ile Tyr
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Asn Asp Gly Ala Asp Ile Ile Tyr
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gly Asp Asp Gly Ala Asp Ile Ile Tyr
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gly Gly Ala Gly Asn Asn Ile Ile Tyr
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Asn Ala Gly Asn Asn Ile Ile Tyr
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Gly Asp Ala Gly Asn Asn Ile Ile Tyr
1               5

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Gly Ser Gly Asn Asn Ile Ile Tyr
1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Gly Asn Ser Gly Asn Asn Ile Ile Tyr
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gly Asp Ser Gly Asn Asn Ile Ile Tyr
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Gly Gly Gly Gly Asn Asn Ile Ile Tyr
1               5

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Asn Gly Gly Asn Asn Ile Ile Tyr
1               5

<210> SEQ ID NO 357

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Asp Gly Gly Asn Asn Ile Ile Tyr
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Gly Asp Gly Asn Asn Ile Ile Tyr
1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gly Asn Asp Gly Asn Asn Ile Ile Tyr
1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Asp Asp Gly Asn Asn Ile Ile Tyr
1               5

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gly Gly Ala Gly Asp Asn Ile Ile Tyr
1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362
```

Gly Asn Ala Gly Asp Asn Ile Ile Tyr
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Asp Ala Gly Asp Asn Ile Ile Tyr
1               5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gly Gly Ser Gly Asp Asn Ile Ile Tyr
1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gly Asn Ser Gly Asp Asn Ile Ile Tyr
1               5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Asp Ser Gly Asp Asn Ile Ile Tyr
1               5

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Gly Gly Gly Asp Asn Ile Ile Tyr
1               5

<210> SEQ ID NO 368
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 368

Gly Asn Gly Gly Asp Asn Ile Ile Tyr
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gly Asp Gly Gly Asp Asn Ile Ile Tyr
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Gly Asp Gly Asp Asn Ile Ile Tyr
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Asn Asp Gly Asp Asn Ile Ile Tyr
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Asp Asp Gly Asp Asn Ile Ile Tyr
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Gly Ala Gly Ala Asn Ile Ile Tyr
1               5
```

```
<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gly Asn Ala Gly Ala Asn Ile Ile Tyr
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Asp Ala Gly Ala Asn Ile Ile Tyr
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Gly Ser Gly Ala Asn Ile Ile Tyr
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Asn Ser Gly Ala Asn Ile Ile Tyr
1               5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gly Asp Ser Gly Ala Asn Ile Ile Tyr
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379
```

Gly Gly Gly Gly Ala Asn Ile Ile Tyr
1               5

<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Asn Gly Gly Ala Asn Ile Ile Tyr
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gly Asp Gly Gly Ala Asn Ile Ile Tyr
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Gly Asp Gly Ala Asn Ile Ile Tyr
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gly Asn Asp Gly Ala Asn Ile Ile Tyr
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gly Asp Asp Gly Ala Asn Ile Ile Tyr
1               5

<210> SEQ ID NO 385
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 385

Gly Gly Ala Gly Asn Asp Val Ile Tyr
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gly Asn Ala Gly Asn Asp Val Ile Tyr
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gly Asp Ala Gly Asn Asp Val Ile Tyr
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Gly Ser Gly Asn Asp Val Ile Tyr
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gly Asn Ser Gly Asn Asp Val Ile Tyr
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gly Asp Ser Gly Asn Asp Val Ile Tyr
1               5
```

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Gly Gly Gly Asn Asp Val Ile Tyr
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gly Asn Gly Gly Asn Asp Val Ile Tyr
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Asp Gly Gly Asn Asp Val Ile Tyr
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Gly Asp Gly Asn Asp Val Ile Tyr
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gly Asn Asp Gly Asn Asp Val Ile Tyr
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 396

Gly Asp Asp Gly Asn Asp Val Ile Tyr
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Gly Ala Gly Asp Asp Val Ile Tyr
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Asn Ala Gly Asp Asp Val Ile Tyr
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Asp Ala Gly Asp Asp Val Ile Tyr
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gly Gly Ser Gly Asp Asp Val Ile Tyr
1               5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Asn Ser Gly Asp Asp Val Ile Tyr
1               5

<210> SEQ ID NO 402
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 402

Gly Asp Ser Gly Asp Asp Val Ile Tyr
1               5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Gly Gly Gly Asp Asp Val Ile Tyr
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Asn Gly Gly Asp Asp Val Ile Tyr
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Asp Gly Gly Asp Asp Val Ile Tyr
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Gly Asp Gly Asp Asp Val Ile Tyr
1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Asn Asp Gly Asp Asp Val Ile Tyr
1               5
```

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Asp Asp Gly Asp Asp Val Ile Tyr
1               5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Gly Ala Gly Ala Asp Val Ile Tyr
1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Asn Ala Gly Ala Asp Val Ile Tyr
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Asp Ala Gly Ala Asp Val Ile Tyr
1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gly Ser Gly Ala Asp Val Ile Tyr
1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gly Asn Ser Gly Ala Asp Val Ile Tyr
1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Asp Ser Gly Ala Asp Val Ile Tyr
1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Gly Gly Gly Ala Asp Val Ile Tyr
1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Asn Gly Gly Ala Asp Val Ile Tyr
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gly Asp Gly Gly Ala Asp Val Ile Tyr
1               5

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Gly Asp Gly Ala Asp Val Ile Tyr
1               5

<210> SEQ ID NO 419
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Asn Asp Gly Ala Asp Val Ile Tyr
1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gly Asp Asp Gly Ala Asp Val Ile Tyr
1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Gly Ala Gly Asn Asn Val Ile Tyr
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Asn Ala Gly Asn Asn Val Ile Tyr
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Asp Ala Gly Asn Asn Val Ile Tyr
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gly Gly Ser Gly Asn Asn Val Ile Tyr
```

```
1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Gly Asn Ser Gly Asn Asn Val Ile Tyr
1               5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Gly Asp Ser Gly Asn Asn Val Ile Tyr
1               5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Gly Gly Gly Gly Asn Asn Val Ile Tyr
1               5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Gly Asn Gly Gly Asn Asn Val Ile Tyr
1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gly Asp Gly Gly Asn Asn Val Ile Tyr
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 430

Gly Gly Asp Gly Asn Asn Val Ile Tyr
1               5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Asn Asp Gly Asn Asn Val Ile Tyr
1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Gly Asp Asp Gly Asn Asn Val Ile Tyr
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Gly Gly Ala Gly Asp Asn Val Ile Tyr
1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Asn Ala Gly Asp Asn Val Ile Tyr
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gly Asp Ala Gly Asp Asn Val Ile Tyr
1               5

<210> SEQ ID NO 436

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gly Gly Ser Gly Asp Asn Val Ile Tyr
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Asn Ser Gly Asp Asn Val Ile Tyr
1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Asp Ser Gly Asp Asn Val Ile Tyr
1               5

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Gly Gly Gly Gly Asp Asn Val Ile Tyr
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Gly Asn Gly Gly Asp Asn Val Ile Tyr
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441
```

```
Gly Asp Gly Gly Asp Asn Val Ile Tyr
1               5
```

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

```
Gly Gly Asp Gly Asp Asn Val Ile Tyr
1               5
```

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

```
Gly Asn Asp Gly Asp Asn Val Ile Tyr
1               5
```

<210> SEQ ID NO 444
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

```
Gly Asp Asp Gly Asp Asn Val Ile Tyr
1               5
```

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

```
Gly Gly Ala Gly Ala Asn Val Ile Tyr
1               5
```

<210> SEQ ID NO 446
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

```
Gly Asn Ala Gly Ala Asn Val Ile Tyr
1               5
```

<210> SEQ ID NO 447
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 447

Gly Asp Ala Gly Ala Asn Val Ile Tyr
1               5

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Gly Ser Gly Ala Asn Val Ile Tyr
1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gly Asn Ser Gly Ala Asn Val Ile Tyr
1               5

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Gly Asp Ser Gly Ala Asn Val Ile Tyr
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Gly Gly Gly Gly Ala Asn Val Ile Tyr
1               5

<210> SEQ ID NO 452
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gly Asn Gly Gly Ala Asn Val Ile Tyr
1               5
```

```
<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Asp Gly Gly Ala Asn Val Ile Tyr
1               5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gly Gly Asp Gly Ala Asn Val Ile Tyr
1               5

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Gly Asn Asp Gly Ala Asn Val Ile Tyr
1               5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Asp Asp Gly Ala Asn Val Ile Tyr
1               5

<210> SEQ ID NO 457
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gly Gly Ala Gly Asn Asp Thr Leu Ile
1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458
```

```
Gly Asn Ala Gly Asn Asp Thr Leu Ile
1               5

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gly Asp Ala Gly Asn Asp Thr Leu Ile
1               5

<210> SEQ ID NO 460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Gly Gly Ser Gly Asn Asp Thr Leu Ile
1               5

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Gly Asn Ser Gly Asn Asp Thr Leu Ile
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Gly Asp Ser Gly Asn Asp Thr Leu Ile
1               5

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Gly Gly Gly Gly Asn Asp Thr Leu Ile
1               5

<210> SEQ ID NO 464
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 464

Gly Asn Gly Gly Asn Asp Thr Leu Ile
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Gly Asp Gly Gly Asn Asp Thr Leu Ile
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Gly Gly Asp Gly Asn Asp Thr Leu Ile
1               5

<210> SEQ ID NO 467
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Gly Asn Asp Gly Asn Asp Thr Leu Ile
1               5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gly Asp Asp Gly Asn Asp Thr Leu Ile
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gly Gly Ala Gly Asp Asp Thr Leu Ile
1               5
```

```
<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gly Asn Ala Gly Asp Asp Thr Leu Ile
1               5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Gly Asp Ala Gly Asp Asp Thr Leu Ile
1               5

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gly Gly Ser Gly Asp Asp Thr Leu Ile
1               5

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gly Asn Ser Gly Asp Asp Thr Leu Ile
1               5

<210> SEQ ID NO 474
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Gly Asp Ser Gly Asp Asp Thr Leu Ile
1               5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 475

Gly Gly Gly Gly Asp Asp Thr Leu Ile
1               5

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Gly Asn Gly Gly Asp Asp Thr Leu Ile
1               5

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gly Asp Gly Gly Asp Asp Thr Leu Ile
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gly Gly Asp Gly Asp Asp Thr Leu Ile
1               5

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gly Asn Asp Gly Asp Asp Thr Leu Ile
1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Gly Asp Asp Gly Asp Asp Thr Leu Ile
1               5

<210> SEQ ID NO 481
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 481

Gly Gly Ala Gly Ala Asp Thr Leu Ile
1               5

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gly Asn Ala Gly Ala Asp Thr Leu Ile
1               5

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Gly Asp Ala Gly Ala Asp Thr Leu Ile
1               5

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Gly Ser Gly Ala Asp Thr Leu Ile
1               5

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gly Asn Ser Gly Ala Asp Thr Leu Ile
1               5

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Asp Ser Gly Ala Asp Thr Leu Ile
1               5

<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Gly Gly Gly Gly Ala Asp Thr Leu Ile
1               5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gly Asn Gly Gly Ala Asp Thr Leu Ile
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gly Asp Gly Gly Ala Asp Thr Leu Ile
1               5

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gly Gly Asp Gly Ala Asp Thr Leu Ile
1               5

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gly Asn Asp Gly Ala Asp Thr Leu Ile
1               5

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Gly Asp Asp Gly Ala Asp Thr Leu Ile
1               5

<210> SEQ ID NO 493
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gly Gly Ala Gly Asn Asn Thr Leu Ile
1               5

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Gly Asn Ala Gly Asn Asn Thr Leu Ile
1               5

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gly Asp Ala Gly Asn Asn Thr Leu Ile
1               5

<210> SEQ ID NO 496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Gly Gly Ser Gly Asn Asn Thr Leu Ile
1               5

<210> SEQ ID NO 497
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Gly Asn Ser Gly Asn Asn Thr Leu Ile
1               5

<210> SEQ ID NO 498
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Gly Asp Ser Gly Asn Asn Thr Leu Ile
1               5

<210> SEQ ID NO 499
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Gly Gly Gly Gly Asn Asn Thr Leu Ile
1               5

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Gly Asn Gly Gly Asn Asn Thr Leu Ile
1               5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Gly Asp Gly Gly Asn Asn Thr Leu Ile
1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Gly Gly Asp Gly Asn Asn Thr Leu Ile
1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Gly Asn Asp Gly Asn Asn Thr Leu Ile
```

```
1               5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Gly Asp Asp Gly Asn Asn Thr Leu Ile
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Gly Gly Ala Gly Asp Asn Thr Leu Ile
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Gly Asn Ala Gly Asp Asn Thr Leu Ile
1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Gly Asp Ala Gly Asp Asn Thr Leu Ile
1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Gly Gly Ser Gly Asp Asn Thr Leu Ile
1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 509

Gly Asn Ser Gly Asp Asn Thr Leu Ile
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gly Asp Ser Gly Asp Asn Thr Leu Ile
1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Gly Gly Gly Gly Asp Asn Thr Leu Ile
1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Gly Asn Gly Gly Asp Asn Thr Leu Ile
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Gly Asp Gly Gly Asp Asn Thr Leu Ile
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gly Gly Asp Gly Asp Asn Thr Leu Ile
1               5

<210> SEQ ID NO 515

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Gly Asn Asp Gly Asp Asn Thr Leu Ile
1               5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Gly Asp Asp Gly Asp Asn Thr Leu Ile
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Gly Ala Gly Ala Asn Thr Leu Ile
1               5

<210> SEQ ID NO 518
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Gly Asn Ala Gly Ala Asn Thr Leu Ile
1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Gly Asp Ala Gly Ala Asn Thr Leu Ile
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520
```

```
Gly Gly Ser Gly Ala Asn Thr Leu Ile
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Gly Asn Ser Gly Ala Asn Thr Leu Ile
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Gly Asp Ser Gly Ala Asn Thr Leu Ile
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Gly Gly Gly Gly Ala Asn Thr Leu Ile
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Gly Asn Gly Gly Ala Asn Thr Leu Ile
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gly Asp Gly Gly Ala Asn Thr Leu Ile
1               5

<210> SEQ ID NO 526
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 526

Gly Gly Asp Gly Ala Asn Thr Leu Ile
1               5

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Gly Asn Asp Gly Ala Asn Thr Leu Ile
1               5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Gly Asp Asp Gly Ala Asn Thr Leu Ile
1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gly Gly Ala Gly Asn Asp Ile Leu Ile
1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gly Asn Ala Gly Asn Asp Ile Leu Ile
1               5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gly Asp Ala Gly Asn Asp Ile Leu Ile
1               5
```

```
<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Gly Gly Ser Gly Asn Asp Ile Leu Ile
1               5

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gly Asn Ser Gly Asn Asp Ile Leu Ile
1               5

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Gly Asp Ser Gly Asn Asp Ile Leu Ile
1               5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gly Gly Gly Gly Asn Asp Ile Leu Ile
1               5

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Gly Asn Gly Gly Asn Asp Ile Leu Ile
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537
```

```
Gly Asp Gly Gly Asn Asp Ile Leu Ile
1               5

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Gly Gly Asp Gly Asn Asp Ile Leu Ile
1               5

<210> SEQ ID NO 539
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Gly Asn Asp Gly Asn Asp Ile Leu Ile
1               5

<210> SEQ ID NO 540
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gly Asp Asp Gly Asn Asp Ile Leu Ile
1               5

<210> SEQ ID NO 541
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Gly Gly Ala Gly Asp Asp Ile Leu Ile
1               5

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gly Asn Ala Gly Asp Asp Ile Leu Ile
1               5

<210> SEQ ID NO 543
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 543

Gly Asp Ala Gly Asp Asp Ile Leu Ile
1               5

<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Gly Gly Ser Gly Asp Asp Ile Leu Ile
1               5

<210> SEQ ID NO 545
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gly Asn Ser Gly Asp Asp Ile Leu Ile
1               5

<210> SEQ ID NO 546
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gly Asp Ser Gly Asp Asp Ile Leu Ile
1               5

<210> SEQ ID NO 547
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Gly Gly Gly Gly Asp Asp Ile Leu Ile
1               5

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gly Asn Gly Gly Asp Asp Ile Leu Ile
1               5
```

-continued

<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gly Asp Gly Gly Asp Asp Ile Leu Ile
1               5

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Gly Gly Asp Gly Asp Asp Ile Leu Ile
1               5

<210> SEQ ID NO 551
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Gly Asn Asp Gly Asp Asp Ile Leu Ile
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Gly Asp Asp Gly Asp Asp Ile Leu Ile
1               5

<210> SEQ ID NO 553
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Gly Gly Ala Gly Ala Asp Ile Leu Ile
1               5

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 554

Gly Asn Ala Gly Ala Asp Ile Leu Ile
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Gly Asp Ala Gly Ala Asp Ile Leu Ile
1               5

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gly Gly Ser Gly Ala Asp Ile Leu Ile
1               5

<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Gly Asn Ser Gly Ala Asp Ile Leu Ile
1               5

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gly Asp Ser Gly Ala Asp Ile Leu Ile
1               5

<210> SEQ ID NO 559
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Gly Gly Gly Gly Ala Asp Ile Leu Ile
1               5

<210> SEQ ID NO 560
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 560

Gly Asn Gly Gly Ala Asp Ile Leu Ile
1               5

<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Gly Asp Gly Gly Ala Asp Ile Leu Ile
1               5

<210> SEQ ID NO 562
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gly Gly Asp Gly Ala Asp Ile Leu Ile
1               5

<210> SEQ ID NO 563
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gly Asn Asp Gly Ala Asp Ile Leu Ile
1               5

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gly Asp Asp Gly Ala Asp Ile Leu Ile
1               5

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Gly Gly Ala Gly Asn Asn Ile Leu Ile
1               5
```

<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gly Asn Ala Gly Asn Asn Ile Leu Ile
1               5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gly Asp Ala Gly Asn Asn Ile Leu Ile
1               5

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Gly Ser Gly Asn Asn Ile Leu Ile
1               5

<210> SEQ ID NO 569
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Gly Asn Ser Gly Asn Asn Ile Leu Ile
1               5

<210> SEQ ID NO 570
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gly Asp Ser Gly Asn Asn Ile Leu Ile
1               5

<210> SEQ ID NO 571
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gly Gly Gly Gly Asn Asn Ile Leu Ile
1               5

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gly Asn Gly Gly Asn Asn Ile Leu Ile
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gly Asp Gly Gly Asn Asn Ile Leu Ile
1               5

<210> SEQ ID NO 574
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Gly Asp Gly Asn Asn Ile Leu Ile
1               5

<210> SEQ ID NO 575
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Gly Asn Asp Gly Asn Asn Ile Leu Ile
1               5

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Gly Asp Asp Gly Asn Asn Ile Leu Ile
1               5

<210> SEQ ID NO 577
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Gly Gly Ala Gly Asp Asn Ile Leu Ile
1               5

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gly Asn Ala Gly Asp Asn Ile Leu Ile
1               5

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Gly Asp Ala Gly Asp Asn Ile Leu Ile
1               5

<210> SEQ ID NO 580
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Gly Gly Ser Gly Asp Asn Ile Leu Ile
1               5

<210> SEQ ID NO 581
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Gly Asn Ser Gly Asp Asn Ile Leu Ile
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gly Asp Ser Gly Asp Asn Ile Leu Ile
```

```
1               5

<210> SEQ ID NO 583
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gly Gly Gly Gly Asp Asn Ile Leu Ile
1               5

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gly Asn Gly Gly Asp Asn Ile Leu Ile
1               5

<210> SEQ ID NO 585
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gly Asp Gly Gly Asp Asn Ile Leu Ile
1               5

<210> SEQ ID NO 586
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gly Gly Asp Gly Asp Asn Ile Leu Ile
1               5

<210> SEQ ID NO 587
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Gly Asn Asp Gly Asp Asn Ile Leu Ile
1               5

<210> SEQ ID NO 588
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 588

Gly Asp Asp Gly Asp Asn Ile Leu Ile
1               5

<210> SEQ ID NO 589
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Gly Gly Ala Gly Ala Asn Ile Leu Ile
1               5

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Gly Asn Ala Gly Ala Asn Ile Leu Ile
1               5

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gly Asp Ala Gly Ala Asn Ile Leu Ile
1               5

<210> SEQ ID NO 592
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Gly Gly Ser Gly Ala Asn Ile Leu Ile
1               5

<210> SEQ ID NO 593
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gly Asn Ser Gly Ala Asn Ile Leu Ile
1               5

<210> SEQ ID NO 594
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gly Asp Ser Gly Ala Asn Ile Leu Ile
1               5

<210> SEQ ID NO 595
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Gly Gly Gly Gly Ala Asn Ile Leu Ile
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Gly Asn Gly Gly Ala Asn Ile Leu Ile
1               5

<210> SEQ ID NO 597
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Gly Asp Gly Gly Ala Asn Ile Leu Ile
1               5

<210> SEQ ID NO 598
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Gly Gly Asp Gly Ala Asn Ile Leu Ile
1               5

<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599
```

Gly Asn Asp Gly Ala Asn Ile Leu Ile
1               5

<210> SEQ ID NO 600
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gly Asp Asp Gly Ala Asn Ile Leu Ile
1               5

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Gly Gly Ala Gly Asn Asp Val Leu Ile
1               5

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Gly Asn Ala Gly Asn Asp Val Leu Ile
1               5

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gly Asp Ala Gly Asn Asp Val Leu Ile
1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Gly Gly Ser Gly Asn Asp Val Leu Ile
1               5

<210> SEQ ID NO 605
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 605

Gly Asn Ser Gly Asn Asp Val Leu Ile
1               5

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gly Asp Ser Gly Asn Asp Val Leu Ile
1               5

<210> SEQ ID NO 607
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Gly Gly Gly Gly Asn Asp Val Leu Ile
1               5

<210> SEQ ID NO 608
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Gly Asn Gly Gly Asn Asp Val Leu Ile
1               5

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Gly Asp Gly Gly Asn Asp Val Leu Ile
1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Gly Gly Asp Gly Asn Asp Val Leu Ile
1               5

```
<210> SEQ ID NO 611
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Gly Asn Asp Gly Asn Asp Val Leu Ile
1               5

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Gly Asp Asp Gly Asn Asp Val Leu Ile
1               5

<210> SEQ ID NO 613
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Gly Gly Ala Gly Asp Asp Val Leu Ile
1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gly Asn Ala Gly Asp Asp Val Leu Ile
1               5

<210> SEQ ID NO 615
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Gly Asp Ala Gly Asp Asp Val Leu Ile
1               5

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616
```

```
Gly Gly Ser Gly Asp Asp Val Leu Ile
1               5

<210> SEQ ID NO 617
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Gly Asn Ser Gly Asp Asp Val Leu Ile
1               5

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Gly Asp Ser Gly Asp Asp Val Leu Ile
1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gly Gly Gly Gly Asp Asp Val Leu Ile
1               5

<210> SEQ ID NO 620
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Gly Asn Gly Gly Asp Asp Val Leu Ile
1               5

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Gly Asp Gly Gly Asp Asp Val Leu Ile
1               5

<210> SEQ ID NO 622
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 622

Gly Gly Asp Gly Asp Asp Val Leu Ile
1               5

<210> SEQ ID NO 623
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Gly Asn Asp Gly Asp Asp Val Leu Ile
1               5

<210> SEQ ID NO 624
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Gly Asp Asp Gly Asp Asp Val Leu Ile
1               5

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Gly Gly Ala Gly Ala Asp Val Leu Ile
1               5

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Gly Asn Ala Gly Ala Asp Val Leu Ile
1               5

<210> SEQ ID NO 627
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Gly Asp Ala Gly Ala Asp Val Leu Ile
1               5
```

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Gly Gly Ser Gly Ala Asp Val Leu Ile
1               5

<210> SEQ ID NO 629
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Gly Asn Ser Gly Ala Asp Val Leu Ile
1               5

<210> SEQ ID NO 630
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Gly Asp Ser Gly Ala Asp Val Leu Ile
1               5

<210> SEQ ID NO 631
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Gly Gly Gly Gly Ala Asp Val Leu Ile
1               5

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Gly Asn Gly Gly Ala Asp Val Leu Ile
1               5

<210> SEQ ID NO 633
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 633

Gly Asp Gly Gly Ala Asp Val Leu Ile
1               5

<210> SEQ ID NO 634
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Gly Gly Asp Gly Ala Asp Val Leu Ile
1               5

<210> SEQ ID NO 635
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Gly Asn Asp Gly Ala Asp Val Leu Ile
1               5

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Gly Asp Asp Gly Ala Asp Val Leu Ile
1               5

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Gly Gly Ala Gly Asn Asn Val Leu Ile
1               5

<210> SEQ ID NO 638
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Gly Asn Ala Gly Asn Asn Val Leu Ile
1               5

<210> SEQ ID NO 639
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 639

Gly Asp Ala Gly Asn Asn Val Leu Ile
1               5

<210> SEQ ID NO 640
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Gly Gly Ser Gly Asn Asn Val Leu Ile
1               5

<210> SEQ ID NO 641
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Gly Asn Ser Gly Asn Asn Val Leu Ile
1               5

<210> SEQ ID NO 642
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Gly Asp Ser Gly Asn Asn Val Leu Ile
1               5

<210> SEQ ID NO 643
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Gly Gly Gly Gly Asn Asn Val Leu Ile
1               5

<210> SEQ ID NO 644
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Gly Asn Gly Gly Asn Asn Val Leu Ile
1               5
```

<210> SEQ ID NO 645
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Gly Asp Gly Gly Asn Asn Val Leu Ile
1               5

<210> SEQ ID NO 646
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Gly Gly Asp Gly Asn Asn Val Leu Ile
1               5

<210> SEQ ID NO 647
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Gly Asn Asp Gly Asn Asn Val Leu Ile
1               5

<210> SEQ ID NO 648
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Gly Asp Asp Gly Asn Asn Val Leu Ile
1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Gly Gly Ala Gly Asp Asn Val Leu Ile
1               5

<210> SEQ ID NO 650
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Gly Asn Ala Gly Asp Asn Val Leu Ile
1               5

<210> SEQ ID NO 651
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Gly Asp Ala Gly Asp Asn Val Leu Ile
1               5

<210> SEQ ID NO 652
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Gly Gly Ser Gly Asp Asn Val Leu Ile
1               5

<210> SEQ ID NO 653
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Gly Asn Ser Gly Asp Asn Val Leu Ile
1               5

<210> SEQ ID NO 654
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Gly Asp Ser Gly Asp Asn Val Leu Ile
1               5

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Gly Gly Gly Gly Asp Asn Val Leu Ile
1               5

<210> SEQ ID NO 656
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Gly Asn Gly Gly Asp Asn Val Leu Ile
1               5

<210> SEQ ID NO 657
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Gly Asp Gly Gly Asp Asn Val Leu Ile
1               5

<210> SEQ ID NO 658
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Gly Gly Asp Gly Asp Asn Val Leu Ile
1               5

<210> SEQ ID NO 659
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Gly Asn Asp Gly Asp Asn Val Leu Ile
1               5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Gly Asp Asp Gly Asp Asn Val Leu Ile
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Gly Gly Ala Gly Ala Asn Val Leu Ile
```

```
1               5

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Gly Asn Ala Gly Ala Asn Val Leu Ile
1               5

<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Gly Asp Ala Gly Ala Asn Val Leu Ile
1               5

<210> SEQ ID NO 664
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Gly Gly Ser Gly Ala Asn Val Leu Ile
1               5

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gly Asn Ser Gly Ala Asn Val Leu Ile
1               5

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Gly Asp Ser Gly Ala Asn Val Leu Ile
1               5

<210> SEQ ID NO 667
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 667

Gly Gly Gly Gly Ala Asn Val Leu Ile
1               5

<210> SEQ ID NO 668
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Gly Asn Gly Gly Ala Asn Val Leu Ile
1               5

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Gly Asp Gly Gly Ala Asn Val Leu Ile
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Gly Gly Asp Gly Ala Asn Val Leu Ile
1               5

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Gly Asn Asp Gly Ala Asn Val Leu Ile
1               5

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Asp Asp Gly Ala Asn Val Leu Ile
1               5

<210> SEQ ID NO 673
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Gly Gly Ala Gly Asn Asp Thr Ile Ile
1               5

<210> SEQ ID NO 674
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Gly Asn Ala Gly Asn Asp Thr Ile Ile
1               5

<210> SEQ ID NO 675
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Gly Asp Ala Gly Asn Asp Thr Ile Ile
1               5

<210> SEQ ID NO 676
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Gly Gly Ser Gly Asn Asp Thr Ile Ile
1               5

<210> SEQ ID NO 677
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gly Asn Ser Gly Asn Asp Thr Ile Ile
1               5

<210> SEQ ID NO 678
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678
```

```
Gly Asp Ser Gly Asn Asp Thr Ile Ile
1               5

<210> SEQ ID NO 679
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Gly Gly Gly Gly Asn Asp Thr Ile Ile
1               5

<210> SEQ ID NO 680
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Gly Asn Gly Gly Asn Asp Thr Ile Ile
1               5

<210> SEQ ID NO 681
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Gly Asp Gly Gly Asn Asp Thr Ile Ile
1               5

<210> SEQ ID NO 682
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Gly Gly Asp Gly Asn Asp Thr Ile Ile
1               5

<210> SEQ ID NO 683
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Gly Asn Asp Gly Asn Asp Thr Ile Ile
1               5

<210> SEQ ID NO 684
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 684

Gly Asp Asp Gly Asn Asp Thr Ile Ile
1               5

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Gly Gly Ala Gly Asp Asp Thr Ile Ile
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Gly Asn Ala Gly Asp Asp Thr Ile Ile
1               5

<210> SEQ ID NO 687
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Gly Asp Ala Gly Asp Asp Thr Ile Ile
1               5

<210> SEQ ID NO 688
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

Gly Gly Ser Gly Asp Asp Thr Ile Ile
1               5

<210> SEQ ID NO 689
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Gly Asn Ser Gly Asp Asp Thr Ile Ile
1               5

```
<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Gly Asp Ser Gly Asp Asp Thr Ile Ile
1               5

<210> SEQ ID NO 691
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Gly Gly Gly Gly Asp Asp Thr Ile Ile
1               5

<210> SEQ ID NO 692
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Gly Asn Gly Gly Asp Asp Thr Ile Ile
1               5

<210> SEQ ID NO 693
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Gly Asp Gly Gly Asp Asp Thr Ile Ile
1               5

<210> SEQ ID NO 694
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Gly Gly Asp Gly Asp Asp Thr Ile Ile
1               5

<210> SEQ ID NO 695
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695
```

```
Gly Asn Asp Gly Asp Asp Thr Ile Ile
1               5

<210> SEQ ID NO 696
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Gly Asp Asp Gly Asp Asp Thr Ile Ile
1               5

<210> SEQ ID NO 697
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Gly Gly Ala Gly Ala Asp Thr Ile Ile
1               5

<210> SEQ ID NO 698
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Gly Asn Ala Gly Ala Asp Thr Ile Ile
1               5

<210> SEQ ID NO 699
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Gly Asp Ala Gly Ala Asp Thr Ile Ile
1               5

<210> SEQ ID NO 700
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Gly Gly Ser Gly Ala Asp Thr Ile Ile
1               5

<210> SEQ ID NO 701
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 701

Gly Asn Ser Gly Ala Asp Thr Ile Ile
1               5

<210> SEQ ID NO 702
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Gly Asp Ser Gly Ala Asp Thr Ile Ile
1               5

<210> SEQ ID NO 703
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Gly Gly Gly Gly Ala Asp Thr Ile Ile
1               5

<210> SEQ ID NO 704
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Gly Asn Gly Gly Ala Asp Thr Ile Ile
1               5

<210> SEQ ID NO 705
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Gly Asp Gly Gly Ala Asp Thr Ile Ile
1               5

<210> SEQ ID NO 706
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Gly Gly Asp Gly Ala Asp Thr Ile Ile
1               5
```

<210> SEQ ID NO 707
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Gly Asn Asp Gly Ala Asp Thr Ile Ile
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Gly Asp Asp Gly Ala Asp Thr Ile Ile
1               5

<210> SEQ ID NO 709
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Gly Gly Ala Gly Asn Asn Thr Ile Ile
1               5

<210> SEQ ID NO 710
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Gly Asn Ala Gly Asn Asn Thr Ile Ile
1               5

<210> SEQ ID NO 711
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Gly Asp Ala Gly Asn Asn Thr Ile Ile
1               5

<210> SEQ ID NO 712
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 712

Gly Gly Ser Gly Asn Asn Thr Ile Ile
1               5

<210> SEQ ID NO 713
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Gly Asn Ser Gly Asn Asn Thr Ile Ile
1               5

<210> SEQ ID NO 714
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Gly Asp Ser Gly Asn Asn Thr Ile Ile
1               5

<210> SEQ ID NO 715
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Gly Gly Gly Gly Asn Asn Thr Ile Ile
1               5

<210> SEQ ID NO 716
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Gly Asn Gly Gly Asn Asn Thr Ile Ile
1               5

<210> SEQ ID NO 717
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Gly Asp Gly Gly Asn Asn Thr Ile Ile
1               5

<210> SEQ ID NO 718
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 718

Gly Gly Asp Gly Asn Asn Thr Ile Ile
1               5

<210> SEQ ID NO 719
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Gly Asn Asp Gly Asn Asn Thr Ile Ile
1               5

<210> SEQ ID NO 720
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Gly Asp Asp Gly Asn Asn Thr Ile Ile
1               5

<210> SEQ ID NO 721
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Gly Gly Ala Gly Asp Asn Thr Ile Ile
1               5

<210> SEQ ID NO 722
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

Gly Asn Ala Gly Asp Asn Thr Ile Ile
1               5

<210> SEQ ID NO 723
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Gly Asp Ala Gly Asp Asn Thr Ile Ile
1               5
```

```
<210> SEQ ID NO 724
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Gly Gly Ser Gly Asp Asn Thr Ile Ile
1               5

<210> SEQ ID NO 725
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Gly Asn Ser Gly Asp Asn Thr Ile Ile
1               5

<210> SEQ ID NO 726
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Gly Asp Ser Gly Asp Asn Thr Ile Ile
1               5

<210> SEQ ID NO 727
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Gly Gly Gly Gly Asp Asn Thr Ile Ile
1               5

<210> SEQ ID NO 728
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Gly Asn Gly Gly Asp Asn Thr Ile Ile
1               5

<210> SEQ ID NO 729
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 729

Gly Asp Gly Gly Asp Asn Thr Ile Ile
1               5

<210> SEQ ID NO 730
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Gly Gly Asp Gly Asp Asn Thr Ile Ile
1               5

<210> SEQ ID NO 731
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Gly Asn Asp Gly Asp Asn Thr Ile Ile
1               5

<210> SEQ ID NO 732
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Gly Asp Asp Gly Asp Asn Thr Ile Ile
1               5

<210> SEQ ID NO 733
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Gly Gly Ala Gly Ala Asn Thr Ile Ile
1               5

<210> SEQ ID NO 734
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gly Asn Ala Gly Ala Asn Thr Ile Ile
1               5

<210> SEQ ID NO 735
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Gly Asp Ala Gly Ala Asn Thr Ile Ile
1               5

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Gly Gly Ser Gly Ala Asn Thr Ile Ile
1               5

<210> SEQ ID NO 737
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Gly Asn Ser Gly Ala Asn Thr Ile Ile
1               5

<210> SEQ ID NO 738
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Gly Asp Ser Gly Ala Asn Thr Ile Ile
1               5

<210> SEQ ID NO 739
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Gly Gly Gly Gly Ala Asn Thr Ile Ile
1               5

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Gly Asn Gly Gly Ala Asn Thr Ile Ile
```

```
1               5

<210> SEQ ID NO 741
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Gly Asp Gly Gly Ala Asn Thr Ile Ile
1               5

<210> SEQ ID NO 742
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Gly Gly Asp Gly Ala Asn Thr Ile Ile
1               5

<210> SEQ ID NO 743
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Gly Asn Asp Gly Ala Asn Thr Ile Ile
1               5

<210> SEQ ID NO 744
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Gly Asp Asp Gly Ala Asn Thr Ile Ile
1               5

<210> SEQ ID NO 745
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Gly Gly Ala Gly Asn Asp Ile Ile Ile
1               5

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 746

Gly Asn Ala Gly Asn Asp Ile Ile Ile
1               5

<210> SEQ ID NO 747
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Gly Asp Ala Gly Asn Asp Ile Ile Ile
1               5

<210> SEQ ID NO 748
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Gly Gly Ser Gly Asn Asp Ile Ile Ile
1               5

<210> SEQ ID NO 749
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Gly Asn Ser Gly Asn Asp Ile Ile Ile
1               5

<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Gly Asp Ser Gly Asn Asp Ile Ile Ile
1               5

<210> SEQ ID NO 751
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Gly Gly Gly Gly Asn Asp Ile Ile Ile
1               5

<210> SEQ ID NO 752

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Gly Asn Gly Gly Asn Asp Ile Ile Ile
1               5

<210> SEQ ID NO 753
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Gly Asp Gly Gly Asn Asp Ile Ile Ile
1               5

<210> SEQ ID NO 754
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Gly Gly Asp Gly Asn Asp Ile Ile Ile
1               5

<210> SEQ ID NO 755
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Gly Asn Asp Gly Asn Asp Ile Ile Ile
1               5

<210> SEQ ID NO 756
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Gly Asp Asp Gly Asn Asp Ile Ile Ile
1               5

<210> SEQ ID NO 757
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757
```

Gly Gly Ala Gly Asp Asp Ile Ile Ile
1               5

<210> SEQ ID NO 758
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Gly Asn Ala Gly Asp Asp Ile Ile Ile
1               5

<210> SEQ ID NO 759
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Gly Asp Ala Gly Asp Asp Ile Ile Ile
1               5

<210> SEQ ID NO 760
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Gly Gly Ser Gly Asp Asp Ile Ile Ile
1               5

<210> SEQ ID NO 761
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Gly Asn Ser Gly Asp Asp Ile Ile Ile
1               5

<210> SEQ ID NO 762
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Gly Asp Ser Gly Asp Asp Ile Ile Ile
1               5

<210> SEQ ID NO 763
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 763

Gly Gly Gly Gly Asp Asp Ile Ile Ile
1               5

<210> SEQ ID NO 764
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Gly Asn Gly Gly Asp Asp Ile Ile Ile
1               5

<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Gly Asp Gly Gly Asp Asp Ile Ile Ile
1               5

<210> SEQ ID NO 766
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Gly Gly Asp Gly Asp Asp Ile Ile Ile
1               5

<210> SEQ ID NO 767
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Gly Asn Asp Gly Asp Asp Ile Ile Ile
1               5

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Gly Asp Asp Gly Asp Asp Ile Ile Ile
1               5
```

```
<210> SEQ ID NO 769
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Gly Gly Ala Gly Ala Asp Ile Ile Ile
1               5

<210> SEQ ID NO 770
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Gly Asn Ala Gly Ala Asp Ile Ile Ile
1               5

<210> SEQ ID NO 771
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Gly Asp Ala Gly Ala Asp Ile Ile Ile
1               5

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Gly Gly Ser Gly Ala Asp Ile Ile Ile
1               5

<210> SEQ ID NO 773
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Gly Asn Ser Gly Ala Asp Ile Ile Ile
1               5

<210> SEQ ID NO 774
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774
```

```
Gly Asp Ser Gly Ala Asp Ile Ile Ile
1               5

<210> SEQ ID NO 775
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Gly Gly Gly Gly Ala Asp Ile Ile Ile
1               5

<210> SEQ ID NO 776
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Gly Asn Gly Gly Ala Asp Ile Ile Ile
1               5

<210> SEQ ID NO 777
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Gly Asp Gly Gly Ala Asp Ile Ile Ile
1               5

<210> SEQ ID NO 778
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Gly Gly Asp Gly Ala Asp Ile Ile Ile
1               5

<210> SEQ ID NO 779
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Gly Asn Asp Gly Ala Asp Ile Ile Ile
1               5

<210> SEQ ID NO 780
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 780

Gly Asp Asp Gly Ala Asp Ile Ile Ile
1               5

<210> SEQ ID NO 781
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Gly Gly Ala Gly Asn Asn Ile Ile Ile
1               5

<210> SEQ ID NO 782
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Gly Asn Ala Gly Asn Asn Ile Ile Ile
1               5

<210> SEQ ID NO 783
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Gly Asp Ala Gly Asn Asn Ile Ile Ile
1               5

<210> SEQ ID NO 784
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Gly Gly Ser Gly Asn Asn Ile Ile Ile
1               5

<210> SEQ ID NO 785
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Gly Asn Ser Gly Asn Asn Ile Ile Ile
1               5
```

```
<210> SEQ ID NO 786
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Gly Asp Ser Gly Asn Asn Ile Ile Ile
1               5

<210> SEQ ID NO 787
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Gly Gly Gly Gly Asn Asn Ile Ile Ile
1               5

<210> SEQ ID NO 788
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Gly Asn Gly Gly Asn Asn Ile Ile Ile
1               5

<210> SEQ ID NO 789
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Gly Asp Gly Gly Asn Asn Ile Ile Ile
1               5

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Gly Gly Asp Gly Asn Asn Ile Ile Ile
1               5

<210> SEQ ID NO 791
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 791

Gly Asn Asp Gly Asn Asn Ile Ile Ile
1               5

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Gly Asp Asp Gly Asn Asn Ile Ile Ile
1               5

<210> SEQ ID NO 793
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Gly Gly Ala Gly Asp Asn Ile Ile Ile
1               5

<210> SEQ ID NO 794
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

Gly Asn Ala Gly Asp Asn Ile Ile Ile
1               5

<210> SEQ ID NO 795
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Gly Asp Ala Gly Asp Asn Ile Ile Ile
1               5

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Gly Gly Ser Gly Asp Asn Ile Ile Ile
1               5

<210> SEQ ID NO 797
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 797

Gly Asn Ser Gly Asp Asn Ile Ile Ile
1               5

<210> SEQ ID NO 798
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Gly Asp Ser Gly Asp Asn Ile Ile Ile
1               5

<210> SEQ ID NO 799
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Gly Gly Gly Gly Asp Asn Ile Ile Ile
1               5

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Gly Asn Gly Gly Asp Asn Ile Ile Ile
1               5

<210> SEQ ID NO 801
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Gly Asp Gly Gly Asp Asn Ile Ile Ile
1               5

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Gly Gly Asp Gly Asp Asn Ile Ile Ile
1               5

```
<210> SEQ ID NO 803
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Gly Asn Asp Gly Asp Asn Ile Ile Ile
1               5

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Gly Asp Asp Gly Asp Asn Ile Ile Ile
1               5

<210> SEQ ID NO 805
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Gly Gly Ala Gly Ala Asn Ile Ile Ile
1               5

<210> SEQ ID NO 806
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Gly Asn Ala Gly Ala Asn Ile Ile Ile
1               5

<210> SEQ ID NO 807
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Gly Asp Ala Gly Ala Asn Ile Ile Ile
1               5

<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 808

Gly Gly Ser Gly Ala Asn Ile Ile Ile
1               5

<210> SEQ ID NO 809
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Gly Asn Ser Gly Ala Asn Ile Ile Ile
1               5

<210> SEQ ID NO 810
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Gly Asp Ser Gly Ala Asn Ile Ile Ile
1               5

<210> SEQ ID NO 811
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Gly Gly Gly Gly Ala Asn Ile Ile Ile
1               5

<210> SEQ ID NO 812
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Gly Asn Gly Gly Ala Asn Ile Ile Ile
1               5

<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Gly Asp Gly Gly Ala Asn Ile Ile Ile
1               5

<210> SEQ ID NO 814
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Gly Gly Asp Gly Ala Asn Ile Ile Ile
1               5

<210> SEQ ID NO 815
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Gly Asn Asp Gly Ala Asn Ile Ile Ile
1               5

<210> SEQ ID NO 816
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816

Gly Asp Asp Gly Ala Asn Ile Ile Ile
1               5

<210> SEQ ID NO 817
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Gly Gly Ala Gly Asn Asp Val Ile Ile
1               5

<210> SEQ ID NO 818
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Gly Asn Ala Gly Asn Asp Val Ile Ile
1               5

<210> SEQ ID NO 819
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Gly Asp Ala Gly Asn Asp Val Ile Ile
```

```
1               5

<210> SEQ ID NO 820
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Gly Gly Ser Gly Asn Asp Val Ile Ile
1               5

<210> SEQ ID NO 821
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Gly Asn Ser Gly Asn Asp Val Ile Ile
1               5

<210> SEQ ID NO 822
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

Gly Asp Ser Gly Asn Asp Val Ile Ile
1               5

<210> SEQ ID NO 823
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Gly Gly Gly Gly Asn Asp Val Ile Ile
1               5

<210> SEQ ID NO 824
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Gly Asn Gly Gly Asn Asp Val Ile Ile
1               5

<210> SEQ ID NO 825
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 825

Gly Asp Gly Gly Asn Asp Val Ile Ile
1               5

<210> SEQ ID NO 826
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Gly Gly Asp Gly Asn Asp Val Ile Ile
1               5

<210> SEQ ID NO 827
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Gly Asn Asp Gly Asn Asp Val Ile Ile
1               5

<210> SEQ ID NO 828
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Gly Asp Asp Gly Asn Asp Val Ile Ile
1               5

<210> SEQ ID NO 829
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Gly Gly Ala Gly Asp Asp Val Ile Ile
1               5

<210> SEQ ID NO 830
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Gly Asn Ala Gly Asp Asp Val Ile Ile
1               5

<210> SEQ ID NO 831

```
<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Gly Asp Ala Gly Asp Asp Val Ile Ile
1               5

<210> SEQ ID NO 832
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 832

Gly Gly Ser Gly Asp Asp Val Ile Ile
1               5

<210> SEQ ID NO 833
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 833

Gly Asn Ser Gly Asp Asp Val Ile Ile
1               5

<210> SEQ ID NO 834
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Gly Asp Ser Gly Asp Asp Val Ile Ile
1               5

<210> SEQ ID NO 835
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Gly Gly Gly Gly Asp Asp Val Ile Ile
1               5

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836
```

Gly Asn Gly Gly Asp Asp Val Ile Ile
1               5

<210> SEQ ID NO 837
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 837

Gly Asp Gly Gly Asp Asp Val Ile Ile
1               5

<210> SEQ ID NO 838
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Gly Gly Asp Gly Asp Asp Val Ile Ile
1               5

<210> SEQ ID NO 839
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Gly Asn Asp Gly Asp Asp Val Ile Ile
1               5

<210> SEQ ID NO 840
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Gly Asp Asp Gly Asp Asp Val Ile Ile
1               5

<210> SEQ ID NO 841
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

Gly Gly Ala Gly Ala Asp Val Ile Ile
1               5

<210> SEQ ID NO 842
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 842

Gly Asn Ala Gly Ala Asp Val Ile Ile
1               5

<210> SEQ ID NO 843
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Gly Asp Ala Gly Ala Asp Val Ile Ile
1               5

<210> SEQ ID NO 844
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Gly Gly Ser Gly Ala Asp Val Ile Ile
1               5

<210> SEQ ID NO 845
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Gly Asn Ser Gly Ala Asp Val Ile Ile
1               5

<210> SEQ ID NO 846
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Gly Asp Ser Gly Ala Asp Val Ile Ile
1               5

<210> SEQ ID NO 847
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Gly Gly Gly Gly Ala Asp Val Ile Ile
1               5
```

```
<210> SEQ ID NO 848
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Gly Asn Gly Gly Ala Asp Val Ile Ile
1               5

<210> SEQ ID NO 849
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Gly Asp Gly Gly Ala Asp Val Ile Ile
1               5

<210> SEQ ID NO 850
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Gly Gly Asp Gly Ala Asp Val Ile Ile
1               5

<210> SEQ ID NO 851
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Gly Asn Asp Gly Ala Asp Val Ile Ile
1               5

<210> SEQ ID NO 852
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

Gly Asp Asp Gly Ala Asp Val Ile Ile
1               5

<210> SEQ ID NO 853
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853
```

```
Gly Gly Ala Gly Asn Asn Val Ile Ile
1               5
```

<210> SEQ ID NO 854
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

```
Gly Asn Ala Gly Asn Asn Val Ile Ile
1               5
```

<210> SEQ ID NO 855
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

```
Gly Asp Ala Gly Asn Asn Val Ile Ile
1               5
```

<210> SEQ ID NO 856
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

```
Gly Gly Ser Gly Asn Asn Val Ile Ile
1               5
```

<210> SEQ ID NO 857
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

```
Gly Asn Ser Gly Asn Asn Val Ile Ile
1               5
```

<210> SEQ ID NO 858
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

```
Gly Asp Ser Gly Asn Asn Val Ile Ile
1               5
```

<210> SEQ ID NO 859
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 859

Gly Gly Gly Gly Asn Asn Val Ile Ile
1               5

<210> SEQ ID NO 860
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Gly Asn Gly Gly Asn Asn Val Ile Ile
1               5

<210> SEQ ID NO 861
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 861

Gly Asp Gly Gly Asn Asn Val Ile Ile
1               5

<210> SEQ ID NO 862
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Gly Gly Asp Gly Asn Asn Val Ile Ile
1               5

<210> SEQ ID NO 863
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Gly Asn Asp Gly Asn Asn Val Ile Ile
1               5

<210> SEQ ID NO 864
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Gly Asp Asp Gly Asn Asn Val Ile Ile
1               5
```

<210> SEQ ID NO 865
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Gly Gly Ala Gly Asp Asn Val Ile Ile
1               5

<210> SEQ ID NO 866
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 866

Gly Asn Ala Gly Asp Asn Val Ile Ile
1               5

<210> SEQ ID NO 867
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 867

Gly Asp Ala Gly Asp Asn Val Ile Ile
1               5

<210> SEQ ID NO 868
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Gly Gly Ser Gly Asp Asn Val Ile Ile
1               5

<210> SEQ ID NO 869
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Gly Asn Ser Gly Asp Asn Val Ile Ile
1               5

<210> SEQ ID NO 870
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 870

Gly Asp Ser Gly Asp Asn Val Ile Ile
1               5

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Gly Gly Gly Gly Asp Asn Val Ile Ile
1               5

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Gly Asn Gly Gly Asp Asn Val Ile Ile
1               5

<210> SEQ ID NO 873
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Gly Asp Gly Gly Asp Asn Val Ile Ile
1               5

<210> SEQ ID NO 874
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Gly Gly Asp Gly Asp Asn Val Ile Ile
1               5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Gly Asn Asp Gly Asp Asn Val Ile Ile
1               5

<210> SEQ ID NO 876
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 876

Gly Asp Asp Gly Asp Asn Val Ile Ile
1               5

<210> SEQ ID NO 877
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Gly Gly Ala Gly Ala Asn Val Ile Ile
1               5

<210> SEQ ID NO 878
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Gly Asn Ala Gly Ala Asn Val Ile Ile
1               5

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Gly Asp Ala Gly Ala Asn Val Ile Ile
1               5

<210> SEQ ID NO 880
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Gly Gly Ser Gly Ala Asn Val Ile Ile
1               5

<210> SEQ ID NO 881
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Gly Asn Ser Gly Ala Asn Val Ile Ile
1               5
```

```
<210> SEQ ID NO 882
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Gly Asp Ser Gly Ala Asn Val Ile Ile
1               5

<210> SEQ ID NO 883
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Gly Gly Gly Gly Ala Asn Val Ile Ile
1               5

<210> SEQ ID NO 884
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Gly Asn Gly Gly Ala Asn Val Ile Ile
1               5

<210> SEQ ID NO 885
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Gly Asp Gly Gly Ala Asn Val Ile Ile
1               5

<210> SEQ ID NO 886
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Gly Gly Asp Gly Ala Asn Val Ile Ile
1               5

<210> SEQ ID NO 887
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 887

Gly Asn Asp Gly Ala Asn Val Ile Ile
1               5

<210> SEQ ID NO 888
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Gly Asp Asp Gly Ala Asn Val Ile Ile
1               5

<210> SEQ ID NO 889
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Gly Gly Ala Gly Asn Asp Thr Leu Val
1               5

<210> SEQ ID NO 890
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Gly Asn Ala Gly Asn Asp Thr Leu Val
1               5

<210> SEQ ID NO 891
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Gly Asp Ala Gly Asn Asp Thr Leu Val
1               5

<210> SEQ ID NO 892
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Gly Gly Ser Gly Asn Asp Thr Leu Val
1               5

<210> SEQ ID NO 893
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Gly Asn Ser Gly Asn Asp Thr Leu Val
1               5

<210> SEQ ID NO 894
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Gly Asp Ser Gly Asn Asp Thr Leu Val
1               5

<210> SEQ ID NO 895
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

Gly Gly Gly Gly Asn Asp Thr Leu Val
1               5

<210> SEQ ID NO 896
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Gly Asn Gly Gly Asn Asp Thr Leu Val
1               5

<210> SEQ ID NO 897
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Gly Asp Gly Gly Asn Asp Thr Leu Val
1               5

<210> SEQ ID NO 898
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Gly Gly Asp Gly Asn Asp Thr Leu Val
```

1               5

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Gly Asn Asp Gly Asn Asp Thr Leu Val
1               5

<210> SEQ ID NO 900
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Gly Asp Asp Gly Asn Asp Thr Leu Val
1               5

<210> SEQ ID NO 901
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Gly Gly Ala Gly Asp Asp Thr Leu Val
1               5

<210> SEQ ID NO 902
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Gly Asn Ala Gly Asp Asp Thr Leu Val
1               5

<210> SEQ ID NO 903
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Gly Asp Ala Gly Asp Asp Thr Leu Val
1               5

<210> SEQ ID NO 904
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 904

Gly Gly Ser Gly Asp Asp Thr Leu Val
1               5

<210> SEQ ID NO 905
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

Gly Asn Ser Gly Asp Asp Thr Leu Val
1               5

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

Gly Asp Ser Gly Asp Asp Thr Leu Val
1               5

<210> SEQ ID NO 907
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907

Gly Gly Gly Gly Asp Asp Thr Leu Val
1               5

<210> SEQ ID NO 908
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Gly Asn Gly Gly Asp Asp Thr Leu Val
1               5

<210> SEQ ID NO 909
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

Gly Asp Gly Gly Asp Asp Thr Leu Val
1               5

<210> SEQ ID NO 910

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

Gly Gly Asp Gly Asp Asp Thr Leu Val
1               5

<210> SEQ ID NO 911
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Gly Asn Asp Gly Asp Asp Thr Leu Val
1               5

<210> SEQ ID NO 912
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Gly Asp Asp Gly Asp Asp Thr Leu Val
1               5

<210> SEQ ID NO 913
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Gly Gly Ala Gly Ala Asp Thr Leu Val
1               5

<210> SEQ ID NO 914
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Gly Asn Ala Gly Ala Asp Thr Leu Val
1               5

<210> SEQ ID NO 915
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915
```

Gly Asp Ala Gly Ala Asp Thr Leu Val
1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Gly Gly Ser Gly Ala Asp Thr Leu Val
1               5

<210> SEQ ID NO 917
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Gly Asn Ser Gly Ala Asp Thr Leu Val
1               5

<210> SEQ ID NO 918
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Gly Asp Ser Gly Ala Asp Thr Leu Val
1               5

<210> SEQ ID NO 919
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Gly Gly Gly Gly Ala Asp Thr Leu Val
1               5

<210> SEQ ID NO 920
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Gly Asn Gly Gly Ala Asp Thr Leu Val
1               5

<210> SEQ ID NO 921
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 921

Gly Asp Gly Gly Ala Asp Thr Leu Val
1               5

<210> SEQ ID NO 922
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Gly Gly Asp Gly Ala Asp Thr Leu Val
1               5

<210> SEQ ID NO 923
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Gly Asn Asp Gly Ala Asp Thr Leu Val
1               5

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Gly Asp Asp Gly Ala Asp Thr Leu Val
1               5

<210> SEQ ID NO 925
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Gly Gly Ala Gly Asn Asn Thr Leu Val
1               5

<210> SEQ ID NO 926
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Gly Asn Ala Gly Asn Asn Thr Leu Val
1               5
```

```
<210> SEQ ID NO 927
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 927

Gly Asp Ala Gly Asn Asn Thr Leu Val
1               5

<210> SEQ ID NO 928
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Gly Gly Ser Gly Asn Asn Thr Leu Val
1               5

<210> SEQ ID NO 929
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 929

Gly Asn Ser Gly Asn Asn Thr Leu Val
1               5

<210> SEQ ID NO 930
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 930

Gly Asp Ser Gly Asn Asn Thr Leu Val
1               5

<210> SEQ ID NO 931
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 931

Gly Gly Gly Gly Asn Asn Thr Leu Val
1               5

<210> SEQ ID NO 932
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932
```

```
Gly Asn Gly Gly Asn Asn Thr Leu Val
1               5

<210> SEQ ID NO 933
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Gly Asp Gly Gly Asn Asn Thr Leu Val
1               5

<210> SEQ ID NO 934
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 934

Gly Gly Asp Gly Asn Asn Thr Leu Val
1               5

<210> SEQ ID NO 935
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 935

Gly Asn Asp Gly Asn Asn Thr Leu Val
1               5

<210> SEQ ID NO 936
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

Gly Asp Asp Gly Asn Asn Thr Leu Val
1               5

<210> SEQ ID NO 937
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Gly Gly Ala Gly Asp Asn Thr Leu Val
1               5

<210> SEQ ID NO 938
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 938

Gly Asn Ala Gly Asp Asn Thr Leu Val
1               5

<210> SEQ ID NO 939
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

Gly Asp Ala Gly Asp Asn Thr Leu Val
1               5

<210> SEQ ID NO 940
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 940

Gly Gly Ser Gly Asp Asn Thr Leu Val
1               5

<210> SEQ ID NO 941
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 941

Gly Asn Ser Gly Asp Asn Thr Leu Val
1               5

<210> SEQ ID NO 942
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 942

Gly Asp Ser Gly Asp Asn Thr Leu Val
1               5

<210> SEQ ID NO 943
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Gly Gly Gly Gly Asp Asn Thr Leu Val
1               5
```

<210> SEQ ID NO 944
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Gly Asn Gly Gly Asp Asn Thr Leu Val
1               5

<210> SEQ ID NO 945
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Gly Asp Gly Gly Asp Asn Thr Leu Val
1               5

<210> SEQ ID NO 946
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 946

Gly Gly Asp Gly Asp Asn Thr Leu Val
1               5

<210> SEQ ID NO 947
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Gly Asn Asp Gly Asp Asn Thr Leu Val
1               5

<210> SEQ ID NO 948
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Gly Asp Asp Gly Asp Asn Thr Leu Val
1               5

<210> SEQ ID NO 949
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 949

Gly Gly Ala Gly Ala Asn Thr Leu Val
1               5

<210> SEQ ID NO 950
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Gly Asn Ala Gly Ala Asn Thr Leu Val
1               5

<210> SEQ ID NO 951
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Gly Asp Ala Gly Ala Asn Thr Leu Val
1               5

<210> SEQ ID NO 952
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 952

Gly Gly Ser Gly Ala Asn Thr Leu Val
1               5

<210> SEQ ID NO 953
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Gly Asn Ser Gly Ala Asn Thr Leu Val
1               5

<210> SEQ ID NO 954
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Gly Asp Ser Gly Ala Asn Thr Leu Val
1               5

<210> SEQ ID NO 955
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 955

Gly Gly Gly Gly Ala Asn Thr Leu Val
1               5

<210> SEQ ID NO 956
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Gly Asn Gly Gly Ala Asn Thr Leu Val
1               5

<210> SEQ ID NO 957
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 957

Gly Asp Gly Gly Ala Asn Thr Leu Val
1               5

<210> SEQ ID NO 958
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Gly Gly Asp Gly Ala Asn Thr Leu Val
1               5

<210> SEQ ID NO 959
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Gly Asn Asp Gly Ala Asn Thr Leu Val
1               5

<210> SEQ ID NO 960
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 960

Gly Asp Asp Gly Ala Asn Thr Leu Val
1               5
```

<210> SEQ ID NO 961
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Gly Gly Ala Gly Asn Asp Ile Leu Val
1               5

<210> SEQ ID NO 962
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 962

Gly Asn Ala Gly Asn Asp Ile Leu Val
1               5

<210> SEQ ID NO 963
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Gly Asp Ala Gly Asn Asp Ile Leu Val
1               5

<210> SEQ ID NO 964
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Gly Gly Ser Gly Asn Asp Ile Leu Val
1               5

<210> SEQ ID NO 965
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Gly Asn Ser Gly Asn Asp Ile Leu Val
1               5

<210> SEQ ID NO 966
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 966

Gly Asp Ser Gly Asn Asp Ile Leu Val
1               5

<210> SEQ ID NO 967
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 967

Gly Gly Gly Gly Asn Asp Ile Leu Val
1               5

<210> SEQ ID NO 968
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968

Gly Asn Gly Gly Asn Asp Ile Leu Val
1               5

<210> SEQ ID NO 969
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 969

Gly Asp Gly Gly Asn Asp Ile Leu Val
1               5

<210> SEQ ID NO 970
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 970

Gly Gly Asp Gly Asn Asp Ile Leu Val
1               5

<210> SEQ ID NO 971
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 971

Gly Asn Asp Gly Asn Asp Ile Leu Val
1               5

<210> SEQ ID NO 972
<211> LENGTH: 9
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 972

Gly Asp Asp Gly Asn Asp Ile Leu Val
1               5

<210> SEQ ID NO 973
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

Gly Gly Ala Gly Asp Asp Ile Leu Val
1               5

<210> SEQ ID NO 974
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

Gly Asn Ala Gly Asp Asp Ile Leu Val
1               5

<210> SEQ ID NO 975
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Gly Asp Ala Gly Asp Asp Ile Leu Val
1               5

<210> SEQ ID NO 976
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 976

Gly Gly Ser Gly Asp Asp Ile Leu Val
1               5

<210> SEQ ID NO 977
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 977

Gly Asn Ser Gly Asp Asp Ile Leu Val
```

```
1               5

<210> SEQ ID NO 978
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Gly Asp Ser Gly Asp Asp Ile Leu Val
1               5

<210> SEQ ID NO 979
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Gly Gly Gly Gly Asp Asp Ile Leu Val
1               5

<210> SEQ ID NO 980
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Gly Asn Gly Gly Asp Asp Ile Leu Val
1               5

<210> SEQ ID NO 981
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Gly Asp Gly Gly Asp Asp Ile Leu Val
1               5

<210> SEQ ID NO 982
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Gly Gly Asp Gly Asp Asp Ile Leu Val
1               5

<210> SEQ ID NO 983
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 983

Gly Asn Asp Gly Asp Asp Ile Leu Val
1               5

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Gly Asp Asp Gly Asp Asp Ile Leu Val
1               5

<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Gly Gly Ala Gly Ala Asp Ile Leu Val
1               5

<210> SEQ ID NO 986
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 986

Gly Asn Ala Gly Ala Asp Ile Leu Val
1               5

<210> SEQ ID NO 987
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 987

Gly Asp Ala Gly Ala Asp Ile Leu Val
1               5

<210> SEQ ID NO 988
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Gly Gly Ser Gly Ala Asp Ile Leu Val
1               5

<210> SEQ ID NO 989
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Gly Asn Ser Gly Ala Asp Ile Leu Val
1               5

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Gly Asp Ser Gly Ala Asp Ile Leu Val
1               5

<210> SEQ ID NO 991
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 991

Gly Gly Gly Gly Ala Asp Ile Leu Val
1               5

<210> SEQ ID NO 992
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 992

Gly Asn Gly Gly Ala Asp Ile Leu Val
1               5

<210> SEQ ID NO 993
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 993

Gly Asp Gly Gly Ala Asp Ile Leu Val
1               5

<210> SEQ ID NO 994
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 994
```

Gly Gly Asp Gly Ala Asp Ile Leu Val
1               5

<210> SEQ ID NO 995
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 995

Gly Asn Asp Gly Ala Asp Ile Leu Val
1               5

<210> SEQ ID NO 996
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 996

Gly Asp Asp Gly Ala Asp Ile Leu Val
1               5

<210> SEQ ID NO 997
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 997

Gly Gly Ala Gly Asn Asn Ile Leu Val
1               5

<210> SEQ ID NO 998
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 998

Gly Asn Ala Gly Asn Asn Ile Leu Val
1               5

<210> SEQ ID NO 999
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 999

Gly Asp Ala Gly Asn Asn Ile Leu Val
1               5

<210> SEQ ID NO 1000
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1000

Gly Gly Ser Gly Asn Asn Ile Leu Val
1               5

<210> SEQ ID NO 1001
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1001

Gly Asn Ser Gly Asn Asn Ile Leu Val
1               5

<210> SEQ ID NO 1002
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1002

Gly Asp Ser Gly Asn Asn Ile Leu Val
1               5

<210> SEQ ID NO 1003
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1003

Gly Gly Gly Gly Asn Asn Ile Leu Val
1               5

<210> SEQ ID NO 1004
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1004

Gly Asn Gly Gly Asn Asn Ile Leu Val
1               5

<210> SEQ ID NO 1005
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1005

Gly Asp Gly Gly Asn Asn Ile Leu Val
1               5
```

```
<210> SEQ ID NO 1006
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1006

Gly Gly Asp Gly Asn Asn Ile Leu Val
1               5

<210> SEQ ID NO 1007
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1007

Gly Asn Asp Gly Asn Asn Ile Leu Val
1               5

<210> SEQ ID NO 1008
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1008

Gly Asp Asp Gly Asn Asn Ile Leu Val
1               5

<210> SEQ ID NO 1009
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1009

Gly Gly Ala Gly Asp Asn Ile Leu Val
1               5

<210> SEQ ID NO 1010
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Gly Asn Ala Gly Asp Asn Ile Leu Val
1               5

<210> SEQ ID NO 1011
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011
```

Gly Asp Ala Gly Asp Asn Ile Leu Val
1               5

<210> SEQ ID NO 1012
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Gly Gly Ser Gly Asp Asn Ile Leu Val
1               5

<210> SEQ ID NO 1013
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Gly Asn Ser Gly Asp Asn Ile Leu Val
1               5

<210> SEQ ID NO 1014
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Gly Asp Ser Gly Asp Asn Ile Leu Val
1               5

<210> SEQ ID NO 1015
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Gly Gly Gly Gly Asp Asn Ile Leu Val
1               5

<210> SEQ ID NO 1016
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Gly Asn Gly Gly Asp Asn Ile Leu Val
1               5

<210> SEQ ID NO 1017
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1017

Gly Asp Gly Gly Asp Asn Ile Leu Val
1               5

<210> SEQ ID NO 1018
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Gly Gly Asp Gly Asp Asn Ile Leu Val
1               5

<210> SEQ ID NO 1019
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1019

Gly Asn Asp Gly Asp Asn Ile Leu Val
1               5

<210> SEQ ID NO 1020
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1020

Gly Asp Asp Gly Asp Asn Ile Leu Val
1               5

<210> SEQ ID NO 1021
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1021

Gly Gly Ala Gly Ala Asn Ile Leu Val
1               5

<210> SEQ ID NO 1022
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1022

Gly Asn Ala Gly Ala Asn Ile Leu Val
1               5
```

<210> SEQ ID NO 1023
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1023

Gly Asp Ala Gly Ala Asn Ile Leu Val
1               5

<210> SEQ ID NO 1024
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1024

Gly Gly Ser Gly Ala Asn Ile Leu Val
1               5

<210> SEQ ID NO 1025
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Gly Asn Ser Gly Ala Asn Ile Leu Val
1               5

<210> SEQ ID NO 1026
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1026

Gly Asp Ser Gly Ala Asn Ile Leu Val
1               5

<210> SEQ ID NO 1027
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1027

Gly Gly Gly Gly Ala Asn Ile Leu Val
1               5

<210> SEQ ID NO 1028
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1028

Gly Asn Gly Gly Ala Asn Ile Leu Val
1               5

<210> SEQ ID NO 1029
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1029

Gly Asp Gly Gly Ala Asn Ile Leu Val
1               5

<210> SEQ ID NO 1030
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1030

Gly Gly Asp Gly Ala Asn Ile Leu Val
1               5

<210> SEQ ID NO 1031
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1031

Gly Asn Asp Gly Ala Asn Ile Leu Val
1               5

<210> SEQ ID NO 1032
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1032

Gly Asp Asp Gly Ala Asn Ile Leu Val
1               5

<210> SEQ ID NO 1033
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1033

Gly Gly Ala Gly Asn Asp Val Leu Val
1               5

<210> SEQ ID NO 1034
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1034

Gly Asn Ala Gly Asn Asp Val Leu Val
1               5

<210> SEQ ID NO 1035
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1035

Gly Asp Ala Gly Asn Asp Val Leu Val
1               5

<210> SEQ ID NO 1036
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1036

Gly Gly Ser Gly Asn Asp Val Leu Val
1               5

<210> SEQ ID NO 1037
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1037

Gly Asn Ser Gly Asn Asp Val Leu Val
1               5

<210> SEQ ID NO 1038
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1038

Gly Asp Ser Gly Asn Asp Val Leu Val
1               5

<210> SEQ ID NO 1039
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1039

Gly Gly Gly Gly Asn Asp Val Leu Val
1               5
```

<210> SEQ ID NO 1040
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1040

Gly Asn Gly Gly Asn Asp Val Leu Val
1               5

<210> SEQ ID NO 1041
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1041

Gly Asp Gly Gly Asn Asp Val Leu Val
1               5

<210> SEQ ID NO 1042
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1042

Gly Gly Asp Gly Asn Asp Val Leu Val
1               5

<210> SEQ ID NO 1043
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1043

Gly Asn Asp Gly Asn Asp Val Leu Val
1               5

<210> SEQ ID NO 1044
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1044

Gly Asp Asp Gly Asn Asp Val Leu Val
1               5

<210> SEQ ID NO 1045
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1045

Gly Gly Ala Gly Asp Asp Val Leu Val
1               5

<210> SEQ ID NO 1046
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1046

Gly Asn Ala Gly Asp Asp Val Leu Val
1               5

<210> SEQ ID NO 1047
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1047

Gly Asp Ala Gly Asp Asp Val Leu Val
1               5

<210> SEQ ID NO 1048
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1048

Gly Gly Ser Gly Asp Asp Val Leu Val
1               5

<210> SEQ ID NO 1049
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1049

Gly Asn Ser Gly Asp Asp Val Leu Val
1               5

<210> SEQ ID NO 1050
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1050

Gly Asp Ser Gly Asp Asp Val Leu Val
1               5

<210> SEQ ID NO 1051
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1051

Gly Gly Gly Gly Asp Asp Val Leu Val
1               5

<210> SEQ ID NO 1052
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1052

Gly Asn Gly Gly Asp Asp Val Leu Val
1               5

<210> SEQ ID NO 1053
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1053

Gly Asp Gly Gly Asp Asp Val Leu Val
1               5

<210> SEQ ID NO 1054
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1054

Gly Gly Asp Gly Asp Asp Val Leu Val
1               5

<210> SEQ ID NO 1055
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1055

Gly Asn Asp Gly Asp Asp Val Leu Val
1               5

<210> SEQ ID NO 1056
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1056

Gly Asp Asp Gly Asp Asp Val Leu Val
```

```
1               5
```

<210> SEQ ID NO 1057
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1057

```
Gly Gly Ala Gly Ala Asp Val Leu Val
1               5
```

<210> SEQ ID NO 1058
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1058

```
Gly Asn Ala Gly Ala Asp Val Leu Val
1               5
```

<210> SEQ ID NO 1059
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1059

```
Gly Asp Ala Gly Ala Asp Val Leu Val
1               5
```

<210> SEQ ID NO 1060
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1060

```
Gly Gly Ser Gly Ala Asp Val Leu Val
1               5
```

<210> SEQ ID NO 1061
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1061

```
Gly Asn Ser Gly Ala Asp Val Leu Val
1               5
```

<210> SEQ ID NO 1062
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1062

Gly Asp Ser Gly Ala Asp Val Leu Val
1               5

<210> SEQ ID NO 1063
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1063

Gly Gly Gly Gly Ala Asp Val Leu Val
1               5

<210> SEQ ID NO 1064
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1064

Gly Asn Gly Gly Ala Asp Val Leu Val
1               5

<210> SEQ ID NO 1065
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1065

Gly Asp Gly Gly Ala Asp Val Leu Val
1               5

<210> SEQ ID NO 1066
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1066

Gly Gly Asp Gly Ala Asp Val Leu Val
1               5

<210> SEQ ID NO 1067
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1067

Gly Asn Asp Gly Ala Asp Val Leu Val
1               5

<210> SEQ ID NO 1068

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1068

Gly Asp Asp Gly Ala Asp Val Leu Val
1               5

<210> SEQ ID NO 1069
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1069

Gly Gly Ala Gly Asn Asn Val Leu Val
1               5

<210> SEQ ID NO 1070
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1070

Gly Asn Ala Gly Asn Asn Val Leu Val
1               5

<210> SEQ ID NO 1071
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1071

Gly Asp Ala Gly Asn Asn Val Leu Val
1               5

<210> SEQ ID NO 1072
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1072

Gly Gly Ser Gly Asn Asn Val Leu Val
1               5

<210> SEQ ID NO 1073
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1073
```

Gly Asn Ser Gly Asn Asn Val Leu Val
1               5

<210> SEQ ID NO 1074
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1074

Gly Asp Ser Gly Asn Asn Val Leu Val
1               5

<210> SEQ ID NO 1075
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1075

Gly Gly Gly Gly Asn Asn Val Leu Val
1               5

<210> SEQ ID NO 1076
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1076

Gly Asn Gly Gly Asn Asn Val Leu Val
1               5

<210> SEQ ID NO 1077
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1077

Gly Asp Gly Gly Asn Asn Val Leu Val
1               5

<210> SEQ ID NO 1078
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1078

Gly Gly Asp Gly Asn Asn Val Leu Val
1               5

<210> SEQ ID NO 1079
<211> LENGTH: 9
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 1079

Gly Asn Asp Gly Asn Asn Val Leu Val
1               5

<210> SEQ ID NO 1080
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 1080

Gly Asp Asp Gly Asn Asn Val Leu Val
1               5

<210> SEQ ID NO 1081
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 1081

Gly Gly Ala Gly Asp Asn Val Leu Val
1               5

<210> SEQ ID NO 1082
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 1082

Gly Asn Ala Gly Asp Asn Val Leu Val
1               5

<210> SEQ ID NO 1083
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 1083

Gly Asp Ala Gly Asp Asn Val Leu Val
1               5

<210> SEQ ID NO 1084
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 1084

Gly Gly Ser Gly Asp Asn Val Leu Val
1               5

```
<210> SEQ ID NO 1085
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1085

Gly Asn Ser Gly Asp Asn Val Leu Val
1               5

<210> SEQ ID NO 1086
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1086

Gly Asp Ser Gly Asp Asn Val Leu Val
1               5

<210> SEQ ID NO 1087
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1087

Gly Gly Gly Gly Asp Asn Val Leu Val
1               5

<210> SEQ ID NO 1088
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1088

Gly Asn Gly Gly Asp Asn Val Leu Val
1               5

<210> SEQ ID NO 1089
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1089

Gly Asp Gly Gly Asp Asn Val Leu Val
1               5

<210> SEQ ID NO 1090
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1090
```

Gly Gly Asp Gly Asp Asn Val Leu Val
1               5

<210> SEQ ID NO 1091
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1091

Gly Asn Asp Gly Asp Asn Val Leu Val
1               5

<210> SEQ ID NO 1092
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1092

Gly Asp Asp Gly Asp Asn Val Leu Val
1               5

<210> SEQ ID NO 1093
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1093

Gly Gly Ala Gly Ala Asn Val Leu Val
1               5

<210> SEQ ID NO 1094
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1094

Gly Asn Ala Gly Ala Asn Val Leu Val
1               5

<210> SEQ ID NO 1095
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1095

Gly Asp Ala Gly Ala Asn Val Leu Val
1               5

<210> SEQ ID NO 1096
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1096

Gly Gly Ser Gly Ala Asn Val Leu Val
1               5

<210> SEQ ID NO 1097
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1097

Gly Asn Ser Gly Ala Asn Val Leu Val
1               5

<210> SEQ ID NO 1098
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1098

Gly Asp Ser Gly Ala Asn Val Leu Val
1               5

<210> SEQ ID NO 1099
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1099

Gly Gly Gly Gly Ala Asn Val Leu Val
1               5

<210> SEQ ID NO 1100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1100

Gly Asn Gly Gly Ala Asn Val Leu Val
1               5

<210> SEQ ID NO 1101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1101

Gly Asp Gly Gly Ala Asn Val Leu Val
1               5
```

<210> SEQ ID NO 1102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1102

Gly Gly Asp Gly Ala Asn Val Leu Val
1               5

<210> SEQ ID NO 1103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1103

Gly Asn Asp Gly Ala Asn Val Leu Val
1               5

<210> SEQ ID NO 1104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1104

Gly Asp Asp Gly Ala Asn Val Leu Val
1               5

<210> SEQ ID NO 1105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1105

Gly Gly Ala Gly Asn Asp Thr Ile Val
1               5

<210> SEQ ID NO 1106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1106

Gly Asn Ala Gly Asn Asp Thr Ile Val
1               5

<210> SEQ ID NO 1107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1107

Gly Asp Ala Gly Asn Asp Thr Ile Val
1               5

<210> SEQ ID NO 1108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1108

Gly Gly Ser Gly Asn Asp Thr Ile Val
1               5

<210> SEQ ID NO 1109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1109

Gly Asn Ser Gly Asn Asp Thr Ile Val
1               5

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1110

Gly Asp Ser Gly Asn Asp Thr Ile Val
1               5

<210> SEQ ID NO 1111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1111

Gly Gly Gly Gly Asn Asp Thr Ile Val
1               5

<210> SEQ ID NO 1112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1112

Gly Asn Gly Gly Asn Asp Thr Ile Val
1               5

<210> SEQ ID NO 1113
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1113

Gly Asp Gly Gly Asn Asp Thr Ile Val
1               5

<210> SEQ ID NO 1114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1114

Gly Gly Asp Gly Asn Asp Thr Ile Val
1               5

<210> SEQ ID NO 1115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1115

Gly Asn Asp Gly Asn Asp Thr Ile Val
1               5

<210> SEQ ID NO 1116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1116

Gly Asp Asp Gly Asn Asp Thr Ile Val
1               5

<210> SEQ ID NO 1117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1117

Gly Gly Ala Gly Asp Asp Thr Ile Val
1               5

<210> SEQ ID NO 1118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1118

Gly Asn Ala Gly Asp Asp Thr Ile Val
1               5
```

<210> SEQ ID NO 1119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1119

Gly Asp Ala Gly Asp Asp Thr Ile Val
1               5

<210> SEQ ID NO 1120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1120

Gly Gly Ser Gly Asp Asp Thr Ile Val
1               5

<210> SEQ ID NO 1121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1121

Gly Asn Ser Gly Asp Asp Thr Ile Val
1               5

<210> SEQ ID NO 1122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1122

Gly Asp Ser Gly Asp Asp Thr Ile Val
1               5

<210> SEQ ID NO 1123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1123

Gly Gly Gly Gly Asp Asp Thr Ile Val
1               5

<210> SEQ ID NO 1124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1124

Gly Asn Gly Gly Asp Asp Thr Ile Val
1               5

<210> SEQ ID NO 1125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1125

Gly Asp Gly Gly Asp Asp Thr Ile Val
1               5

<210> SEQ ID NO 1126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1126

Gly Gly Asp Gly Asp Asp Thr Ile Val
1               5

<210> SEQ ID NO 1127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1127

Gly Asn Asp Gly Asp Asp Thr Ile Val
1               5

<210> SEQ ID NO 1128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1128

Gly Asp Asp Gly Asp Asp Thr Ile Val
1               5

<210> SEQ ID NO 1129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1129

Gly Gly Ala Gly Ala Asp Thr Ile Val
1               5

<210> SEQ ID NO 1130
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1130

Gly Asn Ala Gly Ala Asp Thr Ile Val
1               5

<210> SEQ ID NO 1131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1131

Gly Asp Ala Gly Ala Asp Thr Ile Val
1               5

<210> SEQ ID NO 1132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1132

Gly Gly Ser Gly Ala Asp Thr Ile Val
1               5

<210> SEQ ID NO 1133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1133

Gly Asn Ser Gly Ala Asp Thr Ile Val
1               5

<210> SEQ ID NO 1134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1134

Gly Asp Ser Gly Ala Asp Thr Ile Val
1               5

<210> SEQ ID NO 1135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1135

Gly Gly Gly Gly Ala Asp Thr Ile Val
```

1               5

<210> SEQ ID NO 1136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1136

Gly Asn Gly Gly Ala Asp Thr Ile Val
1               5

<210> SEQ ID NO 1137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1137

Gly Asp Gly Gly Ala Asp Thr Ile Val
1               5

<210> SEQ ID NO 1138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1138

Gly Gly Asp Gly Ala Asp Thr Ile Val
1               5

<210> SEQ ID NO 1139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1139

Gly Asn Asp Gly Ala Asp Thr Ile Val
1               5

<210> SEQ ID NO 1140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1140

Gly Asp Asp Gly Ala Asp Thr Ile Val
1               5

<210> SEQ ID NO 1141
<211> LENGTH: 9
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 1141

Gly Gly Ala Gly Asn Asn Thr Ile Val
1               5

<210> SEQ ID NO 1142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1142

Gly Asn Ala Gly Asn Asn Thr Ile Val
1               5

<210> SEQ ID NO 1143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1143

Gly Asp Ala Gly Asn Asn Thr Ile Val
1               5

<210> SEQ ID NO 1144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1144

Gly Gly Ser Gly Asn Asn Thr Ile Val
1               5

<210> SEQ ID NO 1145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1145

Gly Asn Ser Gly Asn Asn Thr Ile Val
1               5

<210> SEQ ID NO 1146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1146

Gly Asp Ser Gly Asn Asn Thr Ile Val
1               5

<210> SEQ ID NO 1147
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1147

Gly Gly Gly Gly Asn Asn Thr Ile Val
1               5

<210> SEQ ID NO 1148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1148

Gly Asn Gly Gly Asn Asn Thr Ile Val
1               5

<210> SEQ ID NO 1149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1149

Gly Asp Gly Gly Asn Asn Thr Ile Val
1               5

<210> SEQ ID NO 1150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1150

Gly Gly Asp Gly Asn Asn Thr Ile Val
1               5

<210> SEQ ID NO 1151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1151

Gly Asn Asp Gly Asn Asn Thr Ile Val
1               5

<210> SEQ ID NO 1152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1152
```

Gly Asp Asp Gly Asn Asn Thr Ile Val
1               5

<210> SEQ ID NO 1153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1153

Gly Gly Ala Gly Asp Asn Thr Ile Val
1               5

<210> SEQ ID NO 1154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1154

Gly Asn Ala Gly Asp Asn Thr Ile Val
1               5

<210> SEQ ID NO 1155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1155

Gly Asp Ala Gly Asp Asn Thr Ile Val
1               5

<210> SEQ ID NO 1156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1156

Gly Gly Ser Gly Asp Asn Thr Ile Val
1               5

<210> SEQ ID NO 1157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1157

Gly Asn Ser Gly Asp Asn Thr Ile Val
1               5

<210> SEQ ID NO 1158
<211> LENGTH: 9
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 1158

Gly Asp Ser Gly Asp Asn Thr Ile Val
1               5

<210> SEQ ID NO 1159
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1159

Gly Gly Gly Gly Asp Asn Thr Ile Val
1               5

<210> SEQ ID NO 1160
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1160

Gly Asn Gly Gly Asp Asn Thr Ile Val
1               5

<210> SEQ ID NO 1161
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1161

Gly Asp Gly Gly Asp Asn Thr Ile Val
1               5

<210> SEQ ID NO 1162
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1162

Gly Gly Asp Gly Asp Asn Thr Ile Val
1               5

<210> SEQ ID NO 1163
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1163

Gly Asn Asp Gly Asp Asn Thr Ile Val
1               5

```
<210> SEQ ID NO 1164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1164

Gly Asp Asp Gly Asp Asn Thr Ile Val
1               5

<210> SEQ ID NO 1165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1165

Gly Gly Ala Gly Ala Asn Thr Ile Val
1               5

<210> SEQ ID NO 1166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1166

Gly Asn Ala Gly Ala Asn Thr Ile Val
1               5

<210> SEQ ID NO 1167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1167

Gly Asp Ala Gly Ala Asn Thr Ile Val
1               5

<210> SEQ ID NO 1168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1168

Gly Gly Ser Gly Ala Asn Thr Ile Val
1               5

<210> SEQ ID NO 1169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1169
```

```
Gly Asn Ser Gly Ala Asn Thr Ile Val
1               5

<210> SEQ ID NO 1170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1170

Gly Asp Ser Gly Ala Asn Thr Ile Val
1               5

<210> SEQ ID NO 1171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1171

Gly Gly Gly Gly Ala Asn Thr Ile Val
1               5

<210> SEQ ID NO 1172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1172

Gly Asn Gly Gly Ala Asn Thr Ile Val
1               5

<210> SEQ ID NO 1173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1173

Gly Asp Gly Gly Ala Asn Thr Ile Val
1               5

<210> SEQ ID NO 1174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1174

Gly Gly Asp Gly Ala Asn Thr Ile Val
1               5

<210> SEQ ID NO 1175
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1175

Gly Asn Asp Gly Ala Asn Thr Ile Val
1               5

<210> SEQ ID NO 1176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1176

Gly Asp Asp Gly Ala Asn Thr Ile Val
1               5

<210> SEQ ID NO 1177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1177

Gly Gly Ala Gly Asn Asp Ile Ile Val
1               5

<210> SEQ ID NO 1178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1178

Gly Asn Ala Gly Asn Asp Ile Ile Val
1               5

<210> SEQ ID NO 1179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1179

Gly Asp Ala Gly Asn Asp Ile Ile Val
1               5

<210> SEQ ID NO 1180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1180

Gly Gly Ser Gly Asn Asp Ile Ile Val
1               5
```

<210> SEQ ID NO 1181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1181

Gly Asn Ser Gly Asn Asp Ile Ile Val
1               5

<210> SEQ ID NO 1182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1182

Gly Asp Ser Gly Asn Asp Ile Ile Val
1               5

<210> SEQ ID NO 1183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1183

Gly Gly Gly Gly Asn Asp Ile Ile Val
1               5

<210> SEQ ID NO 1184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1184

Gly Asn Gly Gly Asn Asp Ile Ile Val
1               5

<210> SEQ ID NO 1185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1185

Gly Asp Gly Gly Asn Asp Ile Ile Val
1               5

<210> SEQ ID NO 1186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1186

Gly Gly Asp Gly Asn Asp Ile Ile Val
1               5

<210> SEQ ID NO 1187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1187

Gly Asn Asp Gly Asn Asp Ile Ile Val
1               5

<210> SEQ ID NO 1188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1188

Gly Asp Asp Gly Asn Asp Ile Ile Val
1               5

<210> SEQ ID NO 1189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1189

Gly Gly Ala Gly Asp Asp Ile Ile Val
1               5

<210> SEQ ID NO 1190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1190

Gly Asn Ala Gly Asp Asp Ile Ile Val
1               5

<210> SEQ ID NO 1191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1191

Gly Asp Ala Gly Asp Asp Ile Ile Val
1               5

<210> SEQ ID NO 1192
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1192

Gly Gly Ser Gly Asp Asp Ile Ile Val
1               5

<210> SEQ ID NO 1193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1193

Gly Asn Ser Gly Asp Asp Ile Ile Val
1               5

<210> SEQ ID NO 1194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1194

Gly Asp Ser Gly Asp Asp Ile Ile Val
1               5

<210> SEQ ID NO 1195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1195

Gly Gly Gly Gly Asp Asp Ile Ile Val
1               5

<210> SEQ ID NO 1196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1196

Gly Asn Gly Gly Asp Asp Ile Ile Val
1               5

<210> SEQ ID NO 1197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1197

Gly Asp Gly Gly Asp Asp Ile Ile Val
1               5
```

<210> SEQ ID NO 1198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1198

Gly Gly Asp Gly Asp Asp Ile Ile Val
1               5

<210> SEQ ID NO 1199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1199

Gly Asn Asp Gly Asp Asp Ile Ile Val
1               5

<210> SEQ ID NO 1200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1200

Gly Asp Asp Gly Asp Asp Ile Ile Val
1               5

<210> SEQ ID NO 1201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1201

Gly Gly Ala Gly Ala Asp Ile Ile Val
1               5

<210> SEQ ID NO 1202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1202

Gly Asn Ala Gly Ala Asp Ile Ile Val
1               5

<210> SEQ ID NO 1203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1203

Gly Asp Ala Gly Ala Asp Ile Ile Val
1               5

<210> SEQ ID NO 1204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1204

Gly Gly Ser Gly Ala Asp Ile Ile Val
1               5

<210> SEQ ID NO 1205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1205

Gly Asn Ser Gly Ala Asp Ile Ile Val
1               5

<210> SEQ ID NO 1206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1206

Gly Asp Ser Gly Ala Asp Ile Ile Val
1               5

<210> SEQ ID NO 1207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1207

Gly Gly Gly Gly Ala Asp Ile Ile Val
1               5

<210> SEQ ID NO 1208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1208

Gly Asn Gly Gly Ala Asp Ile Ile Val
1               5

<210> SEQ ID NO 1209
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1209

Gly Asp Gly Gly Ala Asp Ile Ile Val
1               5

<210> SEQ ID NO 1210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1210

Gly Gly Asp Gly Ala Asp Ile Ile Val
1               5

<210> SEQ ID NO 1211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1211

Gly Asn Asp Gly Ala Asp Ile Ile Val
1               5

<210> SEQ ID NO 1212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1212

Gly Asp Asp Gly Ala Asp Ile Ile Val
1               5

<210> SEQ ID NO 1213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1213

Gly Gly Ala Gly Asn Asn Ile Ile Val
1               5

<210> SEQ ID NO 1214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1214

Gly Asn Ala Gly Asn Asn Ile Ile Val
```

```
1               5

<210> SEQ ID NO 1215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1215

Gly Asp Ala Gly Asn Asn Ile Ile Val
1               5

<210> SEQ ID NO 1216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1216

Gly Gly Ser Gly Asn Asn Ile Ile Val
1               5

<210> SEQ ID NO 1217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1217

Gly Asn Ser Gly Asn Asn Ile Ile Val
1               5

<210> SEQ ID NO 1218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1218

Gly Asp Ser Gly Asn Asn Ile Ile Val
1               5

<210> SEQ ID NO 1219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1219

Gly Gly Gly Gly Asn Asn Ile Ile Val
1               5

<210> SEQ ID NO 1220
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 1220

Gly Asn Gly Gly Asn Asn Ile Ile Val
1               5

<210> SEQ ID NO 1221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1221

Gly Asp Gly Gly Asn Asn Ile Ile Val
1               5

<210> SEQ ID NO 1222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1222

Gly Gly Asp Gly Asn Asn Ile Ile Val
1               5

<210> SEQ ID NO 1223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1223

Gly Asn Asp Gly Asn Asn Ile Ile Val
1               5

<210> SEQ ID NO 1224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1224

Gly Asp Asp Gly Asn Asn Ile Ile Val
1               5

<210> SEQ ID NO 1225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1225

Gly Gly Ala Gly Asp Asn Ile Ile Val
1               5

<210> SEQ ID NO 1226
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1226

Gly Asn Ala Gly Asp Asn Ile Ile Val
1               5

<210> SEQ ID NO 1227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1227

Gly Asp Ala Gly Asp Asn Ile Ile Val
1               5

<210> SEQ ID NO 1228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1228

Gly Gly Ser Gly Asp Asn Ile Ile Val
1               5

<210> SEQ ID NO 1229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1229

Gly Asn Ser Gly Asp Asn Ile Ile Val
1               5

<210> SEQ ID NO 1230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1230

Gly Asp Ser Gly Asp Asn Ile Ile Val
1               5

<210> SEQ ID NO 1231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1231
```

```
Gly Gly Gly Gly Asp Asn Ile Ile Val
1               5

<210> SEQ ID NO 1232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1232

Gly Asn Gly Gly Asp Asn Ile Ile Val
1               5

<210> SEQ ID NO 1233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1233

Gly Asp Gly Gly Asp Asn Ile Ile Val
1               5

<210> SEQ ID NO 1234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1234

Gly Gly Asp Gly Asp Asn Ile Ile Val
1               5

<210> SEQ ID NO 1235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1235

Gly Asn Asp Gly Asp Asn Ile Ile Val
1               5

<210> SEQ ID NO 1236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1236

Gly Asp Asp Gly Asp Asn Ile Ile Val
1               5

<210> SEQ ID NO 1237
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1237

Gly Gly Ala Gly Ala Asn Ile Ile Val
1               5

<210> SEQ ID NO 1238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1238

Gly Asn Ala Gly Ala Asn Ile Ile Val
1               5

<210> SEQ ID NO 1239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1239

Gly Asp Ala Gly Ala Asn Ile Ile Val
1               5

<210> SEQ ID NO 1240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1240

Gly Gly Ser Gly Ala Asn Ile Ile Val
1               5

<210> SEQ ID NO 1241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1241

Gly Asn Ser Gly Ala Asn Ile Ile Val
1               5

<210> SEQ ID NO 1242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1242

Gly Asp Ser Gly Ala Asn Ile Ile Val
1               5
```

```
<210> SEQ ID NO 1243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1243

Gly Gly Gly Gly Ala Asn Ile Ile Val
1               5

<210> SEQ ID NO 1244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1244

Gly Asn Gly Gly Ala Asn Ile Ile Val
1               5

<210> SEQ ID NO 1245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1245

Gly Asp Gly Gly Ala Asn Ile Ile Val
1               5

<210> SEQ ID NO 1246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1246

Gly Gly Asp Gly Ala Asn Ile Ile Val
1               5

<210> SEQ ID NO 1247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1247

Gly Asn Asp Gly Ala Asn Ile Ile Val
1               5

<210> SEQ ID NO 1248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1248
```

```
Gly Asp Asp Gly Ala Asn Ile Ile Val
1               5

<210> SEQ ID NO 1249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1249

Gly Gly Ala Gly Asn Asp Val Ile Val
1               5

<210> SEQ ID NO 1250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1250

Gly Asn Ala Gly Asn Asp Val Ile Val
1               5

<210> SEQ ID NO 1251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1251

Gly Asp Ala Gly Asn Asp Val Ile Val
1               5

<210> SEQ ID NO 1252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1252

Gly Gly Ser Gly Asn Asp Val Ile Val
1               5

<210> SEQ ID NO 1253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1253

Gly Asn Ser Gly Asn Asp Val Ile Val
1               5

<210> SEQ ID NO 1254
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1254

Gly Asp Ser Gly Asn Asp Val Ile Val
1               5

<210> SEQ ID NO 1255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1255

Gly Gly Gly Gly Asn Asp Val Ile Val
1               5

<210> SEQ ID NO 1256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1256

Gly Asn Gly Gly Asn Asp Val Ile Val
1               5

<210> SEQ ID NO 1257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1257

Gly Asp Gly Gly Asn Asp Val Ile Val
1               5

<210> SEQ ID NO 1258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1258

Gly Gly Asp Gly Asn Asp Val Ile Val
1               5

<210> SEQ ID NO 1259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1259

Gly Asn Asp Gly Asn Asp Val Ile Val
1               5
```

<210> SEQ ID NO 1260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1260

Gly Asp Asp Gly Asn Asp Val Ile Val
1               5

<210> SEQ ID NO 1261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1261

Gly Gly Ala Gly Asp Asp Val Ile Val
1               5

<210> SEQ ID NO 1262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1262

Gly Asn Ala Gly Asp Asp Val Ile Val
1               5

<210> SEQ ID NO 1263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1263

Gly Asp Ala Gly Asp Asp Val Ile Val
1               5

<210> SEQ ID NO 1264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1264

Gly Gly Ser Gly Asp Asp Val Ile Val
1               5

<210> SEQ ID NO 1265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1265

Gly Asn Ser Gly Asp Asp Val Ile Val
1               5

<210> SEQ ID NO 1266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1266

Gly Asp Ser Gly Asp Asp Val Ile Val
1               5

<210> SEQ ID NO 1267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1267

Gly Gly Gly Gly Asp Asp Val Ile Val
1               5

<210> SEQ ID NO 1268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1268

Gly Asn Gly Gly Asp Asp Val Ile Val
1               5

<210> SEQ ID NO 1269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1269

Gly Asp Gly Gly Asp Asp Val Ile Val
1               5

<210> SEQ ID NO 1270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1270

Gly Gly Asp Gly Asp Asp Val Ile Val
1               5

<210> SEQ ID NO 1271
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 1271

Gly Asn Asp Gly Asp Asp Val Ile Val
1               5

<210> SEQ ID NO 1272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1272

Gly Asp Asp Gly Asp Asp Val Ile Val
1               5

<210> SEQ ID NO 1273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1273

Gly Gly Ala Gly Ala Asp Val Ile Val
1               5

<210> SEQ ID NO 1274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1274

Gly Asn Ala Gly Ala Asp Val Ile Val
1               5

<210> SEQ ID NO 1275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1275

Gly Asp Ala Gly Ala Asp Val Ile Val
1               5

<210> SEQ ID NO 1276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1276

Gly Gly Ser Gly Ala Asp Val Ile Val
1               5
```

<210> SEQ ID NO 1277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1277

Gly Asn Ser Gly Ala Asp Val Ile Val
1               5

<210> SEQ ID NO 1278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1278

Gly Asp Ser Gly Ala Asp Val Ile Val
1               5

<210> SEQ ID NO 1279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1279

Gly Gly Gly Gly Ala Asp Val Ile Val
1               5

<210> SEQ ID NO 1280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1280

Gly Asn Gly Gly Ala Asp Val Ile Val
1               5

<210> SEQ ID NO 1281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1281

Gly Asp Gly Gly Ala Asp Val Ile Val
1               5

<210> SEQ ID NO 1282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1282

Gly Gly Asp Gly Ala Asp Val Ile Val
1               5

<210> SEQ ID NO 1283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1283

Gly Asn Asp Gly Ala Asp Val Ile Val
1               5

<210> SEQ ID NO 1284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1284

Gly Asp Asp Gly Ala Asp Val Ile Val
1               5

<210> SEQ ID NO 1285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1285

Gly Gly Ala Gly Asn Asn Val Ile Val
1               5

<210> SEQ ID NO 1286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1286

Gly Asn Ala Gly Asn Asn Val Ile Val
1               5

<210> SEQ ID NO 1287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1287

Gly Asp Ala Gly Asn Asn Val Ile Val
1               5

<210> SEQ ID NO 1288
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1288

Gly Gly Ser Gly Asn Asn Val Ile Val
1               5

<210> SEQ ID NO 1289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1289

Gly Asn Ser Gly Asn Asn Val Ile Val
1               5

<210> SEQ ID NO 1290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1290

Gly Asp Ser Gly Asn Asn Val Ile Val
1               5

<210> SEQ ID NO 1291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1291

Gly Gly Gly Gly Asn Asn Val Ile Val
1               5

<210> SEQ ID NO 1292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1292

Gly Asn Gly Gly Asn Asn Val Ile Val
1               5

<210> SEQ ID NO 1293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1293

Gly Asp Gly Gly Asn Asn Val Ile Val
```

```
1               5

<210> SEQ ID NO 1294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1294

Gly Gly Asp Gly Asn Asn Val Ile Val
1               5

<210> SEQ ID NO 1295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1295

Gly Asn Asp Gly Asn Asn Val Ile Val
1               5

<210> SEQ ID NO 1296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1296

Gly Asp Asp Gly Asn Asn Val Ile Val
1               5

<210> SEQ ID NO 1297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1297

Gly Gly Ala Gly Asp Asn Val Ile Val
1               5

<210> SEQ ID NO 1298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1298

Gly Asn Ala Gly Asp Asn Val Ile Val
1               5

<210> SEQ ID NO 1299
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 1299

Gly Asp Ala Gly Asp Asn Val Ile Val
1               5

<210> SEQ ID NO 1300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1300

Gly Gly Ser Gly Asp Asn Val Ile Val
1               5

<210> SEQ ID NO 1301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1301

Gly Asn Ser Gly Asp Asn Val Ile Val
1               5

<210> SEQ ID NO 1302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1302

Gly Asp Ser Gly Asp Asn Val Ile Val
1               5

<210> SEQ ID NO 1303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1303

Gly Gly Gly Gly Asp Asn Val Ile Val
1               5

<210> SEQ ID NO 1304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1304

Gly Asn Gly Gly Asp Asn Val Ile Val
1               5

<210> SEQ ID NO 1305

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1305

Gly Asp Gly Gly Asp Asn Val Ile Val
1               5

<210> SEQ ID NO 1306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1306

Gly Gly Asp Gly Asp Asn Val Ile Val
1               5

<210> SEQ ID NO 1307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1307

Gly Asn Asp Gly Asp Asn Val Ile Val
1               5

<210> SEQ ID NO 1308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1308

Gly Asp Asp Gly Asp Asn Val Ile Val
1               5

<210> SEQ ID NO 1309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1309

Gly Gly Ala Gly Ala Asn Val Ile Val
1               5

<210> SEQ ID NO 1310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1310
```

Gly Asn Ala Gly Ala Asn Val Ile Val
1               5

<210> SEQ ID NO 1311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1311

Gly Asp Ala Gly Ala Asn Val Ile Val
1               5

<210> SEQ ID NO 1312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1312

Gly Gly Ser Gly Ala Asn Val Ile Val
1               5

<210> SEQ ID NO 1313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1313

Gly Asn Ser Gly Ala Asn Val Ile Val
1               5

<210> SEQ ID NO 1314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1314

Gly Asp Ser Gly Ala Asn Val Ile Val
1               5

<210> SEQ ID NO 1315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1315

Gly Gly Gly Gly Ala Asn Val Ile Val
1               5

<210> SEQ ID NO 1316
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1316

Gly Asn Gly Gly Ala Asn Val Ile Val
1               5

<210> SEQ ID NO 1317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1317

Gly Asp Gly Gly Ala Asn Val Ile Val
1               5

<210> SEQ ID NO 1318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1318

Gly Gly Asp Gly Ala Asn Val Ile Val
1               5

<210> SEQ ID NO 1319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1319

Gly Asn Asp Gly Ala Asn Val Ile Val
1               5

<210> SEQ ID NO 1320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1320

Gly Asp Asp Gly Ala Asn Val Ile Val
1               5

<210> SEQ ID NO 1321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1321

Gly Asp Glu Ala Ser Asp Leu Phe Phe
1               5
```

```
<210> SEQ ID NO 1322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1322

Gly Asp Leu Ala Ser Asp Leu Phe Phe
1               5

<210> SEQ ID NO 1323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1323

Gly Asp Asn Ala Ser Asp Leu Phe Phe
1               5

<210> SEQ ID NO 1324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1324

Gly Asp Glu Ala Ser Asp Leu Phe Thr
1               5

<210> SEQ ID NO 1325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1325

Gly Asp Leu Ala Ser Asp Leu Phe Thr
1               5

<210> SEQ ID NO 1326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1326

Gly Asp Asn Ala Ser Asp Leu Phe Thr
1               5

<210> SEQ ID NO 1327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1327
```

```
Gly Asp Glu Ala Ser Asp Leu Phe Asn
1               5

<210> SEQ ID NO 1328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1328

Gly Asp Leu Ala Ser Asp Leu Phe Asn
1               5

<210> SEQ ID NO 1329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1329

Gly Asp Asn Ala Ser Asp Leu Phe Asn
1               5

<210> SEQ ID NO 1330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1330

Gly Asp Glu Ala Ser Asp Leu Phe Asp
1               5

<210> SEQ ID NO 1331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1331

Gly Asp Leu Ala Ser Asp Leu Phe Asp
1               5

<210> SEQ ID NO 1332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1332

Gly Asp Asn Ala Ser Asp Leu Phe Asp
1               5

<210> SEQ ID NO 1333
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1333

Gly Asp Glu Ala Ser Asp Leu Phe Lys
1               5

<210> SEQ ID NO 1334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1334

Gly Asp Leu Ala Ser Asp Leu Phe Lys
1               5

<210> SEQ ID NO 1335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1335

Gly Asp Asn Ala Ser Asp Leu Phe Lys
1               5

<210> SEQ ID NO 1336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1336

Gly Asp Glu Ala Ser Asp Leu Phe Ser
1               5

<210> SEQ ID NO 1337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1337

Gly Asp Leu Ala Ser Asp Leu Phe Ser
1               5

<210> SEQ ID NO 1338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1338

Gly Gly Ser Gly Asn Asp Asn Leu Ser
1               5
```

-continued

```
<210> SEQ ID NO 1339
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1339

Gly Ser Ala Arg Asp Asp Val Leu Ile Gly Asp Ala Gly Ala Asn Val
1               5                   10                  15

Leu Asn Gly Leu Ala Asp Asn Asp Val Leu Ser Gly Gly Ala Gly Asp
            20                  25                  30

Asp Val Leu Leu Gly Asp Glu Gly Ser Asp Leu Leu Ser Gly Asp Ala
        35                  40                  45

Gly Asn Asp Asp Leu Phe Gly Gly Gln Gly Asp Asp Thr Tyr Leu Phe
    50                  55                  60

Gly Val Gly Tyr Gly His Asp Thr Ile Tyr Glu Ser Gly Gly His
65                  70                  75                  80

Asp Thr Ile Arg Gly Ser Ala Arg Asp Asp Val Leu Ile Gly Asp Ala
                85                  90                  95

Gly Ala Asn Val Leu Asn Gly Leu Ala Asp Asn Asp Val Leu Ser Gly
            100                 105                 110

Gly Ala Gly Asp Asp Val Leu Leu Gly Asp Glu Gly Ser Asp Leu Leu
        115                 120                 125

Ser Gly Asp Ala Gly Asn Asp Asp Leu Phe Gly Gly Gln Gly Asp Asp
    130                 135                 140

Thr Tyr Leu Phe Gly Val Gly Tyr Gly His Asp Thr Ile Tyr Glu Ser
145                 150                 155                 160

Gly Gly Gly His Asp Thr Ile Arg Ile Asn Ala Gly Ala Asp Gln Leu
                165                 170                 175

Trp Phe Ala Arg Gln Gly Asn Asp Leu Glu Ile Arg Ile Leu Gly Thr
            180                 185                 190

Asp Asp Ala Leu Thr Val His Asp Trp Tyr Arg Asp Ala Asp His Arg
        195                 200                 205

Val Glu Ile Ile His Ala Ala Asn Gln Ala Val Asp Gln Ala Gly Ile
    210                 215                 220

Glu Lys Leu Val Glu Ala Met Ala Gln Tyr Pro Asp
225                 230                 235

<210> SEQ ID NO 1340
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1340

Gly Ser Ala Arg Asp Asp Val Leu Ile Gly Asp Ala Gly Ala Asn Val
1               5                   10                  15

Leu Asn Gly Leu Ala Asp Asn Asp Val Leu Ser Gly Gly Ala Gly Asp
            20                  25                  30

Asp Val Leu Leu Gly Asp Glu Gly Ser Asp Leu Leu Ser Gly Asp Ala
        35                  40                  45

Gly Asn Asp Asp Leu Phe Gly Gly Gln Gly Asp Asp Thr Tyr Leu Phe
    50                  55                  60
```

```
Gly Val Gly Tyr Gly His Asp Thr Ile Tyr Glu Ser Gly Gly Gly His
 65                  70                  75                  80

Asp Thr Ile Arg Gly Asp Ala Gly Ala Asn Val Leu Asn Gly Leu Ala
                 85                  90                  95

Asp Asn Asp Val Leu Ser Gly Gly Ala Gly Asp Asp Val Leu Leu Gly
            100                 105                 110

Asp Glu Gly Ser Asp Leu Leu Ser Gly Asp Ala Gly Asn Asp Asp Leu
        115                 120                 125

Phe Gly Gly Gln Gly Asp Asp Thr Tyr Leu Phe Gly Val Gly Tyr Gly
    130                 135                 140

His Asp Thr Ile Tyr Glu Ser Gly Gly Gly His Asp Thr Ile Arg
145                 150                 155
```

<210> SEQ ID NO 1341
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1341

```
Gly Ser Ala Arg Asp Asp Val Leu Ile Gly Asp Ala Gly Ala Asn Val
  1               5                  10                  15

Leu Asn Gly Leu Ala Asp Asn Asp Val Leu Ser Gly Gly Ala Gly Asp
                 20                  25                  30

Asp Val Leu Leu Gly Asp Glu Gly Ser Asp Leu Leu Ser Gly Asp Ala
             35                  40                  45

Gly Asn Asp Asp Leu Phe Gly Gly Gln Gly Asp Asp Thr Tyr Leu Phe
 50                  55                  60

Gly Val Gly Tyr Gly His Asp Thr Ile Tyr Glu Ser Gly Gly Gly His
 65                  70                  75                  80

Asp Thr Ile Arg Gly Asp Ala Gly Ala Asn Val Leu Asn Gly Leu Ala
                 85                  90                  95

Asp Asn Asp Val Leu Ser Gly Gly Ala Gly Asp Asp Val Leu Leu Gly
            100                 105                 110

Asp Glu Gly Ser Asp Leu Leu Ser Gly Asp Ala Gly Asn Asp Asp Leu
        115                 120                 125

Phe Gly Gly Gln Gly Asp Asp Thr Tyr Leu Phe Gly Val Gly Tyr Gly
    130                 135                 140

His Asp Thr Ile Tyr Glu Ser Gly Gly Gly His Asp Thr Ile Arg Ile
145                 150                 155                 160

Asn Ala Gly Ala Asp Gln Leu Trp Phe Ala Arg Gln Gly Asn Asp Leu
                165                 170                 175

Glu Ile Arg Ile Leu Gly Thr Asp Asp Ala Leu Thr Val His Asp Trp
            180                 185                 190

Tyr Arg Asp Ala Asp His Arg Val Glu Ile Ile His Ala Ala Asn Gln
        195                 200                 205

Ala Val Asp Gln Ala Gly Ile Glu Lys Leu Val Glu Ala Met Ala Gln
    210                 215                 220

Tyr Pro Asp
225
```

<210> SEQ ID NO 1342
<211> LENGTH: 139
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1342

Gly Gly Ser Gly Asn Asp Val Ile Val Gly Asn Ala Ala Asn Asn Val
1               5                   10                  15

Leu Lys Gly Gly Ala Gly Asn Asp Val Leu Phe Gly Gly Gly Gly Ala
            20                  25                  30

Asp Glu Leu Trp Gly Gly Ala Gly Lys Asp Ile Phe Val Phe Ser Ala
        35                  40                  45

Ala Ser Asp Ser Ala Pro Gly Ala Ser Asp Trp Ile Arg Asp Phe Gln
50                  55                  60

Lys Gly Ile Asp Lys Ile Asp Leu Ser Phe Phe Asn Lys Glu Ala Asn
65                  70                  75                  80

Ser Ser Asp Phe Ile His Phe Val Asp His Phe Ser Gly Thr Ala Gly
                85                  90                  95

Glu Ala Leu Leu Ser Tyr Asn Ala Ser Ser Asn Val Thr Asp Leu Ser
            100                 105                 110

Val Asn Ile Gly Gly His Gln Ala Pro Asp Phe Leu Val Lys Ile Val
        115                 120                 125

Gly Gln Val Asp Val Ala Thr Asp Phe Ile Val
    130                 135

<210> SEQ ID NO 1343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Asn or Asp
<220> FEATURE:
<221> NAME/KEY: MOD_RES
<222> LOCATION: (3)..(3)
<223> OTHER INFORMATION: Ala, Ser, Gly, Asp, Glu, Leu or Asn
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(5)
<223> OTHER INFORMATION: Asn, Asp, Ala or Ser
<220> FEATURE:
<221> NAME/KEY: MOD_RES
<222> LOCATION: (6)..(6)
<223> OTHER INFORMATION: Asp or Asn
<220> FEATURE:
<221> NAME/KEY: MOD_RES
<222> LOCATION: (7)..(7)
<223> OTHER INFORMATION: Thr, Ile, Val or Leu
<220> FEATURE:
<221> NAME/KEY: MOD_RES
<222> LOCATION: (8)..(8)
<223> OTHER INFORMATION: Leu, Ile or Phe
<220> FEATURE:
<221> NAME/KEY: MOD_RES
<222> LOCATION: (9)..(9)
<223> OTHER INFORMATION: Tyr, Ile, Val, Phe, Thr, Asn, Asp, Lys or Ser

<400> SEQUENCE: 1343

Gly Xaa Xaa Xaa Xaa Xaa Xaa Xaa Xaa
1               5
```

<210> SEQ ID NO 1344
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1344

Gly Gly Ala Gly Asn Asp Thr Leu Tyr Gly Gly Ala Gly Asn Asp Thr
1               5                   10                  15

Leu Tyr Gly Gly Ala Gly Asn Asp Thr Leu Tyr Gly Gly Ala Gly Asn
            20                  25                  30

Asp Thr Leu Tyr Gly Gly Ala Gly Asn Asp Thr Leu Tyr Gly Gly Ala
        35                  40                  45

Gly Asn Asp Thr Leu Tyr Gly Gly Ala Gly Asn Asp Thr Leu Tyr Gly
    50                  55                  60

Gly Ala Gly Asn Asp Thr Leu Tyr Gly Gly Ala Gly Asn Asp Thr Leu
65                  70                  75                  80

Tyr Gly Gly Ala Gly Asn Asp Thr Leu Tyr Gly Gly Ala Gly Asn Asp
                85                  90                  95

Thr Leu Tyr Gly Gly Ala Gly Asn Asp Thr Leu Tyr Gly Gly Ala Gly
            100                 105                 110

Asn Asp Thr Leu Tyr Gly Gly Ala Gly Asn Asp Thr Leu Tyr Gly Gly
        115                 120                 125

Ala Gly Asn Asp Thr Leu Tyr Gly Gly Ala Gly Asn Asp Thr Leu Tyr
    130                 135                 140

Gly Gly Ala Gly Asn Asp Thr Leu Tyr Ile Asn Ala Gly Ala Asp Gln
145                 150                 155                 160

Leu Trp Phe Ala Arg Gln Gly Asn Asp Leu Glu Ile Arg Ile Leu Gly
                165                 170                 175

Thr Asp Asp Ala Leu Thr Val His Asp Trp Tyr Arg Asp Ala Asp His
            180                 185                 190

Arg Val Glu Ile Ile His Ala Ala Asn Gln Ala Val Asp Gln Ala Gly
        195                 200                 205

Ile Glu Lys Leu Val Glu Ala Met Ala Gln Tyr Pro Asp
    210                 215                 220

<210> SEQ ID NO 1345
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1345
ggcggtgcgg gcaacgatac cctgtatggt ggcgccggga atgacacatt atacggaggt    60
gctggcaatg atacgctgta tggcggagca ggtaacgac                          99

<210> SEQ ID NO 1346
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1346

```
attcccagca ccgccataaa gggtatcgtt gcctgccccc ccatacagcg tgtcgttacc    60
ggcgccccca tacaaagtgt cgttacctgc tccgc                              95
```

<210> SEQ ID NO 1347
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1347

```
attaaaaact cggggatgat gatgatgaca agggcggtgc ggg                     43
```

<210> SEQ ID NO 1348
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1348

```
tttttaataa gcttgaggag tattattaat acagtgtatc attgccagca c             51
```

<210> SEQ ID NO 1349
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1349

```
tttttaataa gcttgaggag tattattaat acagcgtgtc gttaccg                 47
```

<210> SEQ ID NO 1350
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1350

```
attaaaaagg atgatggcgg tgcggg                                        26
```

<210> SEQ ID NO 1351
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1351

```
tttttaataa gcttgaggag tattattaat acaaagtgtc gttacctgct c             51
```

<210> SEQ ID NO 1352
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1352
tttttaataa gcttgaggag tattattaat agagggtatc gttacccgc                49

<210> SEQ ID NO 1353
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1353
aatatataga ggagataata atatatgagt aaaggagaag aactttcac tggagt        56

<210> SEQ ID NO 1354
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1354
tattataaag cttttatttg tatagttcat ccatgccatg tgtaat                   46

<210> SEQ ID NO 1355
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1355
aatatataga ggagataata atatatgagt attcaacatt tccgtgtcgc               50

<210> SEQ ID NO 1356
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1356
tattattaag cttttattac caatgcttaa tcagtgaggc acc                      43

<210> SEQ ID NO 1357
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1357
aaagaggagg atcatgaata tggcaaaaag ggtaaatgca ttcaacgacc               50

<210> SEQ ID NO 1358
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1358

```
agtgccaagc ttttattaca cacacctcct tgccatctct ctatcctc          48
```

<210> SEQ ID NO 1359
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1359

```
aaagaggagg atcatgaatg atgatgatga caagatgagt attcaacatt tccgtgtcgc    60
ccttattc                                                             68
```

<210> SEQ ID NO 1360
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1360

```
aaagaggagg atcatgaatg atgatgatga caagatggca aaaagggtaa atgcattcaa    60
cgacc                                                                65
```

<210> SEQ ID NO 1361
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1361

```
cctcggggat gatggtgaca agggcggtgc                                     30
```

<210> SEQ ID NO 1362
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1362

```
gcaccgccct tgtcaccatc atccccgagg                                     30
```

<210> SEQ ID NO 1363
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1363

```
ggggatgatg gtgagcaggg cggtgcgggc                                     30
```

<210> SEQ ID NO 1364
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1364
gcccgcaccg ccctgctcac catcatcccc                                              30

<210> SEQ ID NO 1365
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 1365

Val Pro Gly Xaa Gly
1               5

<210> SEQ ID NO 1366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any amino acid

<400> SEQUENCE: 1366

Gly Gly Xaa Gly Xaa Asp Xaa Xaa Xaa
1               5

<210> SEQ ID NO 1367
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1367
ggcggtgctg ggaatgacac actgtacggc ggggcgggta acgataccct ctatggtggt      60
gctggcaatg atacactgta t                                               81

<210> SEQ ID NO 1368
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 1368

Asp Asp Asp Asp Lys
1               5

<210> SEQ ID NO 1369
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1369

Asp Asp Gly Glu Gln
1               5

<210> SEQ ID NO 1370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1370

Gly Val Gly Val Pro
1               5

<210> SEQ ID NO 1371
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1371

Val Pro Gly Ile Gly Val Pro Gly Ile Gly Val Pro Gly Ile Gly Val
1               5                   10                  15

Pro Gly Ile Gly Val Pro Gly Ile Gly Val Pro Gly Ile Gly Val Pro
            20                  25                  30

Gly Ile Gly Val Pro Gly Ile Gly Val Pro Gly Ile Gly Val Pro Gly
        35                  40                  45

Ile Gly Val Pro Gly Ile Gly Val Pro Gly Ile Gly Val Pro Gly Ile
    50                  55                  60

Gly Val Pro Gly Ile Gly Val Pro Gly Ile Gly Val Pro Gly Ile Gly
65                  70                  75                  80

Val Pro Gly Ile Gly Val Pro Gly Ile Gly Val Pro Gly Ile Gly Val
                85                  90                  95

Pro Gly Ile Gly Val Pro Gly Ile Gly Val Pro Gly Ile Gly Val Pro
            100                 105                 110

Gly Ile Gly Val Pro Gly Ile Gly Val Pro Gly Ile Gly Val Pro Gly
        115                 120                 125

Ile Gly Val Pro Gly Ile Gly Val Pro Gly Ile Gly Val Pro Gly Ile
    130                 135                 140

Gly Val Pro Gly Ile Gly Val Pro Gly Ile Gly Val Pro Gly Ile Gly
145                 150                 155                 160

Val Pro Gly Ile Gly Val Pro Gly Ile Gly Val Pro Gly Ile Gly Val
                165                 170                 175
```

```
Pro Gly Ile Gly Val Pro Gly Ile Gly Val Pro Gly Ile Gly Val Pro
            180                 185                 190
Gly Ile Gly Val Pro Gly Ile Gly
        195                 200

<210> SEQ ID NO 1372
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1372

Gly Gly Ser Gly Asn Asp Val Ile Val Gly Asn Ala Ala Asn Asn Val
1               5                   10                  15
Leu Lys Gly Gly Ala Gly Asn Asp Val Leu Phe Gly Gly Gly Gly Ala
            20                  25                  30
Asp Glu Leu Trp Gly Gly Ala Gly Lys Asp Ile Phe Val
            35                  40                  45
```

US 9,550,805 B2

PRECIPITABLE PEPTIDES

This application is a continuation-in-part of International Application No. PCT/US2012/033293, filed Apr. 12, 2012, which claims priority to U.S. provisional application Ser. No. 61/475,042 filed Apr. 13, 2011, and also claims the benefit of and priority to U.S. provisional application Ser. No. 61/616,341 filed Mar. 27, 2012, the disclosures of all of which are hereby incorporated by reference in their entireties for all purposes.

This invention was made with government support under grant number W9132T-08-2-0012 awarded by the DTRA and under grant number W9132T-08-2-0002 awarded by the US Army. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

SEQUENCE LISTING

The instant application contains a Sequence Listing which has been submitted electronically in ASCII format and is incorporated by reference in its entirety. Said ASCII copy, created on Jan. 16, 2014, is named 19240.924US3_SL.txt and is 335,744 bytes in size.

BACKGROUND OF THE INVENTION

Rapid protein purification is an important requirement in many bioengineering applications where significant amounts of time are currently spent purifying proteins from heterogeneous samples. There are currently a number of approaches for performing bioseparation, but these approaches are expensive, time consuming, can require specialized treatments.

A variety of approaches currently exist for purifying recombinant proteins such as using a poly-histidine tag, glutathione S-transferase (GST) fusions or fusion to an elastin-like peptide (ELP). In the case of ELPs, a fusion protein can be precipitated from solution by increasing the temperature of the sample (Banki, et al., Nat Meth, vol. 2, no. 9, pp. 659-662, 2005; Fong et al, Trends in Biotechnology, vol. 28, no. 5, pp. 272-279, May 2010). One limitation of ELP technology is that increased temperature can adversely affect the stability of fusion proteins. Another limitation of ELP technology is that inducing temperature changes are difficult in large scale preparations.

There is a need for improved purification methods for rapid purification of molecules (e.g. exogenously expressed proteins) from heterogeneous samples in a rapid manner and with high levels of recovery. This invention addresses these needs.

SUMMARY OF THE INVENTION

In certain aspects, the invention relates to a precipitable beta roll cassette (PBRC) comprising one or more beta roll tags (PBRTs) wherein the one or more PBRTs comprise the amino acid sequence of SEQ ID NO: 1

In certain aspects, the invention relates to a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs: 25-1337

In certain aspects, the invention relates to a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine.

In certain aspects, the invention relates to a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT.

In certain aspects, the invention relates to a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT, wherein the PBRC further comprises a capping sequence.

In certain aspects, the invention relates to a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT, wherein the PBRC further comprises a stabilizing polypeptide.

In certain aspects, the invention relates to a PBRC linked purification moiety comprising a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT. In certain embodiments, the PBRC is linked to the purification moiety by a peptide bond. In certain embodiments, the PBRC is linked to the purification moiety by a chemical bond that is not a peptide bond.

In certain aspects, the invention relates to a PBRC linked purification moiety comprising a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT, wherein the PBRC further comprises a cleavage site located N-terminally or C-terminally to one or more of the one or more PBRTs. In certain embodiments, the cleavage site is selected from the group comprising an intein cleavage site, a Factor Xa cleavage site, a thrombin cleavage site, an enterokinase cleavage site, or a signal peptidase cleavage site.

In certain aspects, the invention relates to a polypeptide comprising a PBRC linked purification moiety comprising a precipitable beta roll cassette (PBRC) comprising one or more beta roll tags (PBRTs) wherein the one or more PBRTs are independently any of: (a) a polypeptide having the amino acid sequence of SEQ ID NO: 1, or (b) a polypeptide having the amino acid sequence of any of SEQ ID NOs 25-1337, (c) a polypeptide comprising the amino acid sequence G (SEQ ID NO: 1343), wherein, (i) the X at position 2 is an amino acid selected from the group consisting of glycine, asparagine or aspartic acid, and (ii) the X at position 3 is an amino acid selected from the group consisting of alanine, serine, glycine, aspartic acid, glutamic acid, leucine or asparagine, and (iii) the X at position 4 is an amino acid selected from the group consisting of glycine or alanine, and (iv) the X at position 5 is an amino acid selected from the group consisting of asparagine, aspartic acid, alanine, or serine, and (v) the X at position 6 is an amino acid selected from the group consisting of aspartic acid or asparagine, (vi) the X at position 7 is an amino acid selected from the group consisting of threonine, isoleucine, valine, or leucine, and (vii) the X at position 8 is an amino acid selected from the group consisting of leucine, isoleucine, or phenylalanine, and (viii) the X at position 9 is an amino acid selected from the group consisting of tyrosine, isoleucine, valine, phenylalanine, threonine, asparagine, aspartic acid, lysine or serine, or (c) a variant PBRT; and a purification moiety.

In certain aspects, the invention relates to a nucleic acid encoding any of the polypeptides described herein.

In certain embodiments, the invention relates to a method for purifying a PBRC linked purification moiety, the method comprising (a) expressing the PBRC linked purification moiety in an expression system, (b) collecting the PBRC linked purification moiety in a first medium, (c) adding Ca2+ to the first medium so as to induce precipitation of PBRC linked purification moiety, (d) removing unprecipiated material from the medium from the precipitated PBRC linked purification moiety, (e) resuspending the PBRC linked purification moiety in a second medium having a lower than the free Ca2+ concentration than the free Ca2+ concentration obtained after step (c). In certain embodiments, a calcium chelator is added to the second medium of step (e). In certain embodiments, steps (c) to (e) are repeated one or more times. In certain embodiments, the method further comprises a step of removing precipitated material between step (b) and step (c). In certain embodiments, the PBRC comprises a cleavage site between the PBRC and the purification moiety. In certain embodiments, the method further comprises steps of: (i) cleaving the PBRC linked purification moiety so as to separate the purification moiety from the PBRC, (ii) adding Ca2+ to the medium so as to induce precipitation of the PBRC, and (iii) isolating the unprecipiated purification moiety. In certain embodiments, the cleavage site is an intein cleavage site.

In certain aspects, the invention relates to an expression vector comprising, as arranged from 5' to 3', a promoter, a nucleic acid sequence encoding the PBRC of any of claims 1-4, and at least one cloning site.

In certain aspects, the invention relates to an expression vector comprising, as arranged from 5' to 3', a promoter, at least one cloning site, and a nucleic acid sequence encoding the PBRC of any of claims 1-4.

In certain aspects, the invention relates to an expression vector comprising, as arranged from 5' to 3', a promoter, at least one cloning site, a nucleic acid sequence encoding the PBRC of any of claims 1-4 and at least a second cloning site.

BRIEF DESCRIPTION OF THE FIGURES

FIG. 1A shows purification of precipitatable maltose binding protein comprising a precipitatable beta roll tag and an enterokinase cleavage site (MBP-PBRT). Total lysate is shown in lane 1 and lanes 2-7 are precipitation/wash cycles. After two cycles, the sample consists nearly only of the MBP fusion protein with the precipitating tag attached (MBP-PBRT). Recovery is nearly 100% of the expressed protein. FIG. 1B shows SDS-PAGE analysis of purified MBP-PBRT and MBP-PBRT subjected to digestion of the enterokinase digestion site (FIG. 1B). Lane 1 shows purified MBP-PBRT, lane 2 shows supernatant after overnight digest and lane 3 shows the pellet.

FIG. 4 discloses the consensus sequence as SEQ IN NO: 1343.

FIG. 5 shows a schematic illustration of the corkscrew configuration of tandem Ca2+ binding sequences. The figure shows a crystal structure image of the beta roll domain from the metalloprotease of S. marcescens (1SAT in the Protein Databank). Alternating 9-amino acid repeats are highlighted in green and red. Coordinated calcium ions are in white. The image represents 5 repeats of beta roll sequence. While there is no crystal structure for the adenylate cyclase beta roll domain, the high degree of sequence similarity to the consensus beta roll indicates that the adenylate cyclase beta roll domain is similar.

FIGS. 8A-8D show a characterization of beta roll distribution, sequence deviation and number of repeats. FIG. 8A shows a distribution of beat roll lengths as frequency plotted against the number of beta roll repeats. FIG. 8B shows beta roll sequence deviation from consensus by position plotted as proportion deviation as a function of distance from terminus. FIG. 8C shows a probability of deviation from consensus plotted as probability as a function of the number of beta roll repeats. FIG. 8D shows amount of beta roll in overall protein plotted as the number of beta roll residues as a function of the number of total residues.

FIG. 10A shows a precipitation and resuspension of the MBP-PBRT-GFP polypeptide. FIG. 10B shows SDS-PAGE of multiple precipitation wash cycles. The lanes of the SDS gel are as follows: lane 1—ladder; lane 2—clarified lysate; lane 3—precipitation in 25 mM calcium followed by three washes; lane 4—precipitation in 50 mM calcium followed by three washes; lane 5—precipitation in 75 mM calcium followed by three washes; lane—6 precipitation in 100 mM calcium followed by three washes. All lanes are normalized in terms of concentration. Recovery percentage can be estimated by comparing the band intensity in lane 2 to subsequent lanes.

FIG. 11 discloses SEQ ID NO: 1368.

FIG. 13A shows crystal structure of β roll domain from metalloprotease of S. marcescens (PDB: 1 SAT). FIG. 13B shows amino acid frequencies for single β roll repeat identifying consensus sequence GGAGNDTLY (SEQ ID NO: 1). Height of the letter corresponds to proportion of sequences containing the particular amino acid at that position.

DETAILED DESCRIPTION OF THE INVENTION

Figure 1A:
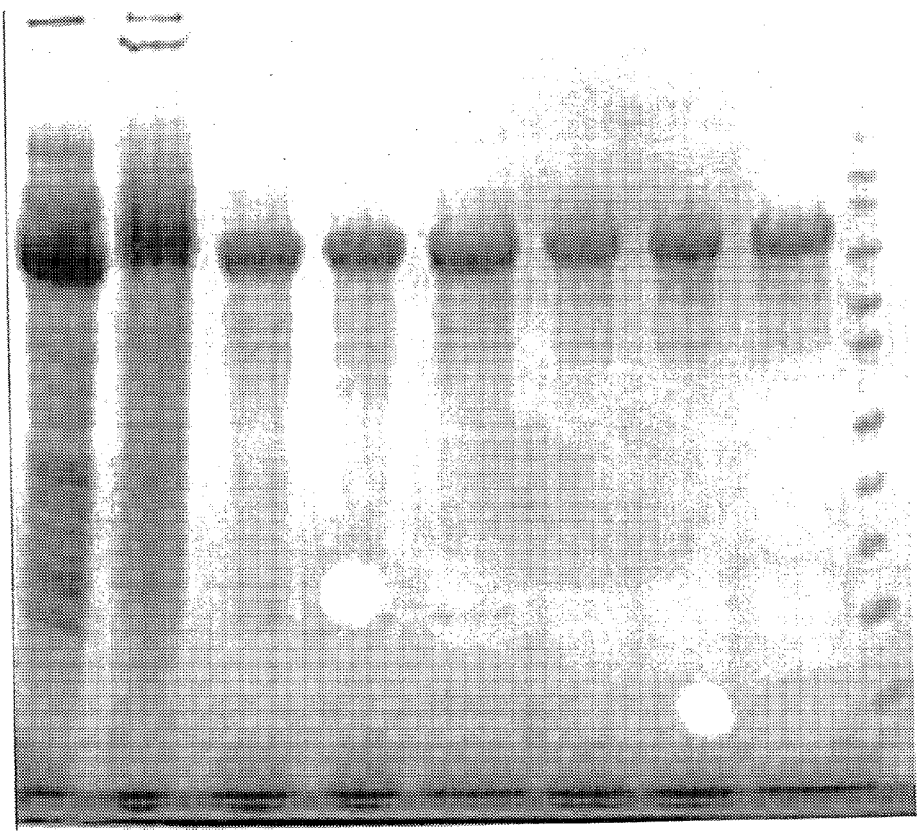
FIGS. 1A-1B show a SDS-PAGE gel showing purification of a molecule comprising a precipitable beta-roll tag.

The issued patents, applications, and other publications that are cited herein are hereby incorporated by reference to the same extent as if each was specifically and individually indicated to be incorporated by reference.

Purification is a major requirement in many bioengineering applications where significant amounts of time are currently spent purifying proteins from heterogeneous samples. The invention described herein relates to methods for rapidly purifying a purification moiety (e.g. a target polypeptide) from a heterogeneous medium using a PBRC. For example, in certain embodiments, a target polypeptide can be produced as a fusion protein in frame with a PBRC. In certain embodiments, the fusion protein comprising the target protein and the PBRC can further comprise a specific cleavage site (e.g. an intein cleavage site or an enterokinase cleavage site) between the target protein sequence and the PBRC sequence. In such embodiments, cleavage at the cleavage site can be used to separate the PBRC from the target polypeptide.

The beta-roll domain is a right-handed beta helix found in a number of proteins. The consensus sequence for beta-roll peptides is tandem repeats of the 9 amino acid sequence GGXGXDX(L/F/I)X (SEQ ID NO: 24). In the presence of calcium, the conformation aligns to adopt the helical turns. Two repeats of the sequence are required to make a complete helical turn and each of these turns binds a calcium atom. In the absence of calcium, the peptide exists in a disordered conformation. Therefore the β-roll domain exhibits natural allosteric regulation. A synthetic version of the β-roll peptide has been produced with 8 repeats of GGSGNDNLS (SEQ ID NO: 1338) and this peptide was found to bind calcium and fold into the β-roll structure (Lilie et al., FEBS Lett 470 (2), 173 (2000)). The domain is capable of reversibly unfolding upon removal of the calcium. Beta roll sequences are known to play a role in secretion as part of the bacterial Type I secretion system (Davidson, et al., Microbiol. Mol. Biol. Rev. 72 (2008), pp. 317-364; Holland et al., Mol. Membr. Biol. 22 (2005), pp. 29-39; Chenal, et al., J. Biol. Chem. 284(2009), pp. 1781-1789; Welch, Pore-Forming Toxins 257 (2001), pp. 85-111; Rose et al., J. Biol. Chem. 270 (1995), pp. 26370-26376; Baumann, J. Mol. Biol. 242 (1994), pp. 244-251; Angkawidjaja, et al., FEBS Lett. 581 (2007), pp. 5060-5064; Meier et al., J. Biol. Chem. 282 (2007), pp. 31477-31483; Bauche et al., J. Biol. Chem. 281 (2006), pp. 16914-16926; Baumann et al., EMBO J. 12 (1993), pp. 3357-3364; Angkawidjaja et al., FEBS Lett. 579(2005), pp. 4707-4712).

The precipitable-beta roll tags and precipitable-beta roll cassettes described herein are class of designed peptides which possess the ability to reversibly precipitate in response to calcium ions. In one aspect, the invention described herein relates to the surprising finding that PBRCs (e.g. PBRTs repeats of sequence GGAGNDTLY (SEQ ID NO: 1)) undergo reversible precipitation upon calcium binding. In another aspect, the invention described herein relates to the surprising finding that attachment of a PBRC to a second molecule (e.g. attachment to a protein as a fusion protein comprising an in-frame) can be used to purify the second molecule through reversible precipitation. In another aspect, the invention described herein relates to the use of calcium concentration changes at room temperature to induce precipitation of recombinant molecules comprising a precipitable beta-roll tag.

In addition to target polypeptides, the PBRCs describe herein are also suitable for purifying non-peptide purification moieties of widely varying types, including, for example, lipids, oligonucleotides and carbohydrates, small organic or inorganic molecules, proteins, single-stranded or double-stranded oligonucleotides, polynucleotides. In certain aspects, applications for the methods and compositions described herein include, but are not limited to, the purification of recombinant proteins the removal of target proteins from a sample, and detection of compounds for diagnostic purposes. The invention also extends to the antibodies that specifically bind to a PBRT or a PBRC and the methods for using the PBRTs and PBRCs described herein.

Without wishing to be bound to theory, in certain embodiments, the PBRTs and PBRCs described herein can undergo a reversible Ca2+ binding dependent transition wherein they are structurally disordered and highly soluble in a medium below a Ca2+ concentration (or free Ca2+) transition concentration, but exhibit a disorder to order phase transition when the Ca2+ or free Ca2+ concentration is raised above the Ca2+ (or free Ca2+) transition concentration. Again, without wishing to be bound by theory, in some embodiments, the disorder to order phase transition leads to precipitation of the PBRTs or PBRCs. Precipitation of PBRC can be used to remove and isolated them from solution (e.g.

by centrifugation). In one embodiment, the invention described herein relates to a PBRC which functions reversible Ca2+ precipitable tag when linked to a purification moiety of interest. In embodiments where the PBRC is linked to a purification moiety of interest, the methods described herein can be used to induce precipitation of the PBRC linked purification moiety. Because the transition concentration dependent phase transition is reversible, the PBRT and PBRC can be resolubilized in a medium having a Ca2+ concentration (or free Ca2+) below the transition concentration. In certain embodiments, this can be accomplished by introducing medium having reduced, or no Ca2+, or by removing, or chelating Ca2+ from the medium. When the precipitate is resuspended in calcium-free buffer or in a buffer comprising a calcium ion chelator (e.g. EGTA or EDTA), the precipitate resuspends into solution.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

In certain embodiments, the term "precipitable-beta roll tag" (PBRT) refers to an amino acid sequence having the sequence GGAGNDTLY (SEQ ID NO: 1). In certain embodiments, a PBRT refers to an amino acid sequence having the amino acid sequence GXXXXXXXX (SEQ ID NO: 1343), wherein (a) the X at position 2 is an amino acid selected from the group consisting of glycine, asparagine or aspartic acid, and (b) the X at position 3 is an amino acid selected from the group consisting of alanine, serine, glycine, aspartic acid, glutamic acid, leucine or asparagine, and (c) the X at position 4 is an amino acid selected from the group consisting of glycine or alanine, and (d) the X at position 5 is an amino acid selected from the group consisting of asparagine, aspartic acid, alanine, or serine, and (e) the X at position 6 is an amino acid selected from the group consisting of aspartic acid or asparagine, (f) the X at position 7 is an amino acid selected from the group consisting of threonine, isoleucine, valine, or leucine, and (g) the X at position 8 is an amino acid selected from the group consisting of leucine, isoleucine, or phenylalanine, and (h) the X at position 9 is an amino acid selected from the group consisting of tyrosine, isoleucine, valine, phenylalanine, threonine, asparagine, aspartic acid, lysine or serine, or a nucleic acid encoding the same. A PBRT refers to an amino acid sequence having the sequence set forth in any of SEQ ID NOs: 25-1337.

TABLE 1

| SEQ ID NOs: 25-1337 |
| --- |
| Sequence (SEQ ID NO) |
| GDNASDLFS SEQ ID NO: 25 |
| GNAGNDTLY SEQ ID NO: 26 |
| GDAGNDTLY SEQ ID NO: 27 |
| GGSGNDTLY SEQ ID NO: 28 |
| GNSGNDTLY SEQ ID NO: 29 |
| GDSGNDTLY SEQ ID NO: 30 |

TABLE 1-continued

| SEQ ID NOs: 25-1337 |
| --- |
| Sequence (SEQ ID NO) |
| GGGGNDTLY SEQ ID NO: 31 |
| GNGGNDTLY SEQ ID NO: 32 |
| GDGGNDTLY SEQ ID NO: 33 |
| GGDGNDTLY SEQ ID NO: 34 |
| GNDGNDTLY SEQ ID NO: 35 |
| GDDGNDTLY SEQ ID NO: 36 |
| GGAGDDTLY SEQ ID NO: 37 |
| GNAGDDTLY SEQ ID NO: 38 |
| GDAGDDTLY SEQ ID NO: 39 |
| GGSGDDTLY SEQ ID NO: 40 |
| GNSGDDTLY SEQ ID NO: 41 |
| GDSGDDTLY SEQ ID NO: 42 |
| GGGGDDTLY SEQ ID NO: 43 |
| GNGGDDTLY SEQ ID NO: 44 |
| GDGGDDTLY SEQ ID NO: 45 |
| GGDGDDTLY SEQ ID NO: 46 |
| GNDGDDTLY SEQ ID NO: 47 |
| GDDGDDTLY SEQ ID NO: 48 |
| GGAGADTLY SEQ ID NO: 49 |
| GNAGADTLY SEQ ID NO: 50 |
| GDAGADTLY SEQ ID NO: 51 |
| GGSGADTLY SEQ ID NO: 52 |
| GNSGADTLY SEQ ID NO: 53 |
| GDSGADTLY SEQ ID NO: 54 |
| GGGGADTLY SEQ ID NO: 55 |
| GNGGADTLY SEQ ID NO: 56 |
| GDGGADTLY SEQ ID NO: 57 |
| GGDGADTLY SEQ ID NO: 58 |
| GNDGADTLY SEQ ID NO: 59 |
| GDDGADTLY SEQ ID NO: 60 |
| GGAGNNTLY SEQ ID NO: 61 |
| GNAGNNTLY SEQ ID NO: 62 |
| GDAGNNTLY SEQ ID NO: 63 |
| GGSGNNTLY SEQ ID NO: 64 |
| GNSGNNTLY SEQ ID NO: 65 |
| GDSGNNTLY SEQ ID NO: 66 |
| GGGGNNTLY SEQ ID NO: 67 |
| GNGGNNTLY SEQ ID NO: 68 |

TABLE 1-continued

SEQ ID NOs: 25-1337

| Sequence (SEQ ID NO) |
|---|
| GDGGNNTLY SEQ ID NO: 69 |
| GGDGNNTLY SEQ ID NO: 70 |
| GNDGNNTLY SEQ ID NO: 71 |
| GDDGNNTLY SEQ ID NO: 72 |
| GGAGDNTLY SEQ ID NO: 73 |
| GNAGDNTLY SEQ ID NO: 74 |
| GDAGDNTLY SEQ ID NO: 75 |
| GGSGDNTLY SEQ ID NO: 76 |
| GNSGDNTLY SEQ ID NO: 77 |
| GDSGDNTLY SEQ ID NO: 78 |
| GGGGDNTLY SEQ ID NO: 79 |
| GNGGDNTLY SEQ ID NO: 80 |
| GDGGDNTLY SEQ ID NO: 81 |
| GGDGDNTLY SEQ ID NO: 82 |
| GNDGDNTLY SEQ ID NO: 83 |
| GDDGDNTLY SEQ ID NO: 84 |
| GGAGANTLY SEQ ID NO: 85 |
| GNAGANTLY SEQ ID NO: 86 |
| GDAGANTLY SEQ ID NO: 87 |
| GGSGANTLY SEQ ID NO: 88 |
| GNSGANTLY SEQ ID NO: 89 |
| GDSGANTLY SEQ ID NO: 90 |
| GGGGANTLY SEQ ID NO: 91 |
| GNGGANTLY SEQ ID NO: 92 |
| GDGGANTLY SEQ ID NO: 93 |
| GGDGANTLY SEQ ID NO: 94 |
| GNDGANTLY SEQ ID NO: 95 |
| GDDGANTLY SEQ ID NO: 96 |
| GGAGNDILY SEQ ID NO: 97 |
| GNAGNDILY SEQ ID NO: 98 |
| GDAGNDILY SEQ ID NO: 99 |
| GGSGNDILY SEQ ID NO: 100 |
| GNSGNDILY SEQ ID NO: 101 |
| GDSGNDILY SEQ ID NO: 102 |
| GGGGNDILY SEQ ID NO: 103 |
| GNGGNDILY SEQ ID NO: 104 |
| GDGGNDILY SEQ ID NO: 105 |
| GGDGNDILY SEQ ID NO: 106 |
| GNDGNDILY SEQ ID NO: 107 |
| GDDGNDILY SEQ ID NO: 108 |
| GGAGDDILY SEQ ID NO: 109 |
| GNAGDDILY SEQ ID NO: 110 |
| GDAGDDILY SEQ ID NO: 111 |
| GGSGDDILY SEQ ID NO: 112 |
| GNSGDDILY SEQ ID NO: 113 |
| GDSGDDILY SEQ ID NO: 114 |
| GGGGDDILY SEQ ID NO: 115 |
| GNGGDDILY SEQ ID NO: 116 |
| GDGGDDILY SEQ ID NO: 117 |
| GGDGDDILY SEQ ID NO: 118 |
| GNDGDDILY SEQ ID NO: 119 |
| GDDGDDILY SEQ ID NO: 120 |
| GGAGADILY SEQ ID NO: 121 |
| GNAGADILY SEQ ID NO: 122 |
| GDAGADILY SEQ ID NO: 123 |
| GGSGADILY SEQ ID NO: 124 |
| GNSGADILY SEQ ID NO: 125 |
| GDSGADILY SEQ ID NO: 126 |
| GGGGADILY SEQ ID NO: 127 |
| GNGGADILY SEQ ID NO: 128 |
| GDGGADILY SEQ ID NO: 129 |
| GGDGADILY SEQ ID NO: 130 |
| GNDGADILY SEQ ID NO: 131 |
| GDDGADILY SEQ ID NO: 132 |
| GGAGNNILY SEQ ID NO: 133 |
| GNAGNNILY SEQ ID NO: 134 |
| GDAGNNILY SEQ ID NO: 135 |
| GGSGNNILY SEQ ID NO: 136 |
| GNSGNNILY SEQ ID NO: 137 |
| GDSGNNILY SEQ ID NO: 138 |
| GGGGNNILY SEQ ID NO: 139 |
| GNGGNNILY SEQ ID NO: 140 |
| GDGGNNILY SEQ ID NO: 141 |
| GGDGNNILY SEQ ID NO: 142 |
| GNDGNNILY SEQ ID NO: 143 |
| GDDGNNILY SEQ ID NO: 144 |

TABLE 1-continued

SEQ ID NOs: 25-1337

| Sequence (SEQ ID NO) |
|---|
| GGAGDNILY SEQ ID NO: 145 |
| GNAGDNILY SEQ ID NO: 146 |
| GDAGDNILY SEQ ID NO: 147 |
| GGSGDNILY SEQ ID NO: 148 |
| GNSGDNILY SEQ ID NO: 149 |
| GDSGDNILY SEQ ID NO: 150 |
| GGGGDNILY SEQ ID NO: 151 |
| GNGGDNILY SEQ ID NO: 152 |
| GDGGDNILY SEQ ID NO: 153 |
| GGDGDNILY SEQ ID NO: 154 |
| GNDGDNILY SEQ ID NO: 155 |
| GDDGDNILY SEQ ID NO: 156 |
| GGAGANILY SEQ ID NO: 157 |
| GNAGANILY SEQ ID NO: 158 |
| GDAGANILY SEQ ID NO: 159 |
| GGSGANILY SEQ ID NO: 160 |
| GNSGANILY SEQ ID NO: 161 |
| GDSGANILY SEQ ID NO: 162 |
| GGGGANILY SEQ ID NO: 163 |
| GNGGANILY SEQ ID NO: 164 |
| GDGGANILY SEQ ID NO: 165 |
| GGDGANILY SEQ ID NO: 166 |
| GNDGANILY SEQ ID NO: 167 |
| GDDGANILY SEQ ID NO: 168 |
| GGAGNDVLY SEQ ID NO: 169 |
| GNAGNDVLY SEQ ID NO: 170 |
| GDAGNDVLY SEQ ID NO: 171 |
| GGSGNDVLY SEQ ID NO: 172 |
| GNSGNDVLY SEQ ID NO: 173 |
| GDSGNDVLY SEQ ID NO: 174 |
| GGGGNDVLY SEQ ID NO: 175 |
| GNGGNDVLY SEQ ID NO: 176 |
| GDGGNDVLY SEQ ID NO: 177 |
| GGDGNDVLY SEQ ID NO: 178 |
| GNDGNDVLY SEQ ID NO: 179 |
| GDDGNDVLY SEQ ID NO: 180 |
| GGAGDDVLY SEQ ID NO: 181 |
| GNAGDDVLY SEQ ID NO: 182 |
| GDAGDDVLY SEQ ID NO: 183 |
| GGSGDDVLY SEQ ID NO: 184 |
| GNSGDDVLY SEQ ID NO: 185 |
| GDSGDDVLY SEQ ID NO: 186 |
| GGGGDDVLY SEQ ID NO: 187 |
| GNGGDDVLY SEQ ID NO: 188 |
| GDGGDDVLY SEQ ID NO: 189 |
| GGDGDDVLY SEQ ID NO: 190 |
| GNDGDDVLY SEQ ID NO: 191 |
| GDDGDDVLY SEQ ID NO: 192 |
| GGAGADVLY SEQ ID NO: 193 |
| GNAGADVLY SEQ ID NO: 194 |
| GDAGADVLY SEQ ID NO: 195 |
| GGSGADVLY SEQ ID NO: 196 |
| GNSGADVLY SEQ ID NO: 197 |
| GDSGADVLY SEQ ID NO: 198 |
| GGGGADVLY SEQ ID NO: 199 |
| GNGGADVLY SEQ ID NO: 200 |
| GDGGADVLY SEQ ID NO: 201 |
| GGDGADVLY SEQ ID NO: 202 |
| GNDGADVLY SEQ ID NO: 203 |
| GDDGADVLY SEQ ID NO: 204 |
| GGAGNNVLY SEQ ID NO: 205 |
| GNAGNNVLY SEQ ID NO: 206 |
| GDAGNNVLY SEQ ID NO: 207 |
| GGSGNNVLY SEQ ID NO: 208 |
| GNSGNNVLY SEQ ID NO: 209 |
| GDSGNNVLY SEQ ID NO: 210 |
| GGGGNNVLY SEQ ID NO: 211 |
| GNGGNNVLY SEQ ID NO: 212 |
| GDGGNNVLY SEQ ID NO: 213 |
| GGDGNNVLY SEQ ID NO: 214 |
| GNDGNNVLY SEQ ID NO: 215 |
| GDDGNNVLY SEQ ID NO: 216 |
| GGAGDNVLY SEQ ID NO: 217 |
| GNAGDNVLY SEQ ID NO: 218 |
| GDAGDNVLY SEQ ID NO: 219 |
| GGSGDNVLY SEQ ID NO: 220 |

TABLE 1-continued

SEQ ID NOs: 25-1337

| Sequence (SEQ ID NO) |
|---|
| GNSGDNVLY SEQ ID NO: 221 |
| GDSGDNVLY SEQ ID NO: 222 |
| GGGGDNVLY SEQ ID NO: 223 |
| GNGGDNVLY SEQ ID NO: 224 |
| GDGGDNVLY SEQ ID NO: 225 |
| GGDGDNVLY SEQ ID NO: 226 |
| GNDGDNVLY SEQ ID NO: 227 |
| GDDGDNVLY SEQ ID NO: 228 |
| GGAGANVLY SEQ ID NO: 229 |
| GNAGANVLY SEQ ID NO: 230 |
| GDAGANVLY SEQ ID NO: 231 |
| GGSGANVLY SEQ ID NO: 232 |
| GNSGANVLY SEQ ID NO: 233 |
| GDSGANVLY SEQ ID NO: 234 |
| GGGGANVLY SEQ ID NO: 235 |
| GNGGANVLY SEQ ID NO: 236 |
| GDGGANVLY SEQ ID NO: 237 |
| GGDGANVLY SEQ ID NO: 238 |
| GNDGANVLY SEQ ID NO: 239 |
| GDDGANVLY SEQ ID NO: 240 |
| GGAGNDTIY SEQ ID NO: 241 |
| GNAGNDTIY SEQ ID NO: 242 |
| GDAGNDTIY SEQ ID NO: 243 |
| GGSGNDTIY SEQ ID NO: 244 |
| GNSGNDTIY SEQ ID NO: 245 |
| GDSGNDTIY SEQ ID NO: 246 |
| GGGGNDTIY SEQ ID NO: 247 |
| GNGGNDTIY SEQ ID NO: 248 |
| GDGGNDTIY SEQ ID NO: 249 |
| GGDGNDTIY SEQ ID NO: 250 |
| GNDGNDTIY SEQ ID NO: 251 |
| GDDGNDTIY SEQ ID NO: 252 |
| GGAGDDTIY SEQ ID NO: 253 |
| GNAGDDTIY SEQ ID NO: 254 |
| GDAGDDTIY SEQ ID NO: 255 |
| GGSGDDTIY SEQ ID NO: 256 |
| GNSGDDTIY SEQ ID NO: 257 |
| GDSGDDTIY SEQ ID NO: 258 |
| GGGGDDTIY SEQ ID NO: 259 |
| GNGGDDTIY SEQ ID NO: 260 |
| GDGGDDTIY SEQ ID NO: 261 |
| GGDGDDTIY SEQ ID NO: 262 |
| GNDGDDTIY SEQ ID NO: 263 |
| GDDGDDTIY SEQ ID NO: 264 |
| GGAGADTIY SEQ ID NO: 265 |
| GNAGADTIY SEQ ID NO: 266 |
| GDAGADTIY SEQ ID NO: 267 |
| GGSGADTIY SEQ ID NO: 268 |
| GNSGADTIY SEQ ID NO: 269 |
| GDSGADTIY SEQ ID NO: 270 |
| GGGGADTIY SEQ ID NO: 271 |
| GNGGADTIY SEQ ID NO: 272 |
| GDGGADTIY SEQ ID NO: 273 |
| GGDGADTIY SEQ ID NO: 274 |
| GNDGADTIY SEQ ID NO: 275 |
| GDDGADTIY SEQ ID NO: 276 |
| GGAGNNTIY SEQ ID NO: 277 |
| GNAGNNTIY SEQ ID NO: 278 |
| GDAGNNTIY SEQ ID NO: 279 |
| GGSGNNTIY SEQ ID NO: 280 |
| GNSGNNTIY SEQ ID NO: 281 |
| GDSGNNTIY SEQ ID NO: 282 |
| GGGGNNTIY SEQ ID NO: 283 |
| GNGGNNTIY SEQ ID NO: 284 |
| GDGGNNTIY SEQ ID NO: 285 |
| GGDGNNTIY SEQ ID NO: 286 |
| GNDGNNTIY SEQ ID NO: 287 |
| GDDGNNTIY SEQ ID NO: 288 |
| GGAGDNTIY SEQ ID NO: 289 |
| GNAGDNTIY SEQ ID NO: 290 |
| GDAGDNTIY SEQ ID NO: 291 |
| GGSGDNTIY SEQ ID NO: 292 |
| GNSGDNTIY SEQ ID NO: 293 |
| GDSGDNTIY SEQ ID NO: 294 |
| GGGGDNTIY SEQ ID NO: 295 |
| GNGGDNTIY SEQ ID NO: 296 |

TABLE 1-continued

SEQ ID NOs: 25-1337

| Sequence (SEQ ID NO) |
|---|
| GDGGDNTIY SEQ ID NO: 297 |
| GGDGDNTIY SEQ ID NO: 298 |
| GNDGDNTIY SEQ ID NO: 299 |
| GDDGDNTIY SEQ ID NO: 300 |
| GGAGANTIY SEQ ID NO: 301 |
| GNAGANTIY SEQ ID NO: 302 |
| GDAGANTIY SEQ ID NO: 303 |
| GGSGANTIY SEQ ID NO: 304 |
| GNSGANTIY SEQ ID NO: 305 |
| GDSGANTIY SEQ ID NO: 306 |
| GGGGANTIY SEQ ID NO: 307 |
| GNGGANTIY SEQ ID NO: 308 |
| GDGGANTIY SEQ ID NO: 309 |
| GGDGANTIY SEQ ID NO: 310 |
| GNDGANTIY SEQ ID NO: 311 |
| GDDGANTIY SEQ ID NO: 312 |
| GGAGNDIIY SEQ ID NO: 313 |
| GNAGNDIIY SEQ ID NO: 314 |
| GDAGNDIIY SEQ ID NO: 315 |
| GGSGNDIIY SEQ ID NO: 316 |
| GNSGNDIIY SEQ ID NO: 317 |
| GDSGNDIIY SEQ ID NO: 318 |
| GGGGNDIIY SEQ ID NO: 319 |
| GNGGNDIIY SEQ ID NO: 320 |
| GDGGNDIIY SEQ ID NO: 321 |
| GGDGNDIIY SEQ ID NO: 322 |
| GNDGNDIIY SEQ ID NO: 323 |
| GDDGNDIIY SEQ ID NO: 324 |
| GGAGDDIIY SEQ ID NO: 325 |
| GNAGDDIIY SEQ ID NO: 326 |
| GDAGDDIIY SEQ ID NO: 327 |
| GGSGDDIIY SEQ ID NO: 328 |
| GNSGDDIIY SEQ ID NO: 329 |
| GDSGDDIIY SEQ ID NO: 330 |
| GGGGDDIIY SEQ ID NO: 331 |
| GNGGDDIIY SEQ ID NO: 332 |
| GDGGDDIIY SEQ ID NO: 333 |
| GGDGDDIIY SEQ ID NO: 334 |
| GNDGDDIIY SEQ ID NO: 335 |
| GDDGDDIIY SEQ ID NO: 336 |
| GGAGADIIY SEQ ID NO: 337 |
| GNAGADIIY SEQ ID NO: 338 |
| GDAGADIIY SEQ ID NO: 339 |
| GGSGADIIY SEQ ID NO: 340 |
| GNSGADIIY SEQ ID NO: 341 |
| GDSGADIIY SEQ ID NO: 342 |
| GGGGADIIY SEQ ID NO: 343 |
| GNGGADIIY SEQ ID NO: 344 |
| GDGGADIIY SEQ ID NO: 345 |
| GGDGADIIY SEQ ID NO: 346 |
| GNDGADIIY SEQ ID NO: 347 |
| GDDGADIIY SEQ ID NO: 348 |
| GGAGNNIIY SEQ ID NO: 349 |
| GNAGNNIIY SEQ ID NO: 350 |
| GDAGNNIIY SEQ ID NO: 351 |
| GGSGNNIIY SEQ ID NO: 352 |
| GNSGNNIIY SEQ ID NO: 353 |
| GDSGNNIIY SEQ ID NO: 354 |
| GGGGNNIIY SEQ ID NO: 355 |
| GNGGNNIIY SEQ ID NO: 356 |
| GDGGNNIIY SEQ ID NO: 357 |
| GGDGNNIIY SEQ ID NO: 358 |
| GNDGNNIIY SEQ ID NO: 359 |
| GDDGNNIIY SEQ ID NO: 360 |
| GGAGDNIIY SEQ ID NO: 361 |
| GNAGDNIIY SEQ ID NO: 362 |
| GDAGDNIIY SEQ ID NO: 363 |
| GGSGDNIIY SEQ ID NO: 364 |
| GNSGDNIIY SEQ ID NO: 365 |
| GDSGDNIIY SEQ ID NO: 366 |
| GGGGDNIIY SEQ ID NO: 367 |
| GNGGDNIIY SEQ ID NO: 368 |
| GDGGDNIIY SEQ ID NO: 369 |
| GGDGDNIIY SEQ ID NO: 370 |
| GNDGDNIIY SEQ ID NO: 371 |
| GDDGDNIIY SEQ ID NO: 372 |

TABLE 1-continued

SEQ ID NOs: 25-1337

| Sequence (SEQ ID NO) |
|---|
| GGAGANIIY SEQ ID NO: 373 |
| GNAGANIIY SEQ ID NO: 374 |
| GDAGANIIY SEQ ID NO: 375 |
| GGSGANIIY SEQ ID NO: 376 |
| GNSGANIIY SEQ ID NO: 377 |
| GDSGANIIY SEQ ID NO: 378 |
| GGGGANIIY SEQ ID NO: 379 |
| GNGGANIIY SEQ ID NO: 380 |
| GDGGANIIY SEQ ID NO: 381 |
| GGDGANIIY SEQ ID NO: 382 |
| GNDGANIIY SEQ ID NO: 383 |
| GDDGANIIY SEQ ID NO: 384 |
| GGAGNDVIY SEQ ID NO: 385 |
| GNAGNDVIY SEQ ID NO: 386 |
| GDAGNDVIY SEQ ID NO: 387 |
| GGSGNDVIY SEQ ID NO: 388 |
| GNSGNDVIY SEQ ID NO: 389 |
| GDSGNDVIY SEQ ID NO: 390 |
| GGGGNDVIY SEQ ID NO: 391 |
| GNGGNDVIY SEQ ID NO: 392 |
| GDGGNDVIY SEQ ID NO: 393 |
| GGDGNDVIY SEQ ID NO: 394 |
| GNDGNDVIY SEQ ID NO: 395 |
| GDDGNDVIY SEQ ID NO: 396 |
| GGAGDDVIY SEQ ID NO: 397 |
| GNAGDDVIY SEQ ID NO: 398 |
| GDAGDDVIY SEQ ID NO: 399 |
| GGSGDDVIY SEQ ID NO: 400 |
| GNSGDDVIY SEQ ID NO: 401 |
| GDSGDDVIY SEQ ID NO: 402 |
| GGGGDDVIY SEQ ID NO: 403 |
| GNGGDDVIY SEQ ID NO: 404 |
| GDGGDDVIY SEQ ID NO: 405 |
| GGDGDDVIY SEQ ID NO: 406 |
| GNDGDDVIY SEQ ID NO: 407 |
| GDDGDDVIY SEQ ID NO: 408 |
| GGAGADVIY SEQ ID NO: 409 |
| GNAGADVIY SEQ ID NO: 410 |
| GDAGADVIY SEQ ID NO: 411 |
| GGSGADVIY SEQ ID NO: 412 |
| GNSGADVIY SEQ ID NO: 413 |
| GDSGADVIY SEQ ID NO: 414 |
| GGGGADVIY SEQ ID NO: 415 |
| GNGGADVIY SEQ ID NO: 416 |
| GDGGADVIY SEQ ID NO: 417 |
| GGDGADVIY SEQ ID NO: 418 |
| GNDGADVIY SEQ ID NO: 419 |
| GDDGADVIY SEQ ID NO: 420 |
| GGAGNNVIY SEQ ID NO: 421 |
| GNAGNNVIY SEQ ID NO: 422 |
| GDAGNNVIY SEQ ID NO: 423 |
| GGSGNNVIY SEQ ID NO: 424 |
| GNSGNNVIY SEQ ID NO: 425 |
| GDSGNNVIY SEQ ID NO: 426 |
| GGGGNNVIY SEQ ID NO: 427 |
| GNGGNNVIY SEQ ID NO: 428 |
| GDGGNNVIY SEQ ID NO: 429 |
| GGDGNNVIY SEQ ID NO: 430 |
| GNDGNNVIY SEQ ID NO: 431 |
| GDDGNNVIY SEQ ID NO: 432 |
| GGAGDNVIY SEQ ID NO: 433 |
| GNAGDNVIY SEQ ID NO: 434 |
| GDAGDNVIY SEQ ID NO: 435 |
| GGSGDNVIY SEQ ID NO: 436 |
| GNSGDNVIY SEQ ID NO: 437 |
| GDSGDNVIY SEQ ID NO: 438 |
| GGGGDNVIY SEQ ID NO: 439 |
| GNGGDNVIY SEQ ID NO: 440 |
| GDGGDNVIY SEQ ID NO: 441 |
| GGDGDNVIY SEQ ID NO: 442 |
| GNDGDNVIY SEQ ID NO: 443 |
| GDDGDNVIY SEQ ID NO: 444 |
| GGAGANVIY SEQ ID NO: 445 |
| GNAGANVIY SEQ ID NO: 446 |
| GDAGANVIY SEQ ID NO: 447 |
| GGSGANVIY SEQ ID NO: 448 |

TABLE 1-continued

SEQ ID NOs: 25-1337

| Sequence (SEQ ID NO) |
|---|
| GNSGANVIY SEQ ID NO: 449 |
| GDSGANVIY SEQ ID NO: 450 |
| GGGGANVIY SEQ ID NO: 451 |
| GNGGANVIY SEQ ID NO: 452 |
| GDGGANVIY SEQ ID NO: 453 |
| GGDGANVIY SEQ ID NO: 454 |
| GNDGANVIY SEQ ID NO: 455 |
| GDDGANVIY SEQ ID NO: 456 |
| GGAGNDTLI SEQ ID NO: 457 |
| GNAGNDTLI SEQ ID NO: 458 |
| GDAGNDTLI SEQ ID NO: 459 |
| GGSGNDTLI SEQ ID NO: 460 |
| GNSGNDTLI SEQ ID NO: 461 |
| GDSGNDTLI SEQ ID NO: 462 |
| GGGGNDTLI SEQ ID NO: 463 |
| GNGGNDTLI SEQ ID NO: 464 |
| GDGGNDTLI SEQ ID NO: 465 |
| GGDGNDTLI SEQ ID NO: 466 |
| GNDGNDTLI SEQ ID NO: 467 |
| GDDGNDTLI SEQ ID NO: 468 |
| GGAGDDTLI SEQ ID NO: 469 |
| GNAGDDTLI SEQ ID NO: 470 |
| GDAGDDTLI SEQ ID NO: 471 |
| GGSGDDTLI SEQ ID NO: 472 |
| GNSGDDTLI SEQ ID NO: 473 |
| GDSGDDTLI SEQ ID NO: 474 |
| GGGGDDTLI SEQ ID NO: 475 |
| GNGGDDTLI SEQ ID NO: 476 |
| GDGGDDTLI SEQ ID NO: 477 |
| GGDGDDTLI SEQ ID NO: 478 |
| GNDGDDTLI SEQ ID NO: 479 |
| GDDGDDTLI SEQ ID NO: 480 |
| GGAGADTLI SEQ ID NO: 481 |
| GNAGADTLI SEQ ID NO: 482 |
| GDAGADTLI SEQ ID NO: 483 |
| GGSGADTLI SEQ ID NO: 484 |
| GNSGADTLI SEQ ID NO: 485 |
| GDSGADTLI SEQ ID NO: 486 |
| GGGGADTLI SEQ ID NO: 487 |
| GNGGADTLI SEQ ID NO: 488 |
| GDGGADTLI SEQ ID NO: 489 |
| GGDGADTLI SEQ ID NO: 490 |
| GNDGADTLI SEQ ID NO: 491 |
| GDDGADTLI SEQ ID NO: 492 |
| GGAGNNTLI SEQ ID NO: 493 |
| GNAGNNTLI SEQ ID NO: 494 |
| GDAGNNTLI SEQ ID NO: 495 |
| GGSGNNTLI SEQ ID NO: 496 |
| GNSGNNTLI SEQ ID NO: 497 |
| GDSGNNTLI SEQ ID NO: 498 |
| GGGGNNTLI SEQ ID NO: 499 |
| GNGGNNTLI SEQ ID NO: 500 |
| GDGGNNTLI SEQ ID NO: 501 |
| GGDGNNTLI SEQ ID NO: 502 |
| GNDGNNTLI SEQ ID NO: 503 |
| GDDGNNTLI SEQ ID NO: 504 |
| GGAGDNTLI SEQ ID NO: 505 |
| GNAGDNTLI SEQ ID NO: 506 |
| GDAGDNTLI SEQ ID NO: 507 |
| GGSGDNTLI SEQ ID NO: 508 |
| GNSGDNTLI SEQ ID NO: 509 |
| GDSGDNTLI SEQ ID NO: 510 |
| GGGGDNTLI SEQ ID NO: 511 |
| GNGGDNTLI SEQ ID NO: 512 |
| GDGGDNTLI SEQ ID NO: 513 |
| GGDGDNTLI SEQ ID NO: 514 |
| GNDGDNTLI SEQ ID NO: 515 |
| GDDGDNTLI SEQ ID NO: 516 |
| GGAGANTLI SEQ ID NO: 517 |
| GNAGANTLI SEQ ID NO: 518 |
| GDAGANTLI SEQ ID NO: 519 |
| GGSGANTLI SEQ ID NO: 520 |
| GNSGANTLI SEQ ID NO: 521 |
| GDSGANTLI SEQ ID NO: 522 |
| GGGGANTLI SEQ ID NO: 523 |
| GNGGANTLI SEQ ID NO: 524 |

TABLE 1-continued

SEQ ID NOs: 25-1337

| Sequence (SEQ ID NO) |
|---|
| GDGGANTLI SEQ ID NO: 525 |
| GGDGANTLI SEQ ID NO: 526 |
| GNDGANTLI SEQ ID NO: 527 |
| GDDGANTLI SEQ ID NO: 528 |
| GGAGNDILI SEQ ID NO: 529 |
| GNAGNDILI SEQ ID NO: 530 |
| GDAGNDILI SEQ ID NO: 531 |
| GGSGNDILI SEQ ID NO: 532 |
| GNSGNDILI SEQ ID NO: 533 |
| GDSGNDILI SEQ ID NO: 534 |
| GGGGNDILI SEQ ID NO: 535 |
| GNGGNDILI SEQ ID NO: 536 |
| GDGGNDILI SEQ ID NO: 537 |
| GGDGNDILI SEQ ID NO: 538 |
| GNDGNDILI SEQ ID NO: 539 |
| GDDGNDILI SEQ ID NO: 540 |
| GGAGDDILI SEQ ID NO: 541 |
| GNAGDDILI SEQ ID NO: 542 |
| GDAGDDILI SEQ ID NO: 543 |
| GGSGDDILI SEQ ID NO: 544 |
| GNSGDDILI SEQ ID NO: 545 |
| GDSGDDILI SEQ ID NO: 546 |
| GGGGDDILI SEQ ID NO: 547 |
| GNGGDDILI SEQ ID NO: 548 |
| GDGGDDILI SEQ ID NO: 549 |
| GGDGDDILI SEQ ID NO: 550 |
| GNDGDDILI SEQ ID NO: 551 |
| GDDGDDILI SEQ ID NO: 552 |
| GGAGADILI SEQ ID NO: 553 |
| GNAGADILI SEQ ID NO: 554 |
| GDAGADILI SEQ ID NO: 555 |
| GGSGADILI SEQ ID NO: 556 |
| GNSGADILI SEQ ID NO: 557 |
| GDSGADILI SEQ ID NO: 558 |
| GGGGADILI SEQ ID NO: 559 |
| GNGGADILI SEQ ID NO: 560 |
| GDGGADILI SEQ ID NO: 561 |
| GGDGADILI SEQ ID NO: 562 |

TABLE 1-continued

SEQ ID NOs: 25-1337

| Sequence (SEQ ID NO) |
|---|
| GNDGADILI SEQ ID NO: 563 |
| GDDGADILI SEQ ID NO: 564 |
| GGAGNNILI SEQ ID NO: 565 |
| GNAGNNILI SEQ ID NO: 566 |
| GDAGNNILI SEQ ID NO: 567 |
| GGSGNNILI SEQ ID NO: 568 |
| GNSGNNILI SEQ ID NO: 569 |
| GDSGNNILI SEQ ID NO: 570 |
| GGGGNNILI SEQ ID NO: 571 |
| GNGGNNILI SEQ ID NO: 572 |
| GDGGNNILI SEQ ID NO: 573 |
| GGDGNNILI SEQ ID NO: 574 |
| GNDGNNILI SEQ ID NO: 575 |
| GDDGNNILI SEQ ID NO: 576 |
| GGAGDNILI SEQ ID NO: 577 |
| GNAGDNILI SEQ ID NO: 578 |
| GDAGDNILI SEQ ID NO: 579 |
| GGSGDNILI SEQ ID NO: 580 |
| GNSGDNILI SEQ ID NO: 581 |
| GDSGDNILI SEQ ID NO: 582 |
| GGGGDNILI SEQ ID NO: 583 |
| GNGGDNILI SEQ ID NO: 584 |
| GDGGDNILI SEQ ID NO: 585 |
| GGDGDNILI SEQ ID NO: 586 |
| GNDGDNILI SEQ ID NO: 587 |
| GDDGDNILI SEQ ID NO: 588 |
| GGAGANILI SEQ ID NO: 589 |
| GNAGANILI SEQ ID NO: 590 |
| GDAGANILI SEQ ID NO: 591 |
| GGSGANILI SEQ ID NO: 592 |
| GNSGANILI SEQ ID NO: 593 |
| GDSGANILI SEQ ID NO: 594 |
| GGGGANILI SEQ ID NO: 595 |
| GNGGANILI SEQ ID NO: 596 |
| GDGGANILI SEQ ID NO: 597 |
| GGDGANILI SEQ ID NO: 598 |
| GNDGANILI SEQ ID NO: 599 |
| GDDGANILI SEQ ID NO: 600 |

TABLE 1-continued

SEQ ID NOs: 25-1337

| Sequence | (SEQ ID NO) |
|---|---|
| GGAGNDVLI | SEQ ID NO: 601 |
| GNAGNDVLI | SEQ ID NO: 602 |
| GDAGNDVLI | SEQ ID NO: 603 |
| GGSGNDVLI | SEQ ID NO: 604 |
| GNSGNDVLI | SEQ ID NO: 605 |
| GDSGNDVLI | SEQ ID NO: 606 |
| GGGGNDVLI | SEQ ID NO: 607 |
| GNGGNDVLI | SEQ ID NO: 608 |
| GDGGNDVLI | SEQ ID NO: 609 |
| GGDGNDVLI | SEQ ID NO: 610 |
| GNDGNDVLI | SEQ ID NO: 611 |
| GDDGNDVLI | SEQ ID NO: 612 |
| GGAGDDVLI | SEQ ID NO: 613 |
| GNAGDDVLI | SEQ ID NO: 614 |
| GDAGDDVLI | SEQ ID NO: 615 |
| GGSGDDVLI | SEQ ID NO: 616 |
| GNSGDDVLI | SEQ ID NO: 617 |
| GDSGDDVLI | SEQ ID NO: 618 |
| GGGGDDVLI | SEQ ID NO: 619 |
| GNGGDDVLI | SEQ ID NO: 620 |
| GDGGDDVLI | SEQ ID NO: 621 |
| GGDGDDVLI | SEQ ID NO: 622 |
| GNDGDDVLI | SEQ ID NO: 623 |
| GDDGDDVLI | SEQ ID NO: 624 |
| GGAGADVLI | SEQ ID NO: 625 |
| GNAGADVLI | SEQ ID NO: 626 |
| GDAGADVLI | SEQ ID NO: 627 |
| GGSGADVLI | SEQ ID NO: 628 |
| GNSGADVLI | SEQ ID NO: 629 |
| GDSGADVLI | SEQ ID NO: 630 |
| GGGGADVLI | SEQ ID NO: 631 |
| GNGGADVLI | SEQ ID NO: 632 |
| GDGGADVLI | SEQ ID NO: 633 |
| GGDGADVLI | SEQ ID NO: 634 |
| GNDGADVLI | SEQ ID NO: 635 |
| GDDGADVLI | SEQ ID NO: 636 |
| GGAGNNVLI | SEQ ID NO: 637 |
| GNAGNNVLI | SEQ ID NO: 638 |
| GDAGNNVLI | SEQ ID NO: 639 |
| GGSGNNVLI | SEQ ID NO: 640 |
| GNSGNNVLI | SEQ ID NO: 641 |
| GDSGNNVLI | SEQ ID NO: 642 |
| GGGGNNVLI | SEQ ID NO: 643 |
| GNGGNNVLI | SEQ ID NO: 644 |
| GDGGNNVLI | SEQ ID NO: 645 |
| GGDGNNVLI | SEQ ID NO: 646 |
| GNDGNNVLI | SEQ ID NO: 647 |
| GDDGNNVLI | SEQ ID NO: 648 |
| GGAGDNVLI | SEQ ID NO: 649 |
| GNAGDNVLI | SEQ ID NO: 650 |
| GDAGDNVLI | SEQ ID NO: 651 |
| GGSGDNVLI | SEQ ID NO: 652 |
| GNSGDNVLI | SEQ ID NO: 653 |
| GDSGDNVLI | SEQ ID NO: 654 |
| GGGGDNVLI | SEQ ID NO: 655 |
| GNGGDNVLI | SEQ ID NO: 656 |
| GDGGDNVLI | SEQ ID NO: 657 |
| GGDGDNVLI | SEQ ID NO: 658 |
| GNDGDNVLI | SEQ ID NO: 659 |
| GDDGDNVLI | SEQ ID NO: 660 |
| GGAGANVLI | SEQ ID NO: 661 |
| GNAGANVLI | SEQ ID NO: 662 |
| GDAGANVLI | SEQ ID NO: 663 |
| GGSGANVLI | SEQ ID NO: 664 |
| GNSGANVLI | SEQ ID NO: 665 |
| GDSGANVLI | SEQ ID NO: 666 |
| GGGGANVLI | SEQ ID NO: 667 |
| GNGGANVLI | SEQ ID NO: 668 |
| GDGGANVLI | SEQ ID NO: 669 |
| GGDGANVLI | SEQ ID NO: 670 |
| GNDGANVLI | SEQ ID NO: 671 |
| GDDGANVLI | SEQ ID NO: 672 |
| GGAGNDTII | SEQ ID NO: 673 |
| GNAGNDTII | SEQ ID NO: 674 |
| GDAGNDTII | SEQ ID NO: 675 |
| GGSGNDTII | SEQ ID NO: 676 |

TABLE 1-continued

SEQ ID NOs: 25-1337

| Sequence (SEQ ID NO) |
|---|
| GNSGNDTII SEQ ID NO: 677 |
| GDSGNDTII SEQ ID NO: 678 |
| GGGGNDTII SEQ ID NO: 679 |
| GNGGNDTII SEQ ID NO: 680 |
| GDGGNDTII SEQ ID NO: 681 |
| GGDGNDTII SEQ ID NO: 682 |
| GNDGNDTII SEQ ID NO: 683 |
| GDDGNDTII SEQ ID NO: 684 |
| GGAGDDTII SEQ ID NO: 685 |
| GNAGDDTII SEQ ID NO: 686 |
| GDAGDDTII SEQ ID NO: 687 |
| GGSGDDTII SEQ ID NO: 688 |
| GNSGDDTII SEQ ID NO: 689 |
| GDSGDDTII SEQ ID NO: 690 |
| GGGGDDTII SEQ ID NO: 691 |
| GNGGDDTII SEQ ID NO: 692 |
| GDGGDDTII SEQ ID NO: 693 |
| GGDGDDTII SEQ ID NO: 694 |
| GNDGDDTII SEQ ID NO: 695 |
| GDDGDDTII SEQ ID NO: 696 |
| GGAGADTII SEQ ID NO: 697 |
| GNAGADTII SEQ ID NO: 698 |
| GDAGADTII SEQ ID NO: 699 |
| GGSGADTII SEQ ID NO: 700 |
| GNSGADTII SEQ ID NO: 701 |
| GDSGADTII SEQ ID NO: 702 |
| GGGGADTII SEQ ID NO: 703 |
| GNGGADTII SEQ ID NO: 704 |
| GDGGADTII SEQ ID NO: 705 |
| GGDGADTII SEQ ID NO: 706 |
| GNDGADTII SEQ ID NO: 707 |
| GDDGADTII SEQ ID NO: 708 |
| GGAGNNTII SEQ ID NO: 709 |
| GNAGNNTII SEQ ID NO: 710 |
| GDAGNNTII SEQ ID NO: 711 |
| GGSGNNTII SEQ ID NO: 712 |
| GNSGNNTII SEQ ID NO: 713 |
| GDSGNNTII SEQ ID NO: 714 |
| GGGGNNTII SEQ ID NO: 715 |
| GNGGNNTII SEQ ID NO: 716 |
| GDGGNNTII SEQ ID NO: 717 |
| GGDGNNTII SEQ ID NO: 718 |
| GNDGNNTII SEQ ID NO: 719 |
| GDDGNNTII SEQ ID NO: 720 |
| GGAGDNTII SEQ ID NO: 721 |
| GNAGDNTII SEQ ID NO: 722 |
| GDAGDNTII SEQ ID NO: 723 |
| GGSGDNTII SEQ ID NO: 724 |
| GNSGDNTII SEQ ID NO: 725 |
| GDSGDNTII SEQ ID NO: 726 |
| GGGGDNTII SEQ ID NO: 727 |
| GNGGDNTII SEQ ID NO: 728 |
| GDGGDNTII SEQ ID NO: 729 |
| GGDGDNTII SEQ ID NO: 730 |
| GNDGDNTII SEQ ID NO: 731 |
| GDDGDNTII SEQ ID NO: 732 |
| GGAGANTII SEQ ID NO: 733 |
| GNAGANTII SEQ ID NO: 734 |
| GDAGANTII SEQ ID NO: 735 |
| GGSGANTII SEQ ID NO: 736 |
| GNSGANTII SEQ ID NO: 737 |
| GDSGANTII SEQ ID NO: 738 |
| GGGGANTII SEQ ID NO: 739 |
| GNGGANTII SEQ ID NO: 740 |
| GDGGANTII SEQ ID NO: 741 |
| GGDGANTII SEQ ID NO: 742 |
| GNDGANTII SEQ ID NO: 743 |
| GDDGANTII SEQ ID NO: 744 |
| GGAGNDIII SEQ ID NO: 745 |
| GNAGNDIII SEQ ID NO: 746 |
| GDAGNDIII SEQ ID NO: 747 |
| GGSGNDIII SEQ ID NO: 748 |
| GNSGNDIII SEQ ID NO: 749 |
| GDSGNDIII SEQ ID NO: 750 |
| GGGGNDIII SEQ ID NO: 751 |
| GNGGNDIII SEQ ID NO: 752 |

TABLE 1-continued

SEQ ID NOs: 25-1337

Sequence (SEQ ID NO)

GDGGNDIII SEQ ID NO: 753

GGDGNDIII SEQ ID NO: 754

GNDGNDIII SEQ ID NO: 755

GDDGNDIII SEQ ID NO: 756

GGAGDDIII SEQ ID NO: 757

GNAGDDIII SEQ ID NO: 758

GDAGDDIII SEQ ID NO: 759

GGSGDDIII SEQ ID NO: 760

GNSGDDIII SEQ ID NO: 761

GDSGDDIII SEQ ID NO: 762

GGGGDDIII SEQ ID NO: 763

GNGGDDIII SEQ ID NO: 764

GDGGDDIII SEQ ID NO: 765

GGDGDDIII SEQ ID NO: 766

GNDGDDIII SEQ ID NO: 767

GDDGDDIII SEQ ID NO: 768

GGAGADIII SEQ ID NO: 769

GNAGADIII SEQ ID NO: 770

GDAGADIII SEQ ID NO: 771

GGSGADIII SEQ ID NO: 772

GNSGADIII SEQ ID NO: 773

GDSGADIII SEQ ID NO: 774

GGGGADIII SEQ ID NO: 775

GNGGADIII SEQ ID NO: 776

GDGGADIII SEQ ID NO: 777

GGDGADIII SEQ ID NO: 778

GNDGADIII SEQ ID NO: 779

GDDGADIII SEQ ID NO: 780

GGAGNNIII SEQ ID NO: 781

GNAGNNIII SEQ ID NO: 782

GDAGNNIII SEQ ID NO: 783

GGSGNNIII SEQ ID NO: 784

GNSGNNIII SEQ ID NO: 785

GDSGNNIII SEQ ID NO: 786

GGGGNNIII SEQ ID NO: 787

GNGGNNIII SEQ ID NO: 788

GDGGNNIII SEQ ID NO: 789

GGDGNNIII SEQ ID NO: 790

TABLE 1-continued

SEQ ID NOs: 25-1337

Sequence (SEQ ID NO)

GNDGNNIII SEQ ID NO: 791

GDDGNNIII SEQ ID NO: 792

GGAGDNIII SEQ ID NO: 793

GNAGDNIII SEQ ID NO: 794

GDAGDNIII SEQ ID NO: 795

GGSGDNIII SEQ ID NO: 796

GNSGDNIII SEQ ID NO: 797

GDSGDNIII SEQ ID NO: 798

GGGGDNIII SEQ ID NO: 799

GNGGDNIII SEQ ID NO: 800

GDGGDNIII SEQ ID NO: 801

GGDGDNIII SEQ ID NO: 802

GNDGDNIII SEQ ID NO: 803

GDDGDNIII SEQ ID NO: 804

GGAGANIII SEQ ID NO: 805

GNAGANIII SEQ ID NO: 806

GDAGANIII SEQ ID NO: 807

GGSGANIII SEQ ID NO: 808

GNSGANIII SEQ ID NO: 809

GDSGANIII SEQ ID NO: 810

GGGGANIII SEQ ID NO: 811

GNGGANIII SEQ ID NO: 812

GDGGANIII SEQ ID NO: 813

GGDGANIII SEQ ID NO: 814

GNDGANIII SEQ ID NO: 815

GDDGANIII SEQ ID NO: 816

GGAGNDVII SEQ ID NO: 817

GNAGNDVII SEQ ID NO: 818

GDAGNDVII SEQ ID NO: 819

GGSGNDVII SEQ ID NO: 820

GNSGNDVII SEQ ID NO: 821

GDSGNDVII SEQ ID NO: 822

GGGGNDVII SEQ ID NO: 823

GNGGNDVII SEQ ID NO: 824

GDGGNDVII SEQ ID NO: 825

GGDGNDVII SEQ ID NO: 826

GNDGNDVII SEQ ID NO: 827

GDDGNDVII SEQ ID NO: 828

TABLE 1-continued

SEQ ID NOs: 25-1337

| Sequence (SEQ ID NO) |
|---|
| GGAGDDVII SEQ ID NO: 829 |
| GNAGDDVII SEQ ID NO: 830 |
| GDAGDDVII SEQ ID NO: 831 |
| GGSGDDVII SEQ ID NO: 832 |
| GNSGDDVII SEQ ID NO: 833 |
| GDSGDDVII SEQ ID NO: 834 |
| GGGGDDVII SEQ ID NO: 835 |
| GNGGDDVII SEQ ID NO: 836 |
| GDGGDDVII SEQ ID NO: 837 |
| GGDGDDVII SEQ ID NO: 838 |
| GNDGDDVII SEQ ID NO: 839 |
| GDDGDDVII SEQ ID NO: 840 |
| GGAGADVII SEQ ID NO: 841 |
| GNAGADVII SEQ ID NO: 842 |
| GDAGADVII SEQ ID NO: 843 |
| GGSGADVII SEQ ID NO: 844 |
| GNSGADVII SEQ ID NO: 845 |
| GDSGADVII SEQ ID NO: 846 |
| GGGGADVII SEQ ID NO: 847 |
| GNGGADVII SEQ ID NO: 848 |
| GDGGADVII SEQ ID NO: 849 |
| GGDGADVII SEQ ID NO: 850 |
| GNDGADVII SEQ ID NO: 851 |
| GDDGADVII SEQ ID NO: 852 |
| GGAGNNVII SEQ ID NO: 853 |
| GNAGNNVII SEQ ID NO: 854 |
| GDAGNNVII SEQ ID NO: 855 |
| GGSGNNVII SEQ ID NO: 856 |
| GNSGNNVII SEQ ID NO: 857 |
| GDSGNNVII SEQ ID NO: 858 |
| GGGGNNVII SEQ ID NO: 859 |
| GNGGNNVII SEQ ID NO: 860 |
| GDGGNNVII SEQ ID NO: 861 |
| GGDGNNVII SEQ ID NO: 862 |
| GNDGNNVII SEQ ID NO: 863 |
| GDDGNNVII SEQ ID NO: 864 |
| GGAGDNVII SEQ ID NO: 865 |
| GNAGDNVII SEQ ID NO: 866 |
| GDAGDNVII SEQ ID NO: 867 |
| GGSGDNVII SEQ ID NO: 868 |
| GNSGDNVII SEQ ID NO: 869 |
| GDSGDNVII SEQ ID NO: 870 |
| GGGGDNVII SEQ ID NO: 871 |
| GNGGDNVII SEQ ID NO: 872 |
| GDGGDNVII SEQ ID NO: 873 |
| GGDGDNVII SEQ ID NO: 874 |
| GNDGDNVII SEQ ID NO: 875 |
| GDDGDNVII SEQ ID NO: 876 |
| GGAGANVII SEQ ID NO: 877 |
| GNAGANVII SEQ ID NO: 878 |
| GDAGANVII SEQ ID NO: 879 |
| GGSGANVII SEQ ID NO: 880 |
| GNSGANVII SEQ ID NO: 881 |
| GDSGANVII SEQ ID NO: 882 |
| GGGGANVII SEQ ID NO: 883 |
| GNGGANVII SEQ ID NO: 884 |
| GDGGANVII SEQ ID NO: 885 |
| GGDGANVII SEQ ID NO: 886 |
| GNDGANVII SEQ ID NO: 887 |
| GDDGANVII SEQ ID NO: 888 |
| GGAGNDTLV SEQ ID NO: 889 |
| GNAGNDTLV SEQ ID NO: 890 |
| GDAGNDTLV SEQ ID NO: 891 |
| GGSGNDTLV SEQ ID NO: 892 |
| GNSGNDTLV SEQ ID NO: 893 |
| GDSGNDTLV SEQ ID NO: 894 |
| GGGGNDTLV SEQ ID NO: 895 |
| GNGGNDTLV SEQ ID NO: 896 |
| GDGGNDTLV SEQ ID NO: 897 |
| GGDGNDTLV SEQ ID NO: 898 |
| GNDGNDTLV SEQ ID NO: 899 |
| GDDGNDTLV SEQ ID NO: 900 |
| GGAGDDTLV SEQ ID NO: 901 |
| GNAGDDTLV SEQ ID NO: 902 |
| GDAGDDTLV SEQ ID NO: 903 |
| GGSGDDTLV SEQ ID NO: 904 |

TABLE 1-continued

SEQ ID NOs: 25-1337

| Sequence (SEQ ID NO) |
|---|
| GNSGDDTLV SEQ ID NO: 905 |
| GDSGDDTLV SEQ ID NO: 906 |
| GGGGDDTLV SEQ ID NO: 907 |
| GNGGDDTLV SEQ ID NO: 908 |
| GDGGDDTLV SEQ ID NO: 909 |
| GGDGDDTLV SEQ ID NO: 910 |
| GNDGDDTLV SEQ ID NO: 911 |
| GDDGDDTLV SEQ ID NO: 912 |
| GGAGADTLV SEQ ID NO: 913 |
| GNAGADTLV SEQ ID NO: 914 |
| GDAGADTLV SEQ ID NO: 915 |
| GGSGADTLV SEQ ID NO: 916 |
| GNSGADTLV SEQ ID NO: 917 |
| GDSGADTLV SEQ ID NO: 918 |
| GGGGADTLV SEQ ID NO: 919 |
| GNGGADTLV SEQ ID NO: 920 |
| GDGGADTLV SEQ ID NO: 921 |
| GGDGADTLV SEQ ID NO: 922 |
| GNDGADTLV SEQ ID NO: 923 |
| GDDGADTLV SEQ ID NO: 924 |
| GGAGNNTLV SEQ ID NO: 925 |
| GNAGNNTLV SEQ ID NO: 926 |
| GDAGNNTLV SEQ ID NO: 927 |
| GGSGNNTLV SEQ ID NO: 928 |
| GNSGNNTLV SEQ ID NO: 929 |
| GDSGNNTLV SEQ ID NO: 930 |
| GGGGNNTLV SEQ ID NO: 931 |
| GNGGNNTLV SEQ ID NO: 932 |
| GDGGNNTLV SEQ ID NO: 933 |
| GGDGNNTLV SEQ ID NO: 934 |
| GNDGNNTLV SEQ ID NO: 935 |
| GDDGNNTLV SEQ ID NO: 936 |
| GGAGDNTLV SEQ ID NO: 937 |
| GNAGDNTLV SEQ ID NO: 938 |
| GDAGDNTLV SEQ ID NO: 939 |
| GGSGDNTLV SEQ ID NO: 940 |
| GNSGDNTLV SEQ ID NO: 941 |
| GDSGDNTLV SEQ ID NO: 942 |
| GGGGDNTLV SEQ ID NO: 943 |
| GNGGDNTLV SEQ ID NO: 944 |
| GDGGDNTLV SEQ ID NO: 945 |
| GGDGDNTLV SEQ ID NO: 946 |
| GNDGDNTLV SEQ ID NO: 947 |
| GDDGDNTLV SEQ ID NO: 948 |
| GGAGANTLV SEQ ID NO: 949 |
| GNAGANTLV SEQ ID NO: 950 |
| GDAGANTLV SEQ ID NO: 951 |
| GGSGANTLV SEQ ID NO: 952 |
| GNSGANTLV SEQ ID NO: 953 |
| GDSGANTLV SEQ ID NO: 954 |
| GGGGANTLV SEQ ID NO: 955 |
| GNGGANTLV SEQ ID NO: 956 |
| GDGGANTLV SEQ ID NO: 957 |
| GGDGANTLV SEQ ID NO: 958 |
| GNDGANTLV SEQ ID NO: 959 |
| GDDGANTLV SEQ ID NO: 960 |
| GGAGNDILV SEQ ID NO: 961 |
| GNAGNDILV SEQ ID NO: 962 |
| GDAGNDILV SEQ ID NO: 963 |
| GGSGNDILV SEQ ID NO: 964 |
| GNSGNDILV SEQ ID NO: 965 |
| GDSGNDILV SEQ ID NO: 966 |
| GGGGNDILV SEQ ID NO: 967 |
| GNGGNDILV SEQ ID NO: 968 |
| GDGGNDILV SEQ ID NO: 969 |
| GGDGNDILV SEQ ID NO: 970 |
| GNDGNDILV SEQ ID NO: 971 |
| GDDGNDILV SEQ ID NO: 972 |
| GGAGDDILV SEQ ID NO: 973 |
| GNAGDDILV SEQ ID NO: 974 |
| GDAGDDILV SEQ ID NO: 975 |
| GGSGDDILV SEQ ID NO: 976 |
| GNSGDDILV SEQ ID NO: 977 |
| GDSGDDILV SEQ ID NO: 978 |
| GGGGDDILV SEQ ID NO: 979 |
| GNGGDDILV SEQ ID NO: 980 |

TABLE 1-continued

SEQ ID NOs: 25-1337

| Sequence (SEQ ID NO) |
|---|
| GDGGDDILV SEQ ID NO: 981 |
| GGDGDDILV SEQ ID NO: 982 |
| GNDGDDILV SEQ ID NO: 983 |
| GDDGDDILV SEQ ID NO: 984 |
| GGAGADILV SEQ ID NO: 985 |
| GNAGADILV SEQ ID NO: 986 |
| GDAGADILV SEQ ID NO: 987 |
| GGSGADILV SEQ ID NO: 988 |
| GNSGADILV SEQ ID NO: 989 |
| GDSGADILV SEQ ID NO: 990 |
| GGGGADILV SEQ ID NO: 991 |
| GNGGADILV SEQ ID NO: 992 |
| GDGGADILV SEQ ID NO: 993 |
| GGDGADILV SEQ ID NO: 994 |
| GNDGADILV SEQ ID NO: 995 |
| GDDGADILV SEQ ID NO: 996 |
| GGAGNNILV SEQ ID NO: 997 |
| GNAGNNILV SEQ ID NO: 998 |
| GDAGNNILV SEQ ID NO: 999 |
| GGSGNNILV SEQ ID NO: 1000 |
| GNSGNNILV SEQ ID NO: 1001 |
| GDSGNNILV SEQ ID NO: 1002 |
| GGGGNNILV SEQ ID NO: 1003 |
| GNGGNNILV SEQ ID NO: 1004 |
| GDGGNNILV SEQ ID NO: 1005 |
| GGDGNNILV SEQ ID NO: 1006 |
| GNDGNNILV SEQ ID NO: 1007 |
| GDDGNNILV SEQ ID NO: 1008 |
| GGAGDNILV SEQ ID NO: 1009 |
| GNAGDNILV SEQ ID NO: 1010 |
| GDAGDNILV SEQ ID NO: 1011 |
| GGSGDNILV SEQ ID NO: 1012 |
| GNSGDNILV SEQ ID NO: 1013 |
| GDSGDNILV SEQ ID NO: 1014 |
| GGGGDNILV SEQ ID NO: 1015 |
| GNGGDNILV SEQ ID NO: 1016 |
| GDGGDNILV SEQ ID NO: 1017 |
| GGDGDNILV SEQ ID NO: 1018 |
| GNDGDNILV SEQ ID NO: 1019 |
| GDDGDNILV SEQ ID NO: 1020 |
| GGAGANILV SEQ ID NO: 1021 |
| GNAGANILV SEQ ID NO: 1022 |
| GDAGANILV SEQ ID NO: 1023 |
| GGSGANILV SEQ ID NO: 1024 |
| GNSGANILV SEQ ID NO: 1025 |
| GDSGANILV SEQ ID NO: 1026 |
| GGGGANILV SEQ ID NO: 1027 |
| GNGGANILV SEQ ID NO: 1028 |
| GDGGANILV SEQ ID NO: 1029 |
| GGDGANILV SEQ ID NO: 1030 |
| GNDGANILV SEQ ID NO: 1031 |
| GDDGANILV SEQ ID NO: 1032 |
| GGAGNDVLV SEQ ID NO: 1033 |
| GNAGNDVLV SEQ ID NO: 1034 |
| GDAGNDVLV SEQ ID NO: 1035 |
| GGSGNDVLV SEQ ID NO: 1036 |
| GNSGNDVLV SEQ ID NO: 1037 |
| GDSGNDVLV SEQ ID NO: 1038 |
| GGGGNDVLV SEQ ID NO: 1039 |
| GNGGNDVLV SEQ ID NO: 1040 |
| GDGGNDVLV SEQ ID NO: 1041 |
| GGDGNDVLV SEQ ID NO: 1042 |
| GNDGNDVLV SEQ ID NO: 1043 |
| GDDGNDVLV SEQ ID NO: 1044 |
| GGAGDDVLV SEQ ID NO: 1045 |
| GNAGDDVLV SEQ ID NO: 1046 |
| GDAGDDVLV SEQ ID NO: 1047 |
| GGSGDDVLV SEQ ID NO: 1048 |
| GNSGDDVLV SEQ ID NO: 1049 |
| GDSGDDVLV SEQ ID NO: 1050 |
| GGGGDDVLV SEQ ID NO: 1051 |
| GNGGDDVLV SEQ ID NO: 1052 |
| GDGGDDVLV SEQ ID NO: 1053 |
| GGDGDDVLV SEQ ID NO: 1054 |
| GNDGDDVLV SEQ ID NO: 1055 |
| GDDGDDVLV SEQ ID NO: 1056 |

TABLE 1-continued

SEQ ID NOs: 25-1337

| Sequence (SEQ ID NO) |
|---|
| GGAGADVLV SEQ ID NO: 1057 |
| GNAGADVLV SEQ ID NO: 1058 |
| GDAGADVLV SEQ ID NO: 1059 |
| GGSGADVLV SEQ ID NO: 1060 |
| GNSGADVLV SEQ ID NO: 1061 |
| GDSGADVLV SEQ ID NO: 1062 |
| GGGGADVLV SEQ ID NO: 1063 |
| GNGGADVLV SEQ ID NO: 1064 |
| GDGGADVLV SEQ ID NO: 1065 |
| GGDGADVLV SEQ ID NO: 1066 |
| GNDGADVLV SEQ ID NO: 1067 |
| GDDGADVLV SEQ ID NO: 1068 |
| GGAGNNVLV SEQ ID NO: 1069 |
| GNAGNNVLV SEQ ID NO: 1070 |
| GDAGNNVLV SEQ ID NO: 1071 |
| GGSGNNVLV SEQ ID NO: 1072 |
| GNSGNNVLV SEQ ID NO: 1073 |
| GDSGNNVLV SEQ ID NO: 1074 |
| GGGGNNVLV SEQ ID NO: 1075 |
| GNGGNNVLV SEQ ID NO: 1076 |
| GDGGNNVLV SEQ ID NO: 1077 |
| GGDGNNVLV SEQ ID NO: 1078 |
| GNDGNNVLV SEQ ID NO: 1079 |
| GDDGNNVLV SEQ ID NO: 1080 |
| GGAGDNVLV SEQ ID NO: 1081 |
| GNAGDNVLV SEQ ID NO: 1082 |
| GDAGDNVLV SEQ ID NO: 1083 |
| GGSGDNVLV SEQ ID NO: 1084 |
| GNSGDNVLV SEQ ID NO: 1085 |
| GDSGDNVLV SEQ ID NO: 1086 |
| GGGGDNVLV SEQ ID NO: 1087 |
| GNGGDNVLV SEQ ID NO: 1088 |
| GDGGDNVLV SEQ ID NO: 1089 |
| GGDGDNVLV SEQ ID NO: 1090 |
| GNDGDNVLV SEQ ID NO: 1091 |
| GDDGDNVLV SEQ ID NO: 1092 |
| GGAGANVLV SEQ ID NO: 1093 |
| GNAGANVLV SEQ ID NO: 1094 |
| GDAGANVLV SEQ ID NO: 1095 |
| GGSGANVLV SEQ ID NO: 1096 |
| GNSGANVLV SEQ ID NO: 1097 |
| GDSGANVLV SEQ ID NO: 1098 |
| GGGGANVLV SEQ ID NO: 1099 |
| GNGGANVLV SEQ ID NO: 1100 |
| GDGGANVLV SEQ ID NO: 1101 |
| GGDGANVLV SEQ ID NO: 1102 |
| GNDGANVLV SEQ ID NO: 1103 |
| GDDGANVLV SEQ ID NO: 1104 |
| GGAGNDTIV SEQ ID NO: 1105 |
| GNAGNDTIV SEQ ID NO: 1106 |
| GDAGNDTIV SEQ ID NO: 1107 |
| GGSGNDTIV SEQ ID NO: 1108 |
| GNSGNDTIV SEQ ID NO: 1109 |
| GDSGNDTIV SEQ ID NO: 1110 |
| GGGGNDTIV SEQ ID NO: 1111 |
| GNGGNDTIV SEQ ID NO: 1112 |
| GDGGNDTIV SEQ ID NO: 1113 |
| GGDGNDTIV SEQ ID NO: 1114 |
| GNDGNDTIV SEQ ID NO: 1115 |
| GDDGNDTIV SEQ ID NO: 1116 |
| GGAGDDTIV SEQ ID NO: 1117 |
| GNAGDDTIV SEQ ID NO: 1118 |
| GDAGDDTIV SEQ ID NO: 1119 |
| GGSGDDTIV SEQ ID NO: 1120 |
| GNSGDDTIV SEQ ID NO: 1121 |
| GDSGDDTIV SEQ ID NO: 1122 |
| GGGGDDTIV SEQ ID NO: 1123 |
| GNGGDDTIV SEQ ID NO: 1124 |
| GDGGDDTIV SEQ ID NO: 1125 |
| GGDGDDTIV SEQ ID NO: 1126 |
| GNDGDDTIV SEQ ID NO: 1127 |
| GDDGDDTIV SEQ ID NO: 1128 |
| GGAGADTIV SEQ ID NO: 1129 |
| GNAGADTIV SEQ ID NO: 1130 |
| GDAGADTIV SEQ ID NO: 1131 |
| GGSGADTIV SEQ ID NO: 1132 |

TABLE 1-continued

SEQ ID NOs: 25-1337

| Sequence (SEQ ID NO) |
|---|
| GNSGADTIV SEQ ID NO: 1133 |
| GDSGADTIV SEQ ID NO: 1134 |
| GGGGADTIV SEQ ID NO: 1135 |
| GNGGADTIV SEQ ID NO: 1136 |
| GDGGADTIV SEQ ID NO: 1137 |
| GGDGADTIV SEQ ID NO: 1138 |
| GNDGADTIV SEQ ID NO: 1139 |
| GDDGADTIV SEQ ID NO: 1140 |
| GGAGNNTIV SEQ ID NO: 1141 |
| GNAGNNTIV SEQ ID NO: 1142 |
| GDAGNNTIV SEQ ID NO: 1143 |
| GGSGNNTIV SEQ ID NO: 1144 |
| GNAGNNTIV SEQ ID NO: 1145 |
| GDSGNNTIV SEQ ID NO: 1146 |
| GGGGNNTIV SEQ ID NO: 1147 |
| GNGGNNTIV SEQ ID NO: 1148 |
| GDGGNNTIV SEQ ID NO: 1149 |
| GGDGNNTIV SEQ ID NO: 1150 |
| GNDGNNTIV SEQ ID NO: 1151 |
| GDDGNNTIV SEQ ID NO: 1152 |
| GGAGDNTIV SEQ ID NO: 1153 |
| GNAGDNTIV SEQ ID NO: 1154 |
| GDAGDNTIV SEQ ID NO: 1155 |
| GGSGDNTIV SEQ ID NO: 1156 |
| GNSGDNTIV SEQ ID NO: 1157 |
| GDSGDNTIV SEQ ID NO: 1158 |
| GGGGDNTIV SEQ ID NO: 1159 |
| GNGGDNTIV SEQ ID NO: 1160 |
| GDGGDNTIV SEQ ID NO: 1161 |
| GGDGDNTIV SEQ ID NO: 1162 |
| GNDGDNTIV SEQ ID NO: 1163 |
| GDDGDNTIV SEQ ID NO: 1164 |
| GGAGANTIV SEQ ID NO: 1165 |
| GNAGANTIV SEQ ID NO: 1166 |
| GDAGANTIV SEQ ID NO: 1167 |
| GGSGANTIV SEQ ID NO: 1168 |
| GNSGANTIV SEQ ID NO: 1169 |
| GDSGANTIV SEQ ID NO: 1170 |
| GGGGANTIV SEQ ID NO: 1171 |
| GNGGANTIV SEQ ID NO: 1172 |
| GDGGANTIV SEQ ID NO: 1173 |
| GGDGANTIV SEQ ID NO: 1174 |
| GNDGANTIV SEQ ID NO: 1175 |
| GDDGANTIV SEQ ID NO: 1176 |
| GGAGNDIIV SEQ ID NO: 1177 |
| GNAGNDIIV SEQ ID NO: 1178 |
| GDAGNDIIV SEQ ID NO: 1179 |
| GGSGNDIIV SEQ ID NO: 1180 |
| GNSGNDIIV SEQ ID NO: 1181 |
| GDSGNDIIV SEQ ID NO: 1182 |
| GGGGNDIIV SEQ ID NO: 1183 |
| GNGGNDIIV SEQ ID NO: 1184 |
| GDGGNDIIV SEQ ID NO: 1185 |
| GGDGNDIIV SEQ ID NO: 1186 |
| GNDGNDIIV SEQ ID NO: 1187 |
| GDDGNDIIV SEQ ID NO: 1188 |
| GGAGDDIIV SEQ ID NO: 1189 |
| GNAGDDIIV SEQ ID NO: 1190 |
| GDAGDDIIV SEQ ID NO: 1191 |
| GGSGDDIIV SEQ ID NO: 1192 |
| GNSGDDIIV SEQ ID NO: 1193 |
| GDSGDDIIV SEQ ID NO: 1194 |
| GGGGDDIIV SEQ ID NO: 1195 |
| GNGGDDIIV SEQ ID NO: 1196 |
| GDGGDDIIV SEQ ID NO: 1197 |
| GGDGDDIIV SEQ ID NO: 1198 |
| GNDGDDIIV SEQ ID NO: 1199 |
| GDDGDDIIV SEQ ID NO: 1200 |
| GGAGADIIV SEQ ID NO: 1201 |
| GNAGADIIV SEQ ID NO: 1202 |
| GDAGADIIV SEQ ID NO: 1203 |
| GGSGADIIV SEQ ID NO: 1204 |
| GNSGADIIV SEQ ID NO: 1205 |
| GDSGADIIV SEQ ID NO: 1206 |
| GGGGADIIV SEQ ID NO: 1207 |
| GNGGADIIV SEQ ID NO: 1208 |

TABLE 1-continued

SEQ ID NOs: 25-1337

| Sequence (SEQ ID NO) |
|---|
| GDGGADIIV SEQ ID NO: 1209 |
| GGDGADIIV SEQ ID NO: 1210 |
| GNDGADIIV SEQ ID NO: 1211 |
| GDDGADIIV SEQ ID NO: 1212 |
| GGAGNNIIV SEQ ID NO: 1213 |
| GNAGNNIIV SEQ ID NO: 1214 |
| GDAGNNIIV SEQ ID NO: 1215 |
| GGSGNNIIV SEQ ID NO: 1216 |
| GNSGNNIIV SEQ ID NO: 1217 |
| GDSGNNIIV SEQ ID NO: 1218 |
| GGGGNNIIV SEQ ID NO: 1219 |
| GNGGNNIIV SEQ ID NO: 1220 |
| GDGGNNIIV SEQ ID NO: 1221 |
| GGDGNNIIV SEQ ID NO: 1222 |
| GNDGNNIIV SEQ ID NO: 1223 |
| GDDGNNIIV SEQ ID NO: 1224 |
| GGAGDNIIV SEQ ID NO: 1225 |
| GNAGDNIIV SEQ ID NO: 1226 |
| GDAGDNIIV SEQ ID NO: 1227 |
| GGSGDNIIV SEQ ID NO: 1228 |
| GNSGDNIIV SEQ ID NO: 1229 |
| GDSGDNIIV SEQ ID NO: 1230 |
| GGGGDNIIV SEQ ID NO: 1231 |
| GNGGDNIIV SEQ ID NO: 1232 |
| GDGGDNIIV SEQ ID NO: 1233 |
| GGDGDNIIV SEQ ID NO: 1234 |
| GNDGDNIIV SEQ ID NO: 1235 |
| GDDGDNIIV SEQ ID NO: 1236 |
| GGAGANIIV SEQ ID NO: 1237 |
| GNAGANIIV SEQ ID NO: 1238 |
| GDAGANIIV SEQ ID NO: 1239 |
| GGSGANIIV SEQ ID NO: 1240 |
| GNSGANIIV SEQ ID NO: 1241 |
| GDSGANIIV SEQ ID NO: 1242 |
| GGGGANIIV SEQ ID NO: 1243 |
| GNGGANIIV SEQ ID NO: 1244 |
| GDGGANIIV SEQ ID NO: 1245 |
| GGDGANIIV SEQ ID NO: 1246 |
| GNDGANIIV SEQ ID NO: 1247 |
| GDDGANIIV SEQ ID NO: 1248 |
| GGAGNDVIV SEQ ID NO: 1249 |
| GNAGNDVIV SEQ ID NO: 1250 |
| GDAGNDVIV SEQ ID NO: 1251 |
| GGSGNDVIV SEQ ID NO: 1252 |
| GNSGNDVIV SEQ ID NO: 1253 |
| GDSGNDVIV SEQ ID NO: 1254 |
| GGGGNDVIV SEQ ID NO: 1255 |
| GNGGNDVIV SEQ ID NO: 1256 |
| GDGGNDVIV SEQ ID NO: 1257 |
| GGDGNDVIV SEQ ID NO: 1258 |
| GNDGNDVIV SEQ ID NO: 1259 |
| GDDGNDVIV SEQ ID NO: 1260 |
| GGAGDDVIV SEQ ID NO: 1261 |
| GNAGDDVIV SEQ ID NO: 1262 |
| GDAGDDVIV SEQ ID NO: 1263 |
| GGSGDDVIV SEQ ID NO: 1264 |
| GNSGDDVIV SEQ ID NO: 1265 |
| GDSGDDVIV SEQ ID NO: 1266 |
| GGGGDDVIV SEQ ID NO: 1267 |
| GNGGDDVIV SEQ ID NO: 1268 |
| GDGGDDVIV SEQ ID NO: 1269 |
| GGDGDDVIV SEQ ID NO: 1270 |
| GNDGDDVIV SEQ ID NO: 1271 |
| GDDGDDVIV SEQ ID NO: 1272 |
| GGAGADVIV SEQ ID NO: 1273 |
| GNAGADVIV SEQ ID NO: 1274 |
| GDAGADVIV SEQ ID NO: 1275 |
| GGSGADVIV SEQ ID NO: 1276 |
| GNSGADVIV SEQ ID NO: 1277 |
| GDSGADVIV SEQ ID NO: 1278 |
| GGGGADVIV SEQ ID NO: 1279 |
| GNGGADVIV SEQ ID NO: 1280 |
| GDGGADVIV SEQ ID NO: 1281 |
| GGDGADVIV SEQ ID NO: 1282 |
| GNDGADVIV SEQ ID NO: 1283 |
| GDDGADVIV SEQ ID NO: 1284 |

TABLE 1-continued

SEQ ID NOs: 25-1337

| Sequence | (SEQ ID NO) |
|---|---|
| GGAGNNVIV | SEQ ID NO: 1285 |
| GNAGNNVIV | SEQ ID NO: 1286 |
| GDAGNNVIV | SEQ ID NO: 1287 |
| GGSGNNVIV | SEQ ID NO: 1288 |
| GNSGNNVIV | SEQ ID NO: 1289 |
| GDSGNNVIV | SEQ ID NO: 1290 |
| GGGGNNVIV | SEQ ID NO: 1291 |
| GNGGNNVIV | SEQ ID NO: 1292 |
| GDGGNNVIV | SEQ ID NO: 1293 |
| GGDGNNVIV | SEQ ID NO: 1294 |
| GNDGNNVIV | SEQ ID NO: 1295 |
| GDDGNNVIV | SEQ ID NO: 1296 |
| GGAGDNVIV | SEQ ID NO: 1297 |
| GNAGDNVIV | SEQ ID NO: 1298 |
| GDAGDNVIV | SEQ ID NO: 1299 |
| GGSGDNVIV | SEQ ID NO: 1300 |
| GNSGDNVIV | SEQ ID NO: 1301 |
| GDSGDNVIV | SEQ ID NO: 1302 |
| GGGGDNVIV | SEQ ID NO: 1303 |
| GNGGDNVIV | SEQ ID NO: 1304 |
| GDGGDNVIV | SEQ ID NO: 1305 |
| GGDGDNVIV | SEQ ID NO: 1306 |
| GNDGDNVIV | SEQ ID NO: 1307 |
| GDDGDNVIV | SEQ ID NO: 1308 |
| GGAGANVIV | SEQ ID NO: 1309 |
| GNAGANVIV | SEQ ID NO: 1310 |
| GDAGANVIV | SEQ ID NO: 1311 |
| GGSGANVIV | SEQ ID NO: 1312 |
| GNSGANVIV | SEQ ID NO: 1313 |
| GDSGANVIV | SEQ ID NO: 1314 |
| GGGGANVIV | SEQ ID NO: 1315 |
| GNGGANVIV | SEQ ID NO: 1316 |
| GDGGANVIV | SEQ ID NO: 1317 |
| GGDGANVIV | SEQ ID NO: 1318 |
| GNDGANVIV | SEQ ID NO: 1319 |
| GDDGANVIV | SEQ ID NO: 1320 |
| GDEASDLFF | SEQ ID NO: 1321 |
| GDLASDLFF | SEQ ID NO: 1322 |
| GDNASDLFF | SEQ ID NO: 1323 |
| GDEASDLFT | SEQ ID NO: 1324 |
| GDLASDLFT | SEQ ID NO: 1325 |
| GDNASDLFT | SEQ ID NO: 1326 |
| GDEASDLFN | SEQ ID NO: 1327 |
| GDLASDLFN | SEQ ID NO: 1328 |
| GDNASDLFN | SEQ ID NO: 1329 |
| GDEASDLFD | SEQ ID NO: 1330 |
| GDLASDLFD | SEQ ID NO: 1331 |
| GDNASDLFD | SEQ ID NO: 1332 |
| GDEASDLFK | SEQ ID NO: 1333 |
| GDLASDLFK | SEQ ID NO: 1334 |
| GDNASDLFK | SEQ ID NO: 1335 |
| GDEASDLFS | SEQ ID NO: 1336 |
| GDLASDLFS | SEQ ID NO: 1337 |

As used herein, the term "precipitable-beta roll cassette" (PBRC) refers to an amino acid sequence comprising at least one PBRT. In certain embodiments, a PBRC will comprise at least two PBRTs. In certain embodiments, a PBRC will comprise at least 3 PBRTs, at least 4 PBRTs, at least 5 PBRTs, at least 6 PBRTs, at least 7 PBRTs, at least 8 PBRTs, at least 9 PBRTs, at least 10 PBRTs, at least 11 PBRTs, at least 12 PBRTs, at least 13 PBRTs, at least 14 PBRTs, at least 15 PBRTs, at least 16 PBRTs, at least 17 PBRTs, at least 18 PBRTs, at least 19 PBRTs, at least 20 PBRTs, or 20 or more PBRTs. In certain embodiments, the PBRCs described herein will comprise a plurality of precipitable beta roll tags arranged in a tandem repeat. For example, in certain embodiments, the PBRCs described herein can comprise at least 2 PBRTs, at least 3 PBRTs, at least 4 PBRTs, at least 5 PBRTs, at least 6 PBRTs, at least 7 PBRTs, at least 8 PBRTs, at least 9 PBRTs, at least 10 PBRTs, at least 11 PBRTs, at least 12 PBRTs, at least 13 PBRTs, at least 14 PBRTs, at least 15 PBRTs, at least 16 PBRTs, at least 17 PBRTs, at least 18 PBRTs, at least 19 PBRTs, at least 20 PBRTs, or 20 or more PBRTs in tandem repeat. In certain embodiments, a PBRC can comprise at least two PBRCs separated by a linking amino acid sequence. Where a linking amino acid sequence in present between two PBRTs, a PBRT located at either end of the linking sequence can be an individual PBRT or it can be a PBRT that is part of a tandem arrangement of two or more PBRTs.

The PBRCs can comprise polymeric or oligomeric repeats of a PBRT. In certain embodiments, the PBRCs described herein can comprise one or more different PBRTs. In one embodiment, all of the PBRTs comprised in a PBRC are identical in amino acid sequence. In one embodiment, all of the PBRTs comprised in a PBRC have different amino acid sequences. In one embodiment, at least one PBRT comprised in a PBRC has a different amino acid sequence as compared to another PBRT in the PBRC. Thus, in certain embodiments, the PBRCs described herein can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 different PBRTs.

In certain embodiments, a PBRC can also comprise a capping sequence ("CS") refers to the an amino acid sequence comprising the amino acid sequence of SEQ ID NO: 3. The term "capping sequence" also refers to a capping sequence having the amino acid sequence of any of SEQ ID NO: 4-23.

Without wishing to be bound to theory, in some embodiments of the invention, the ability of polypeptide comprising one or more PBRT to undergo reversible Ca2+ precipitation, can require that the one or more PBRTs be located N-terminally or C-terminally to a capping sequence. Thus, in certain embodiments, the capping sequence is an amino acid sequence, which, when located C-terminally or N-terminally to one or more PBRTs, allows the one or more PBRTs bind to Ca2+, undergo reversible precipitation in the presence of Ca2+, or induce reversible precipitation of a purification moiety linked to the PBRC.

Thus in certain embodiments, a PBRC will comprise at least 2 PBRTs, at least 3 PBRTs, at least 4 PBRTs, at least 5 PBRTs, at least 6 PBRTs, at least 7 PBRTs, at least 8 PBRTs, at least 9 PBRTs, at least 10 PBRTs, at least 11 PBRTs, at least 12 PBRTs, at least 13 PBRTs, at least 14 PBRTs, at least 15 PBRTs, at least 16 PBRTs, at least 17 PBRTs, at least 18 PBRTs, at least 19 PBRTs, at least 20 PBRTs, or 20 or more PBRTs, all of which are located N-terminally to a CS. In certain embodiments, a PBRC will comprise 2, at least 3 PBRTs, at least 4 PBRTs, at least 5 PBRTs, at least 6 PBRTs, at least 7 PBRTs, at least 8 PBRTs, at least 9 PBRTs, at least 10 PBRTs, at least 11 PBRTs, at least 12 PBRTs, at least 13 PBRTs, at least 14 PBRTs, at least 15 PBRTs, at least 16 PBRTs, at least 17 PBRTs, at least 18 PBRTs, at least 19 PBRTs, at least 20 PBRTs, or 20 or more PBRTs, all of which are located C-terminally to a CS.

In one embodiment, a PBRC is an amino acid sequence comprising at least five tandem PBRTs situated N-terminally to a capping sequence.

In one embodiment, a PBRC is an amino acid sequence comprising at least six to about 16 tandem PBRTs situated N-terminally to a capping sequence.

In one embodiment, a precipitable beta roll cassette is an amino acid sequence comprising 17 or more tandem PBRTs situated N-terminally to a capping sequence.

In one embodiment, the capping sequence comprises the sequence INAGADQLWFARQGNDLEIRILGTDDALT-VHDWYRDADHRVEIIHAANQAVDQAGI EKLVEAMAQYPD (SEQ ID NO: 3) which is a C-terminal sequence on the block V beta roll domain of the adenylate cyclase toxin of *B. pertussis.*

In another embodiment, a PBRC comprises the amino acid sequence GGAGNDTLYGGAGNDTLYGGAGNDT-LYGGAGNDTLYGGAGNDTLYINAGADQLW FAR-QGNDLEIRILGTDDALTVHDWYRDADHRVEIIHAAN-QAVDQAGIEKLVEAMAQ YPD (SEQ ID NO: 4). In another embodiment, a PBRC comprises the amino acid sequence GGAGNDTLYGGAGNDTLYGGAGNDTLYG-GAGNDTLYGGAGNDTLYGGAGNDTL YGGAGNDT-LYGGAGNDTLYGGAGNDTLYGGAGNDTLYG-GAGNDTLYGGAGNDT LYGGAGNDTLYGGAGNDTLYGGAGNDTLYG-GAGNDTLYGGAGNDTLYINAGADQ LWFAR-QGNDLEIRILGTDDALTVHDWYRDADHRVEIIHAAN-QAVDQAGIEKLVEAM AQYPD (SEQ ID NO: 5). In another embodiment, the capping sequence comprises the sequence INAGADQLWFARQGNDLEIRILGTDDALT-VHDWYRDADHRVEAIHAANQAIDPAGI EKLVEAMAQYPD (SEQ ID NO: 6) (adenylate cyclase-hemolysin [*Bordetella bronchiseptica*]). In another embodiment, the capping sequence comprises the sequence INA-GADQLWFARQGNDLEIRILGTDDALTVHDWYRDA-DHRVEAIHAANQAIDPAGI EKLVEAMAQYPD (SEQ ID NO: 7) (adenylate cyclase-hemolysin [*Bordetella bronchiseptica*]). In another embodiment, the capping sequence comprises the sequence INAGADQLWFARQGNDLEIRIL-GTDDALTVHDWYRDADHRVEAIHAANQTVDPAGI EKLVEAMAQYPD (SEQ ID NO: 8) (adenylate cyclase hemolysin [*Bordetella bronchiseptica*]). In another embodiment, the capping sequence comprises the sequence QLWF-SKSGSDLEVRVVGTDDAVTVAGWYSGAEHHMDSI-ETADGTVLLDSMVDRLV QAMAGF (SEQ ID NO: 9) (Azospirillum sp. B510 calcium binding hemolysin protein). In another embodiment, the capping sequence comprises the sequence ADQLWFRHVGNDLEISILGTGDTATVRD-WYLGSRYQIEQIRVDDGRTLVNADVEKL VQAMA (SEQ ID NO: 10) (hemolysin-type calcium-binding region *Burkholderia cenocepacia* MCO-3). In another embodiment, the capping sequence comprises the sequence ADQL-WFRHVGNDLEISILGSSDTATVRDWYSGSRYQIEQ-IRLDDGRTLVNADVEKLV QAMA (SEQ ID NO: 11) (hemolysin-type calcium-binding region [*Burkholderia ambifaria* MC40-6]). In another embodiment, the capping sequence comprises the sequence DARQTNLWFSQVG-KDLQIDVLGSTDQVTVKDWYAGADNRVERIK-TADGKTLYDSD VDKLVQAMASF (SEQ ID NO: 12) (calcium binding secreted hemolysin protein) [Herbaspirillum seropedicae SmR1]). In another embodiment, the capping sequence comprises the sequence DARQTNLWF-SQVGKDLQIDVLGSTDQVTVKDWYAGADNRVERI-KTADGKTLYDSD VDKLVQAMASF (SEQ ID NO: 13) (calcium binding secreted hemolysin protein [Herbaspirillum seropedicae SmR1]). In another embodiment, the capping sequence comprises the sequence ELWFSRENND-LIIKSLLSEDKVTVQNWYSHQDHKIENIRLSNEQTLV-STQVEKMVES MAGF (SEQ ID NO: 14) (RTX toxin protein [*Actinobacillus pleuropneumoniae* serovar). In another embodiment, the capping sequence comprises the sequence EELWFSRDGNDLQINVIGTDNQVEISDWYS-GVNYQLDKVQVGDSVLLNTQLEQLVS AMASF (SEQ ID NO: 15) (hemolysin-type calcium binding protein [*Shewanella piezotolerans* WP3]). In another embodiment, the capping sequence comprises the sequence GLSELWF-SRENNDLIIKSLLSEDKVTVQNWYSHQDHKIENIRL-SNEQMLVSTQVEKM VESMAGF (SEQ ID NO: 16) (RTX toxin protein [*Actinobacillus pleuropneumoniae* serovar 10). In another embodiment, the capping sequence comprises the sequence EDLWFSRDGNNLQINIIGTD-DQVEVNNWYNDTNYQLDQIQVGGSVLLN-NQLEQLVS AMASF (SEQ ID NO: 17) (RTX toxin [*Shewanella violacea* DSS12]). In another embodiment, the capping sequence comprises the sequence ELWFSRENND-LIIKSLLSEDKVTVQNWYSHQDHKIENIRL-SNEQTLVSTQVEKMVES MASF (SEQ ID NO: 18) (RTX toxin protein [*Actinobacillus pleuropneumoniae* serovar 6). In another embodiment, the capping sequence comprises the sequence ADNFWFVKSGNDLEIDILGTHQQVTVADW-FLGGSYQLQEIKAGGLELDTQVTQLVQ AMATY (SEQ ID NO: 19) (protein BRAD06535 [*Bradyrhizobium* sp. ORS278]). In another embodiment, the capping sequence comprises the sequence ELWFSRENNDLIIKSLLSEDK-VTVQNWYSHQDHKIENIRLSNEQTLVSTQVEKMVES MAGF (SEQ ID NO: 20) ([*Actinobacillus pleuropneumoniae* L20]). In another embodiment, the capping sequence comprises the sequence LWFSRENNDLIIKSLLSEDKVT-VQNWYSHQDHKIENIRLSNEQTLVSTQVEKMVESM AGF (SEQ ID NO: 21) (ApxIVA [*Actinobacillus pleuropneumoniae*]). In another embodiment, the capping sequence comprises the sequence LWFRKSGNNLEVSI-IGTSDKLVMSNWYAGSQYQVERFQAGDGKALQAN-QVQSLVQ AMASF (SEQ ID NO: 22) (hemolysin-type calcium-binding protein [*Xanthomonas axonopodis* pv. *citri* str. 306]). In another embodiment, the capping sequence comprises the sequence ELWFSRENNDLIIKSLLSEDK-VTVQNWYSHQDHKIENIRLSNEQTLVSTQVEKMVES MAGF (SEQ ID NO: 23) (RTX toxin IVA [*Actinobacillus pleuropneumoniae*])

Without wishing to be bound to theory, in some embodiments of the invention, the ability of polypeptide comprising one or more PBRT to undergo reversible Ca2+ precipitation, can require that the one or more PBRTs be located N-terminally or C-terminally to a stabilizing polypeptide. It is known that when a certain stabilizing polypeptides (e.g. GFP, maltose binding protein) are attached to the C-terminus of the beta roll, calcium-induced folding can occur (Blenner et al., *Journal of Molecular Biology.* 400 (2010), pp 244-256; Szilvay et al., *Biochemistry,* 48 (2009), pp 11273-11282).

Thus, in one embodiment, a PBRC is an amino acid sequence comprising one or more PBRTs located N-terminally or C-terminally to a stabilizing polypeptide, wherein the stabilizing polypeptide cane be, but is not limited to, glutathione S-transferase (GST), maltose E binding protein (MBP), Green Fluorescent Protein (GFP), and variants thereof. In still a further embodiment, the stabilizing polypeptide is an amino acid sequence of any amino acid composition wherein the sequence comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or at least 68 amino acids.

In another aspect of the invention, the PBRCs described herein can further comprise one or more cleavage sites. In certain embodiments, the cleavage site can be positioned C-terminally or N-terminally to a PBRC so as to allow for cleavage of a PBRC from a linked purification moiety (e.g. a polypeptide purification moiety linked to a PBRC as part of a fusion protein). In embodiments where the PBRC comprises more than one cleavage site, a first cleavage site can be positioned C-terminally or N-terminally to a PBRC so as to allow for cleavage of a PBRC from a linked purification moiety (e.g. a polypeptide purification moiety linked to a PBRC as part of a fusion protein) and a second cleavage site can be positioned between a PBRT and a capping sequence or a PBRT and a stabilizing polypeptide so as to allow so as to allow for cleavage of the capping sequence or the stabilizing polypeptide from the one or more PBRTs in the PBRC. In certain embodiments, cleavage at such cleavage sites can be useful for purification of a purification moiety of interest.

In one embodiment, the cleavage site is a proteolytic cleavage site. Exemplary proteolytic cleavage sites, include, but are not limited to Factor Xa, thrombin, or enterokinase. In another embodiment, the cleavage site is a signal peptidase cleavage site. In another embodiment, the cleavage site is a self cleaving intein cleavage site (Amitai et al., *Proceedings of the National Academy of Sciences, vol.* 106, no. 27, pp. 11005-11010, July 2009; Hiraga et al., *Journal of Molecular Biology, vol.* 393, no. 5, pp. 1106-1117, November 2009). Any other specific cleavage sites known in the art can be used in connection with the methods described herein.

The PBRTs or PBRCs described herein may be linked to a purification moiety by any means known in the art. The PBRTs or PBRCs described herein ca be located at any site in a polypeptide comprising a purification moiety of interest, including a location that is N-terminal, a location that is C-terminal or a location within the sequence of the purification moiety of interest.

In addition to fusion proteins comprising the PBRTs or PBRCs described herein, the PBRTs or PBRCs described herein can also be chemically linked to purification moieties other than by means of a fusion protein. Thus, reference to a PBRC linked purification moiety, or to a PBRT linked purification moiety encompasses for purification moieties linked to a PBRC or PBRT by peptide linkage (e.g. as a fusion protein) or by non-peptide bond chemical linkage.

The chemical modification of PBRTs or PBRCs described herein can be performed according to any method known in the art. For example, amides of the PBRTs or PBRCs described herein can be prepared by techniques well known in the art for converting a carboxylic acid group or precursor, to an amide. One method for amide formation at the C-terminal carboxyl group is to cleave the polypeptide, or fusion thereof from a solid support with an appropriate amine, or to cleave in the presence of an alcohol, yielding an ester, followed by aminolysis with the desired amine.

Salts of carboxyl groups of the PBRTs or PBRCs described herein can be prepared by contacting the polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the PBRTs or PBRCs described herein can be prepared by utilizing an N-acyl protected amino acid for the final condensation, or by acylating a protected or unprotected polypeptide, or fusion thereof. O-acyl derivatives can be prepared, for example, by acylation of a free hydroxy polypeptide or polypeptide resin. Either acylation can be carried out using standard acylating reagents such as acyl halides, anhydrides, acyl imidazoles, and the like. Both N- and O-acylation can be carried out together, if desired.

Formyl-methionine, pyroglutamine and trimethyl-alanine can be substituted at the N-terminal residue of PBRTs or PBRCs described herein. Other amino-terminal modifications include aminooxypentane modifications.

Such chemical linkages can be useful for purifying non-peptide molecules such as lipids, oligonucleotides and carbohydrates, small organic or inorganic molecules, proteins, single-stranded or double-stranded oligonucleotides, polynucleotides, metals (e.g. cobalt, zinc, nickel or copper) and the like. The chemically modified PBRTs or PBRCs described herein can be assayed for the ability to bind to Ca2+, undergo reversible precipitation in the presence of Ca2+, or induce reversible precipitation of a purification moiety linked to the PBRT or PBRC using methods known to those skilled in the art.

The PBRTs and PBRCs described herein can also be coupled with a radioisotope or enzymatic label to facilitate their detection. For example, the PBRTs or PBRCs described herein can be isotopically-labeled where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds can depend on the specific application of that radio-labeled compound.

Alternatively, the PBRTs or PBRCs described herein can be enzymatically labeled with, for example, horseradish peroxidase, alkaline phosphatase, or luciferase, and the enzymatic label detected by determination of conversion of an appropriate substrate to product. In another embodiment, the PBRTs or PBRCs described herein can be labeled with a fluorescent dye, spin label, heavy metal or radio-labeled peptides.

Esters of carboxyl groups of the PBRTs or PBRCs described herein can also be prepared by any of the usual methods known in the art.

The methods and compositions described herein are useful in a broad range of bioseparation applications. The methods and compositions described herein can be used for rapid expression and purification of a purification moiety linked to a PBRC. Such PBRC linked purification moieties can be expressed in any number of expression systems, including in vitro and in vivo expression systems. Exemplary in vivo expression systems suitable for expressing the PBRC linked purification moieties described herein, include, but are not limited to, bacterial systems, yeast systems, and mammalian systems.

In one aspect, the invention relates to a method for purifying purification moieties (e.g. a PBRC or a purification moiety linked to a PBRC). In one aspect, the methods described herein can be used for purifying one or more purification moieties from a heterogeneous mixture of biomaterials in a sample. In another aspect, the methods descried herein can be used to purify chemically synthesized purification moieties or in-vitro synthesized purification moieties.

In certain embodiments, the bioseparation methods described herein can comprise expressing a PBRT linked purification moiety (e.g. a PBRC fusion protein) in a cellular expression system (e.g. a bacterial cell). The PBRC linked purification moiety can then be released into a medium by cell lysis. Any method of cell lysis known in the art can be used in conjunction with the methods described herein, including, but not limited to chemical lysis (e.g. detergents) or physical methods (e.g. sonication or French press). In certain embodiments, the PBRC or PBRC linked purification moiety can be expressed in an in-vitro expression system (e.g. a rabbit reticulocyte system) such that the purification moiety is expressed into the expression system medium.

After expression of the PBRC linked purification moiety, bioseparation can be achieved by increasing the free Ca2+ concentration in the medium comprising the PBRC linked purification moiety to induce precipitation of the PBRC linked purification moiety, followed by removing material that does not precipitate from the medium and then resuspending the precipitated material in a medium having a reduced Ca2+ concentration or in a medium having a reduced concentration of free Ca2+ (e.g. a medium comprising a Ca2+ chelators such as EDTA). These steps can be repeated until the desired level of purity is reached.

In another embodiment, the PBRC linked purification moiety can be expressed in a cellular expression system, and bioseparation can be achieved by increasing the free Ca2+ concentration within the cell prior to cellular lysis. Many methods for increasing intracellular Ca2+ concentrations are known in the art, including, but not limited to adding Ca2+ to a cellular medium, with or without presence of ionophores or cell permeabilization agents. In such embodiments, the cells can then be subjected to lysis conditions (e.g. chemical lysis or physical lysis) and the resulting precipitate can be recovered. Precipitated PBRC or the PBRC linked purification moieties can then be recovered by reducing the free Ca2+ concentration (e.g. through the addition of a Ca2+ chelator) to induce solubilization of the purification moieties from the precipitate and bioseparation can be achieved by eliminating the precipitate. Precipitation and solubilization steps can be repeated until a desired level of purity is reached.

In still other embodiments, the PBRC linked purification moieties described herein can further comprise a peptide sequence to induce secretion into the periplasm of a cell (e.g. an *E. coli* cell) or to the medium outside of a cell. Where the PBRC linked purification moiety is secreted to the periplasm of a cell, cell lysis may be required for further purification of the PBRC linked purification moiety. Where the PBRC linked purification moiety is secreted into the medium outside of the cell, purification can be achieved without cell lysis by eliminating intact cells (e.g. by centrifugation) and purification of the PBRC linked purification moiety from the extracellular medium by increasing the free Ca2+ concentration of the supernatant.

The adjustment of conditions during the purification process can be achieved by numerous methods, including, but not limited to, adjusting the temperature, pH or salt concentration of the aqueous media.

The methods described herein can be used to purify purification moieties of any size. A purified PBRT linked purification moiety can contain less than about 50%, less than about 75%, or less than about 90%, of the materials with which it was originally associated.

In one embodiment, a purification moiety of interest can be linked to PBRC comprising a cleavable peptide sequence (e.g. a self-cleaving peptide sequence such an intein) positioned between the PBRC and the purification moiety. Once the PBRC linked purification moiety is expressed in an expression system, the PBRC linked purification moiety can be recovered using standard techniques as either a homogenous mixture or as a heterogeneous sample. The mixture can then be exposed to calcium to induce precipitation of the PBRC linked purification moiety. The PBRC linked purification moiety can then be resuspended in buffer that has reduced Ca2+, that has reduced free Ca2+ or that contains a calcium chelator (e.g. EDTA). The PBRC linked purification moiety can then be subjected condition that cause cleavage to separate the PBRC from the purification moiety and calcium can be once again added to the mixture. This will precipitate out the PBRC moiety and thereby leaving behind a sample of purified purification moiety of interest.

In another embodiment, PBRC linked purification moiety can be a moiety which binds a second molecule and the second molecule can be used to remove the purification moiety from the sample (e.g. a resin or beads coated with the second molecule) after induced cleavage at a site between the purification moiety and the PBRC.

In some embodiments, immobilization of the PBRC linked purification moieties described herein or its binding proteins can be used to facilitate separation of complexes from uncomplexed forms of one or both of the proteins, as well as to accommodate automation of the assay Immobilization of the PBRC linked purification moieties described herein can be by linking to a solid support, including a plastic or glass plate or bead, a chromatographic resin, a filter or a membrane. Methods of attachment of proteins, or membranes containing same, to such supports are well known in the art Immobilization of the PBRC linked purification moieties described herein can also be accomplished in any vessel suitable for containing the reactants. Examples include microtiter plates, test tubes, and micro-centrifuge tubes.

In one embodiment, a fusion protein can be provided which adds a domain that allows the PBRT linked purification moiety described herein to be bound to a matrix. For example, glutathione-S-transferase fusion proteins can be adsorbed onto glutathione sepharose beads or glutathione derivatized microtiter plates, which are then combined with the cell lysates, and the mixture incubated under conditions conducive to complex formation. Following incubation, the beads can be washed to remove any unbound fraction. Alternatively, the complexes can be dissociated from the matrix using standard electrophoretic techniques.

The methods described herein depend, in part on the finding that PBRCs undergo a reversible Ca2+ binding dependent transition. PBRCs or PBRC linked purification moieties undergo reversible precipitation at a Ca2+ concentration (or free Ca2+) phase transition concentration.

The transition concentrations reversible and the isolated precipitable beta-roll tags or purification moieties comprising a precipitable beta-roll tag can be completely resolubilized in a medium below a certain Ca2+ concentration (or free Ca2+) transition concentration, through, for example the addition of a calcium chelator into the medium comprising the PBRC or PBRC linked purification moiety.

The concentration of Ca2+ required to induce reversible precipitation of a PBRC or PBRC linked purification moiety can be readily determined by adding increasing amounts of Ca2+ until such time as the PBRC or PBRC linked purification moiety begins to precipitate from a the medium. One can readily determine the extent of precipitation by centrifuging the medium. In one embodiment, the amount of Ca2+ required to induce reversible precipitation a PBRC of PBRC linked purification moiety will be about 1 mM Ca2+, more than about 1 mM Ca2+, more than about 5 mM Ca2+, more than about 10 mM Ca2+, more than about 20 mM Ca2+, more than about 30 mM Ca2+, more than about 50 mM Ca2+, more than about 75 mM Ca2+, more than about 100 mM Ca2+, more than about 150 mM Ca2+, more than about 200 mM Ca2+, or more than about 500 mM Ca2+. In certain embodiments, the amount of Ca2+ required to induce precipitation of a PBRC or PBRC linked purification moiety can increase as a function of the number of PBRTs in the PBRC. For example, a PBRC linked purification moiety comprising 8 PBRTs may precipitate in 150 mM Ca2+ wherein a PBRC linked purification moiety comprising 17 PBRTs may precipitate in 25 mM Ca2+. One of skill in the art will readily be capable of determining the amount of Ca2+ required to precipitate a particular PBRC or a particular PBRC linked purification moiety simply by titrating increasing concentrations of Ca2+.

The concentration of Ca2+ required to reverse precipitation of a PBRT or PBRC or of a PBRT or PBRC linked purification moiety can be readily determined by reducing the concentration of free Ca2+ in a medium until such time as a precipitated PBRC or PBRC linked purification moiety begins to solubilize into the medium. One can readily determine the extent of precipitation by centrifuging the medium. In one embodiment, the amount of free Ca2+ in the medium required to solubilize a precipitated PBRT or PBRC or of a PBRT or PBRC linked purification moiety will be less than about 1 mM Ca2+, less than about 1 mM Ca2+, less than about 5 mM Ca2+, less than about 10 mM Ca2+, less than about 20 mM Ca2+, less than about 30 mM Ca2+, less than about 50 mM Ca2+, less than about 75 mM Ca2+, less than about 100 mM Ca2+, less than about 150 mM Ca2+, less than about 200 mM Ca2+, or less than about 500 mM Ca2+. In certain embodiments, the free Ca2+ concentration required to reverse precipitation of a PBRC or a PBRC linked purification moiety can correlated to the number of PBRTs in the PBRC. For example, a PBRC linked purification moiety comprising 8 PBRTs may become soluble in a higher free Ca2+ concentration as compared to a PBRC linked purification moiety comprising 17 PBRTs. One of skill in the art will readily be capable of determining the Ca2+ concentration required to reverse precipitation a particular PBRC or a particular PBRC linked purification moiety simply by decreasing free Ca2+ concentrations.

The free Ca2+ concentration of a medium comprising a PBRC or a PBRC linked purification moiety can be reduced by adding one or more calcium chelators into the medium. Any number of calcium chelators can be used in the connection with the methods described herein. Examples of suitable calcium chelators include, but are not limited to EDTA, EGTA, and BAPTA. In one embodiment, the amount of a calcium chelator required to solubilize a precipitated PBRT or PBRC or of a PBRT or PBRC linked purification moiety will be about 1 mM Ca2+, more than about 1 mM Ca2+, more than about 5 mM Ca2+, more than about 10 mM Ca2+, more than about 20 mM Ca2+, more than about 30 mM Ca2+, more than about 50 mM Ca2+, more than about 75 mM Ca2+, more than about 100 mM Ca2+, more than about 150 mM Ca2+, more than about 200 mM Ca2+, or more than about 500 mM Ca2+.

In addition to temperature and ionic strength, other environmental variables useful for modulating the solubility of PBRT or PBRC or of the PBRT linked purification moieties described herein include pH, the addition of organic solutes and solvents, side-chain ionization or chemical modification, and pressure.

The PBRC linked purification moieties described herein can be further purified or isolated according to any method of protein purification or isolation known in the art. For example, PBRCs or PBRC linked purification moieties can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, the PBRCs or the PBRC linked purification moieties can be produced in a recombinant system in which the protein contains an additional sequence tag that facilitates purification, such as, but not limited to, a polyhistidine sequence, or a sequence that specifically binds to an antibody, such as FLAG and GST. In one embodiment, the PBRCs or the PBRC linked purification moieties can be purified from a crude lysate of the host cell by chromatography on an appropriate solid-phase matrix. Alternatively, antibodies produced against the PBRTs or PBRCs, or a PBRC linked purification moiety or against polypeptides derived therefrom can be used as purification reagents.

The methods and compositions described herein can be useful for the detection of a broad range of purification moieties in biosensing applications. For example, the methods and compositions described herein can be used for the separation of protein of interest from a sample for detection of bimolecular interactions. In one embodiment, if a PBRC is linked to an antibody, the PBRC linked antibody can be added to a sample. Ca2+ can then be added to the sample to induce precipitation of the antibody such that antigen that interact with, or form a complex with, the antibody also precipitate upon the addition of Ca2+. The precipitate can then be collected and resuspended and the sample can be characterized. The presence and quantity of the target in the original sample, as well as any associated purification moieties, can be characterized and determined. Any antibodies, antibody fragments, antibody configurations, classes, or subclasses known in the art can be used in connection with the methods described herein. In another embodiment, if a PBRC is fused to a polypeptide capable of binding to a second purification moiety, it can be added to a sample. Ca2+ can then be added to the sample to induce precipitation of the polypeptide such that other purification moieties that interact with, or form a complex with, the polypeptide also precipitate upon the addition of Ca2+. The precipitate can then be collected and resuspended and the sample can be characterized. The presence and quantity of the target in the original sample, as well as any associated additional purification moieties, can be characterized and determined.

The PBRC linked purification moieties described herein can be produced in prokaryotic or eukaryotic host cells by expression of nucleic acids encoding a polypeptide of this invention. The production of these polypeptides can also be done as part of a larger polypeptide.

The PBRC linked purification moieties described herein can also be synthesized in vitro, e.g., by the solid phase polypeptide synthetic method or by recombinant DNA approaches described herein. The solid phase polypeptide synthetic method is an established and widely used method. These PBRC or PBRC linked purification moieties described herein can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

The PBRC linked purification moieties described herein can also be produced using any in-vitro expression system known in the art or can be synthesized by chemical methods. Methods for expression of heterologous proteins in recombinant hosts, chemical synthesis of polypeptides, and in vitro translation are well known in the art and are described further in Sambrook J et al.; Berger and Kimmel, Methods in Enzymology, Volume 152, Guide to Molecular Cloning Techniques (1987), Academic Press, Inc., San Diego, Calif.; Gutte B and Merrifield R B, J. Am. Chem. Soc. 91:501-02 (1969); Chaiken I M, CRC Crit. Rev. Biochem. 11:255-301 (1981); Kaiser E T et al., Science 243:187-92 (1989); Merrifield B, Science 232:341-47 (1986); Kent S B H, Ann. Rev. Biochem. 57:957-89 (1988); Offord, R. E. (1980) Semisynthetic Proteins, Wiley Publishing. Exemplary peptide synthesis methods known in the art include, but are not limited to those described in Stewart et al., Solid Phase Peptide Synthesis, Pierce Biotechnology, Inc., Rockford, Ill., 1984; Bodanszky, Principles of Peptide Synthesis, Springer-Verlag, New York, 1984; and Pennington et al., Peptide Synthesis Protocols, Humana Press, Totowa, N.J., 1994). Additionally, many companies offer custom peptide synthesis services.

The PBRC linked purification moieties described herein can also be produced by direct chemical synthesis. For example, the PBRC linked purification moieties described herein can be produced as modified polypeptides, with nonpeptide moieties attached by covalent linkage to the N-terminus and/or C-terminus. In certain embodiments, either the carboxy-terminus or the amino-terminus, or both, are chemically modified. Common modifications of the terminal amino and carboxyl groups, include, but are not limited to acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments. Certain amino-terminal and/or carboxy-terminal modifications and/or polypeptide extensions to the core sequence can provide advantageous physical, chemical, biochemical, and pharmacological properties, such as: enhanced stability, increased potency and/or efficacy, resistance to serum proteases, desirable pharmacokinetic properties, and others.

The PBRC linked purification moieties can be prepared using recombinant DNA and molecular cloning techniques. Genes encoding the PBRC linked purification moieties may be produced in heterologous host cells, particularly in the cells of microbial hosts. Any techniques for transfecting host cells and purifying proteins and polypeptides known in the art can be used in connection with the methods described herein. Exemplary epitope tags suitable for use with the methods described herein include, but are not limited to FLAG, HA, Myc and T7 epitope tags. The PBRTs, PBRCs or PBRC linked purification moieties described herein can be synthesized chemically using standard polypeptide synthesis techniques.

The invention also extends to the DNA expression vector comprising DNA coding for the PBRTs or PBRCs described herein, whether or not the encoded products further comprise a linked purification moiety. The invention also provides the expression vector comprising sequences coding for a PBRT or a PBRC configured to allow insertion of a DNA sequence downstream of the sequence coding for the PBRT or the PBRC so as to facilitate production of a fusion protein comprising a PBRT or a PBRC. For example, such vectors can comprise one or more cloning sites between the sequence coding for the PBRT or the PBRC to enable generation of an in-frame translation product. Such vectors may comprise multiple cloning sites in any of three reading frames. Methods for generating such expression vectors are well known in the art.

A variety of expression systems can be used to produce the PBRCs and PBRC linked purification moieties described herein. Such expression systems include vector based expression systems. Exemplary vector base expression systems suitable for use with the methods described herein include, but are not limited to, chromosomal, episomal and virus-derived vectors, e.g., vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids.

The expression system vectors may contain regulatory regions that regulate as well as engender expression. In general, any system or vector suitable to maintain, propagate or express polynucleotide or polypeptide in a host cell may be used for expression in this regard. Expression systems and expression vectors can contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

A number of recombinant expression vectors can be used for expression of the PBRCs and PBRC linked purification moieties described herein. For example, the PBRT linked purification moieties described herein can be expressed in bacterial cells such as E. coli, insect cells (e.g., using baculovirus expression vectors), yeast cells, amphibian cells, or mammalian cells. Suitable host cells are well known to one skilled in the art. Alternatively, the recombinant expression vector can be transcribed and translated in vitro, using, for example T7 promoter regulatory sequences and T7 polymerase.

Examples of E. coli expression vectors include pTrc (Amann E et al., Gene 69:301-15 (1988)) and pET 11d (Studier et al., Gene Expression Technology: Methods in Enzymology 185, Academic Press, San Diego, Calif. (1990) pp. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman S, Gene Expression Technology: Methods in Enzymology 185, Academic Press, San Diego, Calif. (1990) pp. 119-28). Another strategy is to alter the nucleic acid sequence of the nucleic acid to be inserted into an expression vector so that the individual codons for each amino acid are those preferentially utilized in E. coli (Wada K et al., Nucleic Acids Res. 20(Suppl.):2111-18 (1992)). Such alteration of nucleic acid sequences can be carried out by standard DNA synthesis techniques.

In another approach, a nucleic acid can be expressed in mammalian cells using a mammalian expression vector. Examples of mammalian expression vectors include pCDM8 (Seed B, Nature 329:840-41 (1987)) and pMT2PC (Kaufman R J et al., EMBO J. 6:187-95 (1987)). When used in mammalian cells, the expression vector's control functions can be provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989.

A number of these methodologies can also be applied in vivo, systemically or locally, in a complex biological system such as a human. For example, increased copy number of nucleic acids PBRC or PBRC linked purification moieties described herein in expressible from (by DNA transfection), can be employed.

Nucleic acid purification moieties encoding PBRT or PBRC linked purification moieties described herein can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example, Gonzalez et al., Bioconjugate Chem. 10:1068-1074, 1999; Wang et al., International PCT Publication Nos. WO 03/47518 and WO 03/46185), poly(lactic-co-glycolic)ac-id (PLGA) and PLCA microspheres (see for example, U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722).

This invention may also be of use in the pharmaceutical/biotechnology industry where therapeutic compounds need to be purified in large quantities. This approach provides very pure product in a very quick manner.

Purification moieties that can be linked to the PBRTs or PBRCs described herein can be any purification moiety, including a biologically active protein (e.g., a therapeutic peptide, protein or an enzyme useful in industrial biocatalysis).

The purification moieties suitable for use with the methods described herein can be of widely varying types, including, for example, peptides, non-peptide proteins, lipids, oligonucleotides and carbohydrates, or alternatively a ligand-binding protein or an active fragment thereof having binding affinity to a molecule selected from the group consisting of small organic or inorganic molecules, proteins, peptides, single-stranded or double-stranded oligonucleotides, polynucleotides, lipids, and carbohydrates.

Suitable purification moieties include, but are not limited to, molecules useful in medicine, agriculture and other scientific and industrial fields. For example, suitable molecules include those of interest in medicine, agriculture or other scientific or industrial fields. Examples of suitable proteins include enzymes utilized in replacement therapy; hormones for promoting growth in animals, or cell growth in cell culture; and active proteinaceous substances used in various applications, e.g., in biotechnology or in medical diagnostics. One of skill in the art will recognize that many types of recombinant polypeptides can be produced using the methods described herein. The present invention is not limited to any specific types of recombinant polypeptide described herein. Instead, it encompasses any and all recombinant polypeptides.

The PBRTs or PBRCs described herein can be joined to a purification moiety from any source or origin and can include a polypeptide found in prokaryotes, viruses, and eukaryotes, including fungi, plants, yeasts, insects, and animals, including mammals (e.g. humans). Purification moieties suitable for use with the methods described herein include, but are not limited to any polypeptide sequences, known or hypothetical or unknown, which can be identified using common sequence repositories. Examples of such sequence repositories, include, but are not limited to GenBank EMBL, DDBJ and the NCBI. Other repositories can easily be identified by searching on the internet. Polypeptides that can be produced using the methods described herein also include polypeptides have at least about 60%, 70%, 75%, 80%, 90%, 95%, or at least about 99% or more identity to any known or available polypeptide (e.g., a therapeutic polypeptide, a diagnostic polypeptide, an industrial enzyme, or portion thereof, and the like).

Purification moieties suitable for use with the methods described herein include, but are not limited to, polypeptides comprising one or more non-natural amino acids.

Purification moieties suitable for use with the methods described herein include, but are not limited to, cytokines, inflammatory molecules, growth factors, their receptors, and oncogene products or portions thereof. Examples of cytokines, inflammatory molecules, growth factors, their receptors, and oncogene products include, but are not limited to e.g., alpha-1 antitrypsin, Angiostatin, Antihemolytic factor, antibodies (including an antibody or a functional fragment or derivative thereof selected from: Fab, Fab', F(ab)2, Fd, Fv, ScFv, diabody, tribody, tetrabody, dimer, trimer or minibody), angiogenic molecules, angiostatic molecules, Apolipopolypeptide, Apopolypeptide, Asparaginase, Adenosine deaminase, Atrial natriuretic factor, Atrial natriuretic polypeptide, Atrial peptides, Angiotensin family members, Bone Morphogenic Polypeptide (BMP-1, BMP-2, BMP-3, BMP-4, BMP-5, BMP-6, BMP-7, BMP-8a, BMP-8b, BMP-10, BMP-15, etc.); C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant polypeptide-1, Monocyte chemoattractant polypeptide-2, Monocyte chemoattractant polypeptide-3, Monocyte inflammatory polypeptide-1 alpha, Monocyte inflammatory polypeptide-1 beta, RANTES, 1309, R83915, R91733, HCC1, T58847, D31065, T64262), CD40 ligand, C-kit Ligand, Ciliary Neurotrophic Factor, Collagen, Colony stimulating factor (CSF), Complement factor 5a, Complement inhibitor, Complement receptor 1, cytokines, (e.g., epithelial Neutrophil Activating Peptide-78, GRO alpha/MGSA, GRO beta, GRO gamma, MIP-1 alpha, MIP-1 delta, MCP-1), deoxyribonucleic acids, Epidermal Growth Factor (EGF), Erythropoietin ("EPO", representing a preferred target for modification by the incorporation of one or more non-natural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog polypeptides (e.g., Sonic, Indian, Desert), Hemoglobin, Hepatocyte Growth Factor (HGF), Hepatitis viruses, Hirudin, Human serum albumin, Hyalurin-CD44, Insulin, Insulin-like Growth Factor (IGF-I; IGF-II), interferons (e.g., interferon-alpha, interferon-beta, interferon-gamma, interferon-epsilon, interferon-zeta, interferon-eta, interferon-kappa, interferon-lambda, interferon-T, interferon-zeta, interferon-omega), glucagon-like peptide (GLP-1), GLP-2, GLP receptors, glucagon, other agonists of the GLP-1R, natriuretic peptides (ANP, BNP, and CNP), Fuzeon and other inhibitors of HIV fusion, Hurudin and related anticoagulant peptides, Prokineticins and related agonists including analogs of black mamba snake venom, TRAIL, RANK ligand and its antagonists, calcitonin, amylin and other glucoregulatory peptide hormones, and Fc fragments, exendins (including exendin-4), exendin receptors, interleukins (e.g., IL-1, IL-2, IL-3, IL-4, IL-5, IL-6, IL-7, IL-8, IL-9, IL-10, IL-11, IL-12, etc.), I-CAM-1/LFA-1, Keratinocyte Growth Factor (KGF), Lactoferrin, leukemia inhibitory factor, Luciferase, Neurturin, Neutrophil inhibitory factor (NIF), oncostatin M, Osteogenic polypeptide, Parathyroid hormone, PD-ECSF, PDGF, peptide hormones (e.g., Human Growth Hormone), Oncogene products (Mos, Rel, Ras, Raf, Met, etc.), Pleiotropin, Polypeptide A, Polypeptide G, Pyrogenic exotoxins A, B, and C, Relaxin, Renin, ribonucleic acids, SCF/c-kit, Signal transcriptional activators and suppressors (p53, Tat, Fos, Myc, Jun, Myb, etc.), Soluble complement receptor 1, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Steroid hormone receptors (such as those for estrogen, progesterone, testosterone, aldosterone, LDL receptor ligand and corticosterone), Superoxide dismutase (SOD), Toll-like receptors (such as Flagellin), Toxic shock syndrome toxin (TSST-1), Thymosin a 1, Tissue plasminogen activator, transforming growth factor (TGF-alpha, TGF-beta), Tumor necrosis factor beta (TNF beta), Tumor necrosis factor receptor (TNFR), Tumor necrosis factor-alpha (TNF alpha), transcriptional modulators (for example, genes and transcriptional modular polypeptides that regulate cell growth, differentiation and/or cell regulation), Vascular Endothelial Growth Factor (VEGF), virus-like particle, VLA-4NCAM-1, Urokinase, signal transduction molecules, estrogen, progesterone, testosterone, aldosterone, LDL, corticosterone.

Additional purification moieties suitable for use with the methods described herein include, but are not limited to, enzymes (e.g., industrial enzymes) or portions thereof. Examples of enzymes include, but are not limited to amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases. In certain embodiments, such enzymes comprising a PBRT or PBRC can be used as immobilized enzymes in industrial biocatalysis. The enzymes comprising a PBRTs or a PBRC can also be added to a solution to facilitate biocatalysis and then reisolated from the solution.

Additional purification moieties suitable for use with the methods described herein include, but are not limited to, agriculturally related polypeptides such as insect resistance polypeptides (e.g., Cry polypeptides), starch and lipid production enzymes, plant and insect toxins, toxin-resistance polypeptides, Mycotoxin detoxification polypeptides, plant growth enzymes (e.g., Ribulose 1,5-Bisphosphate Carboxylase/Oxygenase), lipoxygenase, and Phosphoenolpyruvate carboxylase.

Additional purification moieties suitable for use with the methods described herein include, but are not limited to, antibodies, immunoglobulin domains of antibodies and their fragments. Examples of antibodies include, but are not limited to antibodies, antibody fragments, antibody derivatives, Fab fragments, Fab' fragments, F(ab)2 fragments, Fd fragments, Fv fragments, single-chain Fv fragments (scFv), diabodies, tribodies, tetrabodies, dimers, trimers, and minibodies.

Additional purification moieties suitable for use with the methods described herein include, but are not limited to, prophylactic vaccine or therapeutic vaccine polypeptides. A prophylactic vaccine is one administered to subjects who are not infected with a condition against which the vaccine is designed to protect. In certain embodiments, a preventive vaccine will prevent a virus from establishing an infection in a vaccinated subject. However, even if it does not provide complete protective immunity, a prophylactic vaccine may still confer some protection to a subject. For example, a prophylactic vaccine may decrease the symptoms, severity, and/or duration of the disease. A therapeutic vaccine, is administered to reduce the impact of a viral infection in subjects already infected with that virus. A therapeutic vaccine may decrease the symptoms, severity, and/or duration of the disease. Vaccine polypeptides include polypeptides, or polypeptide fragments from infectious fungi (e.g., *Aspergillus*, *Candida* species) bacteria (e.g. *E. coli*, *Staphylococci aureus*)), or Streptococci (e.g., *pneumoniae*); protozoa such as sporozoa (e.g., Plasmodia), rhizopods (e.g., *Entamoeba*) and *flagellates* (*Trypanosoma*, *Leishmania*, *Trichomonas*, *Giardia*, etc.); viruses such as (+) RNA viruses (examples include Poxviruses e.g., vaccinia; Picornaviruses, e.g., polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Additional purification moieties suitable for use with the methods described herein include, but are not limited to, molecules that comprise a chemical moiety selected from the group consisting of: cytotoxins, pharmaceutical drugs, dyes or fluorescent labels, a nucleophilic or electrophilic group, a ketone or aldehyde, azide or alkyne compounds, photocaged groups, tags, a peptide, a polypeptide, a polypeptide, an oligosaccharide, polyethylene glycol with any molecular weight and in any geometry, polyvinyl alcohol, metals, metal complexes, polyamines, imidizoles, carbohydrates, lipids, biopolymers, particles, solid supports, a polymer, a targeting agent, an affinity group, any agent to which a complementary reactive chemical group can be attached, biophysical or biochemical probes, isotypically-labeled probes, spin-label amino acids, fluorophores, aryl iodides and bromides.

Reference is also made to a "variant PBRT." A variant PBRT is a PBRT comprising one or more amino acid substitutions any position in the sequence of SEQ ID NO: 1 wherein the substitution replaces any amino acid in position 1 through 9 with an amino acid having a similar side chain group, an amino acid having a similar side chain configuration, an amino acid having an evolutionary positive relatedness, or an amino acid having an evolutionary neutral relatedness.

As used herein, the term "variant precipitable-beta roll cassette" (PBRC) refers to an amino acid sequence comprising at least one variant PBRT. In certain embodiments, a variant PBRC will comprise at least two variant PBRTs. In certain embodiments, a variant PBRC will comprise at least 3 variant PBRTs, at least 4 variant PBRTs, at least 5 variant PBRTs, at least 6 variant PBRTs, at least 7 variant PBRTs, at least 8 variant PBRTs, at least 9 variant PBRTs, at least 10 variant PBRTs, at least 11 variant PBRTs, at least 12 variant PBRTs, at least 13 variant PBRTs, at least 14 variant PBRTs, at least 15 variant PBRTs, at least 16 variant PBRTs, at least 17 variant PBRTs, at least 18 variant PBRTs, at least 19 variant PBRTs, at least 20 variant PBRTs, or 20 or more variant PBRTs. In certain embodiments, the PBRCs described herein will comprise a plurality of variant precipitable beta roll tags arranged in a tandem repeat. For example, in certain embodiments, the variant PBRCs described herein can comprise at least 2 variant PBRTs, at least 3 variant PBRTs, at least 4 variant PBRTs, at least 5 variant PBRTs, at least 6 variant PBRTs, at least 7 variant PBRTs, at least 8 variant PBRTs, at least 9 variant PBRTs, at least 10 variant PBRTs, at least 11 variant PBRTs, at least 12 variant PBRTs, at least 13 variant PBRTs, at least 14 variant PBRTs, at least 15 variant PBRTs, at least 16 variant PBRTs, at least 17 variant PBRTs, at least 18 variant PBRTs, at least 19 variant PBRTs, at least 20 variant PBRTs, or 20 or more variant PBRTs in tandem repeat. In certain embodiments, a PBRC can comprise at least two PBRCs separated by a linking amino acid sequence. Where a linking amino acid sequence in present between two PBRTs, a PBRTs located at either end of the linking sequence can be an individual PBRT or it can be a PBRTs that is part of a tandem arrangement.

Thus in certain embodiments, a variant PBRC will comprise at least 2 variant PBRCs, at least variant 3 PBRTs, at least 4 variant PBRTs, at least 5 variant PBRTs, at least 6 variant PBRTs, at least 7 variant PBRTs, at least 8 variant PBRTs, at least 9 variant PBRTs, at least 10 variant PBRTs, at least 11 variant PBRTs, at least 12 variant PBRTs, at least 13 variant PBRTs, at least 14 variant PBRTs, at least 15 variant PBRTs, at least 16 variant PBRTs, at least 17 variant PBRTs, at least 18 variant PBRTs, at least 19 variant PBRTs, at least 20 variant PBRTs, or 20 or more variant PBRTs, all of which are located N-terminally to a CS. In certain embodiments, a variant PBRC will comprise at least 2 variant PBRCs, at least variant 3 PBRTs, at least 4 variant PBRTs, at least 5 variant PBRTs, at least 6 variant PBRTs, at least 7 variant PBRTs, at least 8 variant PBRTs, at least 9 variant PBRTs, at least 10 variant PBRTs, at least 11 variant PBRTs, at least 12 variant PBRTs, at least 13 variant PBRTs, at least 14 variant PBRTs, at least 15 variant PBRTs, at least 16 variant PBRTs, at least 17 variant PBRTs, at least 18 variant PBRTs, at least 19 variant PBRTs, at least 20 variant PBRTs, or 20 or more variant PBRTs, all of which are located C-terminally to a CS.

In certain aspects, the invention relates to a variant PBRT that contains one or more amino acid insertions, deletions or substitutions as compared to the sequence of SEQ ID NO: 1 and wherein the variant PBRT retains an ability to bind to Ca2+, undergo reversible precipitation in the presence of Ca2+, or induce reversible precipitation of a purification moiety linked to the PBRT.

Changes can be introduced by mutation into nucleic acid sequences, thereby leading to changes in the amino acid sequence of the encoded protein, without altering the functional activity of a PBRT or a PBRC. For example, nucleotide substitutions leading to amino acid substitutions at non-essential amino acid residues can be made in the sequence of a PBRT or a PBRC. A non-essential amino acid residue is a residue that can be altered from the sequence of an amino acid of this invention without altering the ability of the PBRT or PBRC to bind to bind to Ca2+, undergo reversible precipitation in the presence of Ca2+, or induce reversible precipitation of a purification moiety linked to the PBRT or PBRC.

Exemplary residues which are non-essential and therefore amenable to substitution to generate the variant PBRTs and PBRCs described herein can be identified by one of ordinary skill in the art by performing an amino acid alignment of two more PBRTs or PBRCs and determining residues that are not required for the PBRT or PBRC to bind to Ca2+, undergo reversible precipitation in the presence of Ca2+, or induce reversible precipitation of a purification moiety linked to the PBRT or PBRC.

Mutations can be introduced randomly along all or part of a nucleic acid sequence encoding a PBRT or PBRC, such as by saturation mutagenesis, and the resultant mutants can be screened, for example, for their ability bind to Ca2+, undergo reversible precipitation in the presence of Ca2+, or induce reversible precipitation of a purification moiety linked to the variant PBRT or variant PBRC. Following mutagenesis, the purification moiety linked to the variant PBRT or variant PBRC can be expressed recombinantly in a host cell and the functional activity of the precipitable beta-roll tag can be determined using assays available in the art for assessing binding to Ca2+, undergoing reversible precipitation in the presence of Ca2+, or inducing reversible precipitation of purification moiety linked to the variant PBRT or variant PBRC. In certain embodiments, the variant PBRTs described herein can comprise one or more amino acid substitutions, insertions or deletions, wherein the variant PBRT is functionally equivalent a PBRT having the sequence GGAGNDTLY (SEQ ID No. 1). In one embodiment, the variant PBRT has an identical ability bind to Ca2+, undergo reversible precipitation in the presence of Ca2+, or induce reversible precipitation of a purification moiety in a manner similar to, but not necessarily identical to a PBRC comprising only PBRTs of the sequence GGAGNDTLY (SEQ ID NO: 1). In one embodiment, the variant PBRT has a reduced ability bind to Ca2+, undergo reversible precipitation in the presence of Ca2+, or induce reversible precipitation of a purification moiety in a manner similar to, but not necessarily identical to a PBRC comprising only PBRTs of the sequence GGAGNDTLY (SEQ ID NO: 1). In one embodiment, the variant PBRT has an increased ability bind to Ca2+, undergo reversible precipitation in the presence of Ca2+, or induce reversible precipitation of a purification moiety in a manner similar to, but not necessarily identical to a PBRC comprising only PBRTs of the sequence GGAGNDTLY (SEQ ID NO: 1).

The variant PBRCs described herein can also comprise on or more PBRTs in addition to one or more variant PBRTs. The variant PBRCs described herein can also be employed in any embodiments or configuration described herein for a PBRC. Thus, the description of a composition comprising a PBRC, or a method comprising a PBRC applies equally to a variant PBRT or a variant PBRC so long as the variant PBRT or the variant PBRC can bind to Ca2+, undergo reversible precipitation in the presence of Ca2+, or induce reversible precipitation of a purification moiety in a manner similar to, but not necessarily identical to a PBRC comprising only PBRTs of the sequence GGAGNDTLY (SEQ ID NO: 1).

In one embodiment, a variant PBRT comprises the sequence GGXGXDXXX (SEQ ID NO: 2) wherein X can be selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In one embodiment, the variant PBRT has a sequence of GGXGXDXXX (SEQ ID NO: 2), wherein X is not proline. In one embodiment, the variant PBRT comprises the sequence GGXGXDXXX (SEQ ID NO: 2) wherein X is a natural or non-natural amino acid comprising a modification.

In one embodiment, a variant PBRT or PBRC comprises an amino acid sequence having at least about 75%, 80%, 85%, 90%, 95%, 98%, 99% identity with an amino acid sequence of SEQ ID NO: 1.

As used herein, "sequence identity" means the percentage of identical nucleotide or amino acid residues at corresponding positions in two or more sequences when the sequences are aligned to maximize sequence matching, i.e., taking into account gaps and insertions. The comparison of sequences and determination of percent identity between two sequences can be accomplished using a mathematical algorithm. Techniques for determining sequence identity are well known to one skilled in the art, and include, for example, analysis with a sequence comparison algorithm or FASTA version 3.0t78 using default parameters (Pearson and Lipman, Proc Natl Acad Sci USA. 1988 April; 85(8):2444-8). In another non-limiting example, scoring of amino acid can be calculated using the PAM250 matrix as described in Dayhoff et al., (1978) in Atlas of Protein Sequence and Structure, ed. Dayhoff, M. (Natl. Biomed. Res. Found., Silver Spring, Md.), Vol. 5, Suppl. 3, pp. 345-352.

Percent identity or percent similarity of a DNA or peptide sequence can be determined, for example, by comparing sequence information using the GAP computer program. The GAP program utilizes the alignment method of Needleman et al., 1970, as revised by Smith et al., 1981. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See e.g., Schwartz et al., 1979; Gribskov et al., 1986. Nucleic acids that differ due to degeneracy of the genetic code, and still encode the PBRTs or PBRCs, described herein are encompassed by the present disclosure.

Variants can be produced by any number of methods, including but not limited to, error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly, and any combination thereof.

Variant PBRTs or variant PBRCs falling within the scope of this invention, can, in general, be generated by selecting substitutions that do not differ significantly in their effect on maintaining (a) the structure of the polypeptide backbone in the area of the substitution, (b) the charge or hydrophobicity of the purification moiety at the target site, or (c) the bulk of the side chain.

In one embodiment, a variant PBRT or a variant PBRC can comprise a conservative amino acid substitution in which an amino acid residue is replaced with an amino acid residue having a similar side chain configuration Amino acid residues having similar side chain configurations have been defined in the art within in accordance with the following categories: basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), aromatic side chains (e.g., tyrosine, phenylalanine, tryptophan, histidine), aliphatic side chains (e.g., glycine, alanine, valine, leucine, isoleucine), and sulfur-containing side chains (methionine, cysteine). Substitutions can also be made between acidic amino acids and their respective amides (e.g., asparagine and aspartic acid, or glutamine and glutamic acid).

In one embodiment, a variant PBRT or a variant PBRC can comprise a conservative amino acid substitution in which an amino acid residue is replaced with an amino acid residue having a similar side chain group. Amino acid residues having similar side chain groups have been defined in the art within in accordance with the following categories: a no side chain group (glycine), an aliphatic side chain group (alanine, valine, leucine, isoleucine, proline), a hydroxyl side chain group (serine, threonine), an acidic side chain group (aspartic acid, glutamic acid), an amide side chain group (asparagine, glutamine), a basic side chain group (lysine, arginine), an imidazole side chain group (histidine), an aromatic side chain group (phenylalanine, tyrosine, tryptophan), and a sulfur containing side chain group (methionine, cysteine) (see Sambrook et al, (2001) Molecular Cloning: A Laboratory Manual, Volume 3, Table A7-4).

In one embodiment, a variant PBRT or a variant PBRC can comprise a conservative amino acid substitution in which an amino acid residue is replaced an amino acid having evolutionarily positive relatedness. Amino acids having evolutionarily positive relatedness have been defined in the art as follows (wherein the amino acid(s) having evolutionarily positive relatedness are indicated in parentheses): Alanine (serine, threonine, proline, glycine); Arginine (glutamine, histidine, lysine, tryptophan); Asparagine (serine, threonine, aspartic acid, glutamic acid, glutamine, histidine, lysine); Aspartic acid (threonine, glycine, asparagine, glutamine, glutamic acid, histidine); Glutamic acid (threonine, asparagine, aspartic acid, glutamine, histidine); Glutamine (asparagine, aspartic acid, glutamic acid, histidine, arginine, lysine); Glycine (serine, threonine, alanine, aspartic acid); Histidine (asparagine, aspartic acid, glutamine, arginine); Isoleucine (threonine, methionine, leucine, valine, phenylalanine); Leucine (methionine, isoleucine, valine, phenylalanine); Lysine (threonine, asparagine, glutamine, arginine); Methionine (isoleucine, leucine, valine); Phenylalanine (isoleucine, leucine, tyrosine); Proline (serine, threonine, alanine); Serine (threonine, proline, alanine, glycine, asparagine); Threonine (serine, proline, alanine, glycine, asparagine, aspartic acid, glutamic acid, lysine, isoleucine, valine); Tryptophan (arginine, tyrosine); Tyrosine (phenylalanine, tryptophan); Valine (threonine, methionine, isoleucine, leucine) (see Dayhoff et al., (1978) in Atlas of Protein Sequence and Structure, ed. Dayhoff, M., Natl. Biomed. Res. Found., Silver Spring, Md.), Vol. 5, Suppl. 3, pp. 345-352).

In one embodiment, variant of a variant PBRT or a variant PBRC can comprise a conservative amino acid substitution in which an amino acid residue is replaced an amino acid having evolutionarily positive relatedness. Amino acids having evolutionarily neutral relatedness have been defined in the art as follows (wherein the amino acid(s) having evolutionarily neutral relatedness are indicated in parentheses): Alanine (asparagine, aspartic acid, glutamine, glutamic acid, valine); Arginine (serine, proline, asparagine, methionine); Asparagine (alanine, glycine, arginine); Aspartic acid (serine, alanine, lysine); Cysteine (serine, tyrosine); Glutamic acid (serine, alanine, glycine, lysine); Glutamine (proline, alanine); Glycine (asparagine, glutamic acid); Histidine (proline, lysine, tyrosine); Lysine (serine, asparagine, glutamic acid, histidine, methionine); Methionine (arginine, lysine, phenylalanine); Phenylalanine (methionine, tryptophan); Proline (glutamine, histidine, arginine); Serine (cysteine, aspartic acid, glutamic acid, arginine, lysine); Threonine (none); Tryptophan (phenylalanine); Tyrosine (cysteine, histidine); Valine (alanine) (see Dayhoff et al., (1978) in Atlas of Protein Sequence and Structure, ed. Dayhoff, M., Natl. Biomed. Res. Found., Silver Spring, Md.), Vol. 5, Suppl. 3, pp. 345-352).

In one embodiment of a variant PBRT, the glycine at position 1 of SEQ ID NO: 1 is not mutated.

In another embodiment of a variant PBRT, the glycine at position 1 of SEQ ID NO: 1 can be mutated to an amino acid having a similar side chain configuration such that the glycine is replaced with an amino acid having an uncharged polar side chain configuration (e.g., asparagine, glutamine, serine, threonine, tyrosine, or cysteine).

In another embodiment of a variant PBRT, the glycine at position 1 of SEQ ID NO: 1 can be mutated to an amino acid having a similar side chain configuration such that the glycine is replaced with an amino acid having an aliphatic side chain configuration (e.g., alanine, valine, leucine, isoleucine)

In another embodiment of a variant PBRT, the glycine at position 1 of SEQ ID NO: 1 can be mutated to an amino acid having evolutionarily positive relatedness such that the glycine is replaced with any of senile, threonine, alanine, or aspartic acid.

In another embodiment of a variant PBRT, the glycine at position 1 of SEQ ID NO: 1 can be mutated to an amino acid having evolutionarily neutral relatedness such that the glycine is replaced with any of asparagine or glutamic acid.

In one embodiment of a variant PBRT, mutation of the glycine at position 1 of SEQ ID NO: 1 to any of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine wherein mutation of the glycine at position 1 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the glycine at position 1 of SEQ ID NO: 1 is with a non-natural or synthetic amino acid wherein mutation of the glycine at position 1 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the glycine at position 2 of SEQ ID NO: 1 can be mutated to an asparagine residue.

In one embodiment of a variant PBRT, the glycine at position 2 of SEQ ID NO: 1 can be mutated to an aspartic acid residue.

In another embodiment of a variant PBRT, the glycine at position 2 of SEQ ID NO: 1 can be mutated to an amino acid having a similar side chain configuration such that the glycine is replaced with an amino acid having an uncharged polar side chain configuration (e.g., asparagine, glutamine, serine, threonine, tyrosine, or cysteine).

In another embodiment of a variant PBRT, the glycine at position 2 of SEQ ID NO: 1 can be mutated to an amino acid having a similar side chain configuration such that the glycine is replaced with an amino acid having an aliphatic side chain configuration (e.g., alanine, valine, leucine, isoleucine)

In another embodiment of a variant PBRT, the glycine at position 2 of SEQ ID NO: 1 can be mutated to an amino acid having evolutionarily positive relatedness such that the glycine is replaced with any of serine, threonine, alanine, or aspartic acid.

In another embodiment of a variant PBRT, the glycine at position 2 of SEQ ID NO: 1 can be mutated to an amino acid having evolutionarily neutral relatedness such that the glycine is replaced with any of asparagine or glutamic acid.

In one embodiment of a variant PBRT, mutation of the glycine at position 2 of SEQ ID NO: 1 to any of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine wherein mutation of the glycine at position 2 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the glycine at position 2 of SEQ ID NO: 1 is with a non-natural or synthetic amino acid wherein mutation of the glycine at position 2 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the alanine at position 3 of SEQ ID NO: 1 can be mutated to a serine, glycine, or aspartic acid residue.

In one embodiment of a variant PBRT, the alanine at position 3 of SEQ ID NO: 1 can be mutated to a glutamic acid, leucine, or asparagine residue.

In one embodiment of a variant PBRT, the alanine at position 3 of SEQ ID NO: 1 can be mutated to an amino acid having a similar side chain configuration such that the alanine is replaced with an amino acid having a nonpolar side chain configuration (e.g., valine, leucine, isoleucine, proline, phenylalanine, methionine, or tryptophan).

In one embodiment of a variant PBRT, the alanine at position 3 of SEQ ID NO: 1 can be mutated to an amino acid having a similar side chain configuration such that the alanine is replaced with an amino acid having an aliphatic side chain configuration (e.g., glycine, valine, leucine, isoleucine)

In another embodiment of a variant PBRT, the alanine at position 3 of SEQ ID NO: 1 can be mutated to an amino acid having a similar side chain group such that the alanine is replaced with an amino acid having an aliphatic side chain group (e.g., valine, leucine, isoleucine, proline).

In another embodiment of a variant PBRT, the alanine at position 3 of SEQ ID NO: 1 can be mutated to an amino acid having evolutionarily positive relatedness such that the alanine is replaced with any of serine, threonine, proline, or glycine.

In another embodiment of a variant of a precipitable beta-roll tag, the at position 3 of SEQ ID NO: 1 can be mutated to an amino acid having evolutionarily neutral relatedness such that the alanine is replaced with any of asparagine, aspartic acid, glutamine, glutamic acid, or valine.

In one embodiment of a variant PBRT, mutation of the alanine at position 3 of SEQ ID NO: 1 to any of glycine, arginine, asparagine, aspartic acid, cysteine, glutamic acid, glutamine, histidine, isoleucine, leucine, lysine, methionine, phenylalanine, proline, serine, threonine, tryptophan, tyrosine, valine wherein mutation of the alanine at position 3 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the alanine at position 3 of SEQ ID NO: 1 is with a non-natural or synthetic amino acid wherein mutation of the alanine at position 3 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the glycine at position 4 of SEQ ID NO: 1 can be mutated to an alanine residue.

In another embodiment of a variant PBRT, the glycine at position 4 of SEQ ID NO: 1 can be mutated to an amino acid having a similar side chain configuration such that the glycine is replaced with an amino acid having an uncharged polar side chain configuration (e.g., asparagine, glutamine, serine, threonine, tyrosine, or cysteine).

In another embodiment of a variant PBRT, the glycine at position 4 of SEQ ID NO: 1 can be mutated to an amino acid having a similar side chain configuration such that the glycine is replaced with an amino acid having an aliphatic side chain configuration (e.g., alanine, valine, leucine, isoleucine)

In another embodiment of a variant PBRT, the glycine at position 4 of SEQ ID NO: 1 can be mutated to an amino acid having evolutionarily positive relatedness such that the glycine is replaced with any of serine, threonine, alanine, or aspartic acid.

In another embodiment of a variant PBRT, the glycine at position 4 of SEQ ID NO: 1 can be mutated to an amino acid having evolutionarily neutral relatedness such that the glycine is replaced with any of asparagine or glutamic acid.

In one embodiment of a variant PBRT, mutation of the glycine at position 4 of SEQ ID NO: 1 to any of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine wherein mutation of the glycine at position 4 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the glycine at position 4 of SEQ ID NO: 1 is with a non-natural or synthetic amino acid wherein mutation of the glycine at position 4 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the asparagine at position 5 of SEQ ID NO: 1 can be mutated to an aspartic acid or alanine residue.

In one embodiment of a variant PBRT, the asparagine at position 5 of SEQ ID NO: 1 can be mutated to a serine residue.

In one embodiment of a variant PBRT, the asparagine at position 5 of SEQ ID NO: 1 can be mutated to an amino acid having a similar side chain configuration such that the asparagine is replaced with an amino acid having an uncharged polar side chain configuration (e.g., glycine, glutamine, serine, threonine, tyrosine, cysteine)

In one embodiment of a variant PBRT, the asparagine at position 5 of SEQ ID NO: 1 can be mutated to an amino acid having a similar side chain configuration such that the asparagine is replaced with an amino acid having a the side chain configuration of its amide (e.g., aspartic acid).

In another embodiment of a variant PBRT, the asparagine at position 5 of SEQ ID NO: 1 can be mutated to an amino acid having a similar side chain group such that the asparagine is replaced with an amino acid having an amide side chain group (e.g., glutamine).

In another embodiment of a variant PBRT, the asparagine at position 5 of SEQ ID NO: 1 can be mutated to an amino acid having evolutionarily positive relatedness such that the asparagine is replaced with any of serine, threonine, aspartic acid, glutamic acid, glutamine, histidine, or lysine.

In another embodiment of a variant PBRT, the asparagine at position 5 of SEQ ID NO: 1 can be mutated to an amino acid having evolutionarily neutral relatedness such that the asparagine is replaced with any of alanine, glycine, or arginine.

In one embodiment of a variant PBRT, mutation of the asparagine at position 5 of SEQ ID NO: 1 to any of glycine, alanine, arginine, aspartic acid, cysteine, glutamic acid, glutamine, histidine, isoleucine, leucine, lysine, methionine, phenylalanine, proline, serine, threonine, tryptophan, tyrosine, valine wherein mutation of the asparagine at position 5 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the asparagine at position 5 of SEQ ID NO: 1 is with a non-natural or synthetic amino acid wherein mutation of the asparagine at position 5 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the aspartic acid at position 6 of SEQ ID NO: 1 can be mutated to an asparagine residue.

In one embodiment of a variant PBRT, the aspartic acid at position 6 of SEQ ID NO: 1 can be mutated to an amino acid having a similar side chain configuration such that the aspartic acid is replaced with an amino acid having an acidic side chain configuration (e.g., glutamic acid).

In one embodiment of a variant PBRT, the aspartic acid at position 6 of SEQ ID NO: 1 can be mutated to an amino acid having a similar side chain configuration such that the aspartic acid is replaced with an amino acid having a the side chain configuration of its amide (e.g., asparagine).

In another embodiment of a variant PBRT, the aspartic acid at position 6 of SEQ ID NO: 1 can be mutated to an amino acid having a similar side chain group such that the aspartic acid is replaced with an amino acid having an acidic side chain group (e.g., glutamic acid).

In another embodiment of a variant PBRT, the aspartic acid at position 6 of SEQ ID NO: 1 can be mutated to an amino acid having evolutionarily positive relatedness such that the aspartic acid is replaced with any of threonine, glycine, asparagine, glutamine, glutamic acid, or histidine.

In another embodiment of a variant PBRT, the aspartic acid at position 6 of SEQ ID NO: 1 can be mutated to an amino acid having evolutionarily neutral relatedness such that the aspartic acid is replaced with any of serine, alanine, or lysine.

In one embodiment of a variant PBRT, mutation of the aspartic acid at position 6 of SEQ ID NO: 1 to any of glycine, alanine, arginine, asparagine, cysteine, glutamic acid, glutamine, histidine, isoleucine, leucine, lysine, methionine, phenylalanine, proline, serine, threonine, tryptophan, tyrosine, valine wherein mutation of the aspartic acid at position 6 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the aspartic acid at position 6 of SEQ ID NO: 1 is with a non-natural or synthetic amino acid wherein mutation of the aspartic acid at position 6 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the threonine at position 7 of SEQ ID NO: 1 can be mutated to an isoleucine or valine residue.

In one embodiment of a variant PBRT, the threonine at position 7 of SEQ ID NO: 1 can be mutated to a leucine residue.

In one embodiment of a variant PBRT, the threonine at position 7 of SEQ ID NO: 1 can be mutated to an amino acid having a similar side chain configuration such that the threonine is replaced with an amino acid having an uncharged polar side chain configuration (e.g., glycine, asparagine, glutamine, serine, tyrosine, or cysteine).

In one embodiment of a variant PBRT, the threonine at position 7 of SEQ ID NO: 1 can be mutated to an amino acid having a similar side chain configuration such that the threonine is replaced with an amino acid having a beta-branched side chain configuration (e.g., valine, isoleucine).

In another embodiment of a variant PBRT, the threonine at position 7 of SEQ ID NO: 1 can be mutated to an amino acid having a similar side chain group such that the threonine is replaced with an amino acid having an hydroxyl side chain group (e.g., serine).

In another embodiment of a variant PBRT, the threonine at position 7 of SEQ ID NO: 1 can be mutated to an amino acid having evolutionarily positive relatedness such that the threonine is replaced with any of serine, proline, alanine, glycine, asparagine, aspartic acid, glutamic acid, lysine, isoleucine, or valine In one embodiment of a variant PBRT, mutation of the threonine at position 7 of SEQ ID NO: 1 to any of glycine, alanine, arginine, asparagine, aspartic acid, cysteine, glutamic acid, glutamine, histidine, isoleucine, leucine, lysine, methionine, phenylalanine, proline, serine, tryptophan, tyrosine, valine wherein mutation of the threonine at position 7 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the threonine at position 7 of SEQ ID NO: 1 is with a non-natural or synthetic amino acid wherein mutation of the threonine at position 7 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the leucine at position 8 of SEQ ID NO: 1 can be mutated to an isoleucine residue.

In one embodiment of a variant PBRT, the leucine at position 8 of SEQ ID NO: 1 can be mutated to a phenylalanine residue.

In one embodiment of a variant PBRT, the leucine at position 8 of SEQ ID NO: 1 can be mutated to an amino acid having a similar side chain configuration such that the leucine is replaced with an amino acid having a nonpolar side chain configuration (e.g., alanine, valine, isoleucine, proline, phenylalanine, methionine, or tryptophan).

In one embodiment of a variant PBRT, the leucine at position 8 of SEQ ID NO: 1 can be mutated to an amino acid having a similar side chain configuration such that the leucine is replaced with an amino acid having an aliphatic side chain configuration (e.g., glycine, alanine, valine, or isoleucine).

In another embodiment of a variant PBRT, leucine at position 8 of SEQ ID NO: 1 can be mutated to an amino acid having a similar side chain group such that the leucine is replaced with an amino acid having an aliphatic side chain group (e.g., alanine, valine, isoleucine, proline).

In another embodiment of a variant PBRT, the leucine at position 8 of SEQ ID NO: 1 can be mutated to an amino acid having evolutionarily positive relatedness such that the leucine is replaced with any of methionine, isoleucine, valine, or phenylalanine In another embodiment of a variant PBRT, the leucine at position 8 of SEQ ID NO: 1 can be mutated to an amino acid having evolutionarily neutral relatedness such that the leucine is replaced with any of serine, asparagine, glutamic acid, histidine, or methionine.

In one embodiment of a variant PBRT, mutation of the leucine at position 8 of SEQ ID NO: 1 to any of glycine, alanine, arginine, asparagine, aspartic acid, cysteine, glutamic acid, glutamine, histidine, isoleucine, lysine, methionine, phenylalanine, proline, serine, threonine, tryptophan, tyrosine, valine wherein mutation of the leucine at position 8 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the leucine at position 8 of SEQ ID NO: 1 non-natural amino acid wherein mutation of leucine at position 8 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, the tyrosine at position 9 of SEQ ID NO: 1 can be mutated to an isoleucine or valine residue.

In one embodiment of a variant PBRT, the tyrosine at position 9 of SEQ ID NO: 1 can be mutated to a phenylalanine, threonine, asparagine, aspartic acid, lysine, or serine residue.

In one embodiment of a variant PBRT, the tyrosine at position 9 of SEQ ID NO: 1 can be mutated to an amino acid having a similar side chain configuration such that the tyrosine is replaced with an amino acid having an uncharged polar side chain configuration (e.g., glycine, asparagine, glutamine, serine, threonine, or cysteine).

In one embodiment of a variant PBRT, the tyrosine at position 9 of SEQ ID NO: 1 can be mutated to an amino acid having a similar side chain configuration such that the tyrosine is replaced with an amino acid having an aromatic side chain configuration (e.g., tyrosine, phenylalanine, tryptophan, or histidine).

In another embodiment of a variant PBRT, the tyrosine at position 9 of SEQ ID NO: 1 can be mutated to an amino acid having a similar side chain group such that the tyrosine is replaced with an amino acid having an aromatic side chain group (e.g., phenylalanine, tryptophan).

In another embodiment of a variant PBRT, the tyrosine at position 9 of SEQ ID NO: 1 can be mutated to an amino acid having evolutionarily positive relatedness such that the tyrosine is replaced with any of phenylalanine or tryptophan.

In another embodiment of a variant PBRT, the tyrosine at position 9 of SEQ ID NO: 1 can be mutated to an amino acid having evolutionarily neutral relatedness such that the tyrosine is replaced with any of cysteine or histidine.

In one embodiment of a variant PBRT, mutation of the tyrosine at position 9 of SEQ ID NO: 1 to any of glycine, alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine wherein mutation of tyrosine at position 9 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

In one embodiment of a variant PBRT, mutation of the tyrosine at position 9 of SEQ ID NO: 1 is with a non-natural or synthetic amino acid wherein mutation of the tyrosine at position 9 of SEQ ID NO: 1 will result in a precipitable beta-roll tag that is capable of binding to Ca2+, undergo reversible precipitation in the presence of Ca2+, or induce reversible precipitation of a purification moiety linked to the variant PBRT.

As described herein, a variant PBRC can further comprise a capping sequence. In certain embodiments, the capping sequence in a variant PBRC can be a variant capping sequence. A variant capping sequence can be an amino acid sequence having at least 70%, at least 80%, at least 90%, at least 95% or at least 98% identity to SEQ ID NO: 3. In another embodiment, a variant capping sequence is an amino acid sequence having at least 70%, at least 80%, at least 90%, at least 95% or at least 98% identity to any of SEQ ID NO: 4-23.

In still a further embodiment, a variant capping sequence is a sequence comprising one or more amino acid substitutions with an amino acid having a similar side chain group. In one embodiment, the variant capping sequence comprises the sequence of SEQ ID NO: 3 or any of SEQ ID NO: 4-23, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or at least 68, amino acids in the sequence of SEQ ID NO: 3 or any of SEQ ID NO: 4-23 are substituted an amino acid having a similar side chain group.

In still a further embodiment, a variant capping sequence is a sequence comprising one or more amino acid substitutions with an amino acid having a similar side chain configuration. In one embodiment, the variant capping sequence comprises the sequence of SEQ ID NO: 3 or any of SEQ ID NO: 6-23, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or at least 68, amino acids in the sequence of SEQ ID NO: 3 or any of SEQ ID NO: 6-23 are substituted an amino acid having a similar side chain configuration.

In still a further embodiment, a variant capping sequence is a sequence comprising one or more amino acid substitutions with an amino acid having evolutionarily positive relatedness. In one embodiment, the variant capping sequence comprises the sequence of SEQ ID NO: 3 or any of SEQ ID NO: 6-23, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or at least 68, amino acids in the sequence of SEQ ID NO: 3 or any of SEQ ID NO: 6-23 are substituted an amino acid having evolutionarily positive relatedness.

In still a further embodiment, a variant capping sequence is a sequence comprising one or more amino acid substitutions with an amino acid having evolutionarily neutral relatedness. In one embodiment, the variant capping sequence comprises the sequence of SEQ ID NO: 3 or any of SEQ ID NO: 6-23, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or at least 68, amino acids in the sequence of SEQ ID NO: 3 or any of SEQ ID NO: 4-23 are substituted an amino acid having evolutionarily neutral relatedness.

In another embodiment, the PBRT variants or PBRC variants described herein can also comprise a non-natural amino acid. As used herein, a non-natural amino acid can be, but is not limited to, an amino acid comprising a moiety where a chemical moiety is attached, such as an aldehyde- or keto-derivatized amino acid, or a non-natural amino acid that includes a chemical moiety. A non-natural amino acid can also be an amino acid comprising a moiety where a saccharide moiety can be attached, or an amino acid that includes a saccharide moiety. Examples of non-classical amino acids suitable for use with the methods and compositions described herein include, but are not limited to, D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, C alpha-methyl amino acids, N alpha-methyl amino acids, and amino acid analogs in general.

The PBRT variants or PBRC variants described herein can also comprise one or more amino acid analog substitutions, e.g., unnatural amino acids such as alpha alpha-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha.-methyl-alanine, para-benzoyl-phenylalanine, phenylglycine, propargylglycine, sarcosine, .epsilon.-N,N,N-trimethylly-sine, .epsilon.-N-acetyllysine, N-acetylserine, N-formylmethionine, 3-methylhistidine, 5-hydroxylysine, .omega.-N-methylarginine, and other similar amino acids and imino acids and tert-butylglycine. The ability of PBRTs or PBRCs comprising an analog substitutions to bind to Ca2+, undergo reversible precipitation in the presence of Ca2+, or induce reversible precipitation of a purification moiety linked to the PBRT or PBRC using methods known to those skilled in the art.

The PBRT variants or PBRC variants described herein can further comprise polypeptide analogs, such as peptide mimetics (Fauchere J, Adv. Drug Res. 15:29 (1986); Veber D F and Freidinger R M, Trends Neurosci. 8:392-96 (1985); Evans B E et al., J. Med. Chem 30:1229-39 (1987)). Generally, peptidomimetics are structurally similar to a template polypeptide (i.e., a polypeptide that has a biological or pharmacological activity), such as the PBRTs or PBRCs described herein, but have one or more peptide linkages replaced by a linkage selected from the group consisting of: —CH.sub.2NH—, —CH.sub.2S—, —CH.sub.2-CH.sub.2-, —CH.dbd.CH— (cis and trans), —COCH.sub.2-, —CH(OH)CH.sub.2-, and —CH.sub.2SO—, by methods known in the art and further described in the following references: Spatola A F in "Chemistry and Biochemistry of Amino Acids, Peptides, and Proteins," B. Weinstein, ed., Marcel Dekker, New York, p. 267 (1983); Spatola, A F, Vega Data (March 1983), Vol. 1, Issue 3, "Peptide Backbone Modifications" (general review); Morley J S, Trends Pharmcol. Sci. 1:463-68 (1980) (general review); Hudson D et al., Int. J. Pept. Prot. Res. 14:177-85 (1979) (—CH.sub.2NH—, CH.sub.2CH.sub.2-); Spatola A F et al., Life Sci. 38:1243-49 (1986) (—CH.sub.2-S); Hann M M, J. Chem. Soc. Perkin Trans. 1, 307-314 (1982) (—CH—CH—, cis and trans); Almquist R G et al., J. Med. Chem. 23:1392-98 (1980) (—COCH.sub.2-); Jennings-White C et al., Tetrahedron Left. 23:2533-34 (1982) (—COCH.sub.2-); EP 0 045 665 (—CH(OH)CH.sub.2-); Holladay M W et al., Tetrahedron Lett., 24:4401-04 (1983) (—C(OH)CH.sub.2-); Hruby V J, Life Sci. 31:189-99 (1982) (—CH.sub.2-S—). One example of a non-peptide linkage is —CH.sub.2NH—.

Such polypeptide mimetics can have advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics can involve covalent attachment of one or more labels, directly or through a spacer (e.g., an amide group), to non-interfering position(s) on the peptidomimetic that are predicted by quantitative structure-activity data and/or molecular modeling. Such non-interfering positions can be positions that do not from direct contacts with the macromolecules(s) to which the peptidomimetic binds to produce the therapeutic effect. Derivatization (e.g., labeling) of peptidomimetics can be done without substantially interfering with the desired biological or pharmacological activity of the peptidomimetic. The ability of any peptidomimetics to polypeptides can be assayed for the ability to bind 1,4,-benzothiazepine or derivatives thereof using methods know to those skilled in the art.

Systematic substitution of one or more amino acids of the PBRTs or PBRCs described herein with a D-amino acid of the same type (e.g., D-lysine in place of L-lysine) can be used to generate additional PBRT and PBRT variants.

The following methods can be used in connection with the embodiments of the invention.

EXAMPLES

Example 1

Figure 1B:
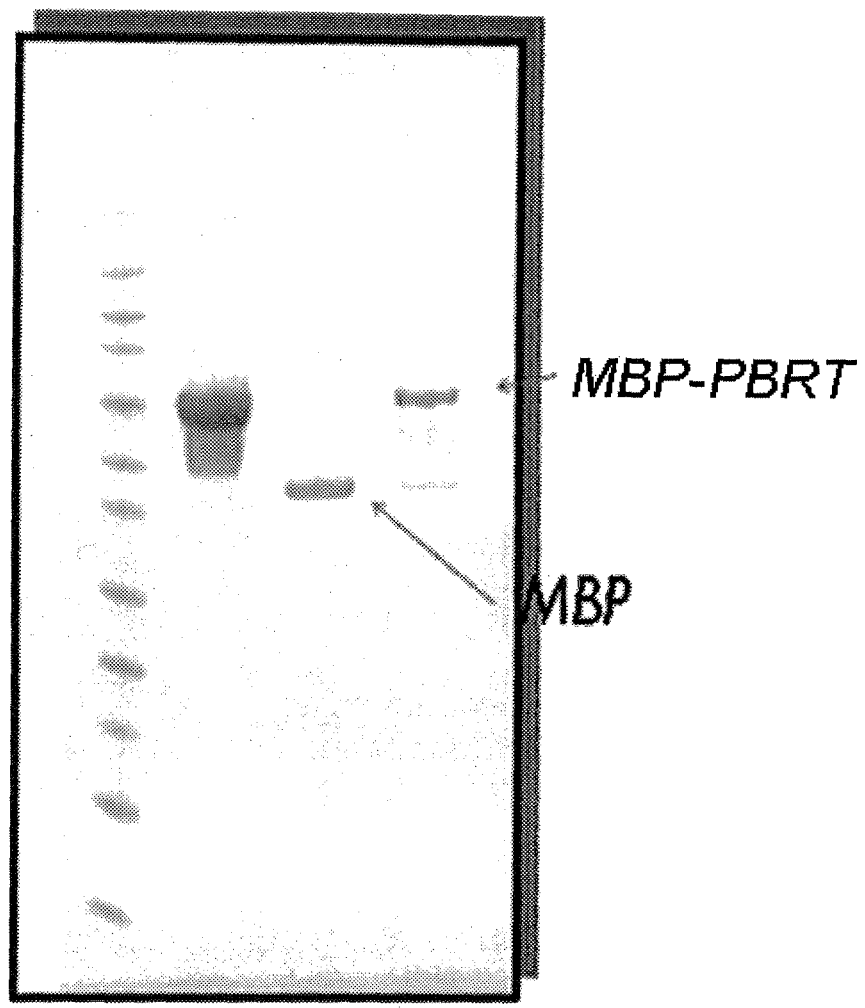

Purification of PBRT or PBRC Linked Purification Moieties 17 tandem repeats of the amino acid sequence GGAGNDTLY (SEQ ID NO: 1) followed by a C-terminal "capping" sequence (the sequence is provided below) were fused to maltose binding protein. This construct was expressed in *E. coli* and the cells are lysed, creating a complex mixture of *E. coli* proteins and the Beta Roll tagged maltose binding protein. The mixture was exposed to 100 mM calcium chloride solution to form a precipitate form. The precipitate was pelleted and resuspended in calcium-free buffer. One precipitation cycle was sufficient to generate a relatively pure protein (FIG. 1). Multiple cycles can be used to achieve better purity.

The capping sequence used in this example is:

```
                                          (SEQ ID NO: 3)
INAGADQLWFARQGNDLEIRILGTDDALTVHDWYRDADHRVEIIHAANQA

VDQAGIEKLVEAMAQYPD
```

Figure 2:
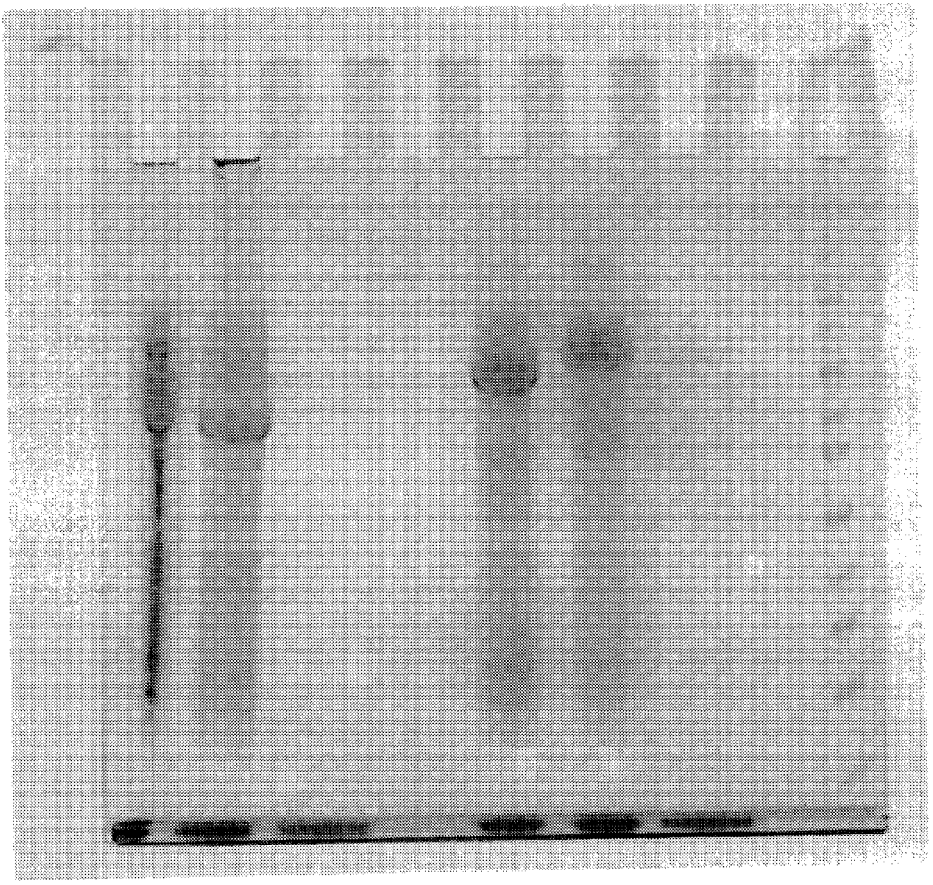
FIG. 2 shows a SDS-PAGE gel showing a successful purification of a polypeptide comprising a 5 or 17 repeat C-capped precipitable beta-roll tags. Lanes (from left to right): 1. MBP-5cap lysate, 2. MBP-5cap supernatant, 3. MBP-5C resuspended precipitate. The 4-6 lanes are the same expect with the capped 17 repeat construct.
Figure 3:
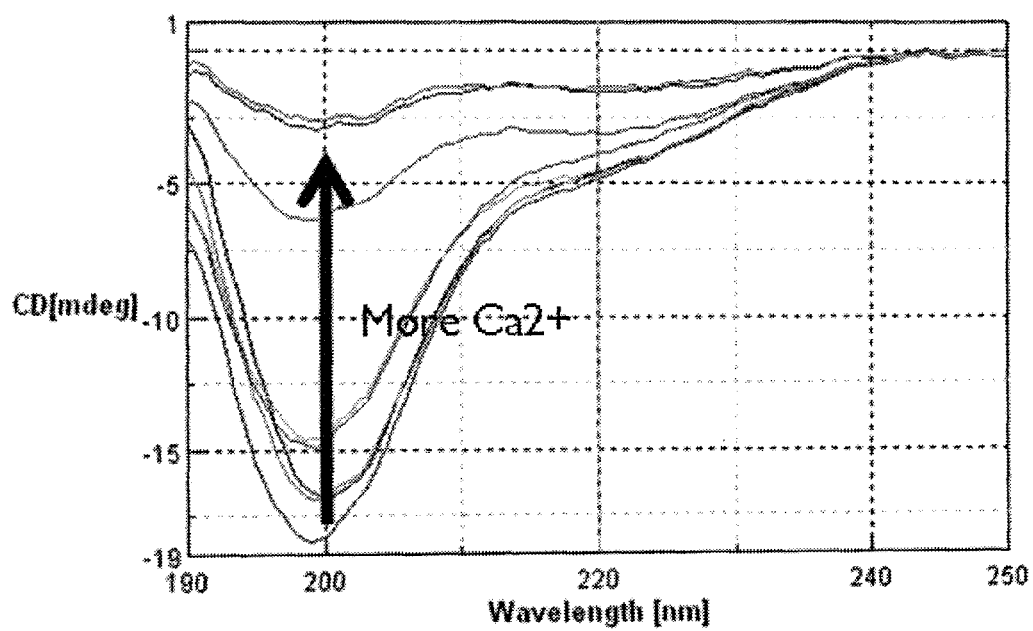
FIG. 3 is circular dichroism data (CD) showing precipitation of a polypeptide comprising a 17 repeat C-capped precipitable beta-roll tag (GGAGNDTLY)17INAGADQL-WFARQGNDLEIRILGTDDALTVHDWYRDADHRVEII HAANQAVDQAGIEKLVEAMAQYPD (SEQ ID NO: 1344) out of solution with increasing calcium concentrations from 0 to 100 mM calcium. Loss of spectra indicates that the peptide is precipitating out of solution and no longer visible via CD.

Polypeptides comprising a 5 or 17 repeat C-capped precipitable beta-roll tags were expressed as MBP fusion proteins. 50 mM calcium was added to clarified cell lysates to induce precipitation of the polypeptides comprising a 5 or 17 repeat C-capped precipitable beta-roll tags. The precipitate was pelleted by centrifugation and the pellet was washed once and resuspended in buffer with 50 mM EGTA. The lysate, the supernatant after calcium addition, and the resuspended pellet were then run on an SDS-PAGE gel (FIG. 2). The results show that the methods described herein can be used to rapidly purify polypeptides comprising a 5 or 17 repeat C-capped precipitable beta-roll tags. Precipitation of purification moieties comprising a precipitable beta-roll tag can be confirmed by circular dichroism analysis (FIG. 3).

An intein domain can be coupled to the construct so that the cleavage reaction and subsequent second precipitation can be examined. Other proteins, in addition to maltose binding protein can be used with the purification protocols described herein.

Example 2

PBRT Sequence Heat Map

Figure 4:
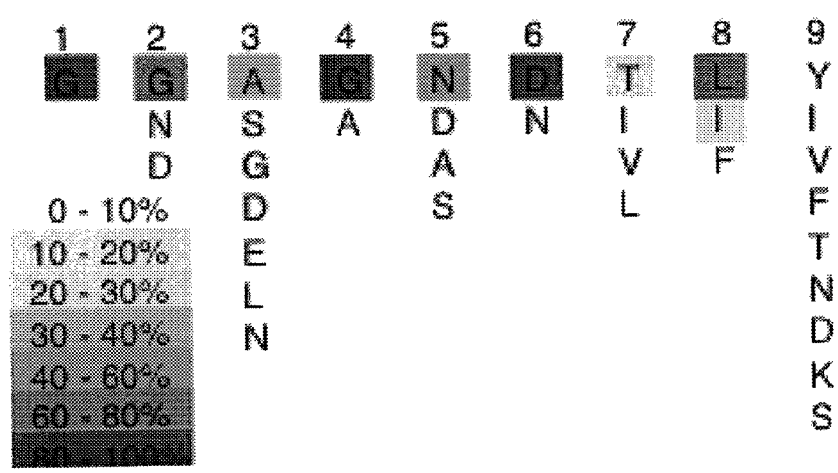
FIG. 4 shows a GGXGXDXXX (SEQ ID NO: 2) sequence heat map. The heat map was determined by using BLAST to find beta roll sequences similar to the metalloprotease of S. marcescens and then quantifying the frequency of amino acids at each of the nine positions after beta roll sequences were identified.
Figure 5:
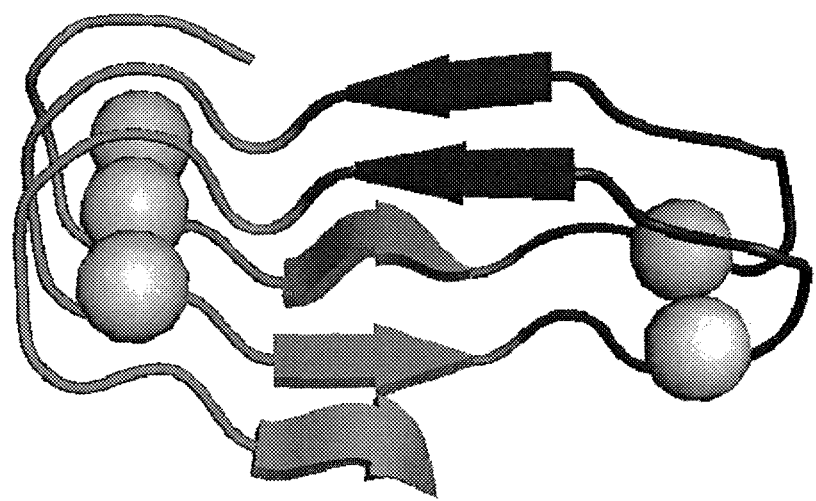
Figure 6:
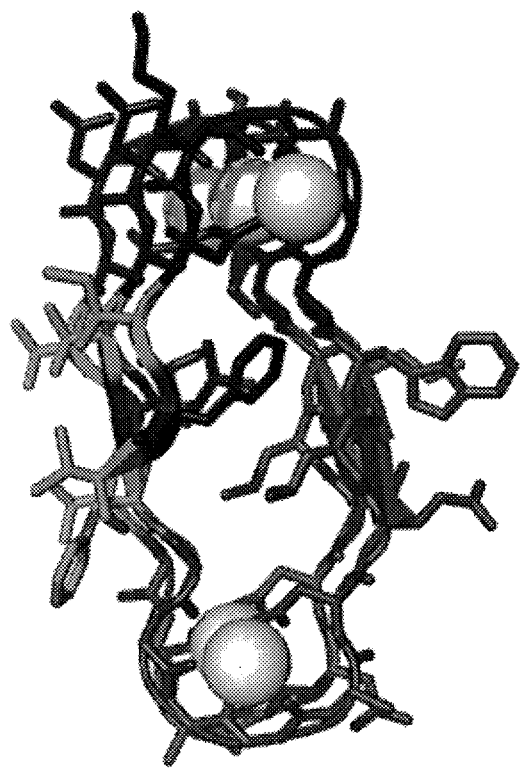
FIG. 6 shows a schematic illustration of the corkscrew configuration of tandem Ca2+ binding sequences from a different angle than shown in FIG. 5. The $6^{th}$ residue binds the calcium ion. The 7th and 9th residues of each repeat are those that face outwards. The $8^{th}$ residue is buried in the hydrophobic core. These residues are threonine and tyrosine, respectively in SEQ ID NO: 1.
Figure 7:
FIG. 7 shows the full crystal structure of the metalloprotease of S. marcescens. The black spheres indicate the position of the calcium ions within the beta roll domain.
Figure 9:
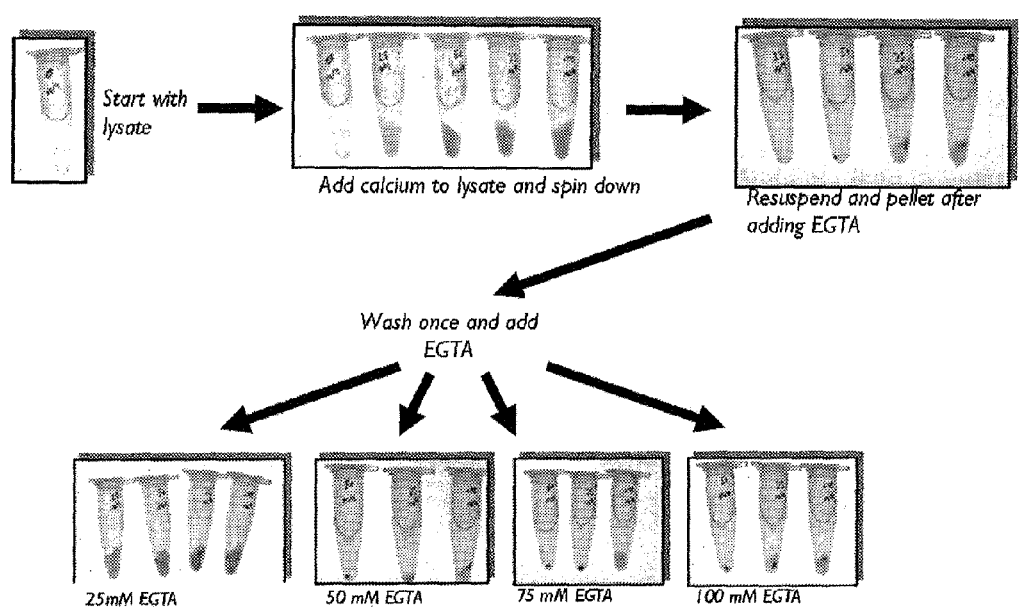
FIG. 9 shows an exemplary protocol for purification of a polypeptide comprising a precipitable beta roll tag. The images depict precipitation of maltose binding protein fused to seventeen repeats of a PBRT. The PBRC comprises 17 repeats of the amino acid sequence of SEQ ID NO: 1. The PBRC does not comprise a capping sequence.
Figure 10:
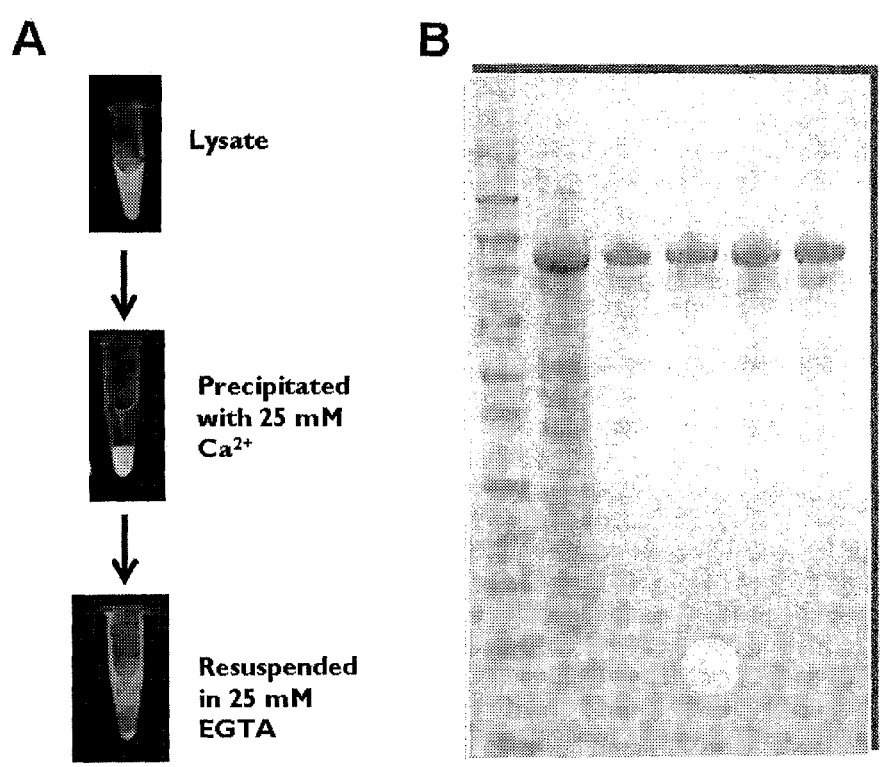
FIG. 10 shows purification of a maltose binding protein/PBRT/green fluorescent protein fusion (MBP-PBRT-GFP).
Figure 11:
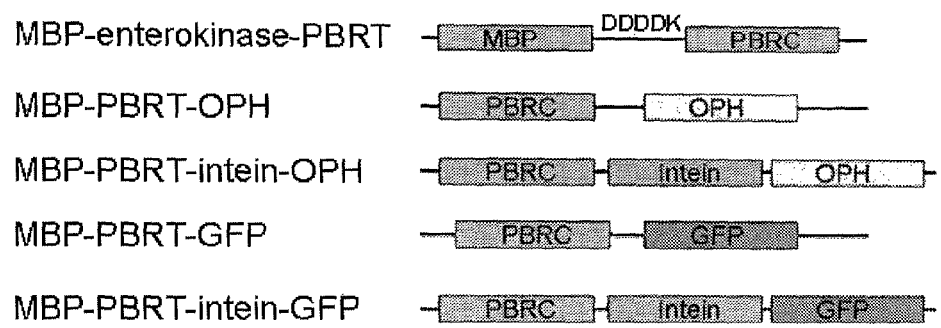
FIG. 11 shows non-limiting examples of polypeptides comprising a PBRT suitable for use with the methods described herein.
Figure 12A:
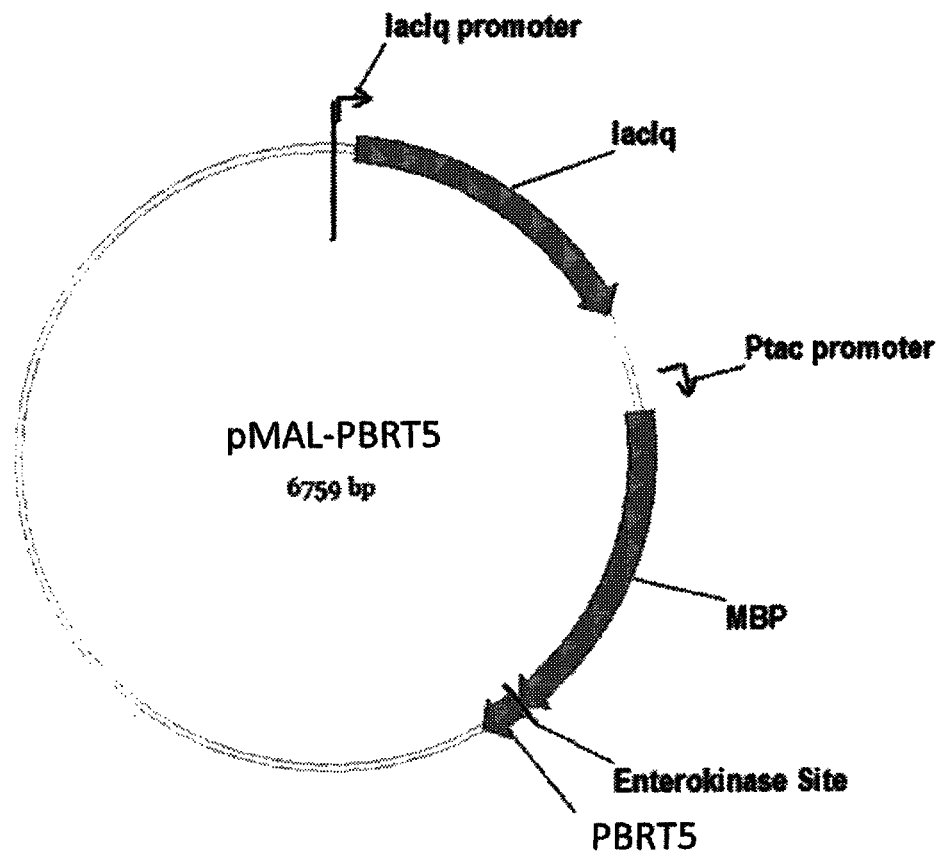
FIGS. 12A-12G show vector Maps at shown in FIG. 12A-G. Vector maps are given for each construct prepared, highlighting the important features.
Figure 12B:
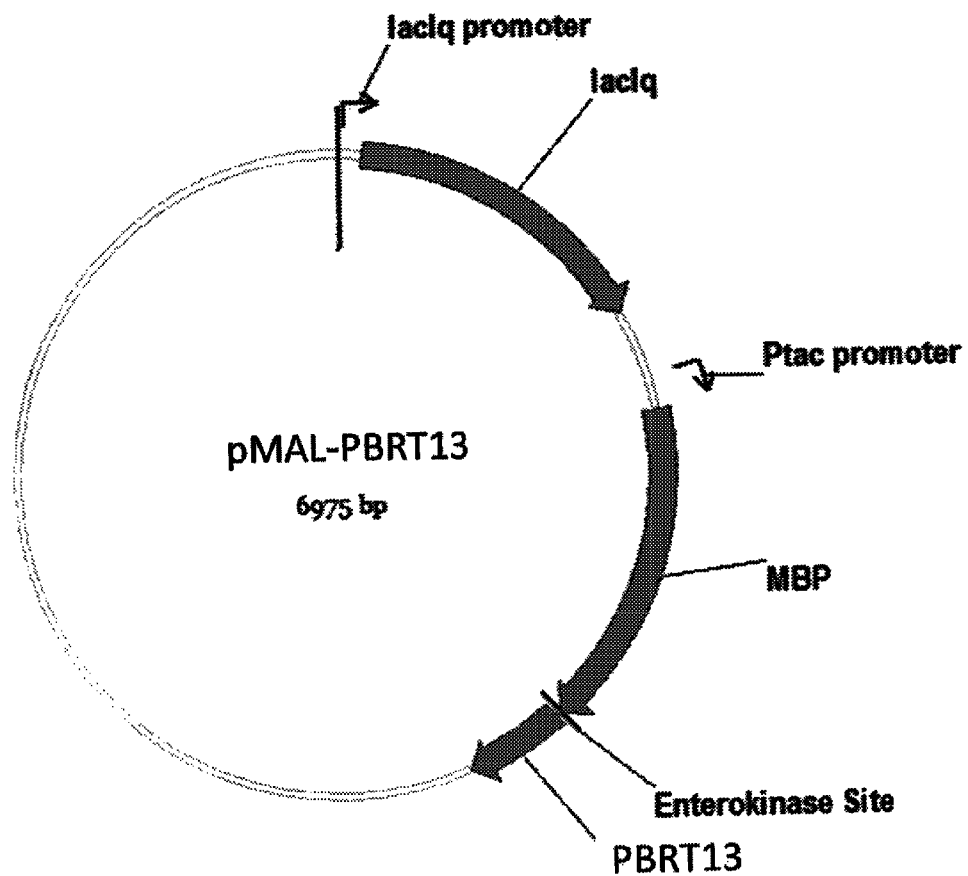
Figure 12C:
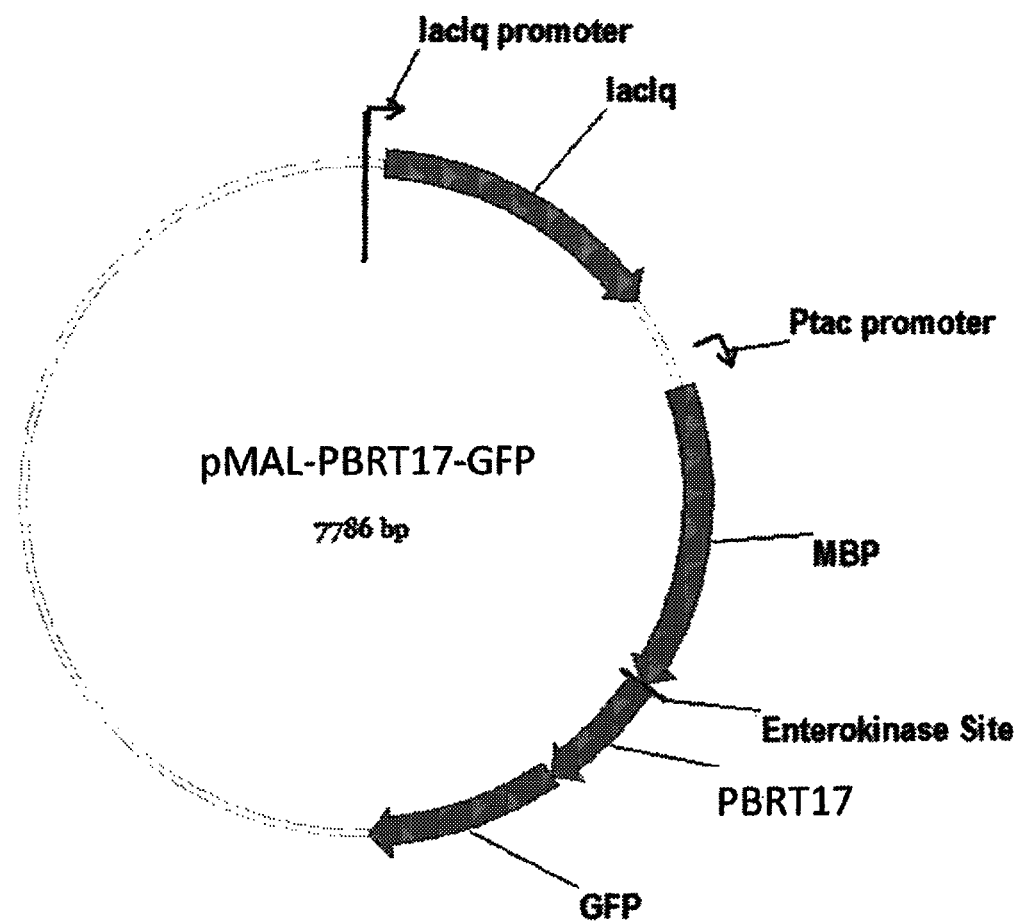
Figure 12D:
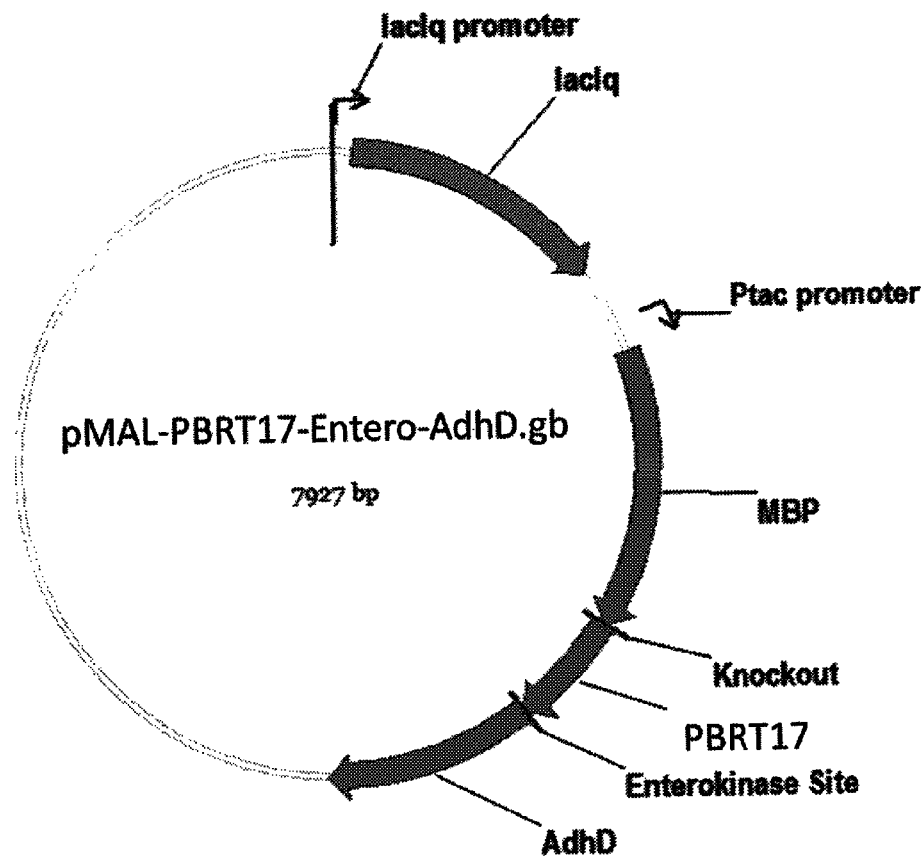
Figure 12E:
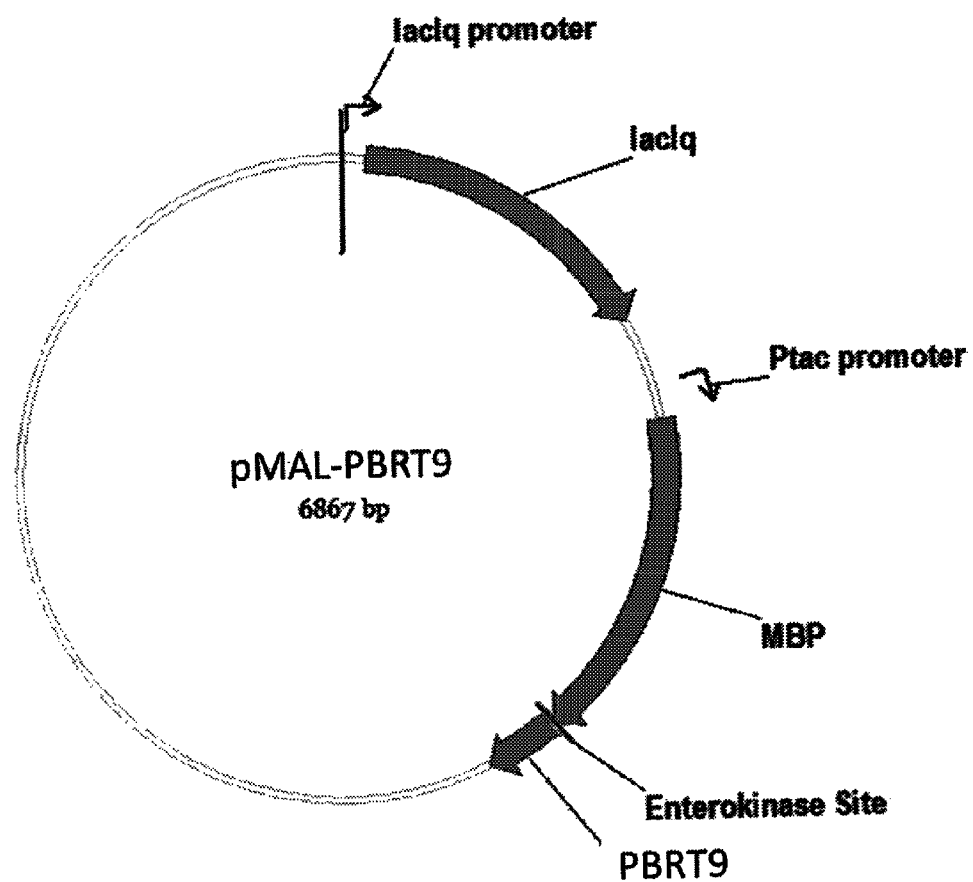
Figure 12F:
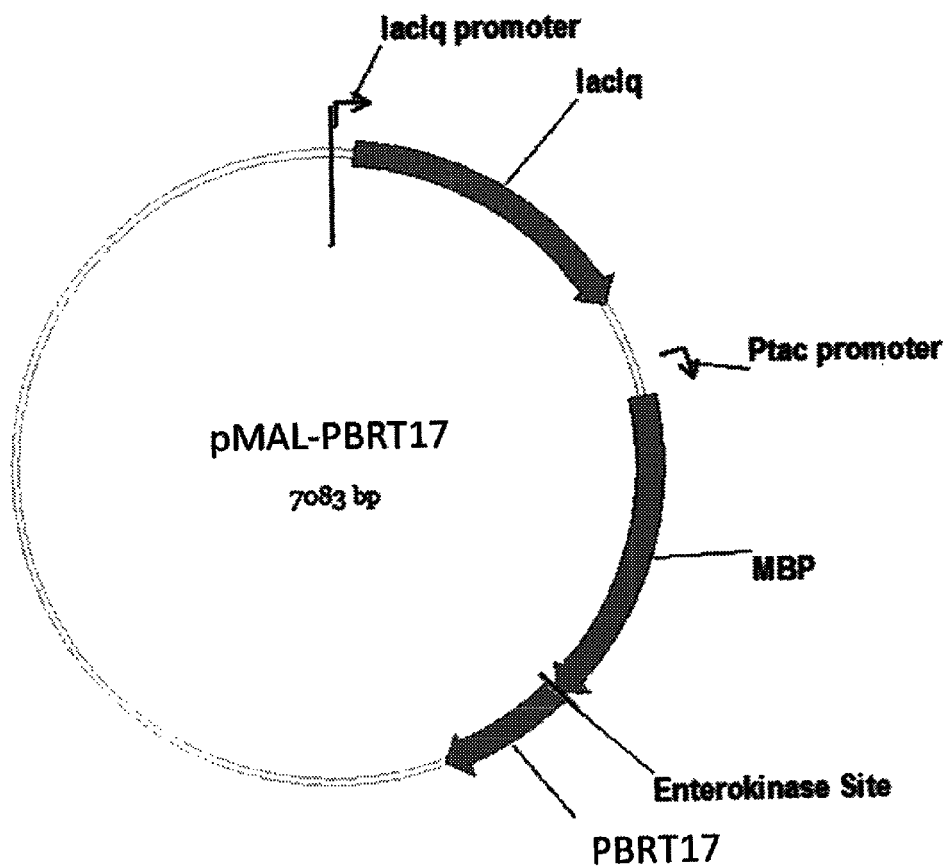
Figure 12G:
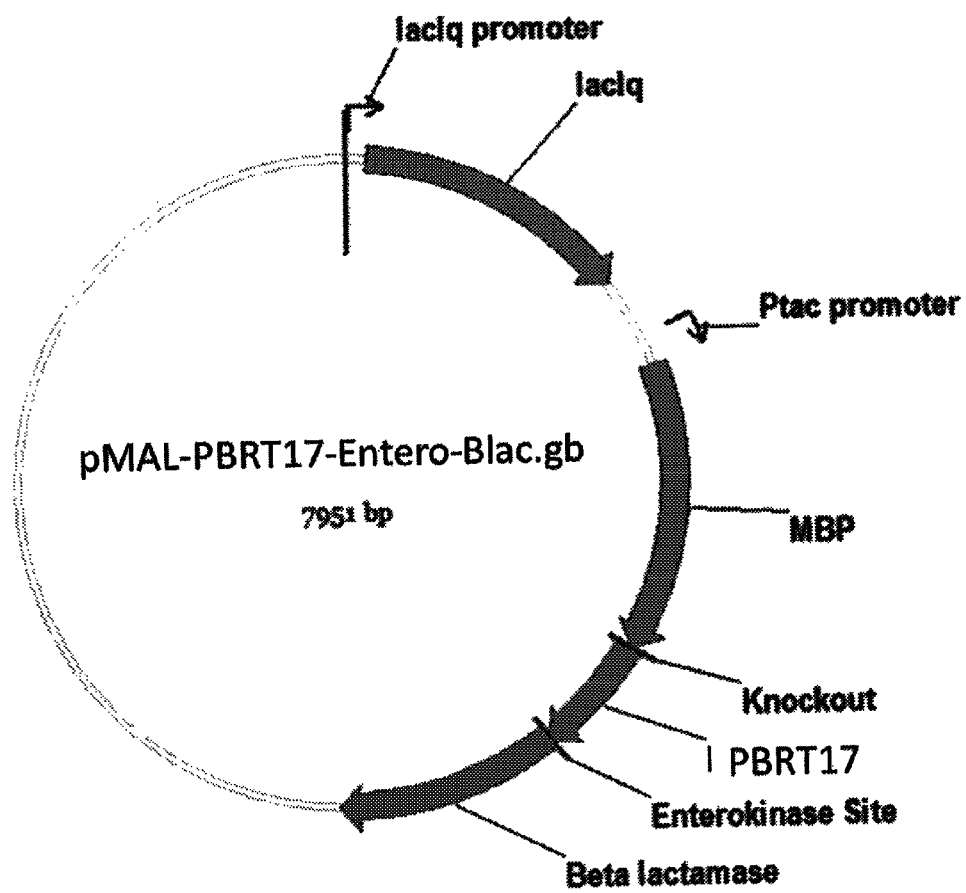

The heat map for the precipitable beta-roll tag sequences described herein was determined by using BLAST to find beta roll sequences similar to the metalloprotease of *S. marcescens* and then quantifying the frequency of amino acids at each of the nine positions after beta roll sequences were identified (FIG. 4). Certain positions in the precipitable beta-roll tag are not highly variable (e.g. positions 1, 2, 4, 6, and 8), whereas other positions, exhibit moderate conservation. Positions 7, 0.9 are highly variable and can be substituted with any natural or non-natural amino acid.

Example 3

A Designed, Phase Changing PBRT-Based Peptide for Efficient Bioseparations

Non-chromatographic purification techniques are of interest since chromatography can be the most expensive step in protein purification (Przybycien et al., (2004). Alternative approaches can rely on targeted precipitation of the protein of interest. One approach is metal chelate affinity precipitation, where thermoresponsive copolymers can be used to specifically precipitate out poly-histidine tagged recombinant proteins (Balan et al., 2003; Kumar et al., 2003). Another purely protein-based approach is the use of thermoresponsive elastin-like peptides (ELPs) that consist of tandem repeats of the sequence VPGXG (SEQ ID NO: 1365) and precipitate with small temperature increases (McPherson et al., 1996; Meyer and Chilkoti. 1999). ELPs undergo an inverse phase transition and aggregation, which is thought to be driven by the exposure of hydrophobic patches in the peptides upon heating (Yamaoka et al., 2003). As part of a purification system, ELPs have been coupled to intein domains that have been genetically engineered into minimal self-cleaving units (Wood et al., 1999). When coupled, the ELP-intein system allows for a simple two-stage purification scheme. In the first step, precipitation of the ELP is triggered and the fusion protein is purified. Then, the intein is induced to cleave off the target protein and the ELP is again precipitated, leaving behind pure target protein in solution (Banki et al., 2005). While effective for many purification applications, the necessary heating of samples or the alternative use of high salt concentrations (Fong et al., 2009) can be problematic in many situations. Another protein-based non-chromatographic purification scheme developed by Ding et al. relies on calcium-dependent precipitation of an annexin B1 tag (Ding et al., 2007). As with ELPs, a self-cleaving intein is also incorporated in the fusion protein to remove the tag following purification.

The compositions and methods described herein relate to repeat scaffolds for protein engineering applications. Repeat scaffolds can have repetitive secondary structures (Courtemanche and Barrick 2008; Grove et al., 2008). Some repeat scaffolds can be engineered for biomolecular recognition, foir example, the ankyrin repeats (Binz et al., 2004). In certain aspects, the compositions and methods described herein relate to consensus design to improve the engineerability of such scaffolds. When used in connetion with the compisitions and methods described herein, consensus design can be used to identify a core repeating peptide unit (Mosavi et al., 2004; Main et al., 2003; Parmeggiani et al., 2008; Binz et al., 2003).

Described herein is a synthetic PBRT peptide, based on the natural repeat-in-toxin (RTX) domain that undergoes calcium-responsive, reversible precipitation. In certain embodiments, when coupled to the maltose binding protein (MBP), the calcium-responsive tag described herein can be ued to purify a fusion protein. In certain embodiments where the MBP is appended to green fluorescent protein (GFP), β-lactamase, or a thermostable alcohol dehydrogenase (AdhD), these constructs can also be purified by calcium-induced precipitation. In certain embodiments, protease cleavage of the precipitating tag enables the recovery of pure and active target protein by cycling precipitation before and after cleavage.

The methods and compositions described herein relate to novel stimulus-responsive repeat scaffolds for protein engineering based on the calcium-responsive repeat-in-toxin (RTX) domain1. The RTX domain is found in proteins secreted through the bacterial type 1 secretion system (Holland et al., 2005). The domain consists of repeats of the consensus amino acid sequence GGXGXDXUX (SEQ ID NO: 1336), where X is variable and U is a hydrophobic amino acid. One RTX domain is the block V RTX domain from the adenylate cyclase toxin (CyaA) of B. pertussis. The domain is intrinsically disordered in the absence of calcium and forms a β roll structure (FIG. 13A) in the presence of calcium (Chenal et al., 2009). The block V RTX domain retains its reversible calcium-responsiveness even when expressed separately from the larger protein (Bauche et al., 2006; Blenner et al., 2010). Previous attempts have been made to use RTX domains in protein engineering, including incorporation into mesh networks, design of synthetic RTX peptides, and generation of hydrogel-forming RTX domains (Lilie et al., 2000; Ringler, P. and G. E. Schulz. 2003; Scotter et al., 2007; Dooley et al., 2012).

Figure 13:
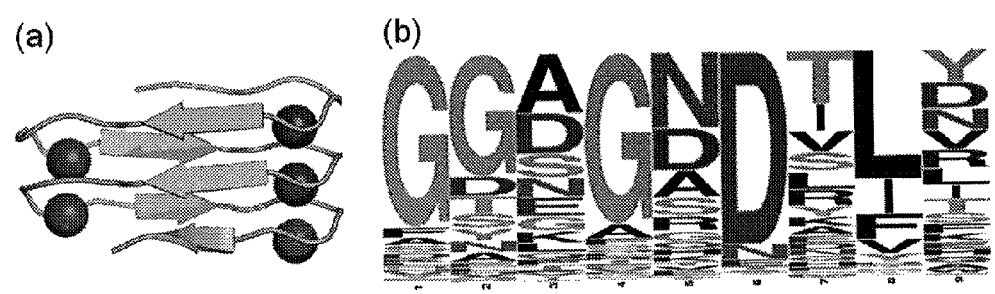
FIG. 13A-13B show beta roll structure and sequence logo.

In certain aspects, the compositions and methods described herein relate to the design of consensus RTX domains. The frequency of amino acids at each position of the nine amino acid repeat unit from a set of RTX-containing proteins have examined and resulted in the identification of a consensus PBRT sequence GGAGNDTLY (SEQ ID NO: 1) (FIG. 13B). A library of consensus constructs consisting of 5, 9, 13, or 17 repeats of the PBRT consensus unit was created. Upon purification of a number of these constructs, many of them were observed to precipitate in the presence of calcium. Therefore, it was decided to explore the possibility of using these consensus precipitable β roll tags (PBRTs) as a tools for bioseparation.

Reported herein is the use of PBRTs to purify recombinant proteins. A maltose binding protein (MBP)-PBRT17 fusion was first purified as a proof of principle. This MBP-PBRT17 construct was fused to green fluorescent protein (GFP), which was used as a reporter during initial purification experiments. β-lactamase and a thermostable alcohol dehydrogenase (AdhD) were also fused to demonstrate the feasibility of purifying enzymatic proteins. In certain embodiments, a specific protease site was engineered downstream of the tag to show that target proteins can be fully purified by protease cleavage while retaining their activity.

Oligonucleotides suitable for used in connection with the methods and compositions described herein are in Table 2.

TABLE 2

Oligonucleotides

| Name | Sequence |
|---|---|
| cons_beta_1 | 5'_ggcggtgcgggcaacgatacccctgtatggtggcgccgggaatgacacattatacg gaggtgctggcaatgatacgctgtatggcggagcaggtaacgac_3' (SEQ ID NO. 1345) |
| cons_beta_2 | 5'_attcccagcaccgccataaagggtatcgttgcctgccccccccatacagcgtgtcgtta ccggcgccccatacaaagtgtcgttacctgctccgc_3' (SEQ ID NO. 1346) |
| cons_beta_3 | 5'_ggcggtgctgggaatgacacactgtacggcggggcgggtaacgataccctctatg gtggtgctggcaatgatacactgtat_3' (SEQ ID NO. 1346) |
| cons1_AvaI_F | 5'_attaaaaactcggggatgatgatgatgacaagggcggtgcggg_3' (SEQ ID NO. 1347) |
| cons9_BseRI_HindIII_R | 5'_tttttaataagcttgaggagtattattaatacagtgtatcattgccagcac_3' (SEQ ID NO. 1348) |
| cons5_BseRI_HindIII_R | 5'_tttttaataagcttgaggagtattattaatacagcgtgtcgttaccg_3' (SEQ ID NO. 1349) |
| cons1_BtsCI_F | 5'_attaaaaaggatgatggcggtgcggg_3' (SEQ ID NO. 1350) |
| cons4_BseRI_HindIII_R | 5'_tttttaataagcttgaggagtattattaatacaaagtgtcgttacctgctc_3' (SEQ ID NO. 1351) |
| cons8_BseRI_HindIII_R | 5'_tttttaataagcttgaggagtattattaatagagggtatcgttacccgc_3' (SEQ ID NO. 1352) |
| GFP_BseRI_F | 5'_aatatatagaggagataataatatatgagtaaaggagaagaacttttcactgga gt_3' (SEQ ID NO. 1353) |
| GFP_HindIII_R | 5'_tattataaagctttatttgtatagttcatccatgccatgtgtaat_3' (SEQ ID NO. 1354) |

TABLE 2-continued

Oligonucleotides

| Name | Sequence |
|---|---|
| blac_BseRI_F | 5'_aatatatagaggagataataatatatgagtattcaacatttccgtgtcgc_3' (SEQ ID NO. 1355) |
| blac_HindIII_R | 5'_tattattaagctttttattaccaatgcttaatcagtgaggcacc_3' (SEQ ID NO. 1356) |
| AdhD_BserI_F | 5'_aaagaggaggatcatgaatatggcaaaaagggtaaatgcattcaacgacc_3' (SEQ ID NO. 1357) |
| AdhD_HindIII_R | 5'_agtgccaagatttattacacacacctccttgccatctctctatcctc_3' (SEQ ID NO. 1358) |
| blac_entero_BseRI_F | 5'_aaagaggaggatcatgaatgatgatgatgacaagatgagtattcaacatttccgtgtcgcccttattc_3' (SEQ ID NO. 1359) |
| AdhD_entero_BseRI_F | 5'_aaagaggaggatcatgaatgatgatgatgacaagatggcaaaaagggtaaatgcattcaacgacc_3' (SEQ ID NO. 1360) |
| entero_KOI_F | 5'_cctcggggatgatggtgacaagggcggtgc_3' (SEQ ID NO. 1361) |
| entero_KOI_R | 5'_gcaccgccatgtcaccatcatccccgagg_3' (SEQ ID NO. 1362) |
| entero_KOII_F | 5'_ggggatgatggtgagcagggcggtgcgggc_3' (SEQ ID NO. 1363) |
| entero_KOII_R | 5'_gcccgcaccgccctgctcaccatcatcccc_3' (SEQ ID NO. 1364) |

Sequences are provided for all oligonucleotides used for cloning experiments.

Four differently sized MBP-PBRT fusions were prepared consisting of 5, 9, 13, or 17 repeats of the consensus PBRT sequence (named PBRT5, PBRT9, PBRT13, and PBRT17). In order to generate the DNA fragment for PBRT9, three oligonucleotides were synthesized: cons_β_1, cons_β_2, and cons_β_3. One ng each of these oligonucleotides was mixed along with the primers cons1_AvaIF and cons9_BseRI_HindIII_R. PCR was performed and a clean product was obtained and gel extracted. This fragment was digested with AvaI and HindIII and cloned into the similarly digested pMAL_c4E vector to generate pMAL_BRT9.

To generate the PBRT5 construct, pMAL_BRT9 was used as a template for PCR with the primers cons1_AvaI_F and cons5_BseRI_HindIII_R. This product was digested with AvaI and HindIII and cloned into the pMAL_c4E vector producing pMAL_BRT5.

BRT13 was produced by concatenation of four additional repeats to PBRT9. Concatenations were achieved using a recursive ligation technique similar to those previously described (Meyer et al., 2002; McDaniel et al., 2010). This four repeat insert was amplified using primers cons1_BtsCI_F and cons4_BseRI_HindIII_R. The product was digested with BtsCI and HindIII and then cloned into pMAL_BRT9 cut with BseRI and HindIII to yield pMAL_BRT13. PBRT17 was produced analogously to PBRT13, except that the reverse primer cons8_BseRI_HindIII_R was used instead of cons4_BseRI_HindIII_R.

The emGFP gene was amplified from the Invitrogen pRSET/emGFP vector using primers GFP_BseRI_F and GFP_HindIII_R. The β-lactamase gene was amplified from the pMAL_c4E vector using primers βlac_BseRI_F and βlac_HindIII_R. The AdhD gene was amplified out of pWUR85 using primers AdhD_BserI_F and AdhD_HindIII_R (Campbell et al., 2010). All three of these inserts were digested with BseRI and HindIII and cloned into similarly digested pMAL_BRT17 to yield pMAL_BRT17_GFP, pMAL_BRT17_βlac and pMAL_PBRT17_AdhD.

The native enterokinase site in the pMAL_c4E vector, which sits between MBP and PBRT17, was knocked out in the pMAL_BRT17_βlac and pMAL_BRT17_AdhD plasmids. Two rounds of site-directed mutagenesis were required to change the native recognition site, DDDDK (SEQ ID NO: 1368), to DDGEQ (SEQ ID NO: 1369), which was shown to be resistant to cleavage. A novel enterokinase recognition site was also engineered downstream of PBRT17 in these constructs to allow for purification of the untagged protein of interest. Full plasmid maps of all cloned constructs are available in FIG. 12.

E. coli cells were used for expression and cloning. One liter cultures of TB supplemented with 100 µg/mL ampicillin and 0.2% glucose were inoculated with 10 mL of overnight culture. Cultures were grown at 37° C. with shaking at 225 RPM to an approximate OD600 of 0.5 and induced with 0.3 mM IPTG. Cells harboring pMAL_BRT17 and pMAL_BRT17_βlac were allowed to express for an additional two hours and then harvested. Cultures transformed with pMAL_BRT17_GFP were transferred to a shaker at 25° C. and allowed to express for an additional 16 h and then harvested as no fluorescence was observed when expressed at 37° C. Cultures transformed with pMAL_BRT17 AdhD were allowed to express at 37° C. for an additional 16 h as previously reported (Campbell et al., 2010). Cells were harvested after expression and resuspended in 1/20 culture volume of 50 mM tris-HCl, pH 7.4 for precipitation purification. For amylose resin purification, cells were resuspended in 1/20 culture volume of MBP column buffer (20 mM tris-HCl, 200 mM NaCl, 1 mM EDTA, pH 7.4). In both cases, cells were subsequently lysed via 150 s. Lysate was then clarified by centrifugation at 15,000 g for 30 mM at 4° C. For amylose resin purification, clarified lysate was diluted with five volumes of column buffer and purified as previously described (Blenner et al., 2010). All subsequent steps were performed at room temperature.

Figure 14:
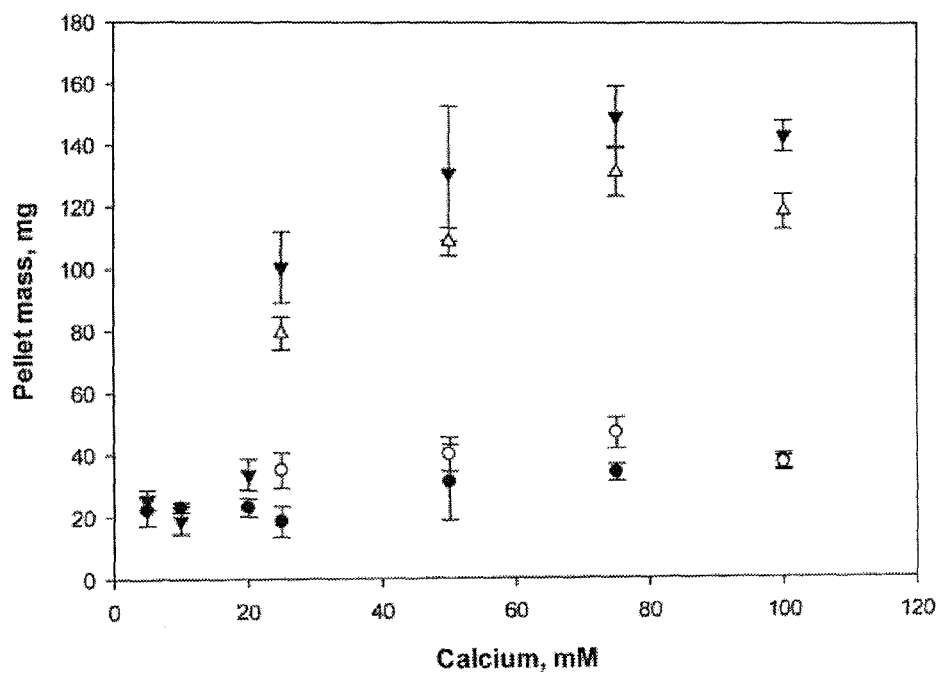
FIG. 14 shows the role of PBRT length in precipitation. Mass of precipitated pellet vs. calcium chloride concentration and PBRT size. Results for MBP-PBRT5(1), MBP-PBRT9(●), MBP-PBRT13(○), and MBP-PBRT17(▼). Error bars represent standard deviations for 3 trials.

For precipitation purification, clarified lysate was added to a concentrated calcium stock according to the data presented in FIG. 14. For example, for precipitation of MBP-PBRT17 lysate in 100 mM CaCl2, 950 µL of clarified lysate was added to 50 µL of 2 M CaCl2 solution. The sample was promptly mixed by gentle pipetting, allowed to sit at room temperature for 2 min and then centrifuged at 16,000 g in a microcentrifuge for 2 min. The supernatant was carefully removed and the pellet was resuspended in the same tris buffer by gentle pipetting. The turbid solution was centrifuged and washed for four additional cycles. For the final step, the pellet was resuspended in tris buffer with a concentration of EGTA equivalent to the original calcium concentration. Gentle pipetting was sufficient to cause the sample to redissolve as confirmed by observation and the lack of a precipitate upon subsequent centrifugation.

Concentrations of all purified proteins were determined by 280 nm absorbance using extinction coefficients predicted by ExPASy (www.expasy.org). All extinction coefficients are provided in Supplementary Table 3. Recovery of MBP-PBRT17 by either amylose resin purification or precipitation was determined solely using this method.

TABLE 3

Calculated Extinction Coefficients

| Construct | $\epsilon$, M−1 · cm−1 |
|---|---|
| MBP-PBRT17 | 91680 |
| MBP-PBRT17-GFP | 113695 |
| MBP-PBRT$_{17}$-βlac | 119765 |
| MBP-PBRT$_{17}$-AdhD | 144175 |
| AdhD | 52370 |

Calculated molar extincton coefficients are given for all protein constructs. The ExPASy ProtParam tool was used for calculation.

MBP-PBRT17-GFP recoveries were estimated by comparing fluorescence emission intensity at 509 nm with excitation at 487 nm. 100-fold dilutions of both clarified lysate and purified protein were made for fluorescence measurements. Purified proteins were resuspended in the same volume as the lysate from which they were extracted, so signals were compared directly.

For estimation of MBP-PBRT17-βlac recovery, protein was added to a nitrocefin solution and the absorbance at 486 nm was tracked corresponding to the hydrolysis of nitrocefin. 500 μL of nitrocefin solution was prepared by placing three nitrocefin disks in 450 μL 50 mM tris-HCl, pH 7.4 and 50 μL DMSO. In each sample well, 50 μL of this solution was mixed with 90 μL of the same tris buffer and 10 μL of protein sample. For each sample tested, serial dilutions from 1× to 1000× were prepared from lysate and purified protein. Initial rates were determined by measuring the change in absorbance at 486 nm over the first 20% of the change in signal between the starting absorbance and the end absorbance. The same nitrocefin stock solution was used for all samples to account for variations in concentration.

MBP-PBRT17-AdhD recovery was also evaluated by enzymatic activity using a protocol previously described (Campbell et al., 2010). Since this AdhD was isolated from the hyperthermofile *Pyrococcus furiosus*, all samples were heat treated at 80° C. for 1 h prior to evaluating activity. All assays were performed at saturated conditions of both cofactor and substrate, 0.5 mM NAD+ and 100 mM 2,3-butanediol, respectively. Reaction mixtures containing 2,3-butanediol and protein sample in 50 mM glycine pH 8.8 were incubated at 45° C. in a 96 well UV microplate in a spectrophotometer. Reactions were initiated by the addition of NAD+. Initial rates were calculated by following the production of NADH at 340 nm. Specific activity of cleaved AdhD was calculated using an NADH extinction coefficient ($\epsilon$=6.22 mM-1 cm-1).

In order to identify the consensus RTX sequence, a database of RTX containing proteins was constructed by searching the UniProt (www.uniprot.org) database for hemolysin-type calcium binding domains. Individual repeats were identified and the frequency of amino acids at each of the nine repeat positions was determined (FIG. 13B). From this result, the repeat sequence GGAGNDTLY (SEQ ID NO: 1) was identified as the consensus sequence. For a few of these positions, other amino acids were found with nearly equal frequency. However, as this sequence was found to be effective for purification, further investigation on sequence variation was not performed. A variety of synthetic RTX domains of different lengths (PBRT5, PBRT9, PBRT13, PBRT17) were prepared as fusions to the C terminus of MBP, with subscripts denoting the number of repeats. These lengths were chosen as they reflect the variability of naturally occurring RTX domains. Upon the addition of calcium to the purified PBRT17 construct, there was significant precipitation out of solution, which was reversed upon the addition of the chelating agent EGTA.

In order to more thoroughly characterize the observed precipitation behavior, cells were induced to express the four MBP-PBRT constructs. Clarified cell lysates were titrated with calcium to assess precipitation behavior by mixing with CaCl2 solution at the indicated concentrations, followed by by centrifugation, and measurement of the mass of the pellet (FIG. 14). Due to possible variations in cell growth rates and densities, all cultures were started from saturated overnight cultures and induced simultaneously. Both PBRT13 and PBRT17 precipitated when calcium concentrations exceeded 25 mM. Some precipitation was observed from PBRT5 and PBRT9 lysate, similar to what was observed with control cell lysate. Addition of an equivalent concentration of EGTA allowed the pellets to quickly dissolve again upon gentle pipetting.

While both PBRT13 and PBRT17 precipitated upon calcium addition, PBRT17 formed a pellet that was easier to clarify and was therefore selected for further examination. Three additional constructs were prepared by fusing MBP-PBRT17 to the N terminus of GFP, β-lactamase, and AdhD (named MBP-PBRT17-GFP and MBP-PBRT17-βlac, MBP-PBRT17-AdhD respectively). These three proteins were fused to MBP to allow for amylose resin chromatography purification as a comparison technique. GFP was chosen as a reporter protein for initial purification experiments to track the location of the PBRT. β-lactamase and AdhD were chosen as they are well characterized enzymes whose activity can be measured with straightforward assays.

Figure 15:
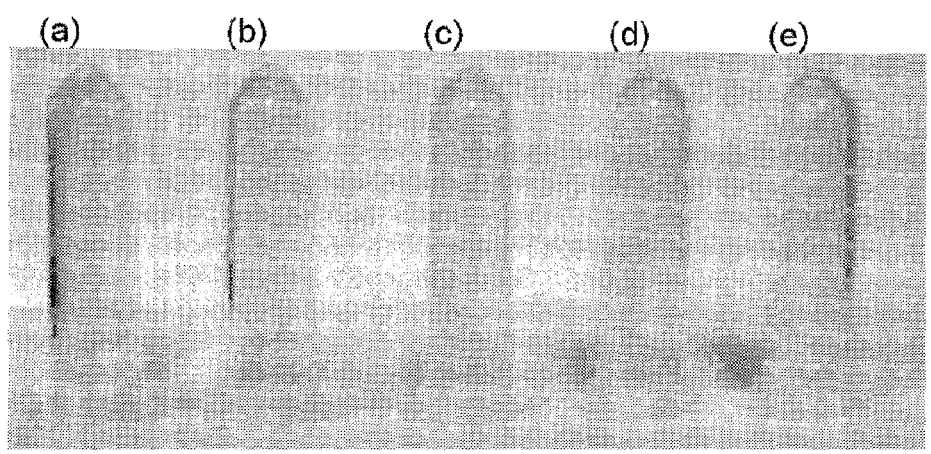
FIG. 15 shows ion specificity of PBRT precipitation. Purified MBP-PBRT17-GFP was mixed with 100 mM of the compound indicated, and centrifuged to collect any pellet. The tube was then inverted so that precipitated protein remained on top. The compounds were as follows: (a) CaCl2, (b) MgCl2, (c) MnCl2, (d) NaCl, and (e) (NH4)2SO4

The folding of RTX domains into β rolls is highly calcium specific. Therefore, investigation was performed to determine whether the precipitation behavior observed was also calcium-specific. To test this, MBP-PBRT17-GFP was purified on an amylose resin and diafiltered into salt-free tris buffer Diafiltration was used as proteins are purified in high salt buffer for the amylose resin step and it was observed that PBRT precipitation was significantly in high salt. This is consistent with previous observations that RTX calcium affinity is reduced with increasing salt concentration (Szilvay et al., 2009). Solutions of various salts were added to final concentrations of 100 mM. The samples were then gently mixed by pipetting, allowed to sit for 2 min, and centrifuged at 16,000 g in a microcentrifuge for 2 min. Tubes were then inverted and the presence of a pellet at the top was indicative of precipitation (FIG. 15). PBRT precipitation was observed to be calcium-specific, with near complete precipitation of MBP-PBRT17-GFP (as indicated by the remaining color in solution) in the presence of calcium and no precipitation with other salts.

Figure 16:
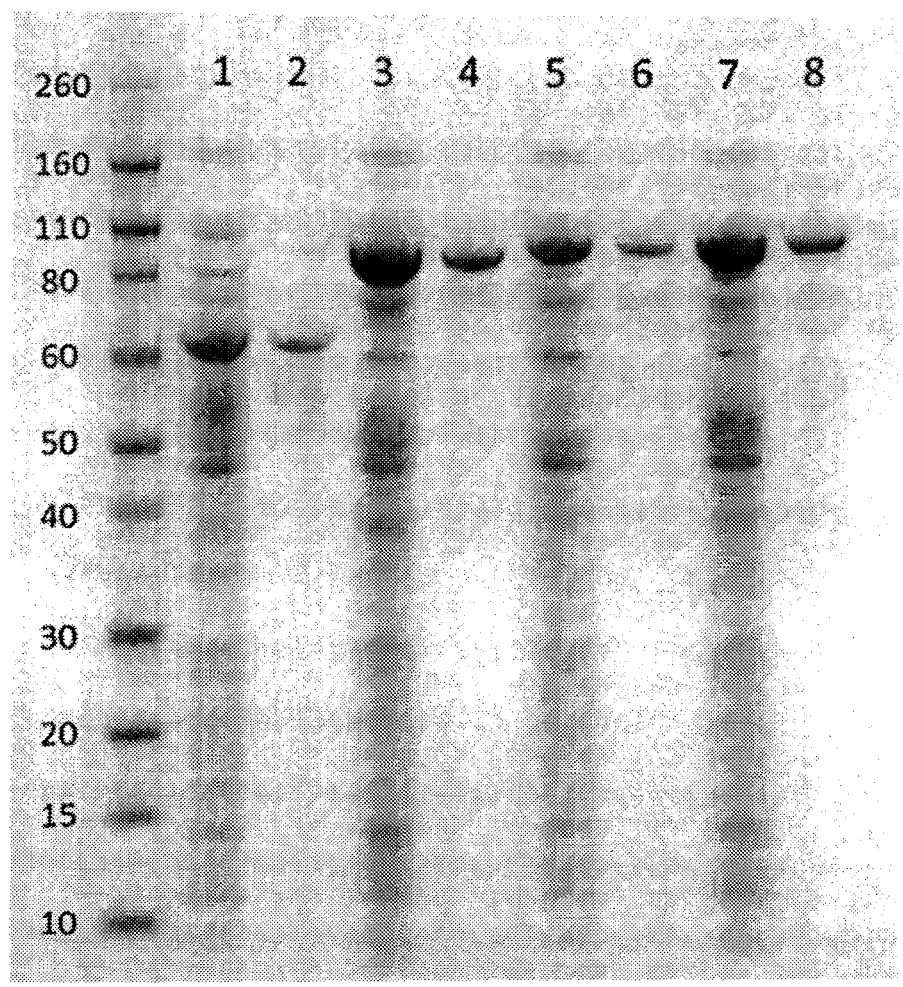
FIG. 16 shows SDS-PAGE results for purification of the four constructs tested. Numbers are standard size in kDa. Expected molecular weights for MBP-PBRT17, MBP-PBRT17-GFP, MBP-PBRT17-βlac, and MBP-PBRT17-AdhD are 57.1, 83.4, 88.6, and 89.1 kDa, respectively. (1-2) Purification of MBP-PBRT 17. Lane 1 is clarified lysate, and Lane 2 is purified fusion protein. (3-4) Same samples for purification of MBP-PBRT17-GFP. (5-6) Same samples for MBP-PBRT17-βlac. (7-8) Same samples for MBP-PBRT17-AdhD.

For all 4 constructs tested, calcium concentrations greater than 25 mM were found to cause precipitation of the fusion protein. To assess the ideal calcium concentration, all 4 constructs were precipitated from 1 mL of clarified cell lysate in 25, 50, 75, and 100 mM CaCl2. Pellets were washed in salt-free tris buffer five times. Pellets were broken up upon washing, but did not redissolve until exposed to an equivalent concentration of EGTA after the final wash. The 100 mM CaCl2 samples were found to not fully redissolve, so only lower CaCl2 concentrations were tested further. A slight increase in recovery was observed at 75 mM CaCl2 (as compared with lower CaCl2 concentrations) as confirmed by SDS-PAGE. All 4 constructs were subsequently purified by precipitation with 75 mM CaCl2 and SDS-PAGE gels were run after 5 washes (FIG. 16). No significant difference was found with increasing number of washes, so further quantification and recovery measurements were performed on samples washed five times. To confirm scalability, the analogous protocol was also performed on 50 mL lysate, and comparable results were obtained. Additionally, the reversibility of the precipitation process was tested. It was found that addition of calcium to the redissolved pellet in EGTA solution did yield a pellet once again. Full pellet size was only recovered after dialysis into EGTA-free buffer.

The recovery and functionality of the purified proteins after precipitation was then qualified. To assess recovery of MBP-PBRT17, the theoretically determined extinction coefficient was used to estimate concentration by absorbance at 280 nm (Gill and Vonhippel, 1989). Results from purifying the construct on an amylose resin were compared with PBRT precipitation. For MBP-PBRT17-GFP, recoveries were calculated as the percentage of fluorescence signal of purified sample compared with lysate (this was normalized against control lysate). Along with total protein recoveries estimated by UV absorbance, recoveries of both MBP-PBRT17-βlac and MBP-PBRT17-AdhD were estimated by comparing lysate activity to the activity of these constructs after purification. MBP-PBRT17-βlac recoveries were calculated using activity measured by tracking the absorbance at 486 nm for the hydrolysis of nitrocefin. MBP-PBRT17-AdhD recoveries were calculated by tracking NADH formation at 340 nm in saturating conditions of both substrate and cofactor. Results of these trials are shown in Table 4.

each fusion protein based on UV absorption at 280 nm. All fusion proteins were shown to be purified in high yields.

TABLE 5

Absolute Protein Yields
Absolute Yield (mg/L)

| Calcium, mM | MBP-PBRT17 | MBP-PBRT17-GFP | MBP-PBRT17-βlac | MBP-PBRT17-AdhD |
|---|---|---|---|---|
| 25 | 268 ± 11 | 333 ± 12 | 124 ± 3 | 198 ± 3 |
| 50 | 305 ± 14 | 434 ± 17 | 160 ± 7 | 273 ± 9 |
| 75 | 295 ± 26 | 336 ± 40 | 176 ± 5 | 214 ± 6 |

Amount of protein recovered for each fusion construct after precipitation and washing. Values were determined using UV absorbance at 280 nm and calculated extinction coefficients available in the Table 3. All data were collected in triplicate and errors represent standard deviations.

Figure 17:
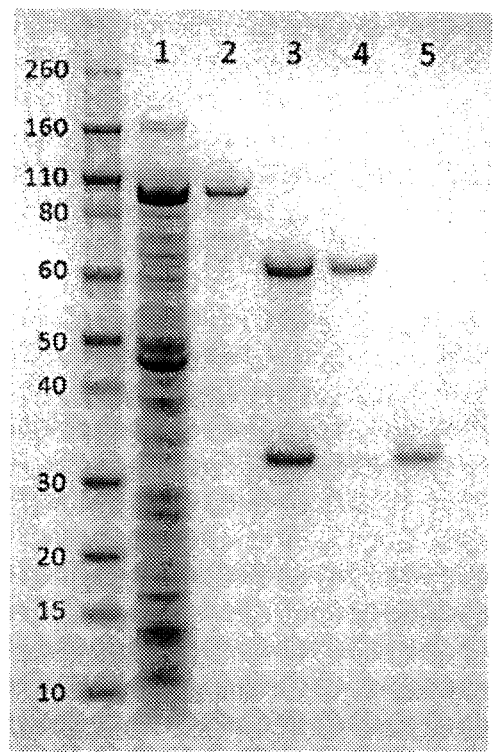
FIG. 17 shows SDS-PAGE results for purification and cleavage of AdhD. Numbers are standard size in kDa. Estimated molecular weight for AdhD is 31.9 kDa. (1) Clarified MBP-PBRT17-AdhD lysate. (2) Purified fusion protein. (3) Enterokinase cleavage. (4) Precipitated MBP-PBRT17. (5) Soluble AdhD. 3× protein concentrations were used in lanes 3, 4, and 5.

In certain embodiments, the PBRTs described herein can be coupled with a cleavage tag to separate the protein of interest from the PBRT. The pMAL_c4E vector used for these assays contains a cleavable enterokinase site between the MBP and PBRT. This recognition sequence was removed via site-directed mutagenesis. A new enterokinase site was engineered between the PBRT and the protein of interest for MBP-PBRT17-βlac and MBP-PBRT17-AdhD. Therefore, as a proof of principle, precipitation purified MBP-PBRT17-βlac and MBP-PBRT17-AdhD was subjected to overnight cleavage by enterokinase digestion. Calcium was then added directly to the cleavage reaction to precipitate MBP-PBRT17, thereby separating the tag from the protein of interest following centrifugation. This is shown in FIG. 17 for MBP-PBRT17-AdhD, showing pure, soluble protein by SDS-PAGE. Recoveries of 93±7% were obtained by tracking UV absorbance at 280 nm, meaning 93% of the AdhD in the precipitation purified sample was recovered after cleav-

TABLE 4

Recovery data for three constructs tested.

| | MBP-PBRT17 | MBP-PBRT17-GFP | | MBP-PBRT17-βlac | | MBP-PBRT17-AdhD | |
|---|---|---|---|---|---|---|---|
| Calcium, mM | Fold versus Resin | Fold versus Resin | Fluorescence | Fold versus Resin | Activity Recovered | Fold versus Resin | Activity Recovered |
| 25 | 2.0 ± 0.1 | 2.8 ± 0.1 | 61 ± 3% | 4.1 ± 0.1 | 1.6 ± 0.1% | 1.6 ± 0.1 | 3.8 ± 0.5% |
| 50 | 2.3 ± 0.1 | 3.7 ± 0.1 | 86 ± 6% | 5.3 ± 0.2 | 4.0 ± 0.1% | 1.7 ± 0.1 | 4.7 ± 0.7% |
| 75 | 2.2 ± 0.2 | 2.8 ± 0.3 | 78 ± 8% | 5.1 ± 0.2 | 3.4 ± 0.1% | 2.2 ± 0.1 | 8.3 ± 1.4% |

"Fold versus Resin" denotes protein quantity recovered relative to amylose resin for equivalent loading amount. For MBP-PBRT17-GFP, MBP-PBRT17-βlac, and MBP-PBRT17-AdhD fluorescence and activity are the respective properties relative to clarified lysate. Errors represent standard deviations. All data were collected in triplicate.

For MBP-PBRT17, calcium precipitation recovers about double the amount of protein as compared with amylose resin purification. For MBP-PBRT17-GFP, up to 86% recovery of fluorescence was observed. MBP-PBRT17-βlac recovery from the lysate was not as high, but was still 5-fold better than the amylose resin, yielding a significant quantity of protein. Similar results were also observed for MBP-PBRT17-AdhD, although the yields were not quite as high compared with the resin (2-fold improvement). The overall values of the activities recovered in Table 4 were all larger than the values obtained using the amylose resin purification. It is also possible that measuring activity in crude extracts may introduce error beyond what was accounted for in the measurement of endogenous hydrolysis (β-lactamase) and reduction (AdhD). Table 5 lists the absolute yield of age and reprecipitation of the tag. Specific activity of the purified enzyme was also calculated to be 20.2±1.3 min-1, which is similar to what has been previously reported, indicating this system has little to no effect on the activities of purified proteins (Campbell et al., 2010). However, in the case of MBP-PBRT17-βlac, the cleaved β-lactamase remained in the insoluble fraction following enterokinase cleavage and calcium precipitation. Upon further investigation it was found that β-lactamase will precipitate in high calcium concentrations. As a control experiment, similar behavior was observed in recombinant β-lactamase. In 75 mM CaCl2, an insoluble pellet was formed upon centrifugation. Activity assays confirmed a significant amount of active protein in the insoluble fraction. In certain embodiments, the protease used could be fused to the precipitating PBRT or a self-cleaving intein could be incorporated. Fusing the protease to the PBRT can be used for its removal from the target protein in the final precipitation. A self-cleaving intein can also be used to fulfill a similar function. PBRT can also precipitate without being fused to the MBP, indicating that the MBP is not essential for this system. In certain embodiments, the MBP may be useful for improving protein expression levels.

The results described herein show a correlation between length and precipitation (FIG. 14). However, there has not been extensive work in studying the role of the number of repeats on RTX behavior. The impact of altering the number of native. RTX repeats in the block V CyaA RTX domain of *B. pertussis* was previously examined without significant size effect and C-terminal capping was required for calcium-responsiveness (Shur and Banta, 2012). As for past efforts to design synthetic RTX domains, the synthetic domains created by Scotter et al. consisted of 4 RTX repeats and those prepared by Lilie et al. consisted of 8 repeats (Lilie et al., 2000; Scotter et al., 2007). The peptides create by Lilie et al. were weakly calcium-responsive, while those of Scotter et al. were only lanthanum-responsive and formed partially insoluble filaments in the presence of lanthanum. In general, β sheets are prone to aggregation and nature uses various strategies to ensure solubility of proteins containing these motifs (Richardson and Richardson, 2002). PBRTs may be a balance between this tendency and the calcium-responsiveness of the β roll.

The technique described herein provides a new stimulus-responsive phase-changing peptide useful in a range of applications similar to those for which ELPs have been used, such as recombinant protein purification or the creation of "smart" biomaterials. The PBRTs described herein possesses certain advantages over ELPs and annexin B1 since precipitation is simpler to achieve and the PBRT peptide is significantly smaller. Additionally, PBRT17 precipitates in as little as 25 mM CaCl2 at room temperature, compared to the larger ionic strength and higher temperature increases required for ELP precipitation. Precipitation also occurs instantaneously, whereas annexin B1-based systems require a 2 h incubation period at 4° C. Overall, PBRTs offer a new tool for rapid purification of recombinant proteins. The protocol described here can be performed to obtain purified fusion protein from lysate in only a few minutes. Further optimization of the PBRT system should enable the use of specific proteases to purify target proteins and further improve the precipitation and resolubilization process, greatly enhancing the ability to rapidly purify recombinant proteins.

REFERENCES

1. Przybycien, T. M., N. S. Pujar, and L. M. Steele. 2004. Alternative bioseparation operations: life beyond packed-bed chromatography. Curr. Opin. Biotechnol. 15:469-478.
2. Balan, S., J. Murphy, I. Galaev, A. Kumar, G. E. Fox, B. Mattiasson, and R. C. Willson. 2003. Metal chelate affinity precipitation of RNA and purification of plasmid DNA. Biotechnol. Lett. 25:1111-1116.
3. Kumar, A., P. O. Wahlund, C. Kepka, I. Y. Galaev, and B. Mattiasson. 2003. Purification of histidine-tagged single-chain Fv-antibody fragments by metal chelate affinity precipitation using thermoresponsive copolymers. Biotechnol. Bioeng. 84:494-503.
4. McPherson, D. T., J. Xu, and D. W. Urry. 1996. Product purification by reversible phase transition following *Escherichia coli* expression of genes encoding up to 251 repeats of the elastomeric pentapeptide GVGVP (SEQ ID NO: 1370). Protein Expr. Purif. 7:51-57.
5. Meyer, D. E. and A. Chilkoti. 1999. Purification of recombinant proteins by fusion with thermally-responsive polypeptides. Nat. Biotechnol. 17:1112-1115.
6. Yamaoka, T., T. Tamura, Y. Seto, T. Tada, S. Kunugi, and D. A. Tirrell. 2003. Mechanism for the phase transition of a genetically engineered elastin model peptide (VPGIG) 40 (SEQ ID NO: 1371) in aqueous solution. Biomacromolecules 4:1680-1685.
7. Wood, D. W., W. Wu, G. Belfort, V. Derbyshire, and M. Belfort. 1999. A genetic system yields self-cleaving inteins for bioseparations. Nat. Biotechnol. 17:889-892.
8. Banki, M. R., L. Feng, and D. W. Wood. 2005. Simple bioseparations using self-cleaving elastin-like polypeptide tags. Nat. Methods 2:659-661.
9. Fong, B. A., W. Y. Wu, and D. W. Wood. 2009. Optimization of ELP-intein mediated protein purification by salt substitution. Protein Expr. Purif. 66:198-202.
10. Ding, F. X., H. L. Yan, Q. Mei, G. Xue, Y. Z. Wang, Y. J. Gao, and S. H. Sun. 2007. A novel, cheap and effective fusion expression system for the production of recombinant proteins. Appl. Microbiol. Biotechnol. 77:483-488.
11. Courtemanche, N. and D. Barrick. 2008. The leucine-rich repeat domain of Internalin B folds along a polarized N-terminal pathway. Structure 16:705-714.
12. Grove, T. Z., A. L. Cortajarena, and L. Regan. 2008. Ligand binding by repeat proteins: natural and designed. Curr. Opin. Struct. Biol. 18:507-515.
13. Binz, H. K., P. Amstutz, A. Kohl, M. T. Stumpp, C. Briand, P. Forrer, M. G. Grutter, and A. Pluckthun. 2004. High-affinity binders selected from designed ankyrin repeat protein libraries. Nat. Biotechnol. 22:575-582.
14. Mosavi, L. K., T. J. Cammett, D. C. Desrosiers, and Z. Y. Peng. 2004. The ankyrin repeat as molecular architecture for protein recognition. Protein Sci. 13:1435-1448.
15. Main, E. R., Y. Xiong, M. J. Cocco, L. D'Andrea, and L. Regan. 2003. Design of stable alpha-helical arrays from an idealized TPR motif Structure 11:497-508.
16. Parmeggiani, F., R. Pellarin, A. P. Larsen, G. Varadamsetty, M. T. Stumpp, O. Zerbe, A. Caflisch, and A. Pluckthun. 2008. Designed armadillo repeat proteins as general peptide-binding scaffolds: Consensus design and computational optimization of the hydrophobic core. J. Mol. Biol. 376:1282-1304.
17. Binz, R K., M. Stumpp, P. Forrer, P. Amstutz, and A. Plückthun. 2003. Designing repeat proteins: well-expressed, soluble and stable proteins from combinatorial libraries of consensus ankyrin repeat proteins. J. Mol. Biol. 332:489-503.
18. Holland, I. B., L. Schmitt, and J. Young. 2005. Type 1 protein secretion in bacteria, the ABC-transporter dependent pathway review. Mol. Membr. Biol. 22:29-39.
19. Chenal, A., J. I. Guijarro, B. Raynal, M. Delepierre, and D. Ladant. 2009. RTX calcium binding motifs are intrinsically disordered in the absence of calcium: implication for protein secretion. J. Biol. Chem. 284:1781-1789.
20. Bauche, C., A. Chenal, O. Knapp, C. Bodenreider, R. Benz, A. Chaffotte, and D. Ladant. 2006. Structural and functional characterization of an essential RTX subdomain of *Bordetella pertussis* adenylate cyclase toxin. J. Biol. Chem. 281:16914-16926.
21. Blenner, M. A., O. Shur, G. R. Szilvay, D. M. Cropek, and S. Banta. 2010. Calcium-induced folding of a beta roll motif requires C-terminal entropic stabilization. J. Mol. Biol. 400:244-256.
22. Lilie, H., W. Haehnel, R. Rudolph, and U. Baumann. 2000. Folding of a synthetic parallel beta-roll protein. FEBS Lett. 470:173-177.

23. Ringler, P. and G. E. Schulz. 2003. Self-assembly of proteins into designed networks. Science 302:106-109.
24. Scotter, A. J., M. Guo, M. M. Tomczak, M. E. Daley, R. L. Campbell, R. J. Oko, D. A. Bateman, A. Chakrabartty, et al. 2007. Metal ion-dependent, reversible, protein filament formation by designed beta-roll polypeptides. BMC Struct. Biol. 7:63.
25. Dooley, K., Y. H. Kim, H. D. Lu, R. Tu, and S. Banta. 2012. Engineering of an Environmentally Responsive Beta Roll Peptide for Use As a Calcium-Dependent Cross-Linking Domain for Peptide Hydrogel Formation. Biomacromolecules 13:1758-1764.
26. Meyer, D. E. and A. Chilkoti. 2002. Genetically encoded synthesis of protein-based polymers with precisely specified molecular weight and sequence by recursive directional ligation: Examples from the elastin-like polypeptide system. Biomacromolecules 3:357-367.
27. McDaniel, J. R., J. A. MacKay, F. G. Quiroz, and A. Chilkoti. 2010. Recursive Directional Ligation by Plasmid Reconstruction Allows Rapid and Seamless Cloning of Oligomeric Genes. Biomacromolecules 11:944-952.
28. Campbell, E., I. R. Wheeldon, and S. Banta. 2010. Broadening the cofactor specificity of a thermostable alcohol dehydrogenase using rational protein design introduces novel kinetic transient behavior. Biotechnol. Bioeng. 107:763-774.
29. Szilvay, G. R., M. A. Blenner, O. Shur, D. M. Cropek, and S. Banta. 2009. A FRET-based method for probing the conformational behavior of an intrinsically disordered repeat domain from *Bordetella pertussis* adenylate cyclase. Biochemistry 48:11273-11282.
30. Gill, S. C. and P. H. Vonhippel. 1989. Calculation of Protein Extinction Coefficients from Amino-Acid Sequence Data. Anal. Biochem. 182:319-326.
31. Shur, O. and S. Banta. 2012. Rearranging and concatenating a native RTX domain to understand sequence modularity. Protein Engineering Design and Selection.
32. Richardson, J. S. and D. C. Richardson. 2002. Natural beta-sheet proteins use negative design to avoid edge-to-edge aggregation. Proc. Natl. Acad. Sci. USA 99:2754-2759.
33. Crooks, G. E., G. Hon, J. M. Chandonia, and S. E. Brenner. 2004. WebLogo: A sequence logo generator. Genome Res. 14:1188-1190.
34. Schneider, T. D. and R. M. Stephens. 1990. Sequence Logos—a New Way to Display Consensus Sequences. Nucleic Acids Res. 18:6097-6100.
35. Hochuli et al., "Genetic Approach to Facilitate Purification of Recombinant Proteins with a Novel Metal Chelate Adsorbent", Nature Biotechnology, Issue 6, pp 1321-1325 (1988)
36. Guana et al., "Vectors that facilitate the expression and purification of foreign peptides in *Escherichia coli* by fusion to maltose-binding protein", Gene, Volume 67, Issue 1, pp 21-30, Jul. 15, 1988
37. Banki et al., "Simple bioseparations using self-cleaving elastin-like polypeptide tags", Nature Methods, Issue 2, pp 659-662, Aug. 2, 2005
38. Wood et al., "A genetic system yields self-cleaving inteins for bioseparations." Nature Biotechnology, Issue 17, Pages 889-892 Sep. 17, 1999.
39. U.S. Ser. No. 11/374,403

Example 4

Exemplary PBRCs

Below are the amino acid sequences of two exemplary PBRCs.

```
                                                    (SEQ ID NO: 4)
GGAGNDTLYGGAGNDTLYGGAGNDTLYGGAGNDTLYGGAGNDTLYINAGA

DQLWFARQGNDLEIRILGTDDALTVHDWYRDADHRVEIIHAANQAVDQAG

IEKLVEAMAQYPD (SEQ ID NO: 5)
GGAGNDTLYGGAGNDTLYGGAGNDTLYGGAGNDTLYGGAGNDTLYGGAGN

DTLYGGAGNDTLYGGAGNDTLYGGAGNDTLYGGAGNDTLYGGAGNDTLYG

GAGNDTLYGGAGNDTLYGGAGNDTLYGGAGNDTLYGGAGNDTLYGGAGND

TLYINAGADQLWFARQGNDLEIRILGTDDALTVHDWYRDADHRVEIIHAA

NQAVDQAGIEKLVEAMAQYPD
```

Example 5

Sequences of PBRT and PBRC Peptides that do not Induce Precipitation in Response to Ca2+

The following peptides are soluble in the presence of calcium.

```
                                                 (SEQ ID NO: 1339)
GSARDDVLIGDAGANVLNGLADNDVLSGGAGDDVLLGDEGSDLLSGDAGN

DDLFGGQGDDTYLFGVGYGHDTIYESGGGHDTIRGSARDDVLIGDAGANV

LNGLADNDVLSGGAGDDVLLGDEGSDLLSGDAGNDDLFGGQGDDTYLFGV

GYGHDTIYESGGGHDTIRINAGADQLWFARQGNDLEIRILGTDDALTVHD

WYRDADHRVEIIHAANQAVDQAGIEKLVEAMAQYPD (SEQ ID NO: 1340)
GSARDDVLIGDAGANVLNGLADNDVLSGGAGDDVLLGDEGSDLLSGDAGN

DDLFGGQGDDTYLFGVGYGHDTIYESGGGHDTIRGDAGANVLNGLADNDV

LSGGAGDDVLLGDEGSDLLSGDAGNDDLFGGQGDDTYLFGVGYGHDTIYE

SGGGHDTIR (SEQ ID NO: 1341)
GSARDDVLIGDAGANVLNGLADNDVLSGGAGDDVLLGDEGSDLLSGDAGN

DDLFGGQGDDTYLFGVGYGHDTIYESGGGHDTIRGDAGANVLNGLADNDV

LSGGAGDDVLLGDEGSDLLSGDAGNDDLFGGQGDDTYLFGVGYGHDTIYE

SGGGHDTIRINAGADQLWFARQGNDLEIRILGTDDALTVHDWYRDADHRV

EIIHAANQAVDQAGIEKLVEAMAQYPD (SEQ ID NO: 1341)
GGSGNDVIVGNAANNVLKGGAGNDVLFGGGGADELWGGAGKDIFV (SEQ ID NO: 1342)
GGSGNDVIVGNAANNVLKGGAGNDVLFGGGGADELWGGAGKDIFVFSAAS

DSAPGASDWIRDFQKGIDKIDLSFFNKEANSSDFIHFVDHFSGTAGEALL

SYNASSNVTDLSVNIGGHQAPDFLVKIVGQVDVATDFIV
```

What is claimed is:

1. A precipitable beta roll cassette (PBRC) comprising at least two beta roll tags (PBRTs) wherein the at least two PBRTs each comprise the amino acid sequence of SEQ ID NO: 1, wherein the PBRC precipitates in response to binding of calcium by the at least two PBRTs.

2. A precipitable beta roll cassette (PBRC) comprising at least two beta roll tags (PBRTs) wherein the at least two PBRTs are independently any of:
   (a) a polypeptide having the amino acid sequence of SEQ ID NO: 1, or
   (b) a polypeptide having the amino acid sequence of any of SEQ ID NOs 25-1337;
   wherein the PBRC precipitates in response to binding of calcium by the at least two PBRTs.

3. A precipitable beta roll cassette (PBRC) comprising at least two beta roll tags (PBRTs) wherein the at least two PBRTs are independently any of:
   (a) a polypeptide having the amino acid sequence of SEQ ID NO: 1; or
   (b) a polypeptide having the amino acid sequence of any of SEQ ID NOs 25-1337; or
   (c) a polypeptide comprising the amino acid sequence GXXXXXXXX, wherein,
      (i) the X at position 2 is an amino acid selected from the group consisting of glycine, asparagine or aspartic acid, and
      (ii) the X at position 3 is an amino acid selected from the group consisting of alanine, glycine, aspartic acid, glutamic acid, leucine or asparagine, and
      (iii) the X at position 4 is an amino acid selected from the group consisting of glycine or alanine, and
      (iv) the X at position 5 is an amino acid selected from the group consisting of asparagine, aspartic acid, alanine, or serine, and
      (v) the X at position 6 is an amino acid selected from the group consisting of aspartic acid or asparagine,
      (vi) the X at position 7 is an amino acid selected from the group consisting of threonine, isoleucine, valine, or leucine, and
      (vii) the X at position 8 is an amino acid selected from the group consisting of leucine, isoleucine, or phenylalanine, and
      (viii) the X at position 9 is an amino acid selected from the group consisting of tyrosine, isoleucine, valine, phenylalanine, threonine, asparagine, aspartic acid, lysine or serine;
   wherein the PBRC precipitates in response to binding of calcium by the at least two PBRTs.

4. The PBRC of any of claims 1-3 further comprising a capping sequence.

5. The PBRC of any of claims 1-3 further comprising a stabilizing polypeptide.

6. A PBRC linked purification moiety comprising the PBRC of any of claims 1-3.

7. The PBRC linked purification moiety of claim 6 wherein the PBRC is linked to the purification moiety by a peptide bond.

8. The PBRC linked purification moiety of claim 6 wherein the PBRC is linked to the purification moiety by a chemical bond that is not a peptide bond.

9. The PBRC of any of claims 1-3 further comprising a cleavage site located N-terminally or C-terminally to one or more of the at least two PBRTs.

10. The PBRC of claim 9, wherein the cleavage site is selected from the group comprising an intein cleavage site, a Factor Xa cleavage site, a thrombin cleavage site, an enterokinase cleavage site, or a signal peptidase cleavage site.

11. A polypeptide comprising the PBRC of any of claims 1-3 and a purification moiety.

* * * * *